US009962689B2

(12) United States Patent
Carney et al.

(10) Patent No.: US 9,962,689 B2
(45) Date of Patent: May 8, 2018

(54) PHOSPHINYL FORMAMIDINE COMPOUNDS, METAL COMPLEXES, CATALYST SYSTEMS, AND THEIR USE TO OLIGOMERIZE OR POLYMERIZE OLEFINS

(71) Applicant: Chevron Phillips Chemical Company LP, The Woodlands, TX (US)

(72) Inventors: Michael J. Carney, Eau Claire, WI (US); Brooke L. Small, Kingwood, TX (US); Orson L. Sydora, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 58 days.

(21) Appl. No.: 15/104,185

(22) PCT Filed: Dec. 18, 2013

(86) PCT No.: PCT/US2013/075936
§ 371 (c)(1),
(2) Date: Jun. 13, 2016

(87) PCT Pub. No.: WO2015/094207
PCT Pub. Date: Jun. 25, 2015

(65) Prior Publication Data
US 2016/0375431 A1    Dec. 29, 2016

(51) Int. Cl.
*B01J 31/18* (2006.01)
*C07F 9/46* (2006.01)
*C07F 11/00* (2006.01)
*C07C 2/36* (2006.01)
*C08F 4/69* (2006.01)
*B01J 31/14* (2006.01)
*C07C 2/30* (2006.01)
*C07F 9/50* (2006.01)

(52) U.S. Cl.
CPC .......... *B01J 31/188* (2013.01); *B01J 31/143* (2013.01); *C07C 2/30* (2013.01); *C07C 2/36* (2013.01); *C07F 9/46* (2013.01); *C07F 9/5004* (2013.01); *C07F 9/5022* (2013.01); *C07F 11/005* (2013.01); *C08F 4/69068* (2013.01); *B01J 2231/20* (2013.01); *C07C 2531/14* (2013.01); *C07C 2531/18* (2013.01); *C07C 2531/34* (2013.01)

(58) Field of Classification Search
None
See application file for complete search history.

(56) References Cited

U.S. PATENT DOCUMENTS

2012/0309965 A1   12/2012   Sydora et al.

FOREIGN PATENT DOCUMENTS

| CH | 513130 A | 9/1971 |
|---|---|---|
| EP | 1997834 A1 | 12/2008 |
| WO | 2011082192 A1 | 7/2011 |
| WO | 2015094207 A1 | 6/2015 |

OTHER PUBLICATIONS

Wong et al. (Journal of Organometallic Chemistry, 612, 2000, 160-171 (Year: 2000).*
Conde-Guadano, Susana, et al., "Amidine- and amidinate-functionalised N-heterocyclic carbene complexes of silver and chromium," Dalton Transactions, 2012, pp. 12558-12567, vol. 41, The Royal Society of Chemistry.
Foreign communication from a related counterpart application—International Search Report and Written Opinion, PCT/US2013/075936, dated Sep. 3, 2014, 8 pages.
Foreign communication from a related counterpart application—International Preliminary Report on Patentability, PCT/US2013/075936, dated Jun. 21, 2016, 6 pages.
Group notation revised in periodic table, C&EN, Feb. 4, 1985, pp. 26-27.
Mahieu, Armelle, et al., "Masked Iminophosphide Anion: Synthesis and Versatile Reactivity," Organometallics, 1995, pp. 944-952, vol. 14, No. 2, American Chemical Society.
McNaught, Alan D., et al., "Compendium of Chemical Terminology," IUPAC Recommendations, Second edition, 1997, 5 pages, Wiley-Blackwell.
Siddiqui, Salimuzzaman, et al., "Some Extensions of the Von Braun (BrCN) Reaction on Organic Bases," Pakistan J. Sci. Ind. Res., Physical Sciences Section, Mar. 1987, pp. 163-181, vol. 30, No. 3.
Son, Kyung-Sun, et al., "Synthesis and Structural Diversity of Mono-, Di- and Trinuclear Complexes with N,N'-Bis [(2-diphenylphosphanyl)phenyl]formamidine," Eur. J. Inorg. Chem., 2011, pp. 4256-4261, Wiley-VCH Verlag GmbH & Co. KGaA, Weinheim.
Tsukada, Naofumi, et al., "Amination of Aryl Iodides Catalyzed by a Palladium—Copper Complex Supported by a Chelate-Bridging Ligand," Organometallics, 2012, pp. 7336-7338, vol. 31, American Chemical Society.
Tsukada, Naofumi, et al., "Palladium-Catalyzed Selective Cross-Addition of Triisopropylsilylacetylene to Internal and Terminal Unactivated Alkynes," Organic Letters, 2007, pp. 2919-2921, vol. 9, No. 15, American Chemical Society.

(Continued)

*Primary Examiner* — Yun Qian
(74) *Attorney, Agent, or Firm* — Conley Rose, P.C.; Rodney B. Carroll; Monte R. Rhodes

(57) ABSTRACT

$N^2$-phosphinyl formamidine compounds and $N^2$-phosphinyl formamidine metal salt complexes are described. Methods for making $N^2$-phosphinyl formamidine compounds and $N^2$-phosphinyl formamidine metal salt complexes are also disclosed. Catalyst systems utilizing the $N^2$-phosphinyl formamidine metal salt complexes are also disclosed along with the use of the $N^2$-phosphinyl amidine compounds and $N^2$-phosphinyl amidinate metal salt complexes for the oligomerization and/or polymerization of olefins.

16 Claims, No Drawings

(56) References Cited

OTHER PUBLICATIONS

Tsukada, Naofumi, et al., "Stereoselective cis-Addition of Aromatic C—H Bonds to Alkynes Catalyzed by Dinuclear Palladium Complexes," J. Am. Chem. Soc., 2003, pp. 12102-12103, vol. 125, No. 40, American Chemical Society.

Tsukada, Naofumi, et al., "Synthesis and Structures of Palladium and Platinum A-Frame Complexes Bridged by a Novel Binucleating Ligand, N,N'-Bis[(2-diphenylphosphino)phenyl]formamidine," Organometallics, 2002, pp. 2521-2528, vol. 21, No. 12, American Chemical Society.

Wawer, Iwona, "13C NMR Study of the Substituent Effects on the Internal Steric Hindrances in Amidines," Magnetic Resonance in Chemistry, 1989, pp. 577-581, vol. 27, John Wiley & Sons, Ltd.

\* cited by examiner

US 9,962,689 B2

PHOSPHINYL FORMAMIDINE COMPOUNDS, METAL COMPLEXES, CATALYST SYSTEMS, AND THEIR USE TO OLIGOMERIZE OR POLYMERIZE OLEFINS

CROSS-REFERENCE TO RELATED APPLICATIONS

This application is a filing under 35 U.S.C. 371 of International Application No. PCT/US2013/075936 filed Dec. 18, 2013, entitled "Phosphinyl Formamidine Compounds, Metal Complexes, Catalyst Systems, and Their Use to Oligomerize or Polymerize Olefins," which application is incorporated by reference herein in its entirety.

TECHNICAL FIELD

This disclosure relates to $N^2$-phosphinyl formamidine compounds, metal complexes of $N^2$-phosphinyl formamidine compounds and their production. The disclosure also relates to methods of producing the $N^2$-phosphinyl formamidine compounds and the metal complexes of $N^2$-phosphinyl formamidine compounds. The disclosure further relates to catalyst systems utilizing the $N^2$-phosphinyl formamidine compounds, metal complexes of $N^2$-phosphinyl formamidine compounds, and their use in the oligomerization or polymerization of olefins.

BACKGROUND

Olefins, also commonly known as alkenes, are important items of commerce. Their many applications include employment as intermediates in the manufacture of detergents, as precursors to more environmentally friendly refined oils, as monomers, and as precursors for many other types of products. An important subset of olefins are olefin oligomers, and one method of making olefin oligomers is via oligomerization of ethylene, which is a catalytic reaction involving various types of catalysts and/or catalyst systems. Examples of catalysts and catalyst systems used commercially in the oligomerization of olefins include alkylaluminum compounds, certain nickel-phosphine complexes, a titanium halide with a Lewis acid (e.g., diethyl aluminum chloride), and a selective 1-hexene catalyst system containing a chromium containing compound (e.g., a chromium carboxylate), a nitrogen containing ligand (e.g., a pyrrole), and a metal alkyl (e.g., alkyl aluminum compounds).

Several non-commercial olefin oligomerization catalyst systems are based upon metal complexes of pyridine bis-imines, metal complexes of α-diimine compounds having a metal complexing group, and selective trimerization and/or tetramerization catalyst system using a metal complex of a compound having a diphosphinylaminyl group. These catalyst systems typically use an alkyl aluminum compound (e.g., aluminoxane) to activate the metal complexes for olefin oligomerization.

Applications and demand for olefin oligomers (e.g., alpha olefins) continue to multiply, and competition to supply them correspondingly intensifies. Thus, additional novel and improved catalysts and methods for olefin oligomerization are desirable.

SUMMARY

In an aspect, the present disclosure relates to a compound comprising an $N^2$-phosphinyl formamidine group. In an aspect, the present disclosure relates to a metal complex comprising a metal salt complexed to a compound having an $N^2$-phosphinyl formamidine group. In an embodiment, the metal salt complex can comprise a Group 4-10 metal salt complexed to a compound comprising an $N^2$-phosphinyl formamidine group. In an embodiment, the metal salt complex can comprise chromium. In an embodiment, the metal salt of the metal salt complex can be a chromium halide or chromium β-diketonate.

In an aspect, the present disclosure relates to a method of preparing a compound comprising an $N^2$-phosphinyl formamidine group. In an embodiment, the method for preparing a compound comprising an $N^2$-phosphinyl formamidine group can comprise: a) contacting an amine having the formula $R^1NH_2$ and a trihydrocarbylformate to form a formamidine compound; b) contacting a metal alkyl with the formamidine compound to form a metal formamidinate; and c) contacting a phosphine halide with the metal formamidinate to form a compound comprising the $N^2$-phosphinyl formamidine group. In some embodiments, the method for preparing an $N^2$-phosphinyl formamidine compound can comprise: a) contacting an amine having the formula $R^1NH_2$ and a trihydrocarbylformate to form a hydrocarboxymethanimine compound; b) contacting an ammonium carbonate with the hydrocarboxymethanimine to form a formamidine compound; c) contacting a metal alkyl with the formamidine compound to form a metal formamidinate; and d) contacting a phosphine halide with the metal formamidinate to form a compound comprising the $N^2$-phosphinyl formamidine group.

In an aspect, the present disclosure relates to a method of preparing an $N^2$-phosphinyl formamidine metal salt complex. In an embodiment, the method of preparing the $N^2$-phosphinyl formamidine metal salt complex can comprise: a) contacting a metal salt with an $N^2$-phosphinyl formamidine compound; and b) forming the $N^2$-phosphinyl formamidine metal salt complex.

In an aspect, the present disclosure relates to a catalyst system comprising a metal salt complexed to a compound having an $N^2$-phosphinyl formamidine group and a metal alkyl. In another aspect, the present disclosure relates to a catalyst system comprising a metal salt, a compound having an $N^2$-phosphinyl formamidine group, and a metal alkyl. In an embodiment, the metal salt of the metal salt complex or the catalyst system can comprise a Group 4-10 metal salt. In some embodiments, the metal salt of the metal salt complex or the catalyst system can comprise chromium. In other embodiments, the metal salt of the metal salt complex or the catalyst system can comprise a chromium halide or chromium β-diketonate.

In an aspect, the present disclosure relates to an oligomerization process or a polymerization process. In an embodiment, a process can comprise: contacting an olefin, a catalyst system comprising i) an $N^2$-phosphinyl formamidine metal salt complex and ii) a metal alkyl, and optionally hydrogen; and b) forming an oligomer product (or polymer product). In an embodiment, a process can comprise: contacting an olefin, a catalyst system comprising i) an $N^2$-phosphinyl formamidine compound, ii) a metal salt, and iii) a metal alkyl, and optionally hydrogen; and b) forming an oligomer product (or polymer product). In some embodiments, a process can comprise: a) forming a catalyst system mixture comprising an $N^2$-phosphinyl formamidine metal salt complex, and a metal alkyl; b) contacting the catalyst system mixture with an olefin, and optionally hydrogen; and c) forming an oligomer product (or polymer product). In other embodiments, a process can comprise: a) forming a catalyst system mixture comprising an $N^2$-phosphinyl formamidine metal salt complex, a metal alkyl, and a first solvent; b) contacting the catalyst system mixture with an olefin, a second solvent, and optionally hydrogen; and c) forming an oligomer product (or polymer product). In yet another embodiment, a process can comprise: a) forming a catalyst system mixture comprising an $N^2$-phosphinyl formamidine compound, a metal salt, and a metal alkyl; b) contacting the catalyst system mixture of step a) with an olefin and optionally hydrogen; and c) forming an oligomer product. In yet another embodiment, a process can comprise: a) forming a catalyst system mixture comprising an $N^2$-phosphinyl formamidine compound, a metal salt, a metal alkyl, and a first solvent; b) contacting the catalyst system mixture with an olefin, a second solvent, and optionally hydrogen; and c) forming an oligomer product.

In an embodiment, the metal salt or the metal salt of the $N^2$-phosphinyl formamidine metal salt complex can comprise a Group 4-10 metal salt; or alternatively, a chromium salt. In some embodiments, the metal salt or the metal salt of the $N^2$-phosphinyl formamidine metal salt complex can comprise a chromium halide or chromium β-diketonate. In an embodiment, the olefin utilized in oligomerization or polymerization process can comprise, or consist essentially of, $C_2$ to $C_{30}$ olefin; alternatively, a $C_2$ to $C_{30}$ alpha olefin; alternatively, a $C_2$ to $C_{30}$ normal alpha olefin; alternatively, ethylene or propylene; or alternatively, ethylene. In an embodiment wherein the olefin is ethylene, the oligomerization process can be an ethylene trimerization process and/or an ethylene tetramerization process. In some embodiments, the ethylene trimerization process and/or ethylene tetramerization process can produce an oligomer product comprising a liquid product comprising at least 60 wt. % $C_6$ and $C_8$ olefins.

Disclosed herein is an $N^2$-phosphinyl formamidine compound having the formula:

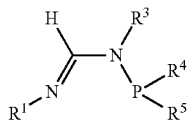

wherein $R^1$ is a $C_1$ to $C_{30}$ organyl group, $R^3$ is hydrogen, a $C_1$ to $C_{30}$ organyl group, or a $C_1$ to $C_{30}$ organyl group consisting essentially of inert functional groups, and $R^4$ and $R^5$ are each independently a $C_1$ to $C_{30}$ organyl group consisting essentially of inert functional groups.

Also disclosed herein is a method of preparing an $N^2$-phosphinyl formamidine compound, comprising a) contacting a metal alkyl with a formamidine compound to form a metal formamidinate; and b) contacting a phosphine halide with the metal formamidinate to form a compound comprising an $N^2$-phosphinyl formamidine group.

Also disclosed herein is a metal salt complex of an $N^2$-phosphinyl formamidine compound having the formula

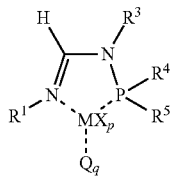

or the formula

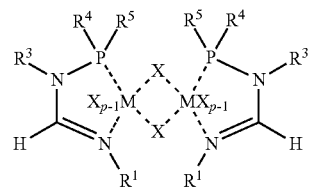

wherein $R^1$ is a $C_1$ to $C_{30}$ organyl group, $R^3$ is hydrogen, a $C_1$ to $C_{30}$ organyl group, or a $C_1$ to $C_{30}$ organyl group consisting essentially of inert functional groups, $R^4$ and $R^5$ are each independently a $C_1$ to $C_{30}$ organyl group consisting essentially of inert functional groups, $MX_p$ represents the metal salt where M is a transition metal, X is a monoanion and p ranges from 2 to 6, or X is a dianion and p ranges from 1 to 3, Q is a neutral ligand, and q ranges from 0 to 6.

Also disclosed herein is a method of preparing an $N^2$-phosphinyl formamidine metal salt complex having the formula

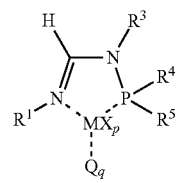

comprising a) contacting a transition metal salt with an $N^2$-phosphinyl formamidine compound; and b) forming the $N^2$-phosphinyl formamidine metal salt complex.

Also disclosed herein is a catalyst system comprising a) an $N^2$-phosphinyl formamidine metal salt complex having the formula

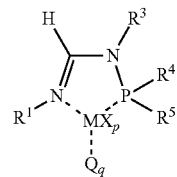

or the formula

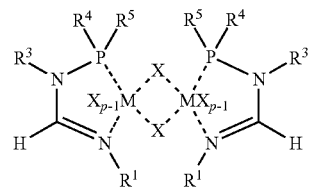

wherein $R^1$ is a $C_1$ to $C_{30}$ organyl group, $R^3$ is hydrogen, a $C_1$ to $C_{30}$ organyl group, or a $C_1$ to $C_{30}$ organyl group consisting essentially of inert functional groups, $R^4$ and $R^5$ are each independently a $C_1$ to $C_{30}$ organyl group consisting essentially of inert functional groups, $MX_p$ represents the metal salt where M is a transition metal, X is a monoanion and p ranges from 2 to 6, or X is a dianion and p ranges from 1 to 3, Q is a neutral ligand, and q ranges from 0 to 6 and b) a metal alkyl.

Also disclosed herein is a process comprising a) contacting an olefin and a catalyst comprising a) an $N^2$-phosphinyl formamidine metal salt complex having the formula

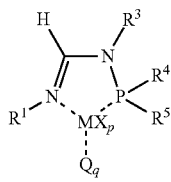

or the formula

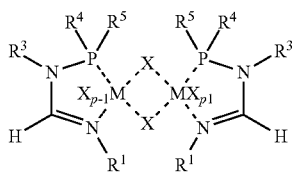

wherein $R^1$ is a $C_1$ to $C_{30}$ organyl group, $R^3$ is hydrogen, a $C_1$ to $C_{30}$ organyl group, or a $C_1$ to $C_{30}$ organyl group consisting essentially of inert functional groups, $R^4$ and $R^5$ are each independently a $C_1$ to $C_{30}$ organyl group consisting essentially of inert functional groups, $MX_p$ represents the metal salt where M is a transition metal, X is a monoanion and p ranges from 2 to 6, or X is a dianion and p ranges from 1 to 3, Q is a neutral ligand, and q ranges from 0 to 6 and b) a metal alkyl wherein the metal alkyl is an aluminoxane; and b) forming an oligomer product. The method disclosed herein further comprises contacting the catalyst system mixture with an olefin and forming an oligomer product.

DETAILED DESCRIPTION

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the table are indicated using the numbering scheme indicated in the version of the periodic table of elements published in *Chemical and Engineering News*, 63(5), 27, 1985. In some instances a group of elements can be indicated using a common name assigned to the group; for example alkali earth metals (or alkali metals) for Group 1 elements, alkaline earth metals (or alkaline metals) for Group 2 elements, transition metals for Group 3-12 elements, and halogens for Group 17 elements.

Regarding claim transitional terms or phrases, the transitional term "comprising", which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter the composition or method to which the term is applied. For example, a feedstock consisting of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class which is utilized and it is possible to have different transitional terms or phrases utilized with different features within a claim. For example, a method can comprise several recited steps (and other non-recited steps) but utilize a catalyst system preparation consisting essentially of specific or alternatively consists of specific steps and/or utilize a catalyst system comprising recited components and other non-recited components.

While compositions and methods are described in terms of "comprising" various components or steps, the compositions and methods can also "consist essentially of" or "consist of" the various components or steps.

The terms "a," "an," and "the" are intended, unless specifically indicated otherwise, to include plural alternatives, e.g., at least one. For instance, the disclosure of "a trialkylaluminum compound" is meant to encompass one trialkylaluminum compound, or mixtures or combinations of more than one trialkylaluminum compound unless otherwise specified.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to pentane includes n-pentane, 2-methyl-butane, and 2,2-dimethylpropane while a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent"

compound, for example, by the number of hydrogen atoms formally removed from the parent compound to generate the group, even if that group is not literally synthesized in this manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout the disclosure a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

A formamidine group is a group having the general structure

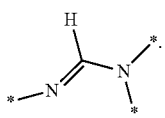

Within the formamidine group the nitrogen participating in a double bond with the central carbon atom is referred to as the $N^1$ nitrogen and the nitrogen atom participating in a single bond with the central carbon atom is referred to as the $N^2$ nitrogen. Similarly, the groups attached to the $N^1$ and $N^2$ nitrogen atoms are referred to as the $N^1$ group and $N^2$ group respectively. An $N^2$-phosphinyl formamidine group has the general structure

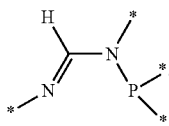

Within the $N^2$-phosphinyl formamidine group the $N^1$ and $N^2$ nitrogen atoms and $N^1$ and $N^2$ groups have the same meaning as described for the formamidine group. Consequently, an $N^2$-phosphinyl formamidine group has the phosphinyl group is attached to the $N^2$ nitrogen atom.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth. In one aspect, the hydrogen atom(s) removed to form the "organyl group," "organylene group," or "organic group" can be attached to a carbon atom belonging to a functional group, for example, an acyl group (—C(O)R), a formyl group (—C(O)H), a carboxy group (—C(O)OH), a hydrocarboxycarbonyl group (—C(O)OR), a cyano group (—C≡N), a carbamoyl group (—C(O)NH$_2$), a N-hydrocarbylcarbamoyl group (—C(O)NHR), or N,N'-dihydrocarbylcarbamoyl group (—C(O)NR$_2$), among other possibilities. In another aspect, the hydrogen atom(s) removed to form the "organyl group," "organylene group," or "organic group" can be attached to a carbon atom not belonging to, and remote from, a functional group, for example, —CH$_2$C(O)CH$_3$, —CH$_2$NR$_2$, and the like. An "organyl group," "organylene group," or "organic group" can be aliphatic, inclusive of being cyclic or acyclic, or can be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the term "organyl group consisting of inert functional groups" definition includes the hydrocarbyl group as a member (among other groups). Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups.

For purposes of this application, an "inert functional group" is a group which does not substantially interfere with the process described herein in which the material having an inert functional group takes part and/or does not complex with the metal compound of the metal complex. The term "does not complex with the metal compound" can include groups that could complex with a metal compound but in particular molecules described herein may not complex with a metal compound due to its positional relationship within a ligand. For example, while an ether group can complex with a metal compound, an ether group located at a para position of a substituted phenyl phosphinyl group may be an inert functional group because a single metal compound cannot complex with both the para ether group and the $N^2$-phosphinyl formamidine group of the same metal complex molecule. Thus, the inertness of a particular functional group is not only related to the functional group's inherent inability to complex the metal compound but can also be related to the functional group's position within the metal complex. Non-limiting examples of inert functional groups which do not substantially interfere with processes described herein can include halo (fluoro, chloro, bromo, and iodo), nitro, hydrocarboxy groups (e.g., alkoxy, and/or aroxy, among others), sulfidyl groups, and/or hydrocarbyl groups, among others.

The term "hydrocarbon" whenever used in this specification and claims refers to a compound containing only carbon and hydrogen. Other identifiers can be utilized to indicate the presence of particular groups in the hydrocarbon (e.g. halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Non-limiting examples of hydrocarbyl groups include ethyl, phenyl, tolyl, propenyl, and the like. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl group are derived by removal of a hydrogen atom from a primary, secondary, tertiary carbon atom, respectively, of an alkane. The n-alkyl group can be derived by removal of a hydrogen atom from a terminal carbon atom of a linear alkane. The groups $RCH_2$ (R≠H), $R_2CH$ (R≠H), and $R_3C$ (R≠H) are primary, secondary, and tertiary alkyl groups, respectively.

A cycloalkane is a saturated cyclic hydrocarbon, with or without side chains, for example, cyclobutane. Unsaturated cyclic hydrocarbons having one or more endocyclic double or one triple bond are called cycloalkenes and cycloalkynes, respectively. Cycloalkenes and cycloalkynes having only one, only two, only three, etc. . . . endocyclic double or triple bonds, respectively, can be identified by use of the term "mono," "di," "tri,: etc. . . . within the name of the cycloalkene or cycloalkyne. Cycloalkenes and cycloalkynes can further identify the position of the endocyclic double or triple bonds.

A "cycloalkyl group" is a univalent group derived by removing a hydrogen atom from a ring carbon atom of a cycloalkane. For example, a 1-methylcyclopropyl group and a 2-methylcyclopropyl group are illustrated as follows.

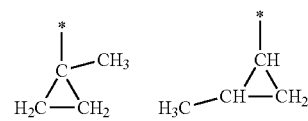

Similarly, a "cycloalkylene group" refers to a group derived by removing two hydrogen atoms from a cycloalkane, at least one of which is a ring carbon. Thus, a "cycloalkylene group" includes both a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon) from a cycloalkane. It should be noted that according to the definitions provided herein, general cycloalkane groups (including cycloalkyl groups and cycloalkylene groups) include those having zero, one, or more than one hydrocarbyl substituent groups attached to a cycloalkane ring carbon atom (e.g. a methylcyclopropyl group) and is member of the group of hydrocarbon groups. However, when referring to a cycloalkane group having a specified number of cycloalkane ring carbon atoms (e.g. cyclopentane group or cyclohexane group, among others), the base name of the cycloalkane group having a defined number of cycloalkane ring carbon atoms refers to the unsubstituted cycloalkane group (including having no hydrocarbyl groups located on cycloalkane group ring carbon atom). Consequently, a substituted cycloalkane group having a specified number of ring carbon atoms (e.g. substituted cyclopentane or substituted cyclohexane, among others) refers to the respective group having one or more substituent groups (including halogens, hydrocarbyl groups, or hydrocarboxy groups, among other substituent groups) attached to a cycloalkane group ring carbon atom. When the substituted cycloalkane group having a defined number of cycloalkane ring carbon atoms is a member of the group of hydrocarbon groups (or a member of the general group of cycloalkane groups), each substituent of the substituted cycloalkane group having a defined number of cycloalkane ring carbon atoms is limited to hydrocarbyl substituent group. One can readily discern and select general groups, specific groups, and/or individual substituted cycloalkane group(s) having a specific number of ring carbons atoms which can be utilized as member of the hydrocarbon group (or a member of the general group of cycloalkane groups).

The term "olefin" whenever used in this specification and claims refers to compounds that have at least one carbon-carbon double bond that is not part of an aromatic ring or ring system. The term "olefin" includes aliphatic and aromatic, cyclic and acyclic, and/or linear and branched compounds having at least one carbon-carbon double bond that is not part of an aromatic ring or ring system unless specifically stated otherwise. The term "olefin," by itself, does not indicate the presence or absence of heteroatoms and/or the presence or absence of other carbon-carbon double bonds unless explicitly indicated. Olefins having only one, only two, only three, etc. . . . carbon-carbon double bonds can be identified by use of the term "mono," "di," "tri," etc. . . . within the name of the olefin. The olefins can be further identified by the position of the carbon-carbon double bond(s).

The term "alkene" whenever used in this specification and claims refers a linear or branched hydrocarbon olefin that has one or more carbon-carbon double bonds. Alkenes having only one, only two, only three, etc. . . . such multiple bond can be identified by use of the term "mono," "di," "tri," etc. . . . within the name. For example, alkamonoenes, alkadienes, and alkatrienes refer to a linear or branched hydrocarbon olefins having only one carbon-carbon double bond (general formula $C_nH_{2n}$), only two carbon-carbon double bonds (general formula $C_nH_{2n-2}$), and only three carbon-carbon double bonds (general formula $C_nH_{2n-4}$), respectively. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atom of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of heteroatoms and/or the presence or absence of other carbon-carbon double bonds unless explicitly indicated. The terms "hydrocarbon alpha olefin" or "alpha olefin hydrocarbon" refer to alpha olefin compounds containing only hydrogen and carbon.

The term "linear alpha olefin" as used herein refers to a linear olefin having a carbon-carbon double bond between the first and second carbon atom. The term "linear alpha olefin" by itself does not indicate the presence or absence of heteroatoms and/or the presence or absence of other carbon-carbon double bonds, unless explicitly indicated. The terms "linear hydrocarbon alpha olefin" or "linear alpha olefin hydrocarbon" refers to linear alpha olefin compounds containing only hydrogen and carbon.

The term "normal alpha olefin" whenever used in this specification and claims refers to a linear hydrocarbon mono-olefin having a carbon carbon double bond between the first and second carbon atom. It is noted that "normal alpha olefin" is not synonymous with "linear alpha olefin" as the term "linear alpha olefin" can include linear olefinic compounds having a double bond between the first and second carbon atoms and having heteroatoms and/or additional double bonds.

The term "consists essentially of normal alpha olefin(s)," or variations thereof, whenever used in this specification and claims refers to commercially available normal alpha olefin product(s). The commercially available normal alpha olefin product can contain non-normal alpha olefin impurities such as vinylidenes, internal olefins, branched alpha olefins, paraffins, and diolefins, among other impurities, which are not removed during the normal alpha olefin production process. One readily recognizes that the identity and quantity of the specific impurities present in the commercial normal alpha olefin product will depend upon the source of commercial normal alpha olefin product. Consequently, the term "consists essentially of normal alpha olefins" and its variants is not intended to limit the amount/quantity of the non-linear alpha olefin components any more stringently than the amounts/quantities present in a particular commercial normal alpha olefin product unless explicitly stated.

A "heterocyclic compound" is a cyclic compound having at least two different elements as ring member atoms. For example, heterocyclic compounds can comprise rings containing carbon and nitrogen (for example, tetrahydropyrrole), carbon and oxygen (for example, tetrahydrofuran), or carbon and sulfur (for example, tetrahydrothiophene), among others. Heterocyclic compounds and heterocyclic groups can be either aliphatic or aromatic.

A "heterocyclyl group" is a univalent group formed by removing a hydrogen atom from a heterocyclic ring or ring system carbon atom of a heterocyclic compound. By specifying that the hydrogen atom is removed from a heterocyclic ring or ring system carbon atom, a "heterocyclyl group" is distinguished from a "cycloheteryl group," in which a hydrogen atom is removed from a heterocyclic ring or ring system heteroatom. For example, a pyrrolidin-2-yl group illustrated below is one example of a "heterocyclyl group," and a pyrrolidin-1-yl group illustrated below is one example of a "cycloheteryl group."

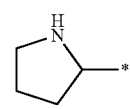 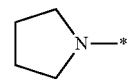

pyrrolidin-2-yl "heterocyclyl group"    pyrrolidin-1-yl "cycloheteryl group"

Similarly, a "heterocyclylene group" or more simply, a "heterocyclene group," refers to a group formed by removing two hydrogen atoms from a heterocyclic compound, at least one of which is from a heterocyclic ring or ring system carbon. Thus, in a "heterocyclylene group," at least one hydrogen is removed from a heterocyclic ring or ring system carbon atom, and the other hydrogen atom can be removed from any other carbon atom, including for example, the same heterocyclic ring or ring system carbon atom, a different heterocyclic ring or ring system ring carbon atom, or a non-ring carbon atom. A "heterocyclic group" refers to a generalized group formed by removing one or more hydrogen atoms (as necessary for the particular group and at least one of which is a heterocyclic ring carbon atom) from a heterocyclic compound. Generally, a heterocyclic compound can be aliphatic or aromatic unless otherwise specified.

A "cycloheteryl group" is a univalent group formed by removing a hydrogen atom from a heterocyclic ring or ring system heteroatom of a heterocyclic compound, as illustrated. By specifying that the hydrogen atom is removed from a heterocyclic ring or ring system heteroatom and not from a ring carbon atom, a "cycloheteryl group" is distinguished from a "heterocyclyl group" in which a hydrogen atom is removed from a heterocyclic ring or ring system carbon atom. Similarly, a "cycloheterylene group" refers to a group formed by removing two hydrogen atoms from an heterocyclic compound, at least one of which is removed from a heterocyclic ring or ring system heteroatom of the heterocyclic compound; the other hydrogen atom can be removed from any other atom, including for example, a heterocyclic ring or ring system ring carbon atom, another heterocyclic ring or ring system heteroatom, or a non-ring atom (carbon or heteroatom). A "cyclohetero group" refers to a generalized group formed by removing one or more hydrogen atoms (as necessary for the particular group and at least one of which is from a heterocyclic ring or ring system heteroatom) from a heterocyclic compound.

An aliphatic compound is an acyclic or cyclic, saturated or unsaturated carbon compound, excluding aromatic compounds. Thus, an aliphatic compound is an acyclic or cyclic, saturated or unsaturated carbon compound, excluding aromatic compounds; that is, an aliphatic compound is a non-aromatic organic compound. An "aliphatic group" is a generalized group formed by removing one or more hydrogen atoms (as necessary for the particular group) from the carbon atom of an aliphatic compound. Thus, an aliphatic compound is an acyclic or cyclic, saturated or unsaturated carbon compound, excluding aromatic compounds. That is, an aliphatic compound is a non-aromatic organic compound. Aliphatic compounds and therefore aliphatic groups can contain organic functional group(s) and/or atom(s) other than carbon and hydrogen.

An aromatic compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds) and "heteroarenes," also termed "hetarenes" (heteroaromatic compounds formally derived from arenes by replacement of one or more methine (—C═) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2). While arene compounds and heteroarene compounds are mutually exclusive members of the group of aromatic compounds, a compound that has both an arene group and a heteroarene group are generally considered a heteroarene compound. Aromatic compounds, arenes, and heteroarenes can be monocyclic (e.g., benzene, toluene, furan, pyridine, methylpyridine) or polycyclic unless otherwise specified. Polycyclic aromatic compounds, arenes, and heteroarenes, include, unless otherwise specified, compounds wherein the aromatic rings can be fused (e.g., naphthalene, benzofuran, and indole), compounds where the aromatic groups can be separate and joined by a bond (e.g., biphenyl or 4-phenylpyridine), or compounds where the aromatic groups are joined by a group containing linking atoms (e.g., carbon—the methylene group in diphenylmethane; oxygen—diphenyl ether; nitrogen—triphenyl amine; among others linking groups). As disclosed herein, the term "substituted" can be used to describe an aromatic group, arene, or heteroarene wherein a non-hydrogen moiety formally replaces a hydrogen in the compound, and is intended to be non-limiting.

An "aromatic group" refers to a generalized group formed by removing one or more hydrogen atoms (as necessary for the particular group and at least one of which is an aromatic ring carbon atom) from an aromatic compound. For a univalent "aromatic group," the removed hydrogen atom must be from an aromatic ring carbon. For an "aromatic group" formed by removing more than one hydrogen atom from an aromatic compound, at least one hydrogen atom must be from an aromatic hydrocarbon ring carbon. Additionally, an "aromatic group" can have hydrogen atoms removed from the same ring of an aromatic ring or ring system (e.g., phen-1,4-ylene, pyridin-2,3-ylene, naphth-1,2-ylene, and benzofuran-2,3-ylene), hydrogen atoms removed from two different rings of a ring system (e.g., naphth-1,8-ylene and benzofuran-2,7-ylene), or hydrogen atoms removed from two isolated aromatic rings or ring systems (e.g., bis(phen-4-ylene)methane).

An arene is an aromatic hydrocarbon, with or without side chains (e.g. benzene, toluene, or xylene, among others. An "aryl group" is a group derived from the formal removal of a hydrogen atom from an aromatic ring carbon of an arene. It should be noted that the arene can contain a single aromatic hydrocarbon ring (e.g., benzene, or toluene), contain fused aromatic rings (e.g., naphthalene or anthracene), and/or contain one or more isolated aromatic rings covalently linked via a bond (e.g., biphenyl) or non-aromatic hydrocarbon group(s) (e.g., diphenylmethane). One example of an "aryl group" is ortho-tolyl (o-tolyl), the structure of which is shown here.

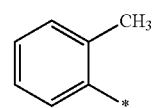 [SMILES: *c1ccccc1C]

Similarly, an "arylene group" refers to a group formed by removing two hydrogen atoms (at least one of which is from an aromatic ring carbon) from an arene. An "arene group" refers to a generalized group formed by removing one or more hydrogen atoms (as necessary for the particular group and at least one of which is an aromatic ring carbon) from an arene. However, if a group contains separate and distinct arene and heteroarene rings or ring systems (e.g. the phenyl and benzofuran moieties in 7-phenylbenzofuran) its classification depends upon the particular ring or ring system from which the hydrogen atom was removed, that is, an arene group if the removed hydrogen came from the aromatic hydrocarbon ring or ring system carbon atom (e.g. the 2 carbon atom in the phenyl group of 6-phenylbenzofuran) and a heteroarene group if the removed hydrogen carbon came from a heteroaromatic ring or ring system carbon atom (e.g. the 2 or 7 carbon atom of the benzofuran group or 6-phenylbenzofuran). It should be noted that according the definitions provided herein, general arene groups (including an aryl group and an araylene group) include those having zero, one, or more than one hydrocarbyl substituent groups located on an aromatic hydrocarbon ring or ring system carbon atom (e.g. a toluene group or a xylene group, among others) and is a member of the group of hydrocarbon groups. However, a phenyl group (or phenylene group) and/or a naphthyl group (or naphthylene group) refer to the specific unsubstituted arene groups (including no hydrocarbyl group located on an aromatic hydrocarbon ring or ring system carbon atom). Consequently, a substituted phenyl group or substituted naphthyl group refers to the respective arene group having one or more substituent groups (including halogens, hydrocarbyl groups, or hydrocarboxy groups, among others) located on an aromatic hydrocarbon ring or ring system carbon atom. When the substituted phenyl group and/or substituted naphtyl group is a member of the group of hydrocarbon groups (or a member of the general group of arene groups), each substituent is limited to a hydrocarbyl substituent group. One having ordinary skill in the art can readily discern and select general phenyl and/or naphthyl groups, specific phenyl and/or naphthyl groups, and/or individual substituted phenyl or substituted naphthyl groups which can be utilized as a member of the group of hydrocarbon groups (or a member of the general group of arene groups).

A heteroarene is an aromatic compound, with or without side chains, having a heteroatom within the aromatic ring or aromatic ring system (e.g. pyridene, indole, or benzofuran, among others). A "heteroaryl group" is a class of "heterocyclyl group" and is a univalent group formed by removing a hydrogen atom from a heteroaromatic ring or ring system carbon atom of a heteroarene compound. By specifying that the hydrogen atom is removed from a ring carbon atom, a "heteroaryl group" is distinguished from an "arylheteryl group," in which a hydrogen atom is removed from a heteroaromatic ring or ring system heteroatom. For example, an indol-2-yl group illustrated below is one example of a "heteroaryl group," and an indol-1-yl group illustrated below is one example of an "arylheteryl group."

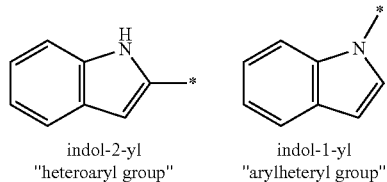

indol-2-yl
"heteroaryl group"

indol-1-yl
"arylheteryl group"

Similarly, a "heteroarylene group" refers to a group formed by removing two hydrogen atoms from a heteroarene compound, at least one of which is from a heteroarene ring or ring system carbon atom. Thus, in a "heteroarylene group," at least one hydrogen is removed from a heteroarene ring or ring system carbon atom, and the other hydrogen atom can be removed from any other carbon atom, including for example, a heteroarene ring or ring system carbon atom, or a non-heteroarene ring or ring system atom. A "heteroarene group" refers to a generalized group formed by removing one or more hydrogen atoms (as necessary for the particular group and at least one of which is a heteroarene ring or ring system carbon atom) from a heteroarene compound. If a hydrogen atom is removed from a heteroaromatic ring or ring system heteroatom and from a heteroaromatic ring or ring system carbon atom or an aromatic hydrocarbon ring or ring system carbon atom, the group is classified as an "arylheterylene group" or an "arylhetero group."

An "arylheteryl group" is a class of "cycloheteryl group" and is a univalent group formed by removing a hydrogen atom from a heteroaromatic ring or ring system heteroatom, as illustrated. By specifying that the hydrogen atom is removed from of a heteroaromatic ring or ring system heteroatom and not from a heteroaromatic ring or ring system carbon atom, an "arylheteryl group" is distinguished from a "heteroaryl group" in which a hydrogen atom is removed from a heteroaromatic ring or a ring system carbon atom. Similarly, an "arylheterylene group" refers to a group formed by removing two hydrogen atoms from a heteroaryl compound, at least one of which is removed from a heteroaromatic ring or ring system heteroatom of the heteroaryl compound; the other hydrogen atom can be removed from any other atom, including for example, a heteroaromatic ring or ring system carbon atom, another heteroaromatic ring or ring system heteroatom, or a non-ring atom (carbon or heteroatom) from a heteroaromatic compound. An "arylhetero group" refers to a generalized group formed by removing one or more hydrogen atoms (as necessary for the particular group and at least one of which is from a heteroaromatic ring or ring system) heteroatom from a heteroarene compound.

An "aralkyl group" is an aryl-substituted alkyl group having a free valance at a non-aromatic carbon atom (e.g. a benzyl group, or a 2-phenyleth-1yl group, among others). Similarly, an "aralkylene group" is an aryl-substituted alkylene group having two free valencies at a single non-aromatic carbon atom or a free valence at two non-aromatic carbon atoms while an "aralkane group" is a generalized aryl-substituted alkane group having one or more free valencies at a non-aromatic carbon atom(s). A "heteroaralkyl group" is a heteroaryl-substituted alkyl group having a free valence at a non-heteroaromatic ring or ring system carbon atom. Similarly a "heteroaralkylene group" is a heteroaryl-substituted alkylene group having two free valencies at a single non-heteroaromatic ring or ring system carbon atom or a free valence at two non-heteroaromatic ring or ring system carbon atoms while a "heteroaralkane group" is a generalized aryl-substituted alkane group having one or more free valencies at a non-heteroaromatic ring or ring system carbon atom(s). It should be noted that according the definitions provided herein, general aralkane groups include those having zero, one, or more than one hydrocarbyl substituent groups located on an aralkane aromatic hydrocarbon ring or ring system carbon atom and is a member of the group of hydrocarbon groups. However, specific aralkane groups specifying a particular aryl group (e.g. the phenyl group in a benzyl group or a 2-phenylethyl group, among others) refer to the specific unsubstituted aralkane groups (including no hydrocarbyl group located on the aralkane aromatic hydrocarbon ring or ring system carbon atom). Consequently, a substituted aralkane group specifying a particular aryl group refers to a respective aralkane group having one or more substituent groups (including halogens, hydrocarbyl groups, or hydrocarboxy groups, among others). When the substituted aralkane group specifying a particular aryl group is a member of the group of hydrocarbon groups (or a member of the general group of aralkane groups), each substituent is limited to a hydrocarbyl substituent group. One can readily discern and select substituted aralkane groups specifying a particular aryl group which can be utilized as a member of the group of hydrocarbon groups (or a member of the general group of aralkane groups).

A "halide" has its usual meaning; therefore, examples of halides include fluoride, chloride, bromide, and iodide.

An "organoheteryl group" is a univalent group containing carbon, which are thus organic, but which have their free valence at an atom other than carbon. Thus, organoheteryl and organyl groups are complementary and mutually exclusive. Organoheteryl groups can be cyclic or acyclic, and/or aliphatic or aromatic, and thus encompass aliphatic "cycloheteryl groups" (e.g. pyrrolidin-1-yl or morpholin-1-yl, among others), aromatic "arylheteryl groups" (e.g. pyrrol-1-yl or indol-1-yl, among others), and acyclic groups (e.g. organylthio, trihydrocarbylsilyl, aryloxy, or alkoxy, among others). Similarly, an "organoheterylene group" is a divalent group containing carbon and at least one heteroatom having two free valencies, at least one of which is at a heteroatom. An "organohetero group" is a generalized group containing carbon and at least one heteroatom having one or more free valencies (as necessary for the particular group and at least one of which is at a heteroatom) from an organohetero compound.

An "organoaluminum compound," is used to describe any compound that contains an aluminum-carbon bond. Thus, organoaluminum compounds include hydrocarbyl aluminum compounds such as trialkyl-, dialkyl-, or monoalkyl-aluminum compounds; hydrocarbyl alumoxane compounds, and aluminate compounds which contain an aluminum-organyl bond such as tetrakis(p-tolyl)aluminate salts.

Within this disclosure the normal rules of organic nomenclature will prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be referenced using comprising or some other alternative language. For example, a reference to a phenyl group comprising a substituent at the 4 position refers to a group having a non-hydrogen atom at the 4 position and hydrogen or any non-hydrogen group at the 2, 3, 5, and 6 positions.

The term "reactor effluent," and it derivatives (e.g. oligomerization reactor effluent) generally refers to all the material which exits the reactor. The term "reactor effluent," and its derivatives, can also be prefaced with other descriptors that limit the portion of the reactor effluent being referenced. For example, while the term "reactor effluent" would refer to all material exiting the reactor (e.g. product and solvent or diluent, among others), the term "olefin reactor effluent" refers to the effluent of the reactor which contains an olefin (i.e. carbon-carbon) double bond.

The term "oligomerization," and its derivatives, refers to processes which produce a mixture of products containing at least 70 weight percent products containing from 2 to 30 monomer units. Similarly, an "oligomer" is a product that contains from 2 to 30 monomer units while an "oligomerization product" includes all product made by the "oligomerization" process including the "oligomers" and products which are not "oligomers" (e.g. product which contain more than 30 monomer units). It should be noted that the monomer units in the "oligomer" or "oligomerization product" do not have to be the same. For example, an "oligomer" or "oligomerization product" of an "oligomerization" process using ethylene and propylene as monomers can contain both ethylene and/or propylene units.

The term "trimerization," and it derivatives, refers to a process which produces a mixture of products containing at least 70 weight percent products containing three and only three monomer units. A "trimer" is a product which contains three and only three monomer units while a "trimerization product" includes all products made by the trimerization process including trimers and products which are not trimers (e.g. dimers or tetramers). Generally, an olefin trimerization reduces the number of olefinic bonds, i.e., carbon-carbon double bonds, by two when considering the number of olefin bonds in the monomer units and the number of olefin bonds in the trimer. It should be noted that the monomer units in the "trimer" or "trimerization product" do not have be the same. For example, a "trimer" of a "trimerization" process using ethylene and butene as monomers can contain ethylene and/or butene monomer units. That is to say the "trimer" will include $C_6$, $C_8$, $C_{10}$, and $C_{12}$ products. In another example, a "trimer" of a "trimerization" process using ethylene as the monomer can contain ethylene monomer units. It should also be noted that a single molecule can contain two monomer units. For example, dienes such as 1,3-butadiene and 1,4-pentadiene have two monomer units within one molecule.

The term "tetramerization," and it derivatives, refers to a process which produces a mixture of products containing at least 70 weight percent products containing four and only four monomer units. A "tetramer" is a product which contains four and only four monomer units while a "tetramerization product" includes all products made by the tetramerization process including tetramers and products which are not tetramers (e.g. dimers or trimer). Generally, an olefin tetramerization reduces the number of olefinic bonds, i.e., carbon-carbon double bonds, by three when considering the number of olefin bonds in the monomer units and the number of olefin bonds in the tetramer. It should be noted that the monomer units in the "tetramer" or "tetramerization product" do not have be the same. For example, a "tetramer" of a "tetramerization" process using ethylene and butene as monomers can contain ethylene and/or butene monomer units. In an example, a "tetramer" of a "tetramerization" process using ethylene as the monomer can contain ethylene monomer units. It should also be noted that a single molecule can contain two monomer units. For example, dienes such as 1,3-butadiene and 1,4-pentadiene have two monomer units within one molecule.

The term "trimerization and tetramerization," and it derivatives, refers to a process which produces a mixture of products containing at least 70 weight percent products containing three and/or four and only three and/or four monomer units. A "trimerization and tetramerization product" includes all products made by the "trimerization and tetramerization" process including trimers, tetramers, and products which are not trimers or tetramers (e.g. dimers). In an example, a "trimerization and tetramerization" process using ethylene as the monomer produces a mixture of products containing at least 70 weight percent hexene and/or octene.

The term or variation of the terms an "oligomerized product having X carbon atoms" and "$C_X$ oligomer product," wherein X can be any positive non-zero integer, refers to materials produced by monomer oligomerization which have X carbon atoms. Thus, the term oligomerized product having X carbon atoms excludes materials having X carbon atoms which were not produced by the oligomerization (e.g. solvent). These terms can also include other descriptive words (e.g. olefin, liquid, and mixture, among others) without detracting from the essence of the term referring to materials having X carbon atoms, produced by monomer oligomerization, and fitting the additional descriptive terms.

This disclosure encompasses $N^2$-phosphinyl formamidine compounds, methods for making $N^2$-phosphinyl formamidine compounds, metal salt complexes comprising $N^2$-phosphinyl formamidine compounds, methods of making metal salt complexes comprising $N^2$-phosphinyl formamidine compounds, catalyst systems comprising $N^2$-phosphinyl formamidine compounds, methods of making catalyst systems comprising $N^2$-phosphinyl formamidine compounds, and methods of oligomerizing olefins utilizing catalysts system comprising $N^2$-phosphinyl formamidine compounds, among other aspects and embodiments. These aspects of this disclosure are further described herein. While these aspects can be disclosed under these headings, the heading does not limit the disclosure found therein. Additionally the various aspects and embodiments disclosed herein can be combined in any manner.

$N^2$-Phosphinyl Formamidine Compounds

In an aspect, the compounds encompassed by the present disclosure include an $N^2$-phosphinyl formamidine compound. Generally, the $N^2$-phosphinyl formamidine compounds encompassed by this disclosure can comprise an $N^2$-phosphinyl formamidine group; or alternatively, comprise two $N^2$-phosphinyl formamidine groups. In an embodiment, the $N^2$-phosphinyl formamidine compounds comprise only one $N^2$-phosphinyl formamidine group; or alternatively, comprise only two $N^2$-phosphinyl formamidine groups. In an embodiment, the compounds, regardless of the number of $N^2$-phosphinyl formamidine groups, or structure, can be non-metallic (i.e., a non-metallic $N^2$-phosphinyl formamidine compound or a non-metallic compound having an $N^2$-phosphinyl formamidine group). In some embodiments, the formamidine group of the $N^2$-phosphinyl formamidine compounds can be an acyclic formamidine group (a formamidine group wherein the two nitrogen atoms and the central carbon atom of the amine group are not contained in a ring).

In an aspect, the $N^2$-phosphinyl formamidine compound can have Structure NPF1 or NPF2, alternatively, Structure NPF1; or alternatively, Structure NPF2.

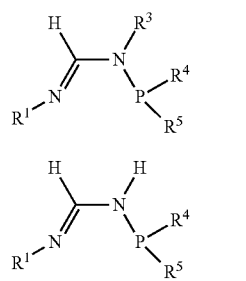

Structure NPF1

Structure NPF2

$R^1$, $R^3$, $R^4$, and $R^5$ within $N^2$-phosphinyl formamidine compound Structures NPF1 and/or NPF2 are independently described herein and can be utilized without limitation to further describe the $N^2$-phosphinyl formamidine compounds having Structures NPF1 and/or NPF2. In other embodiments, the $N^2$-phosphinyl formamidine compounds can have any specific structure disclosed herein.

Generally, $R^1$ can be an organyl group; alternatively, an organyl group consisting essentially of inert functional groups; or alternatively, a hydrocarbyl group. In an embodiment, $R^1$ can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In an embodiment, $R^1$ can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In an embodiment, $R^1$ can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In yet other embodiments, $R^1$ can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group.

In an aspect, $R^1$ can be a $C_1$ to $C_{30}$ alkyl group, a $C_4$ to $C_{30}$ cycloalkyl group, a $C_4$ to $C_{30}$ substituted cycloalkyl group, a $C_6$ to $C_{30}$ aryl group, or a $C_6$ to $C_{30}$ substituted aryl group; alternatively, a $C_4$ to $C_{30}$ cycloalkyl group or a $C_4$ to $C_{30}$ substituted cycloalkyl group; alternatively, a $C_6$ to $C_{30}$ aryl group or a $C_6$ to $C_{30}$ substituted aryl group; alternatively, a $C_1$ to $C_{30}$ alkyl group; alternatively, a $C_4$ to $C_{30}$ cycloalkyl group; alternatively, a $C_4$ to $C_{30}$ substituted cycloalkyl group; alternatively, a $C_6$ to $C_{30}$ aryl group; or alternatively, a $C_6$ to $C_{30}$ substituted aryl group. In an embodiment, $R^1$ can be a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group; alternatively, a $C_4$ to $C_{20}$ cycloalkyl group or a $C_4$ to $C_{20}$ substituted cycloalkyl group; alternatively, a $C_6$ to $C_{20}$ aryl group or a $C_6$ to $C_{20}$ substituted aryl group; alternatively, a $C_1$ to $C_{15}$ alkyl group; alternatively, a $C_4$ to $C_{20}$ cycloalkyl group; alternatively, a $C_4$ to $C_{20}$ substituted cycloalkyl group; alternatively, a $C_6$ to $C_{20}$ aryl group; or alternatively, a $C_6$ to $C_{20}$ substituted aryl group. In other embodiments, $R^1$ can be a $C_1$ to $C_{10}$ alkyl group, a $C_4$ to $C_{15}$ cycloalkyl group, a $C_4$ to $C_{15}$ substituted cycloalkyl group, a $C_6$ to $C_{15}$ aryl group, or a $C_6$ to $C_{15}$ substituted aryl group; alternatively, a $C_4$ to $C_{15}$ cycloalkyl group or a $C_4$ to $C_{15}$ substituted cycloalkyl group; alternatively, a $C_6$ to $C_{15}$ aryl group or a $C_6$ to $C_{15}$ substituted aryl group; alternatively, a $C_1$ to $C_{10}$ alkyl group; alternatively, a $C_4$ to $C_{15}$ cycloalkyl group; alternatively, a $C_4$ to $C_{15}$ substituted cycloalkyl group; alternatively, a $C_6$ to $C_{15}$ aryl group; or alternatively, a $C_6$ to $C_{15}$ substituted aryl group; or alternatively, a $C_3$ to $C_{15}$ heteroaryl group. In further embodiments, $R^1$ can be a $C_1$ to $C_5$ alkyl group.

In an embodiment, $R^1$ can be a methyl group, an ethyl group, a propyl group, a butyl group, a pentyl group, a hexyl group, a heptyl group, an octyl group, a nonyl group, or a decyl group. In some embodiments, $R^1$ can be a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, an n-propyl group; alternatively, an iso-propyl group; alternatively, a tert-butyl group; or alternatively, a neopentyl group. In some embodiments, the alkyl groups which can be utilized as $R^1$ can be substituted. Each substituent of a substituted alkyl group independently can be a halogen or a hydrocarboxy group; alternatively, a halogen; or alternatively, a hydrocarboxy group. Halogens and hydrocarboxy groups (general and specific) that can be utilized as substituents are independently disclosed herein and can be utilized without limitation to further describe the substituted alkyl group which can be utilized as $R^1$.

In an embodiment, $R^1$ can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, $R^1$ can be a cyclopentyl group, a substituted cyclopentyl group, a cyclohexyl group, or a substituted cyclohexyl group. In other embodiments, $R^1$ can be a cyclopentyl group or a substituted cyclopentyl group; or alternatively, a cyclohexyl group or a substituted cyclohexyl group. In further embodiments, $R^1$ can be a cyclopentyl group; alternatively, a substituted cyclopentyl group; a cyclohexyl group; or alternatively, a substituted cyclohexyl group. Substituents (general and specific) are independently disclosed herein and can be utilized without limitation to further describe the substituted cycloalkyl group which can be utilized as $R^1$.

In an aspect, $R^1$ can have Structure G1:

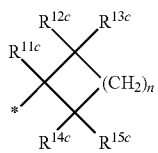

Structure G1 wherein the undesignated valency is attached to the $N^1$ nitrogen atom of the $N^2$-phosphinyl formamidine group. Generally, $R^{11c}$, $R^{12c}$, $R^{13c}$, $R^{14c}$, and $R^{15c}$ can independently be hydrogen or a non-hydrogen substituent, and n can be an integer from 1 to 5. In an embodiment wherein $R^1$ has Structure G1, $R^{11c}$, $R^{13c}$, $R^{14c}$, and $R^{15c}$ can be hydrogen and $R^{12c}$ can be any non-hydrogen substituent disclosed herein; or alternatively, $R^{11c}$, $R^{13c}$, and $R^{15c}$ can be hydrogen and $R^{12c}$ and $R^{14c}$ independently can be any non-hydrogen substituent disclosed herein. In an embodiment, n can be an integer from 1 to 4; or alternatively, from 2 to 4. In other embodiments, n can be 2 or 3; alternatively, 2; or alternatively 3. Substituents (general and specific) are independently disclosed herein and can be utilized without limitation to further describe a non-hydrogen substituent which can be utilized without limitation as $R^{11c}$, $R^{12c}$, $R^{13c}$, $R^{14c}$, and/or $R^{15c}$ for the $R^1$ group having Structure G1.

In an embodiment wherein $R^1$ has Structure G1, $R^{11c}$, $R^{13c}$, $R^{14c}$, and $R^{15c}$ can be hydrogen and $R^{12c}$ can be any non-hydrogen substituent indicated herein; or alternatively, $R^{11c}$, $R^{13c}$, and $R^{15c}$ can be hydrogen and $R^{12c}$ and $R^{14c}$ can be any non-hydrogen substituent indicated herein. In some embodiments, wherein $R^1$ has Structure G1, $R^{11c}$, $R^{13c}$, $R^{14c}$, and $R^{15c}$ can be hydrogen and $R^{12c}$ can be any alkyl group, alkoxy group, or halogen indicated herein; or alternatively, $R^{11c}$, $R^{13c}$, and $R^{15c}$ can be hydrogen and $R^{12c}$ and $R^{14c}$ can be any alkyl group, alkoxy group, or halogen indicated herein. In other embodiments, wherein $R^1$ has Structure G1, $R^{11c}$, $R^{13c}$, $R^{14c}$, and $R^{15c}$ can be hydrogen and $R^{12c}$ can be any alkyl group substituent indicated herein; or alternatively, $R^{11c}$, $R^{13c}$, and $R^{15c}$ can be hydrogen and $R^{12c}$ and $R^{14c}$ can be any alkyl group substituent indicated herein. In another embodiment wherein $R^1$ has Structure G1, $R^{11c}$, $R^{12c}$, $R^{13c}$, $R^{14c}$, and $R^{15c}$ can be hydrogen. In an embodiment, $R^{11c}$, $R^{12c}$, $R^{13c}$, $R^{14c}$, and $R^{15c}$ independently can be hydrogen, or an alkyl group; alternatively, $R^{11c}$, $R^{12c}$, and $R^{14c}$ can be hydrogen and $R^{13c}$ and $R^{15c}$ can be are alkyl groups; or alternatively, $R^{11c}$ can be hydrogen and $R^{12c}$, $R^{13c}$, $R^{14c}$, and $R^{15c}$ can be alkyl groups. Specific substituent halogens, hydrocarbyl groups, hydrocarboxy groups, alkyl group, and alkoxy groups are independently disclosed herein and can be utilized without limitation to further describe the $R^1$ group having Structure G1.

In an aspect, $R^1$ can be a phenyl group, a substituted phenyl group, a naphthyl group, or a substituted naphthyl group; alternatively, a phenyl group or a substituted phenyl group; alternatively, a naphthyl group or a substituted naphthyl group; alternatively, a phenyl group or a naphthyl group; or alternatively, a substituted phenyl group or a substituted naphthyl group. In some embodiments, $R^1$ independently can be a phenyl group; alternatively, a substituted phenyl group; alternatively, a naphthyl group; or alternatively, a substituted naphthyl group. In an embodiment, the $R^1$ substituted phenyl group can be a 2-substituted phenyl group, a 3-substituted phenyl group, a 4-substituted phenyl group, a 2,4 disubstituted phenyl group, a 2,6-disubstituted phenyl group, 3,5-disubstituted phenyl group, or a 2,4,6-trisubstituted phenyl group. In other embodiments, the $R^1$ substituted phenyl group can be a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2 substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,6-di-substituted phenyl group or a 2,4,6-trisubstituted phenyl group; alternatively, a 2,4-disubstituted phenyl group or a 2,6-disubstituted phenyl group; alternatively, a 2-substituted phenyl group; alternatively, a 3 substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Substituents (general and specific) are independently disclosed herein and can be utilized without limitation to further describe any substituted phenyl group which can be utilized as $R^1$.

In an embodiment, $R^1$ can be a naphth-1-yl group, a substituted naphth-1-yl group, a naphth-2-yl group, or a substituted naphth-2-yl group. In some embodiments, $R^1$ can be a naphth-1-yl group or a substituted naphth-1-yl group; alternatively, a naphth-2-yl group or a substituted naphth-2-yl group; alternatively, a naphth-1-yl group; alternatively, a substituted naphth-1-yl group; alternatively, a naphth-2-yl group; or alternatively, a substituted naphth-2-yl group. In other embodiments, $R^1$ can be a 2 substituted naphth-1-yl group, a 3-substituted naphth-1-yl group, a 4-substituted naphth-1-yl group, or a 8-substituted naphth-1-yl group; alternatively, a 2-substituted naphth-1-yl group; alternatively, a 3 substituted naphth-1-yl group; alternatively, a 4-substituted naphth-1-yl group; or alternatively, a 8 substituted naphth-1-yl group. In further embodiments, $R^1$ can be a 1-substituted naphth-2-yl group, a 3 substituted naphth-2-yl group, a 4-substituted naphth-2-yl group, or a 1,3-disubstituted naphth-2-yl group; alternatively, a 1-substituted naphth-2-yl group; alternatively, a 3-substituted naphth-2-yl group; alternatively, a 4-substituted naphth-2-yl group; or alternatively, a 1,3-disubstituted naphth-2-yl group. Substituents (general and specific) are independently disclosed herein can be utilized without limitation to further describe any substituted naphthyl groups which can be utilized as $R^1$.

In an aspect, the $R^1$ can have Structure G2:

Structure G2 wherein the undesignated valency is attached to the $N^1$ nitrogen atom of the $N^2$-phosphinyl formamidine group. Generally, $R^{12}$, $R^{13}$, $R^{14}$, $R^{15}$, and $R^{16}$ independently can be hydrogen or a non-hydrogen substituent. In an embodiment wherein $R^1$ has Structure G2, $R^{12}$, $R^{13}$, $R^{14}$, $R^{15}$, and $R^{16}$ can be hydrogen, $R^{13}$, $R^{14}$, $R^{15}$ and $R^{16}$ can be hydrogen and $R^{12}$ can be a non-hydrogen substituent, $R^{12}$, $R^{14}$, $R^{15}$, and $R^{16}$ can be hydrogen and $R^{13}$ can be a non-hydrogen substituent, $R^{12}$, $R^{13}$, $R^{15}$, and $R^{16}$ can be hydrogen and $R^{14}$ can be a non-hydrogen substituent, $R^{13}$, $R^{15}$, and $R^{16}$ can be hydrogen and $R^{12}$ and $R^{14}$ can be non-hydrogen substituents, $R^{13}$, $R^{14}$, and $R^{15}$ can be hydrogen and $R^{12}$ and $R^{16}$ can be non-hydrogen substituents, $R^{12}$, $R^{14}$, and $R^{16}$ can be hydrogen and $R^{13}$ and $R^{15}$ can be non-hydrogen substituents, or $R^{13}$ and $R^{15}$ can be hydrogen and $R^{12}$, $R^{14}$, and $R^{16}$ can be non-hydrogen substituents. In some embodiments wherein $R^1$ has Structure G2, $R^{13}$, $R^{14}$, $R^{15}$, and $R^{16}$ can be hydrogen and $R^{12}$ can be a non-hydrogen substituent, $R^{12}$, $R^{13}$, $R^{15}$, and $R^{16}$ can be hydrogen and $R^{14}$ can be a non-hydrogen substituent, $R^{13}$, $R^{15}$, and $R^{16}$ can be hydrogen and $R^{12}$ and $R^{14}$ can be non-hydrogen substituents, $R^{13}$, $R^{14}$, and $R^{15}$ can be hydrogen and $R^{12}$ and $R^{16}$ can be non-hydrogen substituents, or $R^{13}$ and $R^{15}$ can be hydrogen and $R^{12}$, $R^{14}$, and $R^{16}$ can be non-hydrogen substituents; alternatively, $R^{13}$, $R^{14}$, $R^{15}$, and $R^{16}$ can be hydrogen and $R^{12}$ can be a non-hydrogen substituent, $R^{12}$, $R^{13}$, $R^{15}$, and $R^{16}$ can be hydrogen and $R^{14}$ can be a non-hydrogen substituent, $R^{13}$, $R^{15}$, and $R^{16}$ can be hydrogen and $R^{12}$ and $R^{14}$ can be non-hydrogen substituents, $R^{13}$, $R^{14}$, and $R^{15}$ can be hydrogen and $R^{12}$ and $R^{16}$ can be non-hydrogen substituents, or $R^{13}$ and $R^{15}$ can be hydrogen and $R^{12}$, $R^{14}$, and $R^{16}$ can be non-hydrogen substituents; alternatively, $R^{12}$, $R^{14}$, $R^{15}$, and $R^{16}$ can be hydrogen and $R^{13}$ can be a non-hydrogen substituent, or $R^{12}$, $R^{14}$, and $R^{16}$ can be hydrogen and $R^{13}$ and $R^{15}$ can be non-hydrogen substituents; alternatively, $R^{13}$, $R^{14}$, $R^{15}$, and $R^{16}$ can be hydrogen and $R^{12}$ can be a non-hydrogen substituent, or $R^{12}$, $R^{13}$, $R^{15}$, and $R^{16}$ can be hydrogen and $R^{14}$ can be a non-hydrogen substituent; alternatively, $R^{13}$, $R^{15}$, and $R^{16}$ can be hydrogen and $R^{12}$ and $R^{14}$ can be non-hydrogen substituents, $R^{13}$, $R^{14}$, and $R^{15}$ can be hydrogen and $R^{12}$ and $R^{16}$ can be non-hydrogen substituents, or $R^{13}$ and $R^{15}$ can be hydrogen and $R^{12}$, $R^{14}$, and $R^{16}$ can be non-hydrogen substituents; or alternatively, $R^{13}$, $R^{15}$, and $R^{16}$ can be hydrogen and $R^{12}$ and $R^{14}$ can be non-hydrogen substituents, or $R^{13}$, $R^{14}$, and $R^{15}$ can be hydrogen and $R^{12}$ and $R^{16}$ can be non-hydrogen substituents. In other embodiments wherein $R^1$ has Structure G2, $R^{12}$, $R^{13}$, $R^{14}$, $R^{15}$, and $R^{16}$ can be hydrogen; alternatively, $R^{13}$, $R^{14}$, $R^{15}$, and $R^{16}$ can be hydrogen and $R^{12}$ can be a non-hydrogen substituent; alternatively, $R^{12}$, $R^{14}$, $R^{15}$, and $R^{16}$ can be hydrogen and $R^{13}$ can be a non-hydrogen substituent; alternatively, $R^{12}$, $R^{13}$, $R^{15}$, and $R^{16}$ can be hydrogen and $R^{14}$ can be a non-hydrogen substituent; alternatively, $R^{13}$, $R^{15}$, and $R^{16}$ can be hydrogen and $R^{12}$ and $R^{14}$ can be non-hydrogen substituents; alternatively, $R^{13}$, $R^{14}$, and $R^{15}$ can be hydrogen and $R^{12}$ and $R^{16}$ can be non-hydrogen substituents; alternatively, $R^{12}$, $R^{14}$, and $R^{16}$ can be hydrogen and $R^{13}$ and $R^{15}$ and can be non-hydrogen substituents; or alternatively, $R^{13}$ and $R^{15}$ can be hydrogen and $R^{12}$, $R^{14}$, and $R^{16}$ can be non-hydrogen substituents. Substituents (general and specific) are independently disclosed herein and can be utilized without limitation as $R^{12}$, $R^{13}$, $R^{14}$, $R^{15}$, and $R^{16}$ for the $R^1$ group having Structure G2.

In an embodiment, when the $N^1$ nitrogen atom of the $N^2$-phosphinyl formamidine group is attached to a carbon atom of a cycloalkane or arene ring or ring system, the cyclic $R^1$ group can comprise at least one substituent located on a carbon atom adjacent to the carbon atom attached to $N^1$ nitrogen atom of the $N^2$-phosphinyl formamidine group. In some embodiments, when the $N^1$ nitrogen atom of the $N^2$-phosphinyl formamidine group is attached to a carbon atom of a cycloalkane or arene ring or ring system, the cyclic $R^1$ group can comprise at least one substituent located on each carbon atom adjacent to the carbon atom attached to $N^1$ nitrogen atom of the $N^2$-phosphinyl formamidine group. In another embodiment, when the $N^1$ nitrogen atom of the $N^2$-phosphinyl formamidine group is attached to a carbon atom of a cycloalkane or arene ring or ring system, the cyclic $R^1$ group can consist of one substituent located on each carbon atom adjacent to the carbon atom attached to $N^1$ nitrogen atom of the $N^2$-phosphinyl formamidine group. In other embodiments, when the $N^1$ nitrogen atom of the $N^2$-phosphinyl formamidine group is attached to a carbon atom of a cycloalkane or arene ring or ring system, the cyclic $R^1$ group can comprise only one substituent located on a carbon atom adjacent to the carbon atom attached to $N^1$ nitrogen atom of the $N^2$-phosphinyl formamidine group. In another embodiment, when the $N^1$ nitrogen atom of the $N^2$-phosphinyl formamidine group is attached to a carbon atom of a cycloalkane or arene ring or ring system, the cyclic $R^1$ group can comprise only one substituent located on each carbon atom adjacent to the carbon atom attached to $N^1$ nitrogen atom of the $N^2$-phosphinyl formamidine group. In yet another embodiment, when the $N^1$ nitrogen atom of the $N^2$-phosphinyl formamidine group is attached to a carbon atom of a cycloalkane or arene ring or ring system, the cyclic $R^1$ group can consist of only one substituent located on each carbon atom adjacent to the carbon atom attached to $N^1$ nitrogen atom of the $N^2$-phosphinyl formamidine group.

In a non-limiting embodiment, $R^1$ can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group, a 2,6-dialkylphenyl group, or a 2,4,6-trialkylphenyl group; alternatively, a 2,4-dialkylphenyl group or a 2,6-dialkylphenyl group; alternatively, a 2,6- dialkylphenyl group, or a 2,4,6-trialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 3-alkylphenyl group; alternatively, a 4-alkylphenyl group; alternatively, a 2,4-dialkylphenyl group; alternatively, a 2,6-dialkylphenyl group; alternatively, a 3,5-dialkylphenyl group; or alternatively, a 2,4,6-trialkylphenyl group. In another non-limiting embodiment, $R^1$ can be a napht-1-yl group, a naphth-2-yl group, a 2-alkylnapht-1-yl group, a 1-alkylnaphth-2-yl group, a 3-alkylnapth-2-yl group, or a 1,3-dialkylnaphth-2-yl group; alternatively, a napht-1-yl group or a 2-alkylnapht-1-yl group; alternatively, a naphth-2-yl group, a 1-alkylnaphth-2-yl group, a 3-alkylnapth-2-yl group, or a 1,3-dialkylnaphth-2-yl group; alternatively, a napht-1-yl group; alternatively, a naphth-2-yl group; alternatively, a 2-alkylnaphth-1-yl group; alternatively, a 1-alkylnaphth-2-yl group; alternatively, a 3-alkylnapth-2-yl group; or alternatively, a 1,3-dialkylnaphth-2-yl group. In other non-limiting embodiments, $R^1$ can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, a 2,5-dialkylcyclopentyl group. Alkyl group substituents (general and specific) are independently described herein and can be utilized, without limitation, to further describe the alkylphenyl, dialkylphenyl, trialkylphenyl, naphthyl, dialkylnaphthyl, alkylcyclohexyl, dialkylcyclohexyl, alkylcyclopentyl, or dialkylcyclopentyl groups that can be utilized $R^1$. Generally, the alkyl substituents of a dialkyl or trialkyl phenyl, naphthyl, cyclohexyl, or cyclopentyl group can be the same; or alternatively, the alkyl substituents of a dialkyl or trialkyl phenyl, naphthyl, cyclohexyl, or cyclopentyl group can be different.

In another non-limiting embodiment, $R^1$ can be a phenyl group, a 2-alkoxyphenyl group, a 3-alkoxyphenyl group, a 4-alkoxyphenyl group, or a 3,5-dialkoxyphenyl group; alternatively, a 2-alkoxyphenyl group or a 4-alkoxyphenyl group; alternatively, a 3-alkoxyphenyl group or a 3,5-dialkoxyphenyl group; alternatively, a 2-alkoxyphenyl group; alternatively, a 3-alkoxyphenyl group; alternatively, a 4-alkoxyphenyl group; alternatively, a 3,5-dialkoxyphenyl group. Alkoxy group substituents (general and specific) are independently described herein and can be utilized, without limitation, to further describe the alkoxyphenyl or dialkoxyphenyl groups that can be utilized $R^1$. Generally, the alkoxy substituents of a dialkoxyphenyl group can be the same; or alternatively, the alkoxy substituents of a dialkoxyphenyl group can be different.

In other non-limiting embodiments, $R^1$ can be a phenyl group, a 2-halophenyl group, a 3-halophenyl group, a 4-halophenyl group, a 2,6-dihalophenyl group, or a 3,5-dialkylphenyl group; alternatively, a 2-halophenyl group, a 4-halophenyl group, or a 2,6-dihalophenyl group; alternatively, a 2-halophenyl group or a 4-halophenyl group; alternatively, a 3-halophenyl group or a 3,5-dihalophenyl group; alternatively, a 2-halophenyl group; alternatively, a 3-halophenyl group; alternatively, a 4-halophenyl group; alternatively, a 2,6-dihalophenyl group; or alternatively, a 3,5-dihalophenyl group. Halides are independently described herein and can be utilized, without limitation, to further describe the halophenyl or dihalophenyl groups that can be utilized as $R^1$. Generally, the halides of a dihalophenyl group can be the same; or alternatively, the halides of a dihalophenyl group can be different.

In a non-limiting embodiment, $R^1$ can be a 2-methylphenyl group, a 2-ethylphenyl group, a 2-n-propylphenyl group, a 2-isopropylphenyl group, a 2-tert-butylphenyl group, a 3-methylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, a 3,5-dimethyl group, or a 2,4,6-trimethylphenyl group; alternatively, a 2-methylphenyl group, a 2-ethylphenyl group, a 2-n-propylphenyl group, a 2-isopropylphenyl group, or a 2-tert-butylphenyl group; alternatively, a 2,6-dimethylphenyl group, a 2,6-diethylphenyl group, a 2,6-di-n-propylphenyl group, a 2,6-diisopropylphenyl group, a 2,6-di-tert-butylphenyl group, or a 2-isopropyl-6-methylphenyl group; alternatively, a 2-methylphenyl group; alternatively, a 2-ethylphenyl group; alternatively, a 2-n-propylphenyl group; alternatively, a 2-isopropylphenyl group; alternatively, a 2-tert-butylphenyl group; alternatively, a 3-methylphenyl group; alternatively, a 2,6-dimethylphenyl group; alternatively, a 2,6-diethylphenyl group; alternatively, a 2,6-di-n-propylphenyl group; alternatively, a 2,6-diisopropylphenyl group; alternatively, a 2,6-di-tert-butylphenyl group; alternatively, a 2-isopropyl-6-methylphenyl group; alternatively, a 3,5-dimethylphenyl group; or alternatively, a 2,4,6-trimethylphenyl group. In another non-limiting embodiment, $R^1$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group, a 2-ethylcyclohexyl group, a 2-isopropylcyclohexyl group, or a 2-tert-butylcyclohexyl group; alternatively, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group; alternatively, a 2-ethylcyclohexyl group; alternatively, a 2-isopropylcyclohexyl group; alternatively, a 2-tert-butylcyclohexyl group; alternatively, a 2,6-dimethylcyclohexyl group; alternatively, a 2,6-diethylcyclohexyl group; alternatively, a 2,6-diisopropylcyclohexyl group; or alternatively, a 2,6-di-tert-butylcyclohexyl group. In another non-limiting embodiment, $R^1$ can be a 2-methylnaphth-1-yl group, a 2-ethylnaphth-1-yl group, a 2-n-propylnaphth-1-yl group, a 2-isopropylnaphth-1-yl group, or a 2-tert-butylnaphth-1-yl group; alternatively, a 2-methylnaphth-1-yl group; alternatively, a 2-ethylnaphth-1-yl group; alternatively, a 2-n-propylnaphth-1-yl group; alternatively, a 2-isopropylnaphth-1-yl group; or alternatively, a 2-tert-butylnaphth-1-yl group.

In a non-limiting embodiment, $R^1$ can be a 3-methoxyphenyl group, a 3-ethoxyphenyl group, a 3-isopropoxyphenyl group, a 3-tert-butoxyphenyl group, a 4-methoxyphenyl group, a 4-ethoxyphenyl group, a 4-isopropoxyphenyl group, a 4-tert-butoxyphenyl group, a 3,5-dimethoxyphenyl group, a 3,5-diethoxyphenyl group, a 3,5-diisopropoxyphenyl group, or a 3,5-di-tert-butoxyphenyl group; alternatively, a 3-methoxyphenyl group, a 3-ethoxyphenyl group, a 3-isopropoxyphenyl group, or a 3-tert-butoxyphenyl group; alternatively, a 4-methoxyphenyl group, a 4-ethoxyphenyl group, a 4-isopropoxy-phenyl group, or a 4-tert-butoxyphenyl group; or alternatively, a 3,5-dimethoxyphenyl group, a 3,5-diethoxyphenyl group, a 3,5-diisopropoxyphenyl group, or a 3,5-di-tert-butoxyphenyl group. In other non-limiting embodiments, $R^1$ can be a 3-methoxyphenyl group; alternatively, a 3-ethoxyphenyl group; alternatively, a 3-isopropoxyphenyl group; alternatively, a 3-tert-butoxyphenyl group; alternatively, a 4-methoxyphenyl group; alternatively, a 4-ethoxyphenyl group; alternatively, a 4-isopropoxyphenyl group; alternatively, a 4-tert-butoxyphenyl group; alternatively, a 3,5-dimethoxyphenyl group; alternatively, a 3,5-diethoxyphenyl group; alternatively, a 3,5-diisopropoxyphenyl group; or alternatively, a 3,5-di-tert-butoxyphenyl group.

In an aspect, $R^3$ can be hydrogen. In another aspect, $R^3$ can be an organyl group; alternatively, an organyl group consisting essentially of inert functional groups; or alternatively, a hydrocarbyl group. In an embodiment, $R^3$ can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In an embodiment, $R^3$ can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In an embodiment, $R^3$ can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In yet other embodiments, $R^3$ can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group.

In an aspect, $R^3$ can be a $C_1$ to $C_{30}$ alkyl group, a $C_4$ to $C_{30}$ cycloalkyl group, a $C_4$ to $C_{30}$ substituted cycloalkyl group, a $C_6$ to $C_{30}$ aryl group, or a $C_6$ to $C_{30}$ substituted aryl group; alternatively, a $C_4$ to $C_{30}$ cycloalkyl group or a $C_4$ to $C_{30}$ substituted cycloalkyl group; alternatively, a $C_6$ to $C_{30}$ aryl group or a $C_6$ to $C_{30}$ substituted aryl group; alternatively, a $C_1$ to $C_{30}$ alkyl group; alternatively, a $C_4$ to $C_{30}$ cycloalkyl group; alternatively, a $C_4$ to $C_{30}$ substituted cycloalkyl group; alternatively, a $C_6$ to $C_{30}$ aryl group; or alternatively, a $C_6$ to $C_{30}$ substituted aryl group. In an embodiment, $R^3$ can be a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group; alternatively, a $C_4$ to $C_{20}$ cycloalkyl group or a $C_4$ to $C_{20}$ substituted cycloalkyl group; alternatively, a $C_6$ to $C_{20}$ aryl group or a $C_6$ to $C_{20}$ substituted aryl group; alternatively, a $C_1$ to $C_{15}$ alkyl group; alternatively, a $C_4$ to $C_{20}$ cycloalkyl group; alternatively, a $C_4$ to $C_{20}$ substituted cycloalkyl group; alternatively, a $C_6$ to $C_{20}$ aryl group; or alternatively, a $C_6$ to $C_{20}$ substituted aryl group. In other embodiments, $R^3$ can be a $C_1$ to $C_{10}$ alkyl group, a $C_4$ to $C_{15}$ cycloalkyl group, a $C_4$ to $C_{15}$ substituted cycloalkyl group, a $C_6$ to $C_{15}$ aryl group, or a $C_6$ to $C_{15}$ substituted aryl group; alternatively, a $C_4$ to $C_{15}$ cycloalkyl group or a $C_4$ to $C_{15}$ substituted cycloalkyl group; alternatively, a $C_6$ to $C_{15}$ aryl group or a $C_6$ to $C_{15}$ substituted aryl group; alternatively, a $C_1$ to $C_{10}$ alkyl group; alternatively, a $C_4$ to $C_{15}$ cycloalkyl group; alternatively, a $C_4$ to $C_{15}$ substituted cycloalkyl group; alternatively, a $C_6$ to $C_{15}$ aryl group; or alternatively, a $C_6$ to $C_{15}$ substituted aryl group. In further embodiments, $R^3$ can be a $C_1$ to $C_5$ alkyl group. Substituents (general and specific) are independently disclosed herein and can be utilized without limitation to further describe substituted groups which can be utilized as $R^3$.

In an embodiment, $R^3$ can be a methyl group, an ethyl group, a propyl group, a butyl group, a pentyl group, a hexyl group, a heptyl group, an octyl group, a nonyl group, or a decyl group. In some embodiments, $R^3$ can be a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, an n-propyl group; alternatively, an iso-propyl group; alternatively, a tert-butyl group; or alternatively, a neopentyl group. In some embodiments, the alkyl groups which can be utilized as $R^3$ can be substituted. Each substituent of a substituted alkyl group independently can be a halogen or a hydrocarboxy group; alternatively, a halogen; or alternatively, a hydrocarboxy group. Halogens and hydrocarboxy groups (general and specific) are independently disclosed herein (e.g., as general substituents and substituents for substituted $R^1$ groups) and can be utilized without limitation to further describe the substituted alkyl group which can be utilized as $R^3$.

In an embodiment, $R^3$ can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, $R^3$ can be a cyclopentyl group, a substituted cyclopentyl group, a cyclohexyl group, or a substituted cyclohexyl group. In other embodiments, $R^3$ can be a cyclopentyl group or a substituted cyclopentyl group; or alternatively, a cyclohexyl group or a substituted cyclohexyl group. In further embodiments, $R^3$ can be a cyclopentyl group; alternatively, a substituted cyclopentyl group; a cyclohexyl group; or alternatively, a substituted cyclohexyl group. Substituents (general and specific) are independently disclosed herein and can be utilized without limitation to further describe the substituted cycloalkyl group which can be utilized as $R^3$.

In an aspect, $R^3$ can have Structure G5:

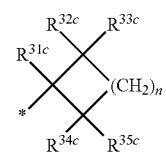

Structure G5 wherein, the undesignated valency is attached to the $N^2$ nitrogen atom of the $N^2$-phosphinyl formamidine group. Generally, $R^{31c}$, $R^{32c}$, $R^{33c}$, $R^{34c}$, and $R^{35c}$ independently can be hydrogen or a non-hydrogen substituent, and n can be an integer from 1 to 5. In an embodiment wherein $R^3$ has Structure G5, $R^{31c}$, $R^{33c}$, $R^{34c}$, and $R^{35c}$ can be hydrogen and $R^{32c}$ can be any non-hydrogen substituent disclosed herein; or alternatively, $R^{31c}$, $R^{33c}$, and $R^{35c}$ can be hydrogen and $R^{32c}$ and $R^{34c}$ independently can be any non-hydrogen substituent disclosed herein. In an embodiment, n can be an integer from 1 to 4; or alternatively, from 2 to 4. In other embodiments, n can be 2 or 3; alternatively, 2; or alternatively 3. Substituents (general and specific) are independently disclosed herein and can be utilized without limitation to further describe a non-hydrogen substituent which can be utilized without limitation as $R^{31c}$, $R^{32c}$, $R^{33c}$, $R^{34c}$, and/or $R^{35c}$ for the $R^3$ group having Structure G5.

In an embodiment, $R^3$ can be a phenyl group or a substituted phenyl group. In some embodiments, $R^3$ can be a phenyl group; or alternatively, a substituted phenyl group. In an embodiment, the $R^3$ substituted phenyl group can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group. In other embodiments, the $R^3$ substituted phenyl group can be a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,6-disubstituted phenyl group or a 2,4,6-trisubstituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Substituents (general and specific) are independently disclosed herein and can be utilized without limitation to further describe any substituted phenyl group which can be utilized as $R^3$.

In an aspect, $R^3$ can have Structure G6:

Structure G6 wherein the undesignated valency is attached to the $N^1$ nitrogen atom of the $N^2$-phosphinyl formamidine group. Generally, $R^{32}$, $R^{33}$, $R^{34}$, $R^{35}$, and $R^{36}$ independently can be hydrogen or a non-hydrogen substituent. In an embodiment wherein $R^3$ has Structure G6, $R^{32}$, $R^{33}$, $R^{34}$, $R^{35}$, and $R^{36}$ can be hydrogen, $R^{33}$, $R^{34}$, $R^{35}$, and $R^{36}$ can be hydrogen and $R^{32}$ can be a non-hydrogen substituent, $R^{32}$, $R^{34}$, $R^{35}$, and $R^{36}$ can be hydrogen and $R^{33}$ can be a non-hydrogen substituent, $R^{32}$, $R^{33}$, $R^{35}$, and $R^{36}$ can be hydrogen and $R^{34}$ can be a non-hydrogen substituent, $R^{33}$, $R^{35}$, and $R^{36}$ can be hydrogen and $R^{32}$ and $R^{34}$ can be non-hydrogen substituents, $R^{33}$, $R^{34}$, and $R^{35}$ can be hydrogen and $R^{32}$ and $R^{36}$ can be non-hydrogen substituents, $R^{32}$, $R^{34}$, and $R^{36}$ can be hydrogen and $R^{33}$ and $R^{35}$ can be non-hydrogen substituents, or $R^{33}$ and $R^{35}$ can be hydrogen and $R^{32}$, $R^{34}$, and $R^{36}$ can be non-hydrogen substituents. In some embodiments wherein $R^3$ has Structure G6, $R^{33}$, $R^{34}$, $R^{35}$, and $R^{36}$ can be hydrogen and $R^{32}$ can be a non-hydrogen substituent, $R^{32}$, $R^{33}$, $R^{35}$, and $R^{36}$ can be hydrogen and $R^{34}$ can be a non-hydrogen substituent, $R^{33}$, $R^{35}$, and $R^{36}$ can be hydrogen and $R^{32}$ and $R^{34}$ can be non-hydrogen substituents, $R^{33}$, $R^{34}$, and $R^{35}$ can be hydrogen and $R^{32}$ and $R^{36}$ can be non-hydrogen substituents, or $R^{33}$ and $R^{35}$ can be hydrogen and $R^{32}$, $R^{34}$, and $R^{36}$ can be non-hydrogen substituents; alternatively, $R^{33}$, $R^{34}$, $R^{35}$, and $R^{36}$ can be hydrogen and $R^{32}$ can be a non-hydrogen substituent, $R^{32}$, $R^{33}$, $R^{35}$, and $R^{36}$ can be hydrogen and $R^{34}$ can be a non-hydrogen substituent, $R^{33}$, $R^{35}$, and $R^{36}$ can be hydrogen and $R^{32}$ and $R^{34}$ can be non-hydrogen substituents, or $R^{33}$, $R^{34}$, and $R^{35}$ can be hydrogen and $R^{32}$ and $R^{36}$ can be non-hydrogen substituents, $R^{33}$, $R^{34}$, $R^{35}$, and $R^{36}$ can be hydrogen and $R^{32}$ can be a non-hydrogen substituent, or $R^{32}$, $R^{34}$, and $R^{36}$ can be hydrogen and $R^{33}$ and $R^{35}$ can be non-hydrogen substituents; alternatively, $R^{33}$, $R^{34}$, $R^{35}$, and $R^{36}$ can be hydrogen and $R^{32}$ can be a non-hydrogen substituent, or $R^{32}$, $R^{33}$, $R^{35}$, and $R^{36}$ can be hydrogen and $R^{34}$ can be a non-hydrogen substituent; alternatively, $R^{33}$, $R^{35}$, and $R^{36}$ can be hydrogen and $R^{32}$ and $R^{34}$ can be non-hydrogen substituents, $R^{33}$, $R^{34}$, and $R^{35}$ can be hydrogen and $R^{32}$ and $R^{36}$ can be non-hydrogen substituents, or $R^{33}$ and $R^{35}$ can be hydrogen and $R^{32}$, $R^{34}$, and $R^{36}$ can be non-hydrogen substituents; or alternatively, $R^{33}$, $R^{35}$, and $R^{36}$ can be hydrogen and $R^{32}$ and $R^{34}$ can be non-hydrogen substituents, or $R^{33}$, $R^{34}$, and $R^{35}$ can be hydrogen and $R^{32}$ and $R^{36}$ can be non-hydrogen substituents. In other embodiments wherein $R^3$ has Structure G6, $R^{32}$, $R^{33}$, $R^{34}$, $R^{35}$, and $R^{36}$ can be hydrogen; alternatively, $R^{33}$, $R^{34}$, $R^{35}$, and $R^{36}$ can be hydrogen and $R^{32}$ can be a non-hydrogen substituent; alternatively, $R^{32}$, $R^{34}$, $R^{35}$, and $R^{36}$ can be hydrogen and $R^{33}$ can be a non-hydrogen substituent; alternatively, $R^{32}$, $R^{33}$, $R^{35}$, and $R^{36}$ can be hydrogen and $R^{34}$ can be a non-hydrogen substituent; alternatively, $R^{33}$, $R^{35}$, and $R^{36}$ can be hydrogen and $R^{32}$ and $R^{34}$ can be non-hydrogen substituents; alternatively, $R^{33}$, $R^{34}$, and $R^{35}$ can be hydrogen and $R^{32}$ and $R^{36}$ can be non-hydrogen substituents; alternatively, $R^{32}$, $R^{34}$, and $R^{36}$ can be hydrogen and $R^{33}$ and $R^{35}$ and can be non-hydrogen substituents; or alternatively, $R^{33}$ and $R^{35}$ can be hydrogen and $R^{32}$, $R^{34}$, and $R^{36}$ can be non-hydrogen substituents. Substituents (general and specific) are independently disclosed herein and can be utilized without limitation as $R^{32}$, $R^{33}$, $R^{34}$, $R^{35}$, and $R^{36}$ for the $R^3$ group having Structure G6.

In a non-limiting embodiment, $R^3$ can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group, a 2,6-dialkylphenyl group, or a 2,4,6-trialkylphenyl group; alternatively, a 2,4-dialkylphenyl group or a 2,6-dialkylphenyl group; alternatively, a 2,6-dialkylphenyl group, or a 2,4,6-trialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 3-alkylphenyl group; alternatively, a 4-alkylphenyl group; alternatively, a 2,4-dialkylphenyl group; alternatively, a 2,6-dialkylphenyl group; alternatively, a 3,5-dialkylphenyl group; or alternatively, a 2,4,6-trialkylphenyl group. In another non-limiting embodiment, $R^3$ can be a phenyl group, a 2-alkoxyphenyl group, a 3-alkoxyphenyl group, a 4-alkoxyphenyl group, or a 3,5-dialkoxyphenyl group; alternatively, a 2-alkoxyphenyl group or a 4-alkoxyphenyl group; alternatively, a 3-alkoxyphenyl group or 3,5-dialkoxyphenyl group; alternatively, a 2-alkoxyphenyl group; alternatively, a 3-alkoxyphenyl group; alternatively, a 4-alkoxyphenyl group; alternatively, a 3,5-dialkoxyphenyl group. In other non-limiting embodiments, $R^1$ can be a phenyl group, a 2-halophenyl group, a 3-halophenyl group, a 4-halophenyl group, a 2,6-dihalophenyl group, or a 3,5-dialkylphenyl group; alternatively, a 2-halophenyl group, a 4-halophenyl group, or a 2,6-dihalophenyl group; alternatively, a 2-halophenyl group or a 4-halophenyl group; alternatively, a 3-halophenyl group or a 3,5-dihalophenyl group; alternatively, a 2-halophenyl group; alternatively, a 3-halophenyl group; alternatively, a 4-halophenyl group; alternatively, a 2,6-dihalophenyl group; or alternatively, a 3,5-dihalophenyl group. Halides, alkyl group substituents (general and specific), and alkoxy group substituents (general and specific) are independently described herein and can be utilized, without limitation, to further describe the alkylphenyl, dialkylphenyl, trialkylphenyl, alkoxyphenyl, dialkoxyphenyl, halophenyl, or dihalophenyl groups that can be utilized as $R^3$. Generally, the halides, alkyl substituents, or alkoxy substituents of a dialkyl, trialkyl phenyl, dialkoxyphenyl, or dihalophenyl group can be the same; or alternatively the halo, alkyl substituents, or alkoxy substituents of alkylphenyl, dialkylphenyl, trialkylphenyl, dialkoxyphenyl, or dihalophenyl groups can be different.

In a non-limiting embodiment, $R^3$ can be a 2-methylphenyl group, a 2-ethylphenyl group, a 2-isopropylphenyl group, a 2-tert-butylphenyl group, a 4-methylphenyl group, a 4-ethylphenyl group, a 4-isopropylphenyl group, a 4-tert-butylphenyl group, a 2,6-dimethylphenyl group, a 2,6-diethylphenyl group, a 2,6-diisopropylphenyl group, or a 2,6-di-tert-butylphenyl group; alternatively, a 2-methylphenyl group, a 2-ethylphenyl group, a 2-isopropylphenyl group, or a 2-tert-butylphenyl group, a 4-methylphenyl group, a 4-ethylphenyl group, a 4-isopropylphenyl group, or a 4-tert-butylphenyl group; alternatively, a 2-methylphenyl group, a 2-ethylphenyl group, a 2-isopropylphenyl group, or a 2-tert-butylphenyl group; alternatively, a 4-methylphenyl group, a 4-ethylphenyl group, a 4-isopropylphenyl group, or a 4-tert-butylphenyl group; or alternatively, a 2,6-dimethylphenyl group, a 2,6-diethylphenyl group, a 2,6-di-n-propylphenyl group, a 2,6-diisopropylphenyl group, or a 2,6-di-tert-butylphenyl group. In another non-limiting embodiment, $R^3$ can be a 2-methylphenyl group; alternatively, a 2-ethylphenyl group; alternatively, a 2-isopropylphenyl group; alternatively, a 2-tert-butylphenyl group; alternatively, a 4-methylphenyl group; alternatively, a 4-ethylphenyl group; alternatively, a 4-isopropylphenyl group; or alternatively, a 4-tert-butylphenyl group.

In an aspect, $R^4$ and/or $R^5$ independently can be an organyl group; alternatively, an organyl group consisting essentially of inert functional groups; or alternatively, a hydrocarbyl group. In an embodiment, $R^4$ and/or $R^5$ independently can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In an embodiment, $R^4$ and/or $R^5$ independently can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In an embodiment, $R^4$ and/or $R^5$ independently can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In yet other embodiments, $R^4$ and $R^5$ can be independently selected from a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group. In an aspect, $R^4$ and $R^5$ can be joined to form a ring (regardless of particular type of group—organyl, organyl consisting of inert functional groups, hydrocarbyl, or any species within) containing the phosphorus atom of the $N^2$-phosphinyl formamidine group.

In another aspect, $R^4$ and/or $R^5$ independently can be a $C_1$ to $C_{30}$ alkyl group, a $C_4$ to $C_{30}$ cycloalkyl group, a $C_4$ to $C_{30}$ substituted cycloalkyl group, a $C_6$ to $C_{30}$ aryl group, or a $C_6$ to $C_{30}$ substituted aryl group; alternatively, a $C_4$ to $C_{30}$ cycloalkyl group or a $C_4$ to $C_{30}$ substituted cycloalkyl group; alternatively, a $C_6$ to $C_{30}$ aryl group or a $C_6$ to $C_{30}$ substituted aryl group; alternatively, a $C_1$ to $C_{30}$ alkyl group; alternatively, a $C_4$ to $C_{30}$ cycloalkyl group; alternatively, a $C_4$ to $C_{30}$ substituted cycloalkyl group; alternatively, a $C_6$ to $C_{30}$ aryl group; or alternatively, a $C_6$ to $C_{30}$ substituted aryl group. In an embodiment, $R^4$ and $R^5$ independently can be a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group; alternatively, a $C_4$ to $C_{20}$ cycloalkyl group or a $C_4$ to $C_{20}$ substituted cycloalkyl group; alternatively, a $C_6$ to $C_{20}$ aryl group or a $C_6$ to $C_{20}$ substituted aryl group; alternatively, a $C_1$ to $C_{15}$ alkyl group; alternatively, a $C_4$ to $C_{20}$ cycloalkyl group; alternatively, a $C_4$ to $C_{20}$ substituted cycloalkyl group; alternatively, a $C_6$ to $C_{20}$ aryl group; or alternatively, a $C_6$ to $C_{20}$ substituted aryl group. In other embodiments, $R^4$ and $R^5$ independently can be a $C_1$ to $C_{10}$ alkyl group, a $C_4$ to $C_{15}$ cycloalkyl group, a $C_4$ to $C_{15}$ substituted cycloalkyl group, a $C_6$ to $C_{15}$ aryl group, or a $C_6$ to $C_{15}$ substituted aryl group; alternatively, a $C_4$ to $C_{15}$ cycloalkyl group or a $C_4$ to $C_{15}$ substituted cycloalkyl group; alternatively, a $C_6$ to $C_{15}$ aryl group or a $C_6$ to $C_{15}$ substituted aryl group; alternatively, a $C_1$ to $C_{10}$ alkyl group; alternatively, a $C_4$ to $C_{15}$ cycloalkyl group; alternatively, a $C_4$ to $C_{15}$ substituted cycloalkyl group; alternatively, a $C_6$ to $C_{15}$ aryl group; or alternatively, a $C_6$ to $C_{15}$ substituted aryl group. In further embodiments, $R^4$ and $R^5$ independently can be a $C_1$ to $C_5$ alkyl group. Substituents (general and specific) are independently disclosed herein and can be utilized without limitation to further describe substituted groups which can be utilized as $R^4$ and/or $R^5$.

In a further aspect, $R^4$ and/or $R^5$ independently can be a methyl group, an ethyl group, a propyl group, a butyl group, a pentyl group, a hexyl group, a heptyl group, an octyl group, a nonyl group, or a decyl group. In some embodiments, $R^4$ and/or $R^5$ independently can be a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group, an ethyl group, an n-propyl group, an n-butyl group, an n-pentyl group, or an n-hexyl group; alternatively, a methyl group; alternatively, an ethyl group; alternatively, an n-propyl group; alternatively, an iso-propyl group; alternatively, an n-butyl group; alternatively, a tert-butyl group; alternatively, an n-pentyl group; alternatively, a neopentyl group; or alternatively, an n-hexyl group. In some embodiments, the alkyl groups which can be utilized as $R^4$ and/or $R^5$ can be substituted. Each substituent of a substituted alkyl group independently can be a halogen or a hydrocarboxy group; alternatively, a halogen; or alternatively, a hydrocarboxy group. Halogens, and hydrocarboxy groups (general and specific) are independently disclosed herein (e.g., as general substituents and/or as substituents for substituted $R^1$ groups) and can be utilized without limitation to further describe the substituted alkyl group which can be utilized as $R^4$ and/or $R^5$.

In a further aspect, $R^4$ and $R^5$ independently can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, $R^4$ and/or $R^5$ independently can be a cyclopentyl group, a substituted cyclopentyl group, a cyclohexyl group, or a substituted cyclohexyl group. In other embodiments, $R^4$ and/or $R^5$ can be a cyclopentyl group or a substituted cyclopentyl group; or alternatively, a cyclohexyl group or a substituted cyclohexyl group. In further embodiments, $R^4$ and/or $R^5$ independently can be a cyclopentyl group; alternatively, a substituted cyclopentyl group; a cyclohexyl group; or alternatively, a substituted cyclohexyl group. Substituents (general and specific) are independently disclosed herein and can be utilized without limitation to further describe the substituted cycloalkyl group which can be utilized as $R^4$ and/or $R^5$.

In an aspect, $R^4$ can have Structure G7:

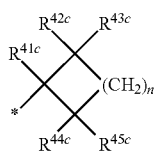

Structure G7 wherein, the undesignated valency is attached to the phosphorus atom of the $N^2$-phosphinyl formamidine group. Generally, $R^{41c}$, $R^{42c}$, $R^{43c}$, $R^{44c}$, and $R^{45c}$ independently can be hydrogen or a non-hydrogen substituent, and n can be an integer from 1 to 5. In an embodiment wherein $R^4$ has Structure G7, $R^{41c}$, $R^{43c}$, $R^{44c}$, and $R^{45c}$ can be hydrogen and $R^{32c}$ can be any non-hydrogen substituent disclosed herein; or alternatively, $R^{41c}$, $R^{43c}$, and $R^{45c}$ can be hydrogen and $R^{42c}$ and $R^{44c}$ independently can be any non-hydrogen substituent disclosed herein. In an embodiment, n can be an integer from 1 to 4; or alternatively, from 2 to 4. In other embodiments, n can be 2 or 3; alternatively, 2; or alternatively 3. Substituents (general and specific) are independently disclosed herein and can be utilized without limitation to further describe a non-hydrogen substituent which can be utilized without limitation as $R^{41c}$, $R^{42c}$, $R^{43c}$, $R^{44c}$, and/or $R^{45c}$ for the $R^4$ group having Structure G7.

In an aspect, $R^5$ can have Structure G8:

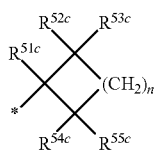

Structure G8 wherein, the undesignated valency is attached to the phosphorus atom of the $N^2$-phosphinyl formamidine group. Generally, $R^{51c}$, $R^{52c}$, $R^{53c}$, $R^{54c}$, and $R^{55c}$ independently can be hydrogen or a non-hydrogen substituent, and n can be an integer from 1 to 5. In an embodiment wherein $R^5$ has Structure G8, $R^{51c}$, $R^{53c}$, $R^{54c}$, and $R^{55c}$ can be hydrogen and $R^{32c}$ can be any non-hydrogen substituent disclosed herein; or alternatively, $R^{51c}$, $R^{53c}$, and $R^{55c}$ can be hydrogen and $R^{52c}$ and $R^{54c}$ independently can be any non-hydrogen substituent disclosed herein. In an embodiment, n can be an integer from 1 to 4; or alternatively, from 2 to 4. In other embodiments, n can be 2 or 3; alternatively, 2; or alternatively 3. Substituents (general and specific) are independently disclosed herein and can be utilized without limitation to further describe a non-hydrogen substituent which can be utilized without limitation as $R^{51c}$, $R^{52c}$, $R^{53c}$, $R^{54c}$, and/or $R^{55c}$ for the $R^5$ group having Structure G8.

In an aspect, $R^4$ and/or $R^5$ independently can be a phenyl group, a substituted phenyl group, a naphthyl group, or a substituted naphthyl group. In an embodiment, $R^4$ and $R^5$ independently can be a phenyl group or a substituted phenyl group; alternatively, a naphthyl group or a substituted naphthyl group; alternatively, a phenyl group or a naphthyl group; or alternatively, a substituted phenyl group or a substituted naphthyl group. In some embodiments, $R^4$ and/or $R^5$ independently can be a phenyl group; alternatively, a substituted phenyl group; alternatively, a naphthyl group; or alternatively, a substituted naphthyl group. Substituents (general and specific) are independently disclosed herein and can be utilized without limitation to further describe any substituted phenyl group and/or substituted naphthyl group which can be utilized as $R^4$ and/or $R^5$.

In an embodiment, the $R^4$ and/or $R^5$ substituted phenyl group can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group. In other embodiments, the $R^4$ and/or $R^5$ substituted phenyl group can be a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,6-disubstituted phenyl group or a 2,4,6-trisubstituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Substituents (general and specific) are independently disclosed herein and can be utilized without limitation to further describe any substituted phenyl group which can be utilized as $R^4$ and/or $R^5$.

In an embodiment, $R^4$ and/or $R^5$ independently can be a naphth-1-yl group, a substituted naphth-1-yl group, a naphth-2-yl group, or a substituted naphth-2-yl group. In some embodiments, $R^4$ and/or $R^5$ independently can be a naphth-1-yl group or a substituted naphth-1-yl group; alternatively, a naphth-2-yl group or a substituted naphth-2-yl group; alternatively, a naphth-1-yl group; alternatively, a substituted naphth-1-yl group; alternatively, a naphth-2-yl group; or alternatively, a substituted naphth-2-yl group. In other embodiments, $R^4$ and/or $R^5$ independently can be a 2-substituted naphth-1-yl group, a 3-substituted naphth-1-yl group, a 4-substituted naphth-1-yl group, or a 8-substituted naphth-1-yl group; alternatively, a 2-substituted naphth-1-yl group; alternatively, a 3-substituted naphth-1-yl group; alternatively, a 4-substituted naphth-1-yl group; or alternatively, a 8-substituted naphth-1-yl group. In further embodiments, $R^4$ and/or $R^5$ independently can be a 1-substituted naphth-2-yl group, a 3-substituted naphth-2-yl group, a 4-substituted naphth-2-yl group, or a 1,3-disubstituted naphth-2-yl group; alternatively, a 1-substituted naphth-2-yl group; alternatively, a 3-substituted naphth-2-yl group; alternatively, a 4-substituted naphth-2-yl group; alternatively, a 1,3-disubstituted naphth-2-yl group. Substituents (general and specific) are independently disclosed herein and can be utilized without limitation to further describe any substituted naphthyl group which can be utilized as $R^4$ and/or $R^5$.

In an aspect, $R^4$ have Structure G9:

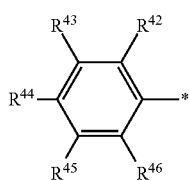

Structure G9 wherein the undesignated valency is attached to the phosphorus atom of the $N^2$-phosphinyl formamidine group. Generally, $R^{42}$, $R^{43}$, $R^{44}$, $R^{45}$, and $R^{46}$ can independently be a hydrogen or a non-hydrogen substituent. In an embodiment wherein $R^4$ has Structure G9, $R^{42}$, $R^{43}$, $R^{44}$, $R^{45}$, and $R^{46}$ can be hydrogen, $R^{43}$, $R^{44}$, $R^{45}$, and $R^{46}$ can be hydrogen and $R^{42}$ can be a non-hydrogen substituent, $R^{42}$, $R^{44}$, $R^{45}$, and $R^{46}$ can be hydrogen and $R^{43}$ can be a non-hydrogen substituent, $R^{42}$, $R^{43}$, $R^{45}$, and $R^{46}$ can be hydrogen and $R^{44}$ can be a non-hydrogen substituent, $R^{43}$, $R^{45}$, and $R^{46}$ can be hydrogen and $R^{42}$ and $R^{44}$ can be non-hydrogen substituents, $R^{43}$, $R^{44}$, and $R^{45}$ can be hydrogen and $R^{42}$ and $R^{46}$ can be non-hydrogen substituents, $R^{42}$, $R^{44}$, and $R^{46}$ can be hydrogen and $R^{43}$ and $R^{45}$ can be non-hydrogen substituents, or $R^{43}$ and $R^{45}$ can be hydrogen and $R^{42}$, $R^{44}$, and $R^{46}$ can be non-hydrogen substituents. In some embodiments wherein $R^4$ has Structure G9, $R^{43}$, $R^{44}$, $R^{45}$, and $R^{46}$ can be hydrogen and $R^{42}$ can be a non-hydrogen substituent, $R^{42}$, $R^{43}$, $R^{45}$, and $R^{46}$ can be hydrogen and $R^{44}$ can be a non-hydrogen substituent, $R^{43}$, $R^{45}$, and $R^{46}$ can be hydrogen and $R^{42}$ and $R^{44}$ can be non-hydrogen substituents, $R^{43}$, $R^{44}$, and $R^{45}$ can be hydrogen and $R^{42}$ and $R^{46}$ can be non-hydrogen substituents, or $R^{43}$ and $R^{45}$ can be hydrogen and $R^{42}$, $R^{44}$, and $R^{46}$ can be non-hydrogen substituents; alternatively, $R^{43}$, $R^{44}$, $R^{45}$, and $R^{46}$ can be hydrogen and $R^{42}$ can be a non-hydrogen substituent, $R^{42}$, $R^{43}$, $R^{45}$, and $R^{46}$ can be hydrogen and $R^{44}$ can be a non-hydrogen substituent, $R^{43}$, $R^{45}$, and $R^{46}$ can be hydrogen and $R^{42}$ and $R^{44}$ can be non-hydrogen substituents, $R^{43}$, $R^{44}$, and $R^{45}$ can be hydrogen and $R^{42}$ and $R^{46}$ can be non-hydrogen substituents, or $R^{43}$ and $R^{45}$ can be hydrogen and $R^{42}$, $R^{44}$, and $R^{46}$ can be non-hydrogen substituents; alternatively, $R^{43}$, $R^{45}$, and $R^{46}$ can be hydrogen and $R^{42}$ and $R^{44}$ can be non-hydrogen substituents, or $R^{43}$, $R^{44}$, and $R^{45}$ can be hydrogen and $R^{42}$ and $R^{46}$ can be non-hydrogen substituents. In other embodiments wherein $R^4$ has Structure G9, $R^{42}$, $R^{43}$, $R^{44}$, $R^{45}$, and $R^{46}$ can be hydrogen; alternatively, $R^{43}$, $R^{44}$, $R^{45}$, and $R^{46}$ can be hydrogen and $R^{42}$ can be a non-hydrogen substituent; alternatively, $R^{42}$, $R^{44}$, $R^{45}$, and $R^{46}$ can be hydrogen and $R^{43}$ can be a non-hydrogen substituent; alternatively, $R^{42}$, $R^{43}$, $R^{45}$, and $R^{46}$ can be hydrogen and $R^{44}$ can be a non-hydrogen substituent; alternatively, $R^{43}$, $R^{45}$, and $R^{46}$ can be hydrogen and $R^{42}$ and $R^{44}$ can be non-hydrogen substituents; alternatively, $R^{43}$, $R^{44}$, and $R^{45}$ can be hydrogen and $R^{42}$ and $R^{46}$ can be non-hydrogen substituents; alternatively, $R^{42}$, $R^{44}$, and $R^{46}$ can be hydrogen and $R^{43}$ and $R^{45}$ can be non-hydrogen substituents; or alternatively, $R^{43}$ and $R^{45}$ can be hydrogen and $R^{42}$, $R^{44}$, and $R^{46}$ can be non-hydrogen substituents. Substituents (general and specific) are independently disclosed herein and can be utilized without limitation as $R^{42}$, $R^{43}$, $R^{44}$, $R^{45}$, and $R^{46}$ for the $R^4$ group having Structure G9.

In an aspect, $R^5$ can have Structure G10:

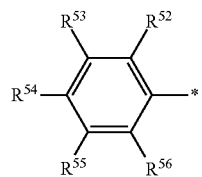

Structure G10 wherein the undesignated valency is attached to the phosphorus atom of the $N^2$-phosphinyl formamidine group. Generally, $R^{52}$, $R^{53}$, $R^{54}$, $R^{55}$, and $R^{56}$ independently can be hydrogen or a non-hydrogen substituent. In an embodiment wherein $R^5$ has Structure G10, $R^{52}$, $R^{53}$, $R^{54}$, $R^{55}$, and $R^{56}$ can be hydrogen, $R^{53}$, $R^{54}$, $R^{55}$, and $R^{56}$ can be hydrogen and $R^{52}$ can be a non-hydrogen substituent, $R^{52}$, $R^{54}$, $R^{55}$, and $R^{56}$ can be hydrogen and $R^{53}$ can be a non-hydrogen substituent, $R^{52}$, $R^{53}$, $R^{55}$, and $R^{56}$ can be hydrogen and $R^{54}$ can be a non-hydrogen substituent, $R^{53}$, $R^{55}$, and $R^{56}$ can be hydrogen and $R^{52}$ and $R^{54}$ can be non-hydrogen substituents, $R^{53}$, $R^{54}$, and $R^{55}$ can be hydrogen and $R^{52}$ and $R^{56}$ can be non-hydrogen substituents, $R^{52}$, $R^{54}$, and $R^{56}$ can be hydrogen and $R^{53}$ and $R^{55}$ can be non-hydrogen substituents, or $R^{53}$ and $R^{55}$ can be hydrogen and $R^{52}$, $R^{54}$, and $R^{56}$ can be non-hydrogen substituents. In some embodiments wherein $R^5$ has Structure G10, $R^{53}$, $R^{54}$, $R^{55}$, and $R^{56}$ can be hydrogen and $R^{52}$ can be a non-hydrogen substituent, $R^{52}$, $R^{53}$, $R^{55}$, and $R^{56}$ can be hydrogen and $R^{54}$ can be a non-hydrogen substituent, $R^{53}$, $R^{55}$, and $R^{56}$ can be hydrogen and $R^{52}$ and $R^{54}$ can be non-hydrogen substituents, $R^{53}$, $R^{54}$, and $R^{55}$ can be hydrogen and $R^{52}$ and $R^{56}$ can be non-hydrogen substituents, or $R^{53}$ and $R^{55}$ can be hydrogen and $R^{52}$, $R^{54}$, and $R^{56}$ can be non-hydrogen substituents; alternatively, $R^{53}$, $R^{54}$, $R^{55}$, and $R^{56}$ can be hydrogen and $R^{52}$ can be a non-hydrogen substituent, $R^{52}$, $R^{53}$, $R^{55}$, and $R^{56}$ can be hydrogen and $R^{54}$ can be a non-hydrogen substituent, $R^{53}$, $R^{55}$, and $R^{56}$ can be hydrogen and $R^{52}$ and $R^{54}$ can be non-hydrogen substituents, or $R^{53}$, $R^{54}$, and $R^{55}$ can be hydrogen and $R^{52}$ and $R^{56}$ can be non-hydrogen substituents; alternatively, $R^{52}$, $R^{54}$, $R^{55}$, and $R^{56}$ can be hydrogen and $R^{53}$ can be a non-hydrogen substituent, or $R^{52}$, $R^{54}$, and $R^{56}$ can be hydrogen and $R^{53}$ and $R^{55}$ can be non-hydrogen substituents; alternatively, $R^{53}$, $R^{54}$, $R^{55}$, and $R^{56}$ can be hydrogen and $R^{52}$ can be a non-hydrogen substituent, or $R^{52}$, $R^{53}$, $R^{55}$, and $R^{56}$ can be hydrogen and $R^{54}$ can be a non-hydrogen substituent; alternatively, $R^{53}$, $R^{55}$, and $R^{56}$ can be hydrogen and $R^{52}$ and $R^{54}$ can be non-hydrogen substituents, $R^{53}$, $R^{54}$, and $R^{55}$ can be hydrogen and $R^{52}$ and $R^{56}$ can be non-hydrogen substituents, or $R^{53}$ and $R^{55}$ can be hydrogen and $R^{52}$, $R^{54}$, and $R^{56}$ can be non-hydrogen substituents; or alternatively, $R^{53}$, $R^{55}$, and $R^{56}$ can be hydrogen and $R^{52}$ and $R^{54}$ can be non-hydrogen substituents, or $R^{53}$, $R^{54}$, and $R^{55}$ can be hydrogen and $R^{52}$ and $R^{56}$ can be non-hydrogen substituents. In other embodiments wherein $R^5$ has Structure G10, $R^{52}$, $R^{53}$, $R^{54}$, $R^{55}$, and $R^{56}$ can be hydrogen; alternatively, $R^{53}$, $R^{54}$, $R^{55}$, and $R^{56}$ can be hydrogen and $R^{52}$ can be a non-hydrogen substituent; alternatively, $R^{52}$, $R^{54}$, $R^{55}$, and $R^{56}$ can be hydrogen and $R^{53}$ can be a non-hydrogen substituent; alternatively, $R^{52}$, $R^{53}$, $R^{55}$, and $R^{56}$ can be hydrogen and $R^{54}$ can be a non-hydrogen substituent; alternatively, $R^{53}$, $R^{55}$, and $R^{56}$ can be hydrogen and $R^{52}$ and $R^{54}$ can be non-hydrogen substituents; alternatively, $R^{53}$, $R^{54}$, and $R^{55}$ can be hydrogen and $R^{52}$ and $R^{56}$ can be non-hydrogen substituents; alternatively, $R^{52}$, $R^{54}$, and $R^{56}$ can be hydrogen and $R^{53}$ and $R^{55}$ and can be non-hydrogen substituents; or alternatively, $R^{53}$ and $R^{55}$ can be hydrogen and $R^{52}$, $R^{54}$, and $R^{56}$ can be non-hydrogen substituents. Substituents (general and specific) are independently disclosed herein and can be utilized without limitation as $R^{52}$, $R^{53}$, $R^{54}$, $R^{55}$, and $R^{56}$ for the $R^5$ group having Structure G10.

In an aspect, $R^4$ and $R^5$ can be joined to form a cyclic group including the phosphorus atom. In an embodiment when $R^4$ and $R^5$ are joined to form a cyclic group including the phosphorus atom of the $N^2$-phosphinyl formamidine group, the phosphinyl group can be a phosphol-1-yl group, a substituted phosphol-1-yl group, a 2,3-dihydrophosphol-1-yl group, a substituted 2,3-dihydrophosphol-1-yl group, a 3,5-dihydrophosphol-1-yl group, a substituted 3,5-dihydrophosphol-1-yl group, a phospholan-1-yl group, a substituted phospholan-1-yl group, a 1,2-dihydrophosphinin-1-yl group, a substituted, 1,2-dihydrophosphinin-1-yl group, a 1,4-dihydrophosphinin-1-yl group, a substituted 1,4-dihydrophosphinin-1-yl group, a 1,2,3,4-tetrahydrophosphinin-1-yl group, a substituted 1,2,3,4-tetrahydrophosphinin-1-yl group, a 1,2,3,6-tetrahydrophosphinin-1-yl group, a substituted 1,2,3,6-tetrahydrophosphinin-1-yl group, a phosphinan-1-yl group, or a substituted phosphinan-1-yl group. In some embodiments, when $R^4$ and $R^5$ are joined to form a cyclic group including the phosphorus atom of the $N^2$-phosphinyl formamidine group, the phosphinyl group can be a phosphol-1-yl group or a substituted phosphol-1-yl group; alternatively, a 2,3-dihydrophosphol-1-yl group or a substituted 2,3-dihydrophosphol-1-yl group; alternatively, a 3,5-dihydrophosphol-1-yl group or a substituted 3,5-dihydrophosphol-1-yl group; alternatively, a phospholan-1-yl group or a substituted phospholan-1-yl group; alternatively, a 1,2-dihydrophosphinin-1-yl group or a substituted, 1,2-dihydrophosphinin-1-yl group; alternatively, a 1,4-dihydrophosphinin-1-yl group or a substituted 1,4-dihydrophosphinin-1-yl group; alternatively, a 1,2,3,4-tetrahydrophosphinin-1-yl group or a substituted 1,2,3,4-tetrahydrophosphinin-1-yl group; alternatively, a 1,2,3,6-tetrahydrophosphinin-1-yl group or a substituted 1,2,3,6-tetrahydrophosphinin-1-yl group; or alternatively, a phosphinan-1-yl group or a substituted phosphinan-1-yl group. In some embodiments, when $R^4$ and $R^5$ are joined to form a cyclic group including the phosphorus atom of the $N^2$-phosphinyl formamidine group, the phosphinyl group can be a phosphol-1-yl group, a 2,3-dihydrophosphol-1-yl group, a 3,5-dihydrophosphol-1-yl group, a phospholan-1-yl group, a 1,2-dihydrophosphinin-1-yl group, a 1,4-dihydrophosphinin-1-yl group, a 1,2,3,4-tetrahydrophosphinin-1-yl group, a 1,2,3,6-tetrahydrophosphinin-1-yl group, or a phosphinan-1-yl group. In other embodiments, when $R^4$ and $R^5$ are joined to form a cyclic group including the phosphorus atom of the $N^2$-phosphinyl formamidine group, the phosphinyl group can be a substituted phosphol-1-yl group, a substituted 2,3-dihydrophosphol-1-yl group, a substituted 3,5-dihydrophosphol-1-yl group, a substituted phospholan-1-yl group, a substituted, 1,2-dihydrophosphinin-1-yl group, a substituted 1,4-dihydrophosphinin-1-yl group, a substituted 1,2,3,4-tetrahydrophosphinin-1-yl group, a substituted 1,2,3,6-tetrahydrophosphinin-1-yl group, or a substituted phosphinan-1-yl group. In yet other embodiments, when $R^4$ and $R^5$ are joined to form a cyclic group including the phosphorus atom of the $N^2$-phosphinyl formamidine group a phospholan-1-yl group, a substituted phospholan-1-yl group, a phosphinan-1-yl group, or a substituted phosphinan-1-yl group; alternatively, a phospholan-1-yl group or a phosphinan-1-yl group; or alternatively, a substituted phospholan-1-yl group or a substituted phosphinan-1-yl group. In further embodiments, when $R^4$ and $R^5$ are joined to form a cyclic group including the phosphorus atom of the $N^2$-phosphinyl formamidine group, the phosphinyl group can be a phosphol-1-yl group; alternatively, a substituted phosphol-1-yl group; alternatively, a 2,3-dihydrophosphol-1-yl group; alternatively, a substituted 2,3-dihydrophosphol-1-yl group; alternatively, a 3,5-dihydrophosphol-1-yl group; alternatively, a substituted 3,5-dihydrophosphol-1-yl group; alternatively, a phospholan-1-yl group; alternatively, a substituted phospholan-1-yl group; alternatively, a 1,2-dihydrophosphinin-1-yl group; alternatively, a substituted, 1,2-dihydrophosphinin-1-yl group; alternatively, a 1,4-dihydrophosphinin-1-yl group; alternatively, a substituted 1,4-dihydrophosphinin-1-yl group; alternatively, a 1,2,3,4-tetrahydrophosphinin-1-yl group; alternatively, a substituted 1,2,3,4-tetrahydrophosphinin-1-yl group; alternatively, a 1,2,3,6-tetrahydrophosphinin-1-yl group; alternatively, a substituted 1,2,3,6-tetrahydrophosphinin-1-yl group; alternatively, a phosphinan-1-yl group; or alternatively, a substituted phosphinan-1-yl group. Substituents (general and specific) are independently disclosed herein and can be utilized without limitation to further describe substituted groups where $R^4$ and $R^5$ are joined to form a cyclic group including the phosphorus atom.

In an embodiment, when $R^4$ and $R^5$ are joined to form a cyclic group including the phosphorus atom of the $N^2$-phosphinyl formamidine group, the cyclic group including the phosphorus atom can comprise at least one substituent on a carbon atom adjacent to the phosphorus atom attached to the $N^2$ nitrogen atom of the $N^2$-phosphinyl formamidine group. In some embodiments, when $R^4$ and $R^5$ are joined to form a cyclic group including the phosphorus atom of the $N^2$-phosphinyl formamidine group, the cyclic group including the phosphorus atom can comprise at least one substituent on each carbon atom adjacent to the phosphorus atom attached to the $N^2$ nitrogen atom of the $N^2$-phosphinyl formamidine group. In other embodiments, when $R^4$ and $R^5$ are joined to form a cyclic group including the phosphorus atom of the $N^2$-phosphinyl formamidine group, the cyclic group including the phosphorus atom can comprise, or consist of, only one substituent on a carbon atom adjacent to the phosphorus atom attached to the $N^2$ nitrogen atom of the $N^2$-phosphinyl formamidine group. In yet other embodiments, when $R^4$ and $R^5$ are joined to form a cyclic group including the phosphorus atom of the $N^2$-phosphinyl formamidine group, the cyclic group including the phosphorus atom can comprise, or consist of, only one substituent on each carbon atom adjacent to the phosphorus atom attached to the $N^2$ nitrogen atom of the $N^2$-phosphinyl formamidine group. Substituents (general and specific) are independently disclosed herein and can be utilized without limitation to further describe substituted group(s) where $R^4$ and $R^5$ are joined to form a cyclic group including the phosphorus atom.

In an embodiment, $R^4$ and/or $R^5$ independently can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group, a 2,6-dialkylphenyl group, or a 2,4,6-trialkylphenyl group; alternatively, a 2,4-dialkylphenyl group or a 2,6-dialkylphenyl group; alternatively, a 2,6-dialkylphenyl group, or a 2,4,6-trialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 3-alkylphenyl group; alternatively, a 4-alkylphenyl group; alternatively, a 2,4-dialkylphenyl group; alternatively, a 2,6-dialkylphenyl group; alternatively, a 3,5-dialkylphenyl group; or alternatively, a 2,4,6-trialkylphenyl group. In another non-limiting embodiment, $R^4$ and/or $R^5$ independently can be a napht-1-yl group, a 2-naphth-2-yl group, a 2-alkylnaphth-1-yl group, a 1-alkylnaphth-2-yl group, a 3-alkylnapth-2-yl group, or a 1,3-dialkylnaphth-2-yl group; alternatively, a napht-1-yl group or a 2-alkylnaphth-1-yl group; alternatively, a naphth-2-yl group, a 1-alkylnaphth-2-yl group, a 3-alkylnapth-2-yl group, or a 1,3-dialkylnaphth-2-yl group; alternatively, a napht-1-yl group; alternatively, a 2-naphth-2-yl group; alternatively, a 2-alkylnaphth-1-yl group; alternatively, a 1-alkylnaphth-2-yl group; alternatively, a 3-alkylnapth-2-yl group; or alternatively, a 1,3-dialkylnaphth-2-yl group. In other non-limiting embodiments, $R^4$ and/or $R^5$ independently can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, cyclopentyl group; alternatively, a 2-alkylcyclopentyl group; or alternatively, a 2,5-dialkylcyclopentyl group. Alkyl group substituents (general and specific) are independently described herein and can be utilized, without limitation, to further describe the alkylphenyl, dialkylphenyl, trialkylphenyl, naphthyl, dialkylnaphthyl, alkylcyclohexyl, dialkylcyclohexyl, alkylcyclopentyl, or dialkylcyclopentyl groups that can be utilized as $R^4$ and/or $R^5$. Generally, the alkyl substituents of a dialkyl or trialkyl phenyl, naphthyl, cyclohexyl, or cyclopentyl group can be the same; or alternatively the alkyl substituents of a dialkyl or trialkyl phenyl, naphthyl, cyclohexyl, or cyclopentyl group can be different.

In another non-limiting embodiment, $R^4$ and/or $R^5$ independently can be a phenyl group, a 2-alkoxyphenyl group, a 3-alkoxyphenyl group, a 4-alkoxyphenyl group, or a 3,5-dialkoxyphenyl group; alternatively, a 2-alkoxyphenyl group or a 4-alkoxyphenyl group; alternatively, a 3-alkoxyphenyl group or a 3,5-dialkoxyphenyl group; alternatively, a 2-alkoxyphenyl group, alternatively, a 3-alkoxyphenyl group; alternatively, a 4-alkoxyphenyl group; alternatively, a 3,5-dialkoxyphenyl group. Alkoxy group substituents (general and specific) are independently described herein and can be utilized, without limitation, to further describe the alkoxyphenyl or dialkoxyphenyl groups that can be utilized as $R^4$ and/or $R^5$. Generally, the alkoxy substituents of a dialkoxyphenyl groups can be the same; or alternatively the alkoxy substituents of a dialkoxyphenyl group can be different.

In other non-limiting embodiments, $R^4$ and/or $R^5$ independently can be a phenyl group, a 2-halophenyl group, a 3-halophenyl group, a 4-halophenyl group, a 2,6-dihalophenyl group, or a 3,5-dialkylphenyl group; alternatively, a 2-halophenyl group, a 4-halophenyl group, or a 2,6-dihalophenyl group; alternatively, a 2-halophenyl group or a 4-halophenyl group; alternatively, a 3-halophenyl group or a 3,5-dihalophenyl group; alternatively, a 2-halophenyl group; alternatively, a 3-halophenyl group; alternatively, a 4-halophenyl group; alternatively, a 2,6-dihalophenyl group; or alternatively, a 3,5-dihalophenyl group. Halides are independently described herein and can be utilized, without limitation, to further describe the halophenyl or dihalophenyl groups that can be utilized $R^4$ and/or $R^5$. Generally, the halides of a dihalophenyl group can be the same; or alternatively the halides of a dihalophenyl group can be different.

In a non-limiting embodiment, $R^4$ and/or $R^5$ independently can be a 2-methylphenyl group, a 2-ethylphenyl group, a 2-isopropylphenyl group, a 2-tert-butylphenyl group, a 3-methylphenyl group, a 2,6-dimethylphenyl group, a 2,6-diethylphenyl group, a 2,6-diisopropylphenyl group, a 2,6-di-tert-butyl-phenyl group, a 3,5-dimethyl group, or a 2,4,6-trimethylphenyl group; alternatively, a 2-methylphenyl group, a 2-ethylphenyl group, a 2-isopropylphenyl group, or a 2-tert-butylphenyl group; alternatively, a 2,6-dimethylphenyl group, a 2,6-diethylphenyl group, a 2,6-diisopropylphenyl group, or a 2,6-di-tert-butylphenyl group; alternatively, 2-methylphenyl group; alternatively, a 2-ethylphenyl group; alternatively, a 2-isopropylphenyl group; alternatively, a 2-tert-butylphenyl group; alternatively, a 3-methylphenyl group; alternatively, a 2,6-dimethylphenyl group; alternatively, a 2,6-diethylphenyl group; alternatively, a 2,6-diisopropylphenyl group; alternatively, a 2,6-di-tert-butylphenyl group; alternatively, a 3,5-dimethyl group; or alternatively, a 2,4,6-trimethylphenyl group. In another non-limiting embodiment, $R^4$ and/or $R^5$ independently can be a cyclohexyl group, a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group, a 2-ethylcyclohexyl group, a 2-isopropylcyclohexyl group, or a 2-tert-butylcyclohexyl group; alternatively, a 2,6-dimethylcyclohexyl group, a 2,6-diethylcyclohexyl group, a 2,6-diisopropylcyclohexyl group, or a 2,6-di-tert-butylcyclohexyl group; alternatively, a cyclohexyl group; alternatively, a 2-methylcyclohexyl group; alternatively, a 2-ethylcyclohexyl group; alternatively, a 2-isopropylcyclohexyl group; alternatively, a 2-tert-butylcyclohexyl group; alternatively, a 2,6-dimethylcyclohexyl group; alternatively, a 2,6-diethylcyclohexyl group; alternatively, a 2,6-diisopropylcyclohexyl group; or alternatively, a 2,6-di-tert-butylcyclohexyl group. In another non-limiting embodiment, $R^4$ and/or $R^5$ independently can be a 2-methylnaphth-1-yl group, a 2-ethylnaphth-1-yl group, a 2-n-propylnaphth-1-yl group, a 2-isopropylnaphth-1-yl group, or a 2-tert-butyl-naphth-1-yl group; alternatively, a 2-methylnaphth-1-yl group; alternatively, a 2-ethylnaphth-1-yl group; alternatively, a 2-n-propylnaphth-1-yl group; alternatively, a 2-isopropylnaphth-1-yl group; or alternatively, a 2-tert-butyl-naphth-1-yl group.

In a non-limiting embodiment, $R^4$ and/or $R^5$ independently can be a 2-methoxyphenyl group, a 2-ethoxyphenyl group, a 2-isopropoxyphenyl group, a 2-tert-butoxyphenyl group, a 3-methoxyphenyl group, a 3-ethoxyphenyl group, a 3-isopropoxyphenyl group, a 3-tert-butoxyphenyl group, a 4-methoxy-phenyl group, a 4-ethoxyphenyl group, a 4-isopropoxyphenyl group, a 4-tert-butoxyphenyl group, a 2,4-dimethoxyphenyl group, a 2,4-diethoxyphenyl group, a 2,4-diisopropoxyphenyl group, a 2,4-di-tert-butoxyphenyl group, a 3,5-dimethoxyphenyl group, a 3,5-diethoxyphenyl group, a 3,5-diisopropoxyphenyl group, a 3,5-di-tert-butoxyphenyl group, a 2,6-dimethoxyphenyl group, a 2,6-diethoxyphenyl group, a 2,6-diisopropoxyphenyl group, a 2,6-di-tert-butoxyphenyl group, or a 2,4,6-trimethoxyphenyl group; alternatively, a 2-methoxyphenyl group, a 2-ethoxyphenyl group, a 2-isopropoxyphenyl group, or a 2-tert-butoxyphenyl group; alternatively, a 3-methoxyphenyl group, a 3-ethoxyphenyl group, a 3-isopropoxyphenyl group, or a 3-tert-butoxyphenyl group; alternatively, a 4-methoxyphenyl group, a 4-ethoxyphenyl group, a 4-isopropoxyphenyl group, or a 4-tert-butoxyphenyl group; alternatively, a 2,4-dimethoxyphenyl group, a 2,4-diethoxyphenyl group, a 2,4-diisopropoxyphenyl group, or a 2,4-di-tert-butoxyphenyl group, alternatively, a 3,5-dimethoxyphenyl group, a 3,5-diethoxyphenyl group, a 3,5-diisopropoxyphenyl group, or a 3,5-di-tert-butoxyphenyl group; or alternatively, a 2,6-dimethoxyphenyl group, a 2,6-diethoxyphenyl group, a 2,6-diisopropoxyphenyl group, or a 2,6-di-tert-butoxyphenyl group. In other non-limiting embodiments, $R^4$ and/or $R^5$ independently can be a 2-methoxyphenyl group; alternatively, a 2-ethoxyphenyl group; alternatively, a 2-isopropoxyphenyl group; alternatively, a 2-tert-butoxyphenyl group; alternatively, a 3-methoxyphenyl group; alternatively, a 3-ethoxyphenyl group; alternatively, a 3-isopropoxyphenyl group; alternatively, a 3-tert-butoxyphenyl group; alternatively, a 4-methoxyphenyl group; alternatively, a 4-ethoxyphenyl group; alternatively, a 4-isopropoxyphenyl group; alternatively, a 4-tert-butoxyphenyl group; alternatively, a 2,4-dimethoxyphenyl group; alternatively, a 2,4-diethoxyphenyl group; alternatively, a 2,4-diisopropoxyphenyl group; alternatively, a 2,4-di-tert-butoxyphenyl group; alternatively, a 3,5-dimethoxyphenyl group; alternatively, a 3,5-diethoxyphenyl group; alternatively, a 3,5-diisopropoxyphenyl group; alternatively, a 3,5-di-tert-butoxyphenyl group; alternatively, a 2,6-dimethoxyphenyl group; alternatively, a 2,6-diethoxyphenyl group; alternatively, a 2,6-diisopropoxyphenyl group; alternatively, a 2,6-di-tert-butoxyphenyl group; or alternatively, a 2,4,6-trimethoxyphenyl group.

In another non-limiting embodiment, $R^4$ and/or $R^5$ independently can be a 2-fluorophenyl group, a 2-chlorophenyl group, a 3-fluorophenyl group, a 3-chlorophenyl group, a 4-fluorophenyl group, a 4-chlorophenyl group, a 3,5-difluorophenyl group, or a 3,5-dichlorophenyl group; alternatively, a 2-fluorophenyl group or a 2-chlorophenyl group; alternatively, a 3-fluorophenyl group or a 3-chlorophenyl group; alternatively, a 4-fluorophenyl group or a 4-chlorophenyl group; alternatively, a 3,5-difluorophenyl group or a 3,5-dichlorophenyl group; alternatively, a 3-fluorophenyl group, a 3-chlorophenyl group, a 3,5-difluorophenyl group or a 3,5-dichlorophenyl group; or alternatively, a 3-fluorophenyl group or a 3,5-difluorophenyl group. In another non-limiting embodiment, $R^4$ and/or $R^5$ independently can be a 2-fluorophenyl group; alternatively, a 2-chlorophenyl group; alternatively, a 3-fluorophenyl group; alternatively, a 3-chlorophenyl group; alternatively, a 4-fluorophenyl group; alternatively, a 4-chlorophenyl group; alternatively, a 3,5-difluorophenyl group; or alternatively, a 3,5-dichlorophenyl group.

Generally, the $R^4$ and/or $R^5$ groups of the phosphinyl group independently can be any $R^4$ or $R^5$ group described herein and utilized in any combination to further describe the phosphinyl group of any $N^2$-phosphinyl formamidine compound described herein. In an embodiment, $R^4$ and $R^5$ can be the same. In other embodiments $R^4$ and $R^5$ can be different.

In an aspect, the phosphinyl group of the $N^2$-phosphinyl formamidine compound can be a diphenylphosphinyl group, a dialkylphosphinyl group, a bis(mono-halo substituted phenyl)phosphinyl group, a bis(mono-alkyl substituted phenyl) phosphinyl group, or a bis(mono-alkoxy substituted phenyl)-phosphinyl group; alternatively, a diphenylphosphinyl group; alternatively, a dialkylphosphinyl group; alternatively, a bis(mono-halo substituted phenyl)phosphinyl group; alternatively, a bis(mono-alkyl substituted phenyl) phosphinyl group; alternatively, a bis(mono-alkoxy substituted phenyl)phosphinyl group. In another aspect, the phosphinyl group of the $N^2$-phosphinyl formamidine compound can be an (alkyl)(phenyl)phosphinyl group, a (mono-halo substituted phenyl)(phenyl)phosphinyl group, a (mono-alkyl substituted phenyl)(phenyl)phosphinyl group, a (mono-alkoxy substituted phenyl)(phenyl)phosphinyl group, a (mono-alkyl substituted phenyl)(mono-halo substituted phenyl) phosphinyl group, or a (mono-alkyl substituted phenyl)(mono-alkoxy substituted phenyl) phosphinyl group; alternatively, an (alkyl)(phenyl)phosphinyl group; alternatively, a (mono-halo substituted phenyl)(phenyl)phosphinyl group; alternatively, a (mono-alkyl substituted phenyl)(phenyl) phosphinyl group; alternatively, a (mono-alkoxy substituted phenyl)(phenyl)phosphinyl group; alternatively, a (mono-alkyl substituted phenyl)-(mono-halo substituted phenyl) phosphinyl group; or alternatively, a (mono-alkyl substituted phenyl)-(mono-alkoxy substituted phenyl) phosphinyl group. In another aspect, the phosphinyl group of the $N^2$-phosphinyl formamidine compound can be a bis(dihalo substituted phenyl)phosphinyl group, a bis(dialkyl substituted phenyl)phosphinyl group, a bis(dialkoxy substituted phenyl)phosphinyl group, a bis(trialkylphenyl)phosphinyl group, or a bis(trialkoxyphenyl)phosphinyl group; alternatively, a bis(dihalo substituted phenyl)phosphinyl group; alternatively, a bis(dialkyl substituted phenyl)phosphinyl group; alternatively, a bis(dialkoxy substituted phenyl)phosphinyl group; alternatively, a bis(trialkylphenyl)phosphinyl group; or alternatively, a bis(trialkoxyphenyl)phosphinyl group. Halogens, alkyl group substituents (general and specific), and alkoxy group substituents (general and specific) are independently described herein (e.g., as substituents for substituted $R^1$ groups) and can be utilized, without limitation to further describe the phosphinyl group which can be utilized in the $N^2$-phosphinyl formamidine compound.

In a non-limiting aspect, the phosphinyl group of the $N^2$-phosphinyl formamidine compound can be a dimethylphosphinyl group, a diethylphosphinyl group, a diisopropylphosphinyl group, a di-tert-butylphosphinyl group, or a di-neo-pentylphosphinyl group. In a non-limiting embodiment, the phosphinyl group of the $N^2$-phosphinyl formamidine compound can be a dimethylphosphinyl group; alternatively, a diethyl phosphinyl group; alternatively, a diisopropylphosphinyl group; alternatively, a di-tert-butylphosphinyl group; or alternatively, a di-neo-pentylphosphinyl group. In a non-limiting aspect, the phosphinyl group of the $N^2$-phosphinyl formamidine compound can be a (methyl)(phenyl)-phosphinyl group, an (ethyl)(phenyl) phosphinyl group, a (isopropyl)(phenyl)phosphinyl group, a (tert-butyl)(phenyl)phosphinyl group, or a (neo-pentyl)(phenyl)phosphinyl group. In an embodiment, the phosphinyl group of the $N^2$-phosphinyl formamidine compound can be a (methyl)(phenyl)phosphinyl group; alternatively, an (ethyl)(phenyl) phosphinyl group; alternatively, an (isopropyl)(phenyl)phosphinyl group; alternatively, a (tert-butyl)(phenyl)phosphinyl group; or alternatively, a (neo-pentyl)(phenyl)phosphinyl group. In some non-limiting embodiments, the phosphinyl group of the $N^2$-phosphinyl formamidine compound can be a dicyclopentyl phosphinyl group, a dicyclohexyl phosphinyl group; alternatively, a dicyclopentylphosphinyl group; or alternatively, a dicyclohexylphosphinyl group.

In yet another non-limiting aspect, the phosphinyl group of the $N^2$-phosphinyl formamidine compound can be a bis(2-fluorophenyl)phosphinyl group, a bis(2-chlorophenyl)phosphinyl group, a bis(3-fluorophenyl)phosphinyl group, a bis(3-chlorophenyl)phosphinyl group, a bis(4-fluorophenyl)-phosphinyl group, or a bis(4-chlorophenyl)phosphinyl group. In some non-limiting embodiments, the phosphinyl group of the $N^2$-phosphinyl formamidine compound can be a bis(2-fluorophenyl)phosphinyl group, a bis(3-fluorophenyl)phosphinyl group, or a bis(4-fluorophenyl)phosphinyl group; or alternatively, a bis(2-chlorophenyl)phosphinyl group, a bis(3-chlorophenyl)phosphinyl group, or a bis(4-chlorophenyl)-phosphinyl group. In other non-limiting embodiments, the phosphinyl group of the $N^2$-phosphinyl formamidine compound can be a bis(2-fluorophenyl)phosphinyl group; alternatively, a bis(2-chlorophenyl)phosphinyl group; alternatively, a bis(3-fluorophenyl)phosphinyl group; alternatively, a bis(3-chlorophenyl)phosphinyl group; alternatively, a bis(4-fluorophenyl)phosphinyl group; or alternatively, a bis(4-chlorophenyl)phosphinyl group.

In yet another non-limiting aspect, the phosphinyl group of the $N^2$-phosphinyl formamidine compound can be a (2-fluorophenyl)(phenyl)phosphinyl group, a (2-chlorophenyl)(phenyl)phosphinyl group, a (3-fluorophenyl)(phenyl) phosphinyl group, a (3-chlorophenyl)(phenyl)phosphinyl group, a (4-fluorophenyl)(phenyl)phosphinyl group, or a (4-chlorophenyl)(phenyl)phosphinyl group. In some non-limiting embodiments, the phosphinyl group of the $N^2$-phosphinyl formamidine compound can be a (2-fluorophenyl)(phenyl)phosphinyl group, a (3-fluorophenyl)(phenyl)phosphinyl group, or a (4-fluoro-phenyl)(phenyl)phosphinyl group; or alternatively, a (2-chlorophenyl)(phenyl)phosphinyl group, a (3-chlorophenyl)(phenyl)phosphinyl group, or a (4-chlorophenyl)(phenyl)phosphinyl group. In other non-limiting embodiments, the phosphinyl group of the $N^2$-phosphinyl formamidine compound can be a (2-fluorophenyl)(phenyl)phosphinyl group; alternatively, a (2-chlorophenyl)(phenyl)phosphinyl group; alternatively, a (3-fluorophenyl)(phenyl)phosphinyl group; alternatively, a (3-chlorophenyl)(phenyl)-phosphinyl group; alternatively, a (4-fluorophenyl)(phenyl)phosphinyl group; or alternatively, a (4-chlorophenyl)(phenyl)phosphinyl group.

In yet another non-limiting aspect, the phosphinyl group of the $N^2$-phosphinyl formamidine compound can be a diphenylphosphinyl group, a bis(2-methylphenyl)phosphinyl group, a bis(2-ethyl-phenyl)phosphinyl group, a bis(2-isopropylphenyl)phosphinyl group, a bis(2-tert-butylphenyl)phosphinyl group, a bis(3-methylphenyl)phosphinyl group, a bis(3-ethylphenyl)phosphinyl group, bis(3-isopropyl-phenyl)phosphinyl group, a bis(3-tert-butylphenyl)phosphinyl group, a diphenylphosphinyl group, a bis(4-methylphenyl)phosphinyl group, a bis(4-ethylphenyl)phosphinyl group, a bis(4-isopropylphenyl)-phosphinyl group, or a bis(4-tert-butylphenyl)phosphinyl group. In a non-limiting embodiment, the phosphinyl group of the $N^2$-phosphinyl formamidine compound can be a bis(2-methylphenyl)phosphinyl group, a bis(2-ethylphenyl)phosphinyl group, a bis(2-isopropylphenyl)phosphinyl group, or a bis(2-tert-butylphenyl)phosphinyl group; alternatively, a diphenylphosphinyl group, a bis(3-methyl-phenyl)phosphinyl group, a bis(3-ethylphenyl)phosphinyl group, a bis(3-isopropylphenyl)phosphinyl group, or a bis(3-tert-butylphenyl) phosphinyl group; or alternatively, a diphenylphosphinyl group, a bis(4-methylphenyl)phosphinyl group, a bis(4-ethylphenyl)phosphinyl group, a bis(4-isopropylphenyl)-phosphinyl group, or a bis(4-tert-butylphenyl)phosphinyl group. In other non-limiting embodiments, the phosphinyl group of the $N^2$-phosphinyl formamidine compound can be a diphenylphosphinyl group; alternatively, a bis(2-methylphenyl) phosphinyl group; alternatively, a bis(2-ethylphenyl)phosphinyl group; alternatively, a bis(2-isopropylphenyl) phosphinyl group; alternatively, a bis(2-tert-butylphenyl)-phosphinyl group; alternatively, a bis(3-methylphenyl) phosphinyl group; alternatively, a bis(3-ethyl-phenyl) phosphinyl group; alternatively, a bis(3-isopropylphenyl) phosphinyl group; alternatively, a bis(3-tert-butylphenyl) phosphinyl group; alternatively, a diphenylphosphinyl group; alternatively, a bis(4-methylphenyl)phosphinyl group; alternatively, a bis(4-ethylphenyl)phosphinyl group; alternatively, a bis(4-isopropylphenyl)phosphinyl group; or alternatively, a bis(4-tert-butylphenyl)phosphinyl group.

In yet another non-limiting aspect, the phosphinyl group of the $N^2$-phosphinyl formamidine compound can be a diphenylphosphinyl group, a (2-methylphenyl)(phenyl) phosphinyl group, a (2-ethyl-phenyl)(phenyl)phosphinyl group, a (2-isopropylphenyl)(phenyl)phosphinyl group, a (2-tert-butyl-phenyl)(phenyl)phosphinyl group, a (3-methylphenyl)(phenyl)phosphinyl group, a (3-ethylphenyl)-(phenyl)phosphinyl group, (3-isopropylphenyl)(phenyl)phosphinyl group, a (3-tert-butylphenyl)-(phenyl)phosphinyl group, a diphenylphosphinyl group, a (4-methylphenyl)(phenyl) phosphinyl group, a (4-ethylphenyl)(phenyl)phosphinyl group, a (4-isopropylphenyl)(phenyl)phosphinyl group, or a (4-tert-butylphenyl)(phenyl)phosphinyl group. In a non-limiting embodiment, the phosphinyl group of the $N^2$-phosphinyl formamidine compound can be a (2-methylphenyl)(phenyl)phosphinyl group, a (2-ethylphenyl)(phenyl) phosphinyl group, a (2-isopropylphenyl)(phenyl)phosphinyl group, or a (2-tert-butylphenyl)(phenyl)phosphinyl group; alternatively, a diphenylphosphinyl group, a (3-methylphenyl)(phenyl)phosphinyl group, a (3-ethylphenyl)(phenyl) phosphinyl group, a (3-isopropylphenyl)(phenyl)phosphinyl group, or a (3-tert-butylphenyl)(phenyl)phosphinyl group; or alternatively, a diphenylphosphinyl group, a (4-methylphenyl)(phenyl)phosphinyl group, a (4-ethylphenyl)(phenyl)phosphinyl group, a (4-isopropylphenyl)(phenyl)phosphinyl group, or a (4-tert-butylphenyl)(phenyl)phosphinyl group. In other non-limiting embodiments, the phosphinyl group of the $N^2$-phosphinyl formamidine compound can be a diphenylphosphinyl group; alternatively, a (2-methylphenyl)(phenyl)phosphinyl group; alternatively, a (2-ethylphenyl)(phenyl)phosphinyl group; alternatively, a (2-isopropylphenyl)(phenyl)phosphinyl group; alternatively, a (2-tert-butylphenyl)(phenyl)phosphinyl group; alternatively, a (3-methylphenyl)(phenyl)phosphinyl group; alternatively, a (3-ethylphenyl)(phenyl)phosphinyl group; alternatively, a (3-isopropylphenyl)(phenyl)phosphinyl group; alternatively, a (3-tert-butylphenyl)(phenyl)phosphinyl group; alternatively, a diphenylphosphinyl group; alternatively, a (4-methylphenyl)(phenyl)phosphinyl group; alternatively, a (4-ethylphenyl)(phenyl)phosphinyl group; alternatively, a (4-isopropylphenyl)(phenyl)phosphinyl group; or alternatively, a (4-tert-butylphenyl)(phenyl)phosphinyl group.

In yet another non-limiting aspect, the phosphinyl group of the $N^2$-phosphinyl formamidine compound can be a diphenylphosphinyl group, a bis(2-methoxyphenyl)phosphinyl group, a bis(2-ethoxy-phenyl)phosphinyl group, a bis(2-isopropoxyphenyl)phosphinyl group, a bis(2-tert-butoxy-phenyl)-phosphinyl group, a bis(3-methoxyphenyl) phosphinyl group, a bis(3-ethoxyphenyl)phosphinyl group, a bis(3-isopropoxyphenyl)phosphinyl group, a bis(3-tert-butoxyphenyl)phosphinyl group, a diphenoxyphosphinyl group, a bis(4-methoxyphenyl)phosphinyl group, a bis(4-ethoxyphenyl)phosphinyl group, bis(4-isopropoxyphenyl) phosphinyl group, or a bis(4-tert-butoxyphenyl)phosphinyl group. In a non-limiting embodiment, the phosphinyl group of the $N^2$-phosphinyl formamidine compound can be a bis(2-methoxyphenyl)phosphinyl group, a bis(2-ethoxyphenyl)phosphinyl group, a bis(2-isopropoxy-phenyl)phosphinyl group, or a bis(2-tert-butoxyphenyl)phosphinyl group; alternatively, a diphenoxyphosphinyl group, a bis(3-methoxyphenyl)phosphinyl group, a bis(3-ethoxyphenyl) phosphinyl group, a bis(3-isopropoxyphenyl)phosphinyl group, or a bis(3-tert-butoxyphenyl)phosphinyl group; or alternatively, a diphenoxyphosphinyl group, a bis(4-methoxyphenyl)phosphinyl group, a bis(4-ethoxy-phenyl) phosphinyl group, a bis(4-isopropoxyphenyl)phosphinyl group, or a bis(4-tert-butoxyphenyl)-phosphinyl group. In other non-limiting embodiments, the phosphinyl group of the $N^2$-phosphinyl formamidine compound can be a diphenylphosphinyl group; alternatively, a bis(2-methoxyphenyl) phosphinyl group; alternatively, a bis(2-ethoxyphenyl)phosphinyl group; alternatively, a bis(2-isopropoxyphenyl) phosphinyl group; alternatively, a bis(2-tert-butoxyphenyl) phosphinyl group; alternatively, a bis(3-methoxyphenyl) phosphinyl group; alternatively, a bis(3-ethoxyphenyl) phosphinyl group; alternatively, a bis(3-isopropoxyphenyl) phosphinyl group; alternatively, a bis(3-tert-butoxyphenyl) phosphinyl group; alternatively, a diphenoxyphosphinyl group; alternatively, a bis(4-methoxyphenyl)phosphinyl group; alternatively, a bis(4-ethoxyphenyl)phosphinyl group; alternatively, a bis(4-isopropoxyphenyl)phosphinyl group; or alternatively, a bis(4-tert-butoxyphenyl)phosphinyl group.

In yet another non-limiting aspect, the phosphinyl group of the $N^2$-phosphinyl formamidine compound can be a diphenylphosphinyl group, a (2-methoxyphenyl)(phenyl) phosphinyl group, a (2-ethoxyphenyl)(phenyl)phosphinyl group, a (2-isopropoxyphenyl)(phenyl)phosphinyl group, a (2-tert-butoxyphenyl)(phenyl)phosphinyl group, a (3-methoxyphenyl)(phenyl)phosphinyl group, a (3-ethoxyphenyl)(phenyl)phosphinyl group, a (3-isopropoxyphenyl) (phenyl)phosphinyl group, a (3-tert-butoxyphenyl)(phenyl) phosphinyl group, a diphenoxyphosphinyl group, a (4-methoxyphenyl)-(phenyl)phosphinyl group, a (4-ethoxyphenyl)(phenyl)phosphinyl group, a (4-isopropoxyphenyl)-(phenyl)phosphinyl group, or a (4-tert-butoxyphenyl)(phenyl)phosphinyl group. In a non-limiting embodiment, the phosphinyl group of the $N^2$-phosphinyl formamidine compound can be a (2-methoxy-phenyl)(phenyl)phosphinyl group, a (2-ethoxyphenyl)(phenyl)phosphinyl group, a (2-isopropoxyphenyl)-(phenyl)phosphinyl group, or a (2-tert-butoxyphenyl)(phenyl)phosphinyl group; alternatively, a diphenoxyphosphinyl group, a (3-methoxyphenyl) (phenyl)phosphinyl group, a (3-ethoxyphenyl)(phenyl)-phosphinyl group, a (3-isopropoxyphenyl)(phenyl) phosphinyl group, or a (3-tert-butoxyphenyl)(phenyl)-phosphinyl group; or alternatively, a diphenoxyphosphinyl group, a (4-methoxyphenyl)(phenyl)-phosphinyl group, a (4-ethoxyphenyl)(phenyl)phosphinyl group, (4-isopropoxy-phenyl)(phenyl)-phosphinyl group, or a (4-tert-butoxyphenyl)(phenyl)phosphinyl group. In other non-limiting embodiments, the phosphinyl group of the $N^2$-phosphinyl formamidine compound can be a diphenylphosphinyl group; alternatively, a (2-methoxyphenyl)(phenyl)phosphinyl group; alternatively, a (2-ethoxyphenyl)(phenyl)phosphinyl group; alternatively, a (2-isopropoxyphenyl)(phenyl)phosphinyl group; alternatively, a (2-tert-butoxyphenyl)(phenyl) phosphinyl group; alternatively, a (3-methoxy-phenyl)(phenyl)phosphinyl group; alternatively, a (3-ethoxyphenyl) (phenyl)phosphinyl group; alternatively, a (3-isopropoxyphenyl)(phenyl)phosphinyl group; alternatively, a (3-tert-butoxyphenyl)-(phenyl)phosphinyl group; alternatively, a diphenoxyphosphinyl group; alternatively, a (4-methoxy-phenyl)(phenyl)phosphinyl group; alternatively, a (4-ethoxyphenyl)(phenyl)phosphinyl group; alternatively, (4-isopropoxyphenyl)(phenyl)phosphinyl group; or alternatively, a (4-tert-butoxy-phenyl)(phenyl)phosphinyl group.

$N^2$-Phosphinyl Formamidine Metal Salt Complexes

In an aspect, this disclosure provides for an $N^2$-phosphinyl formamidine metal salt complex. Generally, the $N^2$-phosphinyl formamidine metal salt complex can comprise a metal salt complexed to an $N^2$-phosphinyl formamidine compound. In some embodiments, the $N^2$-phosphinyl formamidine metal salt complex can further comprise a neutral ligand, Q. In other embodiments, the $N^2$-phosphinyl formamidine metal salt complex can be dimeric. $N^2$-phosphinyl formamidine compounds are generally described herein and can be utilized, without limitation, to further describe the $N^2$-phosphinyl formamidine metal salt complex comprising a metal salt complexed to an $N^2$-phosphinyl formamidine compound. In an embodiment, the $N^2$-phosphinyl formamidine metal salt complex can have Structure NPFMC1 or NPFMC2; alternatively, Structure NPFMC1; or alternatively, Structure NPFMC2.

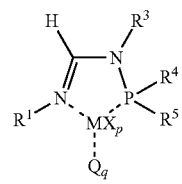

Structure NPFMC1

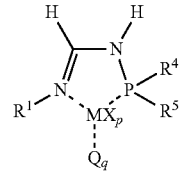

Structure NPFMC2

In some embodiments, the the $N^2$-phosphinyl formamidine metal salt complex can have Structure NPFMC3 or NPFMC4; alternatively, Structure NPFMC3; or alternatively, Structure NPFMC4.

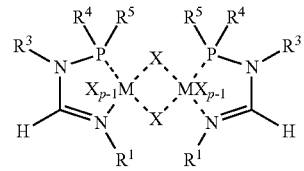

Structure NPFMC3

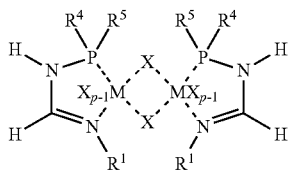

Structure NPFMC4

$R^1$, $R^3$, $R^4$, $R^5$, M, X, Q, p, and q within the $N^2$-phosphinyl formamidine metal salt complex Structures NPFMC1, NPFMC2, NPFMC3, and/or NPFMC4 are independently described herein and these description can be utilized in any combination to further describe the $N^2$-phosphinyl formamidine metal salt complexes of this disclosure. Generally, $MX_p$ or $MX_pQ_q$ represents the metal salt of the metal complex, Q represents a neutral ligand, and q represents the number of neutral ligands in the $N^2$-phosphinyl formamidine metal salt complex. The $N^2$-phosphinyl formamidine compound features $R^1$, $R^3$, $R^4$, and $R^5$ are described for $N^2$-phosphinyl formamidine compounds having Structures NPFMC1, NPFMC2, NPFMC3, and/or NPFMC4 can be utilized without limitation to describe the $N^2$-phosphinyl formamidine metal salt complexes having Structures NPFMC1, NPFMC2, NPFMC3, and/or NPFMC4.

Metal Salt

Generally, the metal salt, $MX_p$ or $MX_pQ_q$, of the $N^2$-phosphinyl formamidine metal salt complex comprising a metal salt complexed to an $N^2$-phosphinyl formamidine compound can comprise a cationic metal, M, and an anionic ligand, X. In some embodiments, the metal salt can further comprise a neutral ligand which may or may not be present in the $N^2$-phosphinyl formamidine metal salt complex comprising a metal salt complexed to an $N^2$-phosphinyl formamidine compound.

Generally, the metal atom of the metal salt, $MX_p$ or $MX_pQ_q$ can be any metal atom. In an aspect, the metal atom of the metal salt can be a transition metal. In an embodiment, suitable metal salts can comprise, or consist essentially of, a Group 3-12 transition metal; alternatively, a Group 4-10 transition metal; alternatively, a Group 6-9 transition metal; alternatively, a Group 7-8 transition metal; alternatively, a Group 4 transition metal; alternatively, a Group 5 transition metal, alternatively, a Group 6 transition metal; alternatively, a Group 7 transition metal; alternatively, a Group 8 transition metal; alternatively, a Group 9 transition metal; or alternatively, a Group 10 transition metal. In some embodiments, the metal salt can comprise titanium, zirconium, hafnium, vanadium, niobium, tantalum, chromium, molybdenum, tungsten, manganese, iron, cobalt, nickel, palladium, platinum, copper, or zinc. In other embodiments, the metal salt can comprise titanium, zirconium, vanadium, chromium, molybdenum, tungsten, iron, cobalt, nickel, palladium, or platinum; alternatively, chromium, iron, cobalt, or nickel; alternatively, titanium, zirconium or hafnium; alternatively, vanadium or niobium; alternatively, chromium, molybdenum or tungsten; alternatively, iron or cobalt; or alternatively, nickel, palladium, platinum, copper, or zinc. In other embodiments, the metal salt can comprise titanium; alternatively, zirconium; alternatively, hafnium; alternatively, vanadium; alternatively, niobium; alternatively, tantalum; alternatively, chromium; alternatively, molybdenum; alternatively, tungsten; alternatively, manganese; alternatively, iron; alternatively, cobalt; alternatively, nickel; alternatively, palladium; alternatively, platinum; alternatively, copper; or alternatively, zinc.

Generally, the metal atom of the transition metal salt can have any positive oxidation state available to the metal atom. In an embodiment, the transition metal can have an oxidation state of from +2 to +6; alternatively, from +2 to +4; or alternatively, from +2 to +3. In some embodiments, the metal atom of the transition metal salt can have an oxidation state or +1; alternatively, +2; alternatively, +3; or alternatively, +4.

In some embodiments, the anionic ligand can be a monoanionic ligand or a dianionic ligand; alternatively, a monoanionic ligand; or alternatively, a dianionic ligand. When the anionic ligand is a monoanionic ligand, the metal salt can have the formula $MX_p$ or $MX_pQ_q$ where M can be any metal atom described herein, X can be any monoanionic ligand described herein, Q can be any neutral ligand described herein, q can be any number described herein, and p can range from 2 to 6; alternatively, range from 2 to 4; alternatively, range from 2 to 3; alternatively, can be 1; alternatively, can be 2; alternatively, can be 3; or alternatively, can be 4. In some embodiments where the anionic ligand is a monoanionic ligand, p can equal the oxidation state of the metal atom.

When the anionic ligand is a dianionic ligand the metal salt can have the formula $M_yX_p$ or $M_yX_pQ_q$ where M can be any metal atom described herein, y equals 2 divided by the greatest common divisor of oxidation state of the metal atom and 2, X can be any dianionic ligand described herein, p equals the oxidation state of the metal atom divided by the greatest common divisor of oxidation state of the metal atom and 2, Q can be any neutral ligand described herein, and q can be any number described herein. In some embodiment when the anionic ligand is a dianionic ligand, p can range from, 1 to 3; alternatively, range from 1 to 2; alternatively, can be 1; alternatively, can be 2; or alternatively, can be 3.

In an embodiment, the monoanionic ligand, X, can be a halide, a carboxylate, a β-diketonate, a hydrocarboxide, a nitrate, or a chlorate. In some embodiments, the monoanionic ligand, X, can be a halide, a carboxylate, a β-diketonate, or a hydrocarboxide. In any aspect or embodiment, the hydrocarboxide can be an alkoxide, an aryloxide, or an aralkoxide. Generally, hydrocarboxide (and subdivisions of hydrocarboxide) are the anion analogues of the hydrocarboxy group. In other embodiments, the monoanionic ligand, X, can be a halide, a carboxylate, a β-diketonate, or an alkoxide; or alternatively, a halide or a β-diketonate. In other embodiments, the monoanion X can be a halide; alternatively, a carboxylate; alternatively, a β-diketonate; alternatively, a hydrocarboxide; alternatively, an alkoxide; or alternatively, an aryloxide.

Generally, each halide monoanion independently can be fluorine, chlorine, bromine, or iodine; or alternatively, chlorine, bromine, or iodine. In an embodiment, each halide monoanion can be chlorine; alternatively, bromine; or alternatively, iodine.

Generally, the carboxylate, a β-diketonate, hydrocarboxide (also alkoxide, aryloxide, or aralkoxide) can be any $C_1$ to $C_{20}$ carboxylate, a β-diketonate, hydrocarboxide (also alkoxide, aryloxide or aralkoxide); or alternatively, any $C_1$ to $C_{10}$ carboxylate, a β-diketonate, hydrocarboxide (also alkoxide, aryloxide, or aralkoxide). In some embodiments, the monoanionic ligand, X, can be a $C_1$ to $C_{20}$ carboxylate; alternatively, a $C_1$ to $C_{20}$ carboxylate; alternatively, a $C_1$ to $C_{20}$ β-diketonate; alternatively, a $C_1$ to $C_{10}$ β-diketonate; alternatively, a $C_1$ to $C_{20}$ hydrocarboxide; alternatively, a $C_1$ to $C_{10}$ hydrocarboxide; alternatively, a $C_1$ to $C_{20}$ alkoxide; alternatively, a $C_1$ to $C_{10}$ alkoxide; alternatively, a $C_6$ to $C_{20}$ aryloxide; or alternatively, a $C_6$ to $C_{10}$ aryloxide.

In an aspect, each carboxylate monoanionic ligand independently can be acetate, a propionate, a butyrate, a pentanoate, a hexanoate, a heptanoate, an octanoate, a nonanoate, a decanoate, an undecanoate, a dodecanoate, a tridecanoate, a tetradecanoate, a pentadecanoate, a hexadecanoate, a heptadecanoate, or an octadecanoate; or alternatively, a pentanoate, a hexanoate, a heptanoate, an octanoate, a nonanoate, a decanoate, an undecanoate, or a dodecanoate. In an embodiment, each carboxylate monoanionic ligand independently can be acetate, propionate, n-butyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, laurate (n-dodecanoate), or stearate (n-octadecanoate); alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, capronate (n-hexanoate); alternatively, n-heptanoate; alternatively, caprylate (n-octanoate); or alternatively, 2-ethylhexanoate. In some embodiments, the carboxylate monoanionic ligand can be triflate (trifluoroacetate).

In an aspect, each β-diketonate monoanionic ligand independently can be acetylacetonate (alternatively 2,4-pentanedionate), hexafluoroacetylacetone (alternatively, 1,1,1,5,5,5-hexafluoro-2,4-pentanediuonate, or benzoylacetonate); alternatively, acetylacetonate; alternatively, hexafluoroacetylacetone; or alternatively, benzoylacetonate. In an aspect, each alkoxide monoanionic ligand independently can be methoxide, ethoxide, a propoxide, or a butoxide. In an embodiment, each alkoxide monoanionic ligand independently can be methoxide, ethoxide, iso-propoxide, or tert-butoxide; alternatively, methoxide; alternatively, an ethoxide; alternatively, an iso-propoxide; or alternatively, a tert-butoxide. In an aspect, the aryloxide can be phenoxide.

In an embodiment, the dianionic ligand, X, can be a catecholate or a dicarboxylate; alternatively, a catecholate; or alternatively, a dicarboxylate. In an embodiment, the catecholate can be a $C_6$ to $C_{20}$ catecholate; alternatively, $C_6$ to $C_{15}$ catecholate; or alternatively, $C_6$ to $C_{10}$ catecholate. In an embodiment, the dicarboxylate can be a $C_2$ to $C_{20}$ dicarboxylate; alternatively, $C_2$ to $C_{10}$ dicarboxylate; or alternatively, a $C_2$ to $C_6$ dicarboxylate. In some embodiments, the catecholate can be 1,2-catecholate, or a substituted 1,2-catecholate; alternatively, 1,2-catecholate; or alternatively, a substituted 1,2-catecholate.

In some embodiments, the dicarboxylate can be oxalate, a malonate, a succinate, acetylenedicarboxylate, phthalate, or a substituted phthalate; alternatively, oxalate, a succinate, phthalate, or a substituted phthalate; alternatively, oxalate; alternatively, a succinate; alternatively, phthalate or a substituted phthalate; alternatively, phthalate; or alternatively, a substituted phthalate. In some embodiments, the dicarboxylate ligand can be oxalate, 1,3 propanedioate, 1,4 butanedioate, 1,2-benzene dicarboxylate, or a substituted 1,2-benzene dicarboxylate; alternatively, 1,2-benzene dicarboxylate or a substituted 1,2-benzene dicarboxylate; alternatively, oxalate; alternatively, 1,3 propanedioate; alternatively, 1,4 butanedioate; alternatively, 1,2-benzene dicarboxylate; or alternatively, a substituted 1,2-benzene dicarboxylate. Substituents (general and specific) are independently disclosed herein and can be utilized without limitation to further describe the substituted 1,2-benzene dicarboxylates which can be utilized as the dianionic ligand.

Neutral Ligand

Generally, each neutral ligand of the transition metal salt or the $N^2$-phosphinyl formamidine metal salt complex comprising a transition metal salt complexed to an $N^2$-phosphinyl formamidine compound, if present, independently can be any neutral ligand that forms an isolatable compound of the metal salt or $N^2$-phosphinyl formamidine metal salt complex comprising a transition metal salt complexed to an $N^2$-phosphinyl formamidine compound. In an aspect, each neutral ligand independently can be a nitrile or an ether. In an embodiment, the neutral ligand can be a nitrile; or alternatively, an ether. The number of neutral ligands, q, of the metal salt or $N^2$-phosphinyl formamidine metal salt complex comprising a transition metal salt complexed to an $N^2$-phosphinyl formamidine compound can be any number that forms an isolatable metal salt or $N^2$-phosphinyl formamidine metal salt complex comprising a transition metal salt complexed to an $N^2$-phosphinyl formamidine compound. In an aspect, the number of neutral ligands, q, can be from 0 to 6, alternatively, from 0 to 3; alternatively, 0, alternatively, 1; alternatively, 2, alternatively, 3; or alternatively, 4. It should be noted that the neutral ligand of the $N^2$-phosphinyl formamidine metal salt complex comprising a transition metal salt complexed to an $N^2$-phosphinyl formamidine compound does not have to be the same, if present, as the neutral ligand of the transition metal salt used to form the $N^2$-phosphinyl formamidine metal salt complex. Additionally, a metal salt not having a neutral ligand can be utilized to prepare an $N^2$-phosphinyl formamidine metal salt complex comprising a transition metal salt complexed to an $N^2$-phosphinyl formamidine compound having a neutral ligand.

Generally, each neutral nitrile ligand independently can be a $C_2$ to $C_{20}$ nitrile; or alternatively, a $C_2$ to $C_{10}$ nitrile. In an embodiment, each neutral nitrile ligand independently can be a $C_2$-$C_{20}$ aliphatic nitrile, a $C_7$-$C_{20}$ aromatic nitrile, a $C_8$-$C_{20}$ aralkane nitrile, or any combination thereof; alternatively, a $C_2$-$C_{20}$ aliphatic nitrile; alternatively, a $C_7$-$C_{20}$ aromatic nitrile; or alternatively, a $C_8$-$C_{20}$ aralkane nitrile. In some embodiments, each neutral nitrile ligand independently can be a $C_2$-$C_{10}$ aliphatic nitrile, a $C_7$-$C_{10}$ aromatic nitrile, a $C_8$-$C_{10}$ aralkane nitrile, or any combination thereof; alternatively, a $C_1$-$C_{10}$ aliphatic nitrile; alternatively, a $C_7$-$C_{10}$ aromatic nitrile; or alternatively, a $C_8$-$C_{10}$ aralkane nitrile.

In an embodiment, each aliphatic nitrile independently can be acetonitrile, propionitrile, a butyronitrile, or any combination thereof; alternatively, acetonitrile; alternatively, propionitrile; or alternatively, a butyronitrile. In an embodiment, each aromatic nitrile independently can be benzonitrile, 2-methylbenzonitrile, 3-methylbenzonitrile, 4-methylbenzonitrile, 2-ethylbenzonitrile, 3-ethylbenzonitrile, 4-ethylbenzonitrile, or any combination thereof; alternatively, benzonitrile; alternatively, 2-methylbenzonitrile; alternatively, 3-methylbenzonitrile; alternatively, 4-methylbenzonitrile; alternatively, 2-ethylbenzonitrile; alternatively, 3-ethylbenzonitrile; or alternatively, 4-ethylbenzonitrile.

Generally, each neutral ether ligand independently can be a $C_2$ to $C_{40}$ ether; alternatively, a $C_2$ to $C_{30}$ ether; or alternatively, a $C_2$ to $C_{20}$ ether. In an embodiment, neutral ligand independently can be a $C_2$ to $C_{40}$ aliphatic acyclic ether, a $C_3$ to $C_{40}$ aliphatic cyclic ether, a $C_4$ to $C_{40}$ aromatic cyclic ether, or a $C_{12}$ to $C_{40}$ diaryl ether; alternatively, a $C_2$ to $C_{40}$ aliphatic acyclic ether; alternatively, a $C_3$ to $C_{40}$ aliphatic cyclic ether; alternatively, a $C_4$ to $C_{40}$ aromatic cyclic ether; or alternatively, a $C_{12}$ to $C_{40}$ diaryl ether. In some embodiments, each neutral ligand independently can be a $C_2$ to $C_{30}$ aliphatic acyclic ether, a $C_3$ to $C_{30}$ aliphatic cyclic ether, a $C_4$ to $C_{30}$ aromatic cyclic ether, or a $C_{12}$ to $C_{30}$ diaryl ether; alternatively, a $C_2$ to $C_{30}$ aliphatic acyclic ether; alternatively, a $C_3$ to $C_{30}$ aliphatic cyclic ether; alternatively, a $C_4$ to $C_{30}$ aromatic cyclic ether; or alternatively, a $C_{12}$ to $C_{30}$ diaryl ether. In other embodiments, each neutral ligand independently can be a $C_2$ to $C_{20}$ aliphatic acyclic ether, a $C_3$ to $C_{20}$ aliphatic cyclic ether, a $C_4$ to $C_{20}$ aromatic cyclic ether, or a $C_{12}$ to $C_{20}$ diaryl ether; alternatively, a $C_2$ to $C_{20}$ aliphatic acyclic ether; alternatively, a $C_3$ to $C_{20}$ aliphatic cyclic ether; alternatively, a $C_4$ to $C_{20}$ aromatic cyclic ether; or alternatively, a $C_{12}$ to $C_{20}$ diaryl ether.

In an embodiment, the aliphatic acyclic ether can be dimethyl ether, diethyl ether, a dipropyl ether, a dibutyl ether, methyl ethyl ether, a methyl propyl ether, a methyl butyl ether, or any combination thereof. In some embodiments, the aliphatic acyclic ether can be dimethyl ether; alternatively, diethyl ether; alternatively, a dipropyl ether; alternatively, a dibutyl ether; alternatively, methyl ethyl ether; alternatively, a methyl propyl ether; or alternatively, a methyl butyl ether.

In an embodiment, the aliphatic cyclic ether can be tetrahydrofuran, a substituted tetrahydrofuran, a dihydrofuran, a substituted dihydrofuran, 1,3-dioxolane, a substituted 1,3-dioxolane, tetrahydropyran, a substituted tetrahydropyran, a dihydropyran, a substituted dihydropyran, pyran, a substituted pyran, a dioxane, or a substituted dioxane; alternatively, tetrahydrofuran or a substituted tetrahydrofuran; alternatively, a dihydrofuran or a substituted dihydrofuran; alternatively, 1,3-dioxolane or a substituted 1,3-dioxolane; alternatively, tetrahydropyran or a substituted tetrahydropyran; alternatively, a dihydropyran or a substituted dihydropyran; alternatively, pyran or a substituted pyran; or alternatively, a dioxane or a substituted dioxane. In some embodiments, the aliphatic cyclic ether can be tetrahydrofuran, tetrahydropyran, or dioxane, or any combination thereof; alternatively, tetrahydrofuran, alternatively tetrahydropyran; or alternatively, dioxane. Substituents (general and specific) are independently disclosed herein and can be utilized without limitation to further describe a substituted tetrahydrofuran, dihydrofuran, 1,3-dioxolane, tetrahydrofuran, tetrahydropyran, pyran or dioxane which can be utilized as the neutral ligand.

In an embodiment, the aromatic cyclic ether can be furan, a substituted furan, benzofuran, a substituted benzofuran, isobenzofuran, a substituted isobenzofuran, dibenzofuran, a substituted dibenzofuran, or any combination thereof; alternatively, furan or a substituted furan; alternatively, benzofuran or a substituted benzofuran; alternatively, isobenzofuran or a substituted isobenzofuran; or alternatively, a dibenzofuran or a substituted dibenzofuran. In some embodiments, the aromatic cyclic ether can be furan, benzofuran, isobenzofuran, dibenzofuran, or any combination thereof; alternatively, furan; alternatively, benzofuran; alternatively, isobenzofuran; or alternatively, dibenzofuran. In an embodiment, the diaryl ether can be diphenyl ether, a substituted diphenyl ether, ditolyl ether, a substituted ditolyl ether, or any combination thereof; alternatively, diphenyl ether or a substituted diphenyl ether; or alternatively, ditolyl ether or a substituted ditolyl ether. In some embodiments, the diaryl ether can be diphenyl ether or ditolyl ether; alternatively, diphenyl ether; or ditolyl ether. Substituents (general and specific) are independently disclosed herein and can be utilized without limitation to further describe a substituted furan, benzofuran, or dibenzofuran which can be utilized as the neutral ligand.

The features of the transition metal salts have been independently described herein and can be utilized in any combination to describe the transition metal salt of the $N^2$-phosphinyl formamidine metal salt complex comprising a transition metal salt complexed to an $N^2$-phosphinyl formamidine compound.

In a non-limiting embodiment, the transition metal salt which can be utilized includes chromium(II) halides, chromium(III) halides, chromium(II) carboxylates, chromium (III) carboxylates, chromium(II) β-diketonates, chromium (III) β-diketonates, chromium(II) halide (THF) complexes, chromium(III) halide (THF) complexes, iron(II) halides, iron(III) halides, iron(II) carboxylates, iron(III) carboxylates, iron(II) β-diketonates, iron(III) β-diketonates, cobalt (II) halides, cobalt(III) halides, cobalt(II) carboxylates, cobalt(III) carboxylates, cobalt(II) β-diketonates, cobalt(III) β-diketonates, nickel(II) halides, nickel(II) carboxylates, nickel(II) β-diketonates, palladium(II) halides, palladium(II) carboxylates, palladium(II) β-diketonates, platinum(II) halides, platinum(IV) halides, platinum(II) carboxylates, or platinum(IV) carboxylates. In some non-limiting embodiments, the transition metal salt can be a chromium(II) halide, a chromium(III) halide, a chromium (II) carboxylate, a chromium(III) carboxylate, a chromium(II) β-diketonate, a chromium(III) β-diketonate, a chromium(II) halide (THF) complex, or a chromium(III) halide (THF) complex; alternatively, an iron(II) halide, an iron(III) halide, an iron(II) carboxylate, an iron(III) carboxylate, an iron(II) β-diketonate, or an iron(III) β-diketonate; alternatively, a cobalt(II) halide, a cobalt(III) halide, a cobalt(II) carboxylate, a cobalt (III) carboxylate, a cobalt(II) β-diketonate, or a cobalt(III) β-diketonate; alternatively, a nickel(II) halide, a nickel(II) carboxylate, or a nickel(II) β-diketonate; alternatively, a palladium(II) halide, a palladium(II) carboxylate, or a palladium(II) β-diketonate; or alternatively, a platinum(II) halide, a platinum(IV) halide, a platinum(II) carboxylate, or a platinum(IV) carboxylate. In some embodiments, the transition metal salt can be a chromium(III) halide, a chromium(III) carboxylate, a chromium(III) β-diketonate, a chromium(III) halide (THF) complex; alternatively, an iron (III) halide, an iron(III) carboxylate, or an iron(III) β-diketonate; or alternatively, a cobalt(III) halide, a cobalt(III) carboxylate, or a cobalt(III) β-diketonate. In other embodiments, the transition metal salt can be a be a chromium(II) halide; alternatively, a chromium(III) halide; alternatively, a chromium (II) carboxylate; alternatively, a chromium(III) carboxylate; alternatively, a chromium(II) β-diketonate; alternatively, a chromium(III) β-diketonate; alternatively, a chromium(II) halide (THF) complex; alternatively, a chromium(III) halide (THF) complex; alternatively, an iron(II) halide; alternatively, an iron(III) halide; alternatively, an iron(II) carboxylate; alternatively, an iron(III) carboxylate; alternatively, an iron(II) β-diketonate; alternatively, an iron (III) β-diketonate; alternatively, a cobalt(II) halide; alternatively, a cobalt(III) halide; alternatively, a cobalt(II) carboxylate; alternatively, a cobalt(III) carboxylate; alternatively, a cobalt(II) β-diketonate; alternatively, a cobalt (III) β-diketonate; alternatively, a nickel(II) halide; alternatively, a nickel(II) carboxylate; alternatively, a nickel(II) β-diketonate; alternatively, a palladium(II) halide; alternatively, a palladium(II) carboxylate; alternatively, a palladium (II) β-diketonate; alternatively, a platinum(II) halide; alternatively, a platinum(IV) halide; alternatively, a platinum(II) carboxylate; or alternatively, a platinum(IV) carboxylate.

In some non-limiting embodiments, transition metal salts which can be utilized includes chromium(II) chloride, chromium(III) chloride, chromium(II) fluoride, chromium(III) fluoride, chromium(II) bromide, chromium(III) bromide, chromium(II) iodide, chromium(III) iodide, chromium(III) chloride (THF) complex, chromium(II) acetate, chromium (III) acetate, chromium(II) 2-ethylhexanoate, chromium(III) 2-ethylhexanoate, chromium(II) triflate, chromium(III) triflate, chromium(III) nitrate, chromium(III) acetylacetonate, chromium(III) hexafluoracetylacetonate, chromium(III) benzoylacetonate, iron(II) chloride, iron(III) chloride, iron (II) fluoride, iron(III) fluoride, iron(II) bromide, iron(III) bromide, iron(II) iodide, iron(III) iodide, iron(II) acetate, iron(III) acetate, iron(II) acetylacetonate, iron(III) acetylacetonate, iron(II) 2-ethylhexanoate, iron(III) 2-ethylhexanoate, iron(II) triflate, iron(III) triflate, iron(III) nitrate, cobalt (II) chloride, cobalt(III) chloride, cobalt(II) fluoride, cobalt (III) fluoride, cobalt(II) bromide, cobalt(III) bromide, cobalt (II) iodide, cobalt(III) iodide, cobalt(II) acetate, cobalt(III) acetate, cobalt(II) acetylacetonate, cobalt(III) acetylacetonate, cobalt(II) 2-ethylhexanoate, cobalt(III) 2-ethylhexanoate, cobalt(II) triflate, cobalt(III) triflate, cobalt(III) nitrate, nickel(II) chloride, nickel(II) fluoride, nickel(II) bromide, nickel(II) iodide, nickel(II) acetate, nickel(II) 2-ethylhexanoate, nickel(II) triflate, nickel(II) nitrate, nickel(II) acetylacetonate, nickel(II) benzoylacetonate, nickel(II) hexafluoracetylacetonate, palladium(II) chloride, palladium (II) fluoride, palladium(II) bromide, palladium(II) iodide, palladium(II) acetate, palladium(II) acetylacetonate, palladium(II) nitrate, platinum(II) chloride, platinum(II) bromide, platinum(II) iodide, or platinum(IV) chloride. In other embodiments, the transition metal salt can be chromium(II) chloride, chromium(III) chloride, chromium(II) fluoride, chromium(III) fluoride, chromium(II) bromide, chromium (III) bromide, chromium(II) iodide, chromium(III) iodide, chromium(III) chloride (THF) complex, chromium(II) acetate, chromium(III) acetate, chromium(II) 2-ethylhexanoate, chromium(III) 2-ethylhexanoate chromium(II) triflate, chromium(III) triflate, chromium(III) nitrate, chromium(III) acetylacetonate, chromium(III) hexafluoracetylacetonate, or chromium(III) benzoylacetonate; alternatively, iron(II) chloride, iron(III) chloride, iron(II) fluoride, iron(III) fluoride, iron(II) bromide, iron(III) bromide, iron (II) iodide, iron(III) iodide, iron(II) acetate, iron(III) acetate, iron(II) acetylacetonate, iron(III) acetylacetonate, iron(II) 2-ethylhexanoate, iron(III) 2-ethylhexanoate, iron(II) triflate, iron(III) triflate, or iron(III) nitrate; alternatively, cobalt(II) chloride, cobalt(III) chloride, cobalt(II) fluoride, cobalt(III) fluoride, cobalt(II) bromide, cobalt(III) bromide, cobalt(II) iodide, cobalt(III) iodide, cobalt(II) acetate, cobalt (III) acetate, cobalt(II) acetylacetonate, cobalt(III) acetylacetonate, cobalt(II) 2-ethylhexanoate, cobalt(III) 2-ethylhexanoate, cobalt(II) triflate, cobalt(III) triflate, or cobalt (III) nitrate; alternatively, nickel(II) chloride, nickel(II) fluoride, nickel(II) bromide, nickel(II) iodide, nickel(II) acetate, nickel(II) 2-ethylhexanoate, nickel(II) triflate, nickel(II) nitrate, nickel(II) acetylacetonate, nickel(II) benzoylacetonate, or nickel(II) hexafluoracetylacetonate; alternatively, palladium(II) chloride, palladium(II) fluoride, palladium(II) bromide, palladium(II) iodide, palladium(II) acetate, palladium(II) acetylacetonate, or palladium(II) nitrate; or alternatively, platinum(II) chloride, platinum(II) bromide, platinum(II) iodide, or platinum(IV) chloride. In yet other embodiments, the transition metal salt can be chromium(III) chloride, chromium(III) fluoride, chromium (III) bromide, chromium(III) iodide, chromium(III) chloride (THF) complex, chromium(III) acetate, chromium(III) 2-ethylhexanoate, chromium(III) triflate, chromium(III) nitrate, chromium(III) acetylacetonate, chromium(III) hexafluoracetylacetonate, or chromium(III) benzoylacetonate; or alternatively, iron(III) chloride, iron(III) fluoride, iron(III) bromide, iron(III) iodide, iron(III) acetate, iron(III) acetylacetonate, iron(III) 2-ethylhexanoate, iron(III) triflate, or iron(III) nitrate. In further embodiments, the transition metal salt can be chromium(III) chloride, chromium(III) chloride (THF) complex, or chromium(III) acetylacetonate; or alternatively, iron(III) chloride, or iron(III) acetylacetonate.

In some non-limiting embodiments, transition metal salts which can be utilized includes chromium(II) chloride; alternatively, chromium(III) chloride; alternatively, chromium (II) fluoride; alternatively, chromium(III) fluoride; alternatively, chromium(II) bromide; alternatively, chromium(III) bromide; alternatively, chromium(II) iodide; alternatively, chromium(III) iodide; alternatively, chromium(III) chloride (THF) complex; alternatively, chromium(II) acetate; alternatively, chromium(III) acetate; alternatively, chromium(II) 2-ethylhexanoate; alternatively, chromium(III) 2-ethylhexanoate; alternatively, chromium(II) triflate; alternatively, chromium(III) triflate; alternatively, chromium(III) nitrate; alternatively, chromium(III) acetylacetonate; alternatively, chromium(III) hexafluoracetylacetonate; alternatively, chromium(III) benzoylacetonate; alternatively, iron(II) chloride; alternatively, iron(III) chloride; alternatively, iron(II) fluoride; alternatively, iron(III) fluoride; alternatively, iron(II) bromide; alternatively, iron(III) bromide; alternatively, iron (II) iodide; alternatively, iron(III) iodide; alternatively, iron (II) acetate; alternatively, iron(III) acetate; alternatively, iron(II) acetylacetonate; alternatively, iron(III) acetylacetonate; alternatively, iron(II) 2-ethylhexanoate; alternatively, iron(III) 2-ethylhexanoate; alternatively, iron(II) triflate; alternatively, iron(III) triflate; alternatively, iron(III) nitrate; alternatively, cobalt(II) chloride; alternatively, cobalt(III) chloride; alternatively, cobalt(II) fluoride; alternatively, cobalt(III) fluoride; alternatively, cobalt(II) bromide; alternatively, cobalt(III) bromide; alternatively, cobalt(II) iodide; alternatively, cobalt(III) iodide; alternatively, cobalt(II) acetate; alternatively, cobalt(III) acetate; alternatively, cobalt(II) acetylacetonate; alternatively, cobalt(III) acetylacetonate; alternatively, cobalt(II) 2-ethylhexanoate; alternatively, cobalt(III) 2-ethylhexanoate; alternatively, cobalt(II) triflate; alternatively, cobalt(III) triflate; alternatively, cobalt (III) nitrate; alternatively, nickel(II) chloride; alternatively, nickel(II) fluoride; alternatively, nickel(II) bromide; alternatively, nickel(II) iodide; alternatively, nickel(II) acetate; alternatively, nickel(II) 2-ethylhexanoate; alternatively, nickel(II) triflate; alternatively, nickel(II) nitrate; alternatively, nickel(II) acetylacetonate; alternatively, nickel(II) benzoylacetonate; alternatively, nickel(II) hexafluoracetylacetonate; alternatively, palladium(II) chloride; alternatively, palladium(II) fluoride; alternatively, palladium(II) bromide; alternatively, palladium(II) iodide; alternatively, palladium(II) acetate; alternatively, palladium(II) acetylacetonate; alternatively, palladium(II) nitrate; alternatively, platinum(II) chloride; alternatively, platinum(II) bromide; alternatively, platinum(II) iodide; or alternatively, platinum (IV) chloride.

In a non-limiting embodiment, the transition metal salt which can be utilized includes a chromium(II) dicarboxylate, chromium(III) dicarboxylate, iron(II) dicarboxylate, iron(III) dicarboxylate, cobalt(II) dicarboxylate, cobalt(III) dicarboxylate, nickel(II) dicarboxylate, palladium(II) dicarboxylate, or platinum(II) carboxylate; alternatively, a chromium(II) dicarboxylate or chromium(III) dicarboxylate; alternatively, an iron(II) dicarboxylate or an iron(III) dicarboxylate; alternatively, a cobalt(II) dicarboxylate or cobalt (III) dicarboxylate; alternatively, a chromium(II) dicarboxylate; alternatively, a chromium(III) dicarboxylate; alternatively, an iron(II) dicarboxylate; alternatively, an iron (III) dicarboxylate; alternatively, a cobalt(II) dicarboxylate;

alternatively, a cobalt(III) dicarboxylate; alternatively, a nickel(II) dicarboxylate; alternatively, a palladium(II) dicarboxylate; or alternatively, a platinum(II) carboxylates. Dicarboxylate dianionic ligands are described herein and these dicarboxylate dianionic ligands can be utilized without limitation to further name the transition metal salts which can be utilized as the transition metal salt.

It should be appreciated, that a given $N^2$-phosphinyl formamidine metal salt complex can have one or more neutral ligands even when the metal salt utilized to produce the $N^2$-phosphinyl formamidine metal salt complex did not have any neutral ligands.

Catalyst Systems

In an aspect, the present disclosure relates to catalyst systems comprising an $N^2$-phosphinyl formamidine compound and a metal salt; alternatively, an $N^2$-phosphinyl formamidine metal salt complex. In an embodiment, the catalyst system can comprise, or consist essentially of, an $N^2$-phosphinyl formamidine metal salt complex and a metal alkyl; or alternatively, an $N^2$-phosphinyl formamidine metal salt complex and an aluminoxane. In another aspect, the catalyst system can comprise, or consist essentially of, an $N^2$-phosphinyl formamidine compound, a metal salt, and a metal alkyl; or alternatively, an $N^2$-phosphinyl formamidine compound, a metal salt, and an aluminoxane. The $N^2$-phosphinyl formamidine metal salt complex, metal salt, $N^2$-phosphinyl formamidine compound, metal alkyl, and aluminoxane which can be utilized in various aspects and/or embodiments of the catalyst system are independently described herein and can be utilized in any combination and without limitation to describe various catalyst systems of this disclosure.

The $N^2$-phosphinyl formamidine metal salt complex(es) and metal alkyls which can be utilized in various catalyst systems of this disclosure can comprise a metal salt complexed to an $N^2$-phosphinyl formamidine compound. The $N^2$-phosphinyl formamidine metal salt complexes, metal salts, and $N^2$-phosphinyl formamidine compounds are independently described herein and can be utilized without limitation to describe an $N^2$-phosphinyl formamidine metal salt complex which can be utilized in various catalyst systems of this disclosure.

Metal Alkyl

Generally, the metal alkyl compound which can be utilized in the catalyst system of this disclosure can be any heteroleptic or homoleptic metal alkyl compound. In an embodiment, the metal alkyl can comprise, consist essentially of, or consist of, a non-halide metal alkyl, a metal alkyl halide, or any combination thereof; alternatively a non-halide metal alkyl; or alternatively, a metal alkyl halide.

In an embodiment, the metal of the metal alkyl can comprise, consist essentially of, or consist of, a group 1, 2, 11, 12, 13, or 14 metal; or alternatively a group 13 or 14 metal; or alternatively, a group 13 metal. In some embodiments, the metal of the metal alkyl (non-halide metal alkyl or metal alkyl halide) can be lithium, sodium, potassium, rubidium, cesium, beryllium, magnesium, calcium, strontium, barium, zinc, cadmium, boron, aluminum, or tin; alternatively, lithium, sodium, potassium, magnesium, calcium, zinc, boron, aluminum, or tin; alternatively, lithium, sodium, or potassium; alternatively magnesium, calcium; alternatively, lithium; alternatively, sodium; alternatively, potassium; alternatively, magnesium; alternatively, calcium; alternatively, zinc; alternatively, boron; alternatively, aluminum; or alternatively, tin. In some embodiments, the metal alkyl (non-halide metal alkyl or metal alkyl halide) can comprise, consist essentially of, or consist of, a lithium alkyl, a sodium alkyl, a magnesium alkyl, a boron alkyl, a zinc alkyl, or an aluminum alkyl. In some embodiments, the metal alkyl (non-halide metal alkyl or metal alkyl halide) can comprise, consist essentially of, or consist of, an aluminum alkyl.

In an embodiment, the aluminum alkyl can be a trialkylaluminum, an alkylaluminum halide, an alkylaluminum alkoxide, an aluminoxane, or any combination thereof. In some embodiments, the aluminum alkyl can be a trialkylaluminum, an alkylaluminum halide, an aluminoxane, or any combination thereof; or alternatively, a trialkylaluminum, an aluminoxane, or any combination thereof. In other embodiments, the aluminum alkyl can be a trialkylaluminum; alternatively, an alkylaluminum halide; alternatively, an alkylaluminum alkoxide; or alternatively, an aluminoxane.

In a non-limiting embodiment, the aluminoxane can have a repeating unit characterized by the Formula I:

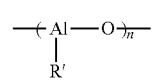

Formula I wherein R' is a linear or branched alkyl group. Alkyl groups for metal alkyls have been independently described herein and can be utilized without limitation to further describe the aluminoxanes having Formula I. Generally, n of Formula I is greater than 1; or alternatively greater than 2. In an embodiment, n can range from 2 to 15; or alternatively, range from 3 to 10.

In an aspect, each halide of any metal alkyl halide disclosed herein can independently be fluoride, chloride, bromide, or iodide; alternatively, chloride, bromide, or iodide. In an embodiment, each halide of any metal alkyl halide disclosed herein can be fluoride; alternatively, chloride; alternatively, bromide; or alternatively, iodide.

In an aspect, each alkyl group of any metal alkyl disclosed herein (non-halide metal alkyl or metal alkyl halide) independently can be a $C_1$ to $C_{20}$ alkyl group; alternatively, a $C_1$ to $C_{10}$ alkyl group; or alternatively, a $C_1$ to $C_6$ alkyl group. In an embodiment, each alkyl group(s) independently can be a methyl group, an ethyl group, a propyl group, a butyl group, a pentyl group, a hexyl group, a heptyl group, or an octyl group; alternatively, a methyl group, an ethyl group, a butyl group, a hexyl group, or an octyl group. In some embodiments, each alkyl group independently can be a methyl group, an ethyl group, an n-propyl group, a n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In an aspect, the alkoxide group of any metal alkyl alkoxide disclosed herein independently can be a $C_1$ to $C_{20}$ alkoxy group; alternatively, a $C_1$ to $C_{10}$ alkoxy group; or alternatively, a $C_1$ to $C_6$ alkoxy group. In an embodiment, each alkoxide group of any metal alkyl alkoxide disclosed herein independently can be a methoxy group, an ethoxy group, a propoxy group, a butoxy group, a pentoxy group, a hexoxy group, a heptoxy group, or an octoxy group; alternatively, a methoxy group, an ethoxy group, a butoxy group, a hexoxy group, or an octoxy group. In some embodiments, each alkoxide group of any metal alkyl alkoxide disclosed herein independently can be a methoxy group, an ethoxy group, an n-propoxy group, an n-butoxy group, an iso-butoxy group, an n-hexoxy group, or an n-octoxy group; alternatively, a methoxy group, an ethoxy group, an n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, an n-hexoxy group; or alternatively, an n-octoxy group.

In a non-limiting embodiment, useful metal alkyls can include methyl lithium, n-butyl lithium, sec-butyl lithium, tert-butyl lithium, diethyl magnesium, di-n-butylmagnesium, ethylmagnesium chloride, n-butylmagnesium chloride, and diethyl zinc. In a non-limiting embodiment, useful trialkylaluminum compounds can include trimethylaluminum, triethylaluminum, tripropylaluminum, tributylaluminum, trihexylaluminum, trioctylaluminum, or mixtures thereof. In some non-limiting embodiments, trialkylaluminum compounds can include trimethylaluminum, triethylaluminum, tripropylaluminum, tri-n-butylaluminum, tri-isobutylaluminum, trihexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof; alternatively, triethylaluminum, tri-n-butylaluminum, trihexylaluminum, tri-n-octylaluminum, or mixtures thereof. In other non-limiting embodiments, useful trialkylaluminum compounds can include trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum.

In a non-limiting embodiment, useful alkylaluminum halides can include diethylaluminum chloride, diethylaluminum bromide, ethylaluminum dichloride, ethylaluminum sesquichloride, and mixtures thereof. In some non-limiting embodiments, useful alkylaluminum halides can include diethylaluminum chloride, ethylaluminum dichloride, ethylaluminum sesquichloride, and mixtures thereof. In other non-limiting embodiments, useful alkylaluminum halides can include diethylaluminum chloride; alternatively, diethylaluminum bromide; alternatively, ethylaluminum dichloride; or alternatively, ethylaluminum sesquichloride.

In a non-limiting embodiment, useful aluminoxanes can include methylaluminoxane (MAO), ethylaluminoxane, modified methylaluminoxane (MMAO), n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, or mixtures thereof. In some non-limiting embodiments, useful aluminoxanes can include methylaluminoxane (MAO), modified methylaluminoxane (MMAO), isobutyl aluminoxane, t-butyl aluminoxane, or mixtures thereof. In other non-limiting embodiments, useful aluminoxanes can include methylaluminoxane (MAO); alternatively, ethylaluminoxane; alternatively, modified methylaluminoxane (MMAO); alternatively, n-propylaluminoxane; alternatively, iso-propylaluminoxane; alternatively, n-butylaluminoxane; alternatively, sec-butylaluminoxane; alternatively, iso-butylaluminoxane; alternatively, t-butyl aluminoxane; alternatively, 1-pentylaluminoxane; alternatively, 2-pentylaluminoxane; alternatively, 3-pentylaluminoxane; alternatively, iso-pentylaluminoxane; or alternatively, neopentylaluminoxane.

Catalyst System Component Ratios

In an aspect, the metal alkyl and $N^2$-phosphinyl formamidine metal salt complex can be combined in any ratio that forms an active catalyst system. In an embodiment, the metal of the metal alkyl to the metal of the $N^2$-phosphinyl formamidine metal salt complex molar ratio can be greater than or equal to 5:1; alternatively, greater than or equal to 10:1; alternatively, greater than or equal to 25:1; alternatively, greater than or equal to 50:1; or alternatively, greater than or equal to 100:1. In some embodiments, the metal of the metal alkyl to the metal of the $N^2$-phosphinyl formamidine metal salt complex molar ratio can range from 5:1 to 100,000:1; alternatively, range from 10:1 to 50,000:1; alternatively, range from 25:1 to 10,000:1; alternatively, range from 50:1 to 5,000:1; or alternatively, range from 100:1 to 2,500:1. When a metal alkyl having a specific metal and an $N^2$-phosphinyl formamidine metal salt complex having a specific metal is utilized the metal of the metal alkyl to the metal of the $N^2$-phosphinyl formamidine metal salt complex molar ratio can be stated as a specific metal of the metal alkyl to specific metal of the $N^2$-phosphinyl formamidine metal salt complex molar ratio. For example, when the metal alkyl is an alkylaluminum compound (e.g. trialkylaluminum, alkylaluminum halide, alkylaluminum alkoxide, and/or aluminoxane) and the $N^2$-phosphinyl formamidine metal salt complex is an $N^2$-phosphinyl formamidine chromium salt complex, the metal of the metal alkyl to metal of the metal salt can be an aluminum to chromium molar ratio. In some non-limiting embodiments, the aluminum to chromium molar ratio can be greater than or equal to 5:1; alternatively, greater than or equal to 10:1; alternatively, greater than or equal to 25:1; alternatively, greater than or equal to 50:1; alternatively, greater than or equal to 100:1; alternatively, range from 5:1 to 100,000:1; alternatively, range from 10:1 to 50,000:1; alternatively, range from 25:1 to 10,000:1; alternatively, range from 50:1 to 5,000:1; or alternatively, range from 100:1 to 2,500:1.

In another aspect, the metal alkyl, metal salt, and $N^2$-phosphinyl formamidine compound can be combined in any ratio that forms an active catalyst system. Generally the ratio of the components of the catalyst system comprising, consisting essentially of, or consisting of a metal alkyl, metal salt, and $N^2$-phosphinyl formamidine compound can be provided as a molar ratio of the metal of the metal alkyl to metal of the metal salt and an equivalent ratio of the $N^2$-phosphinyl formamidine compound to metal salt.

In an embodiment, the metal of the metal alkyl to the metal of the metal salt molar ratio can be greater than or equal to 5:1; alternatively, greater than or equal to 10:1; alternatively, greater than or equal to 25:1; alternatively, greater than or equal to 50:1; or alternatively, greater than or equal to 100:1. In some embodiments, the metal of the metal alkyl to the metal of the metal salt molar ratio can range from 5:1 to 100,000:1; alternatively, ranges from 10:1 to 50,000:1; alternatively, ranges from 25:1 to 10,000:1; alternatively, ranges from 50:1 to 5,000:1; or alternatively, ranges from 100:1 to 2,500:1. When a metal alkyl having a specific metal and a metal salt having a specific metal is utilized the metal of the metal alkyl to the metal of the metal salt molar ratio can be stated as a specific metal of the metal alkyl to specific metal of the metal salt molar ratio. For example, when the metal alkyl is an alkylaluminum compound (e.g. trialkylaluminum, alkylaluminum halide, alkylaluminum alkoxide, and/or aluminoxane) and the metal salt is a chromium salt, the metal of the metal alkyl to metal of the metal salt can be an aluminum to chromium molar ratio. In some non-limiting embodiments, the aluminum to chromium molar ratio can be greater than or equal to 5:1; alternatively, greater than or equal to 10:1; alternatively, greater than or equal to 25:1; alternatively, greater than or equal to 50:1; alternatively, greater than or equal to 100:1; alternatively, range from 5:1 to 100,000:1; alternatively, range from 10:1 to 50,000:1; alternatively, range from 25:1 to 10,000:1; alternatively, range from 50:1 to 5,000:1; or alternatively, range from 100:1 to 2,500:1

In an embodiment, the $N^2$-phosphinyl formamidine compound to metal salt equivalent ratio can be greater than or equal to 0.8:1; alternatively, greater than or equal to 0.9:1; or alternatively, greater than or equal to 0.95:1; or alternatively, greater than or equal to 0.98:1. In some embodiments, the $N^2$-phosphinyl formamidine compound to metal salt equivalent ratio can be range from 0.8:1 to 5:1; alternatively, range from 0.9:1 to 4:1; or alternatively, range from 0.95:1 to 3:1; or alternatively, range from 0.98:1 to 2.5:1. In other embodiments, the $N^2$-phosphinyl formamidine compound to metal salt equivalent ratio can be about 1:1.

Methods of Preparing an $N^2$-Phosphinyl Formamidine Compound and $N^2$-Phosphinyl Formamidine Compound Metal Salt Complex In an aspect, this disclosure relates to a method of preparing an $N^2$-phosphinyl formamidine compound and/or an $N^2$-phosphinyl formamidine metal salt complex. $N^2$-phosphinyl formamidine compounds and $N^2$-phosphinyl formamidine metal salt complexes are generally described herein and methods of preparing them can be generally applied to any $N^2$-phosphinyl formamidine compound and/or $N^2$-phosphinyl formamidine metal salt complex described herein.

Method of Preparing an $N^2$-Phosphinyl Formamidine Compound

In an aspect, this disclosure relates to a method of preparing an $N^2$-phosphinyl formamidine compound. Generally, the method of preparing an $N^2$-phosphinyl formamidine compound can comprise: a) contacting a phosphine halide with a metal formamidinate, and b) forming the $N^2$-phosphinyl formamidinate. Generally, the $N^2$-phosphinyl formamidine compound can be formed under conditions capable of forming an $N^2$-phosphinyl formamidine group. In some embodiments, the $N^2$-phosphinyl formamidine compound can be isolated; alternatively, purified; or alternatively, isolated and purified. General and specific phosphine halides and metal formamidinate are disclosed herein and can be utilized, without limitation, to further describe the method to prepare the $N^2$-phosphinyl formamidine compound.

In an embodiment, the $N^2$-phosphinyl formamidine compound can have any Structure described herein. In some embodiments, the $N^2$-phosphinyl formamidine compound may not have an $N^2$ hydrogen atom (e.g., the $N^2$-phosphinyl formamidine compound Structures NPF1, NPF2, and/or NPF4 where $R^3$ is a non-hydrogen group). In other embodiments, the $N^2$-phosphinyl formamidine compound can have an $N^2$ hydrogen atom (e.g., the $N^2$-phosphinyl formamidine compound Structures NPF6, NPF7, and/or NPF9).

Generally, the metal formamidinate utilized in the method of preparing the $N^2$-phosphinyl formamidine compound can have Structure MFA1 or MFA2; alternatively, Structure MFA1; or alternatively, Structure MFA2.

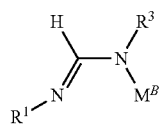

Structure MFA1

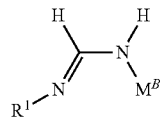

Structure MFA2

Generally, the metal formamidinate structures prefaced with the designation MFA correspond with the $N^2$-phosphinyl formamidine structures prefaced with the designation NPF having the same number designation. $R^1$ and $R^3$ within metal formamidine Structures MFA1 and/or MFA2 and/or are independently described as features of the $N^2$-phosphinyl formamidine compound having Structures NPF1 and/or NPF2. Since metal formamidinate Structures MFA1 and/or MFA2 are utilized to prepare embodiments of $N^2$-phosphinyl formamidine compounds having Structures NPF1 and/or NPF2, the $R^1$ and $R^3$ descriptions for the $N^2$-phosphinyl formamidine compounds can be utilized without limitation to further describe metal formamidinate Structures MFA1 and/or MFA2.

Within this disclosure, phosphine halides can be used to ultimately prepare the $N^2$-phosphinyl formamidine compounds and/or the $N^2$-phosphinyl formamidine metal salt complexes utilized in various aspects of this disclosure. In various embodiments, phosphine halides which can be utilized have Structure PH1.

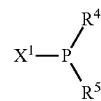

Structure PH1

$R^4$ and $R^5$ are described as features of $N^2$-phosphinyl formamidine compounds having Structures NPF1, NPF2, NPF4, NPF6, NPF7, and/or NPF9 and are described herein. Additionally, $X^1$ is described herein as a feature of the phosphine halides. Since the phosphine halides are utilized to ultimately prepare embodiments of the $N^2$-phospinyl formamidine compounds having Structures NPF1, NPF2, NPF4, NPF6, NPF7, and/or NPF9, $X^1$, $R^4$, and $R^5$ can utilized without limitation to further describe the phosphine halides having StructurePH1. In an embodiment, $X^1$ of the phosphine halide can be fluoro, chloro, bromo, or iodo; alternatively, fluoro; alternatively, chloro; alternatively, bromo; or alternatively, iodo.

In an aspect, the phosphine halide can be a diphenylphosphine halide, a dialkylphosphine halide, a bis(mono-halo substituted phenyl)phosphine halide, a bis(mono-alkyl substituted phenyl)phosphine halide, or a bis(mono-alkoxy substituted phenyl)phosphine halide; alternatively, a diphenylphosphine halide; alternatively, a dialkylphosphine halide; alternatively, a bis(mono-halo substituted phenyl)phosphine halide; alternatively, a bis(mono-alkyl substituted phenyl) phosphine halide; or alternatively, a bis(mono-alkoxy substituted phenyl)phosphine halide. In another aspect, phosphine halide can be an (alkyl)(phenyl)phosphine halide, a (mono-halo substituted phenyl)(phenyl)phosphine halide, a (mono-alkyl substituted phenyl)(phenyl)phosphine halide, a (mono-alkoxy substituted phenyl)(phenyl)phosphine halide, a (mono-alkyl substituted phenyl)(mono-halo substituted phenyl) phosphine halide, or a (mono-alkyl substituted phenyl)(mono-alkoxy substituted phenyl) phosphine halide; alternatively, (alkyl)(phenyl)phosphine halide; alternatively, a (mono-halo substituted phenyl)(phenyl)phosphine halide; alternatively, a (mono-alkyl substituted phenyl)(phenyl) phosphine halide; alternatively, a (mono-alkoxy substituted phenyl)(phenyl)phosphine halide; alternatively, a (mono-alkyl substituted phenyl)(mono-halo substituted phenyl) phosphine halide; or alternatively, a (mono-alkyl substituted phenyl)(mono-alkoxy substituted phenyl) phosphine halide. In another aspect, phosphine halide can be a bis(dihalo substituted phenyl)phosphine halide, a bis(dialkyl substituted phenyl)phosphine halide, a bis(dialkoxy substituted phenyl)phosphine halide, a bis(trialkylphenyl)phosphine halide, or a bis(trialkoxyphenyl)phosphine halide; alternatively, a bis(dihalo substituted phenyl)phosphine halide; alternatively, a bis(dialkyl substituted phenyl)phosphine halide; alternatively, a bis(dialkoxy substituted phenyl)phosphine halide; alternatively, a bis(trialkylphenyl)phosphine halide; or alternatively, a bis(trialkoxyphenyl)phosphine halide. Halo, alkyl, and alkoxy substituents for the substituted phenyl group embodiments of the phosphine halides have been disclosed herein and can be utilized, without limitation to further describe the phosphine halides which can be utilized in aspects and embodiments described herein.

In a non-limiting aspect, the phosphine halide can be dimethylphosphine chloride, diethylphosphine chloride, diisopropylphosphine chloride, di-tert-butylphosphine chloride, or di-neo-pentylphosphine chloride; alternatively, dimethylphosphine chloride, diethylphosphine chloride, di-n-propylphosphine chloride, di-n-butylphosphine chloride, di-n-pentylphosphine chloride, or di-n-hexylphosphine chloride. In an embodiment, the phosphine halide can be dimethylphosphine chloride; alternatively, diethylphosphine chloride; alternatively, di-n-propylphosphine chloride; alternatively, diisopropylphosphine chloride; alternatively, di-n-butylphosphine chloride; alternatively, di-tert-butylphosphine chloride; alternatively, di-n-pentylphosphine chloride; alternatively, di-neo-pentylphosphine chloride; or alternatively, di-n-hexylphosphine chloride.

In a non-limiting aspect, the phosphine halide can be (methyl)(phenyl)phosphine chloride, (ethyl)(phenyl)phosphine chloride, (isopropyl)(phenyl)phosphine chloride, (tert-butyl)(phenyl)phosphine chloride, or (neo-pentyl)(phenyl)phosphine chloride. In an embodiment, the phosphine halide can be (methyl)(phenyl)phosphine chloride; alternatively, (ethyl)(phenyl)phosphine chloride; alternatively, (isopropyl)(phenyl)phosphine chloride; alternatively, (tert-butyl)(phenyl)phosphine chloride; or alternatively, (neo-pentyl)(phenyl)phosphine chloride.

In some non-limiting embodiments, the phosphine halide can be dicyclopentylphosphine chloride, dicyclohexylphosphine chloride; alternatively, dicyclopentylphosphine chloride; or alternatively, dicyclohexylphosphine chloride.

In yet another non non-limiting aspect, the phosphine halide can be bis(2-fluorophenyl)-phosphine chloride, bis(2-chlorophenyl)phosphine chloride, bis(3-fluorophenyl)phosphine chloride, bis(3-chlorophenyl)phosphine chloride, bis(4-fluorophenyl)phosphine chloride, or bis(4-chlorophenyl)-phosphine chloride. In some embodiments, the phosphine halide can be bis(2-fluorophenyl)phosphine chloride, bis(3-fluorophenyl)phosphine chloride, or bis(4-fluorophenyl) phosphine chloride; or alternatively, bis(2-chlorophenyl) phosphine chloride, bis(3-chlorophenyl)phosphine chloride, or bis(4-chlorophenyl)phosphine chloride. In other embodiments, the phosphine halide can be bis(2-fluoro-phenyl) phosphine chloride; alternatively, bis(2-chlorophenyl)phosphine chloride; alternatively, bis(3-fluorophenyl)phosphine chloride; alternatively, bis(3-chlorophenyl)phosphine chloride; alternatively, bis(4-fluorophenyl)phosphine chloride; or alternatively, bis(4-chlorophenyl)phosphine chloride.

In yet another non non-limiting aspect, the phosphine halide can be (2-fluorophenyl)(phenyl)-phosphine chloride, (2-chlorophenyl)(phenyl)phosphine chloride, (3-fluorophenyl)(phenyl)phosphine chloride, (3-chlorophenyl)(phenyl) phosphine chloride, (4-fluorophenyl)(phenyl)phosphine chloride, or (4-chlorophenyl)(phenyl)phosphine chloride. In some embodiments, the phosphine halide can be (2-fluorophenyl)(phenyl)phosphine chloride, (3-fluorophenyl)(phenyl)phosphine chloride, or (4-fluorophenyl)(phenyl)phosphine chloride; or alternatively, (2-chlorophenyl)(phenyl) phosphine chloride, (3-chlorophenyl)(phenyl)phosphine chloride, or (4-chlorophenyl)(phenyl)phosphine chloride. In other embodiments, the phosphine halide can be (2-fluorophenyl)(phenyl)phosphine chloride; alternatively, (2-chlorophenyl)(phenyl)phosphine chloride; alternatively, (3-fluorophenyl)(phenyl)-phosphine chloride; alternatively, (3-chlorophenyl)(phenyl)phosphine chloride; alternatively, (4-fluorophenyl)(phenyl)phosphine chloride; or alternatively, (4-chlorophenyl)(phenyl)phosphine chloride.

In yet another non non-limiting aspect, the phosphine halide can be diphenylphosphine chloride, bis(2-methylphenyl)phosphine chloride, bis(2-ethylphenyl)phosphine chloride, bis(2-isopropyl-phenyl)phosphine chloride, bis(2-tert-butylphenyl)phosphine chloride, bis(3-methylphenyl) phosphine chloride, bis(3-ethylphenyl)phosphine chloride, bis(3-isopropylphenyl)phosphine chloride, bis(3-tert-butylphenyl)phosphine chloride, diphenylphosphine chloride, bis (4-methylphenyl)phosphine chloride, bis(4-ethylphenyl) phosphine chloride, bis(4-isopropylphenyl)phosphine chloride, or bis(4-tert-butylphenyl)phosphine chloride. In an embodiment, the phosphine halide can be bis(2-methylphenyl)phosphine chloride, bis(2-ethylphenyl)phosphine chloride, bis(2-isopropylphenyl)phosphine chloride, or bis (2-tert-butylphenyl)phosphine chloride; alternatively, diphenylphosphine chloride, bis(3-methylphenyl)phosphine chloride, bis(3-ethylphenyl)phosphine chloride, bis(3-isopropylphenyl)-phosphine chloride, or bis(3-tert-butylphenyl)phosphine chloride; or alternatively, diphenylphosphine chloride, bis(4-methylphenyl)phosphine chloride, bis(4-ethylphenyl)phosphine chloride, bis(4-isopropyl-phenyl)phosphine chloride, or bis(4-tert-butylphenyl)phosphine chloride. In other embodiments, the phosphine halide can be diphenylphosphine chloride; alternatively, bis(2-methylphenyl)phosphine chloride; alternatively, bis(2-ethylphenyl)phosphine chloride; alternatively, bis(2-isopropylphenyl)-phosphine chloride; alternatively, bis(2-tert-butylphenyl)phosphine chloride; alternatively, bis(3-methyl-phenyl)phosphine chloride; alternatively, bis(3-ethylphenyl)phosphine chloride; alternatively, bis(3-isopropylphenyl)phosphine chloride; alternatively, bis(3-tert-butylphenyl)phosphine chloride; alternatively, diphenylphosphine chloride; alternatively, bis(4-methylphenyl)phosphine chloride; alternatively, bis(4-ethylphenyl)phosphine chloride, bis(4-isopropylphenyl) phosphine chloride; or alternatively, bis(4-tert-butylphenyl) phosphine chloride.

In yet another non non-limiting aspect, the phosphine halide can be diphenylphosphine chloride, (2-methylphenyl)(phenyl)phosphine chloride, (2-ethylphenyl)(phenyl)phosphine chloride, (2-isopropylphenyl)(phenyl)phosphine chloride, (2-tert-butylphenyl)(phenyl)phosphine chloride, (3-methylphenyl)(phenyl)phosphine chloride, (3-ethylphenyl)(phenyl)phosphine chloride, (3-isopropyl-phenyl)(phenyl)phosphine chloride, (3-tert-butylphenyl)(phenyl)phosphine chloride, diphenylphosphine chloride, (4-methylphenyl)(phenyl)phosphine chloride, (4-ethylphenyl)(phenyl)phosphine chloride, (4-isopropylphenyl)(phenyl)phosphine chloride, or (4-tert-butylphenyl)(phenyl)phosphine chloride. In an embodiment, the phosphine halide can be (2-methylphenyl)(phenyl)phosphine chloride, (2-ethylphenyl)-(phenyl)phosphine chloride, (2-isopropylphenyl)(phenyl)phosphine chloride, or (2-tert-butylphenyl)-(phenyl)phosphine chloride; alternatively, diphenylphosphine chloride, (3-methylphenyl)(phenyl)-phosphine chloride, (3-ethylphenyl)(phenyl)phosphine chloride, (3-isopropylphenyl)(phenyl)phosphine chloride, or (3-tert-butylphenyl)(phenyl)phosphine chloride; or alternatively, diphenylphosphine chloride, (4-methylphenyl)(phenyl)phosphine chloride, (4-ethylphenyl)(phenyl)phosphine chloride, (4-isopropyl-phenyl)(phenyl)phosphine chloride, or (4-tert-butylphenyl)(phenyl)phosphine chloride. In other embodiments, the phosphine halide can be diphenylphosphine chloride; alternatively, (2-methylphenyl)-(phenyl)phosphine chloride; alternatively, (2-ethylphenyl)(phenyl)phosphine chloride; alternatively, (2-isopropylphenyl)(phenyl)phosphine chloride; alternatively, (2-tert-butylphenyl)(phenyl)phosphine chloride; alternatively, (3-methylphenyl)(phenyl)phosphine chloride; alternatively, (3-ethylphenyl)-(phenyl)phosphine chloride; alternatively, (3-isopropylphenyl)(phenyl)phosphine chloride; alternatively, (3-tert-butylphenyl)(phenyl)phosphine chloride; alternatively, diphenylphosphine chloride; alternatively, (4-methylphenyl)(phenyl)phosphine chloride; alternatively, (4-ethylphenyl)(phenyl)phosphine chloride, (4-isopropylphenyl)(phenyl)phosphine chloride; or alternatively, (4-tert-butylphenyl)(phenyl)phosphine chloride.

In yet another non-limiting aspect, the phosphine halide can be diphenylphosphine chloride, bis(2-methoxyphenyl)phosphine chloride, bis(2-ethoxyphenyl)phosphine chloride, bis(2-isopropoxy-phenyl)phosphine chloride, bis(2-tert-butoxyphenyl)phosphine chloride, bis(3-methoxyphenyl)phosphine chloride, bis(3-ethoxyphenyl)phosphine chloride, bis(3-isopropoxyphenyl)phosphine chloride, bis(3-tert-butoxyphenyl)phosphine chloride, diphenoxyphosphine chloride, bis(4-methoxyphenyl)-phosphine chloride, bis(4-ethoxyphenyl)phosphine chloride, bis(4-isopropoxyphenyl)phosphine chloride, or bis(4-tert-butoxyphenyl)phosphine chloride. In an embodiment, the phosphine halide can be bis(2-methoxyphenyl)phosphine chloride, bis(2-ethoxyphenyl)phosphine chloride, bis(2-isopropoxy-phenyl)phosphine chloride, or bis(2-tert-butoxyphenyl)phosphine chloride; alternatively, diphenoxyphosphine chloride, bis(3-methoxyphenyl)phosphine chloride, bis(3-ethoxyphenyl)phosphine chloride, bis(3-isopropoxyphenyl)phosphine chloride, or bis(3-tert-butoxyphenyl)phosphine chloride; or alternatively, diphenoxyphosphine chloride, bis(4-methoxyphenyl)phosphine chloride, bis(4-ethoxy-phenyl)phosphine chloride, bis(4-isopropoxyphenyl)phosphine chloride, or bis(4-tert-butoxyphenyl)-phosphine chloride. In other embodiments, the phosphine halide can be diphenylphosphine chloride; alternatively, bis(2-methoxyphenyl)phosphine chloride; alternatively, bis(2-ethoxyphenyl)phosphine chloride; alternatively, bis(2-isopropoxyphenyl)phosphine chloride; alternatively, bis(2-tert-butoxy-phenyl)phosphine chloride; alternatively, bis(3-methoxyphenyl)phosphine chloride; alternatively, bis(3-ethoxyphenyl)phosphine chloride; alternatively, bis(3-isopropoxyphenyl)phosphine chloride; alternatively, bis(3-tert-butoxyphenyl)phosphine chloride; alternatively, diphenoxyphosphine chloride; alternatively, bis(4-methoxyphenyl)phosphine chloride; alternatively, bis(4-ethoxyphenyl)phosphine chloride, bis(4-isopropoxyphenyl)phosphine chloride; or alternatively, bis(4-tert-butoxyphenyl)phosphine chloride.

In yet another non non-limiting aspect, the phosphine halide can be diphenylphosphine chloride, (2-methoxyphenyl)(phenyl)phosphine chloride, (2-ethoxyphenyl)(phenyl)phosphine chloride, (2-isopropoxyphenyl)(phenyl)phosphine chloride, (2-tert-butoxyphenyl)(phenyl)phosphine chloride, (3-methoxyphenyl)(phenyl)phosphine chloride, (3-ethoxyphenyl)(phenyl)phosphine chloride, (3-isopropoxyphenyl)(phenyl)phosphine chloride, (3-tert-butoxyphenyl)(phenyl)phosphine chloride, diphenoxyphosphine chloride, (4-methoxyphenyl)(phenyl)phosphine chloride, (4-ethoxyphenyl)(phenyl)-phosphine chloride, (4-isopropoxyphenyl)(phenyl)phosphine chloride, or (4-tert-butoxyphenyl)(phenyl)-phosphine chloride. In an embodiment, the phosphine halide can be (2-methoxyphenyl)(phenyl)-phosphine chloride, (2-ethoxyphenyl)(phenyl)phosphine chloride, (2-isopropoxyphenyl)(phenyl)-phosphine chloride, or (2-tert-butoxyphenyl)(phenyl)phosphine chloride; alternatively, diphenoxyphosphine chloride, (3-methoxyphenyl)(phenyl)phosphine chloride, (3-ethoxyphenyl)(phenyl)phosphine chloride, (3-isopropoxyphenyl)(phenyl)phosphine chloride, or (3-tert-butoxyphenyl)(phenyl)phosphine chloride; or alternatively, diphenoxyphosphine chloride, (4-methoxyphenyl)(phenyl)phosphine chloride, (4-ethoxyphenyl)(phenyl)phosphine chloride, (4-isopropoxyphenyl)(phenyl)phosphine chloride, or (4-tert-butoxyphenyl)(phenyl)phosphine chloride. In other embodiments, the phosphine halide can be diphenylphosphine chloride; alternatively, (2-methoxyphenyl)(phenyl)phosphine chloride; alternatively, (2-ethoxyphenyl)(phenyl)phosphine chloride; alternatively, (2-isopropoxyphenyl)(phenyl)phosphine chloride; alternatively, (2-tert-butoxyphenyl)(phenyl)phosphine chloride; alternatively, (3-methoxy-phenyl)(phenyl)phosphine chloride; alternatively, (3-ethoxyphenyl)(phenyl)phosphine chloride; alternatively, (3-isopropoxyphenyl)(phenyl)phosphine chloride; alternatively, (3-tert-butoxyphenyl)-(phenyl)phosphine chloride; alternatively, diphenoxyphosphine chloride; alternatively, (4-methoxy-phenyl)(phenyl)phosphine chloride; alternatively, (4-ethoxyphenyl)(phenyl)phosphine chloride, (4-isopropoxyphenyl)(phenyl)phosphine chloride; or alternatively, (4-tert-butoxyphenyl)(phenyl)-phosphine chloride.

Generally, the phosphine halide and the metal formamidinate can be combined at a phosphine halide to metal formamidinate equivalent ratio of at least 0.9:1. In some embodiments, the phosphine halide and the metal formamidinate can be combined at a phosphine halide to metal formamidinate equivalent ratio of at least 0.95:1; alternatively, of at least 0.975:1; or alternatively, of at least 0.99:1. In some embodiments, the phosphine halide and the metal formamidinate can be combined at a phosphine halide to metal formamidinate equivalent ratio ranging from 0.9:1 to 1.25:1; alternatively, ranging from 0.95:1 to 1.20:1; alternatively, ranging from 0.975:1 to 1.15:1; or alternatively, ranging from 0.99:1 to 1.10:1. In other embodiments, the phosphine halide and the metal formamidinate can be combined at a phosphine halide to metal formamidinate equivalent ratio of about 1:1.

In an embodiment, the conditions capable of forming an $N^2$-phosphinyl formamidine compound can include a reaction temperature of at least 0° C.; alternatively, of at least 5° C.; alternatively, of at least 10° C.; or alternatively, of at least 15° C. In some embodiments, the conditions capable of forming an $N^2$-phosphinyl formamidine compound can include a reaction temperature ranging from 0° C. to 60° C.;

alternatively, ranging from 5° C. to 50° C.; alternatively, ranging from 10° C. to 45° C.; or alternatively, ranging from 15° C. to 40° C. In an embodiment, the conditions capable of forming an $N^2$-phosphinyl formamidine compound can include a reaction time of at least 5 minutes; alternatively, of at least 10 minutes; alternatively, of at least 15 minutes; or alternatively, of at least 20 minutes. In some embodiments, the conditions capable of forming an $N^2$-phosphinyl formamidine compound can include a reaction time ranging from 5 minutes to 6 hours; alternatively, ranging from 10 minutes to 5 hours; alternatively, ranging from 15 minutes to 4.5 hours; or alternatively, ranging from 20 minutes to 4 hours.

In an embodiment, the phosphine halide and the metal formamidinate can be contacted in an aprotic solvent. In some embodiments, the phosphine halide and the metal formamidinate can be contacted in a polar aprotic solvent. Aprotic solvents which can be utilized include hydrocarbon solvents and ether solvents. Polar aprotic solvents which can be utilized include ether solvents. Solvents are generally disclosed herein and any general or specific aprotic solvent and/or polar aprotic solvent described herein can be utilized to further describe the method of preparing an $N^2$-phosphinyl formamidine compound comprising contacting a phosphine halide with a metal amidinate and forming the $N^2$-phosphinyl amidinate.

In an embodiment, the $N^2$-phosphinyl formamidine compound can be utilized without further isolation or purification. In some embodiments, the $N^2$-phosphinyl formamidine compound can be isolated; or alternatively isolated and purified. In an embodiment, wherein the $N^2$-phosphinyl formamidine compound can be prepared in a solvent (aprotic or polar aprotic), the method to prepare the $N^2$-phosphinyl formamidine compound can include a step of isolating the $N^2$-phosphinyl formamidine compound by evaporating the solvent. In an embodiment wherein the $N^2$-phosphinyl formamidine compound can prepared in a solvent (aprotic or polar aprotic), the method to prepare the $N^2$-phosphinyl formamidine compound can include the step of isolating the $N^2$-phosphinyl formamidine compound by filtering the solution to remove particulate materials and/or byproducts of the reaction and evaporating the solvent. In embodiments, the method to prepare the $N^2$-phosphinyl formamidine compound can include a purification step wherein the $N^2$-phosphinyl formamidine compound can be purified by dissolving the $N^2$-phosphinyl formamidine compound in a solvent and filtering the solution to remove particulate materials and/or byproducts of the reaction. The solvent utilized to purify the $N^2$-phosphinyl formamidine compound can be the same solvent utilized to form the $N^2$-phosphinyl formamidine compound or it can be different than the solvent utilized to form the $N^2$-phosphinyl formamidine compound. In some embodiments, the method to prepare the $N^2$-phosphinyl formamidine compound can include a purification step of washing the $N^2$-phosphinyl formamidine compound with a solvent. In other embodiments, the method to prepare the $N^2$-phosphinyl formamidine compound can include a purification step of recrystallizing the $N^2$-phosphinyl formamidine compound.

Generally, evaporation of the solvent can be performed using any suitable method. In some embodiments, the solvent can be evaporated at ambient temperature (15-35° C.—no applied external heat source). In other embodiments, the solvent can be evaporated with gentle heating (e.g., at a temperature ranging from 25° C. to 50° C.). In further embodiments, the solvent can be evaporated at ambient temperature under reduced pressure. In yet other embodiments, the solvent can be evaporated with gentle heating under reduced pressure.

Method of Preparing Metal Formamidinates

In an aspect, the metal formamidinate utilized in the method to prepare the $N^2$-phosphinyl formamidine can be prepared by a) contacting an formamidine compound having an $N^2$ hydrogen atom with a metallic compound capable of abstracting a proton from a —$NH_2$ group or a >NH group; and b) forming the metal formamidinate. Generally, the metal formamidinate can be formed under conditions capable of forming a metal formamidinate. In some embodiments, the metal formamidinate can be isolated; alternatively, purified; or alternatively, isolated and purified.

In an embodiment, the formamidine compound can have Structure FA1 or FA2; alternatively, Structure FA1; or alternatively, Structure FA2. In some embodiments, the formamidine compounds can have only one $N^2$ hydrogen atom (i.e., $R^3$ is a non-hydrogen group in the formamidine compound FA1). In other embodiments, the formamidine can have two $N^2$ hydrogen atoms (i.e., $R^3$ is a hydrogen group in the formamidine compound FA2).

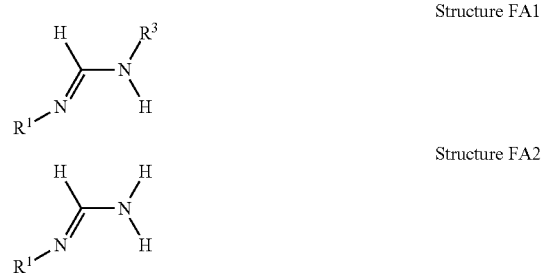

Structure FA1

Structure FA2

Generally, the formamidine structure prefaced with FA corresponds to the metal formamidinate structure prefaced with MFA having the same number designation. However, it should be noted that methods described herein provide for the conversion of formamidine compounds having Structure FA2 (wherein $R^3$ is hydrogen) into formamidine compounds having Structure FA1 (wherein $R^3$ is not hydrogen), respectively. $R^1$ and $R^3$ within formamidine compound Structures FA1 and/or FA2 are independently described as features of the $N^2$-phosphinyl formamidine compound Structures NPF1 and/or NPF2. Since formamidine FA1 and/or FA2 can be utilized to prepare embodiments of $N^2$-phosphinyl formamidine compounds having Structures NPF1 and/or NPF2, the $R^1$ and $R^3$ descriptions for the $N^2$-phosphinyl formamidine compounds can be utilized without limitation to further describe the formamidine Structures FA1 and/or FA2.

In an embodiment, the metallic compound capable of abstracting a proton from a —$NH_2$ group or a >NH group can be a metal hydride or a metal alkyl; alternatively, a metal hydride; or alternatively, a metal alkyl. In an embodiment the metal hydride can be sodium hydride, calcium hydride, lithium aluminum hydride or sodium borohydride; alternatively, sodium hydride or calcium hydride; alternatively, lithium aluminum hydride or sodium borohydride; alternatively, sodium hydride; alternatively, calcium hydride; alternatively, lithium aluminum hydride; or alternatively, sodium borohydride. Metal alkyl compounds are described herein and can be utilized, without limitation, as the metal alkyl for abstracting the proton from the formamidine compound. Useful metal alkyls for abstracting the proton from the formamidine compound can be Group 1 metal alkyls or Group 2 metal alkyls; alternatively, Group 1 metal alkyls; or alternatively, Group 2 metal alkyls. In an embodiment, the metal alkyl can be a lithium alkyl, a sodium alkyl, or a potassium alkyl; alternatively, a lithium alkyl or a sodium alkyl; alternatively, a lithium alkyl; alternatively, a sodium alkyl; or alternatively, a potassium alkyl. Alkyl groups for the metal alkyl are described herein and can be utilized without limitation to further describe the metal alkyls which can be contacted with the formamidine compound. In some exemplary embodiments, the metal alkyl can be methyl lithium, n-butyl lithium, sec-butyl lithium, or tert-butyl lithium; alternatively, methyl lithium; alternatively, n-butyl lithium; alternatively, sec-butyl lithium; or alternatively, tert-butyl lithium.

Generally, the formamidine compound and the metallic compound capable of abstracting a proton from a —$NH_2$ group or a >NH group can be combined in a formamidine compound to metallic compound equivalent ratio of at least 0.9:1. In an embodiment, the formamidine compound and the metallic compound capable of abstracting a proton from a —$NH_2$ group or a >NH group can be combined in a formamidine compound to metallic compound equivalent ratio of at least 0.95:1; alternatively, of at least 0.975:1; or alternatively, of at least 0.99:1. In some embodiments, the formamidine compound and the metallic compound capable of abstracting a proton from a —$NH_2$ group or a >NH group can be combined in a formamidine compound and metallic compound equivalent ratio ranging from 0.9:1 to 1.25:1; alternatively, ranging from 0.95:1 to 1.20:1; alternatively, ranging from 0.975:1 to 1.15:1; or alternatively, ranging from 0.99:1 to 1.10:1. In other embodiments, the formamidine compound and the metallic compound capable of abstracting a proton from a —$NH_2$ group or a >NH group can be combined in a formamidine compound to metallic compound equivalent ratio of about 1:1.

In an embodiment, the conditions capable of forming the metal formamidinate can include a temperature of at least −45° C.; alternatively, of at least −30° C.; alternatively, of at least −25° C.; or alternatively, of at least −20° C. In some embodiments, the reaction conditions capable of forming a metal formamidinate can include a temperature ranging from −45° C. to 60° C.; alternatively, ranging from −30° C. to 50° C.; alternatively, ranging from −25° C. to 45° C.; or alternatively, ranging from −20° C. to 40° C.

In some embodiments, the conditions capable of forming the metal formamidinate can include an initial metallic compound capable of abstracting a proton from a —$NH_2$ group or a >NH group and formamidine compound, contact temperature, and a second temperature to form the metal formamidinate. It should be noted the when the conditions capable of forming the metal formamidinate is described as occurring at two temperatures (one for the contact of the metallic compound capable of abstracting a proton from a —$NH_2$ group or a >NH group and the formamidine compound and one for the formation of the metal formamidinate) that this description does not exclude the prospect that metal formamidinate can be formed at the contact temperature. The description just relates that, in some embodiments, the metal formamidinate formation can proceed better when the initial contact between the metallic compound capable of abstracting a proton from a —$NH_2$ group or a >NH group and formamidine compound is performed at one temperature and the formation of the metal formamidinate is completed at a second different temperature.

In an embodiment, the metallic compound capable of abstracting the proton from a formamidine compound and formamidine compound can be contacted at a temperature ranging from −45° C. to 20° C.; alternatively, ranging from −30° C. to 15° C.; alternatively, ranging from −25° C. to 45° C.; or alternatively, ranging from −20° C. to 40° C. In an embodiment, the metal formamidinate can be formed at a temperature ranging from 0° C. to 20° C.; alternatively, ranging from 5° C. to 15° C.; alternatively, ranging from 10° C. to 45° C.; or alternatively, ranging from 15° C. to 40° C.

In an embodiment, the conditions capable of forming the metal formamidinate can include a metal formamidinate formation time of at least 5 minutes; alternatively, of at least 10 minutes; alternatively, of at least 15 minutes; or alternatively, of at least 20 minutes. In some embodiments, the conditions capable of forming the metal formamidinate can include a metal formamidinate formation time ranging from 5 minutes to 6 hours; alternatively, ranging from 10 minutes to 5 hours; alternatively, ranging from 15 minutes to 4.5 hours; or alternatively, ranging from 20 minutes to 4 hours.

In an embodiment, the metallic compound capable of abstracting a proton from a —$NH_2$ group or a >NH group and the formamidine compound can be contacted in an aprotic solvent. In some embodiments, the metallic compound capable of abstracting a proton from a —$NH_2$ group or a >NH group and the formamidine compound can be contacted in a polar aprotic solvent. Aprotic solvents which can be utilized include hydrocarbon solvents and ether solvents. Polar aprotic solvents which can be utilized include ether solvents. Solvents are generally disclosed herein and any general or specific aprotic solvent and/or polar aprotic solvent described herein can be utilized to further describe the method of preparing the metal formamidinate by contacting a metallic compound capable of abstracting a proton from a —$NH_2$ group or a >NH group and an formamidine compound and forming a metal amidinate.

In an embodiment, the metal formamidinate can be utilized without further isolation or purification. In some embodiments, the metal formamidinate can be isolated; alternatively, purified; or alternatively, isolated and purified. In an embodiment, the method to prepare the metal formamidinate can include a step of isolating the metal formamidinate by filtering the metal formamidate from the solution. In some embodiments, the method to prepare the metal formamidinate can include a step of purifying the metal formamidinate by washing the metal formamidinate with a solvent. Generally, the washing solvent can be an aprotic solvent. In other embodiments, the washing solvent can be a polar aprotic solvent. In other embodiments, the washing solvent can be a non-polar aprotic solvent.

Formamidine Compounds and Hydrocarboxymethanimine Compounds

In an aspect, the formamidine compounds which can be utilized to form the $N^2$-phosphinyl formamidine compound can be prepared by a method comprising contacting an amine and a trihydrocarbylformate to form a formamidine compound; or alternatively, 1) contacting an amine and a trihydrocarbylformate to form a hydrocarboxymethanimine compound and 2) contacting the hydrocarboxymethanimine compound and an ammonium compound to form a formamidine compound. In some embodiments, the formamidine compound which can be utilized to form the $N^2$-phosphinyl formamidine compound can be prepared by a method comprising: a) contacting an amine and a trihydrocarbylformate; and b) forming the formamidine compound; alternatively, a) contacting an amine and a trihydrocarbylformate, b) forming a hydrocarboxymethanimine compound, c) contacting the hydrocarboxymethanimine compound and an ammonium compound, and d) forming the formamidine compound. In an embodiment, the amine and the trihydrocarbylformate are contacted in the presence of acid catalyst. In such embodiments, a formamidine compound can be prepared by a method comprising contacting an amine, a trihydrocarbylformate, and an acid catalyst to form the formamidine compound; or alternatively, a hydrocarboxymethanime compound can be prepared by the method comprising contacting an amine, a trihydrocarbylformate, and an acid catalyst to form the hydrocarboxymethanime compound. The formamidine compound can be formed under conditions capable of forming a formamidine. In some embodiments, the formamidine compound can be isolated; alternatively, purified; or alternatively, isolated and purified. The hydrocarboxymethanimine compound can be formed under conditions capable of forming a hydrocarboxymethanimine. In some embodiments, the hydrocarboxymethanimine compound can be isolated; alternatively, purified; or alternatively, isolated and purified. General and specific amines and trihydrocarbylformates are disclosed herein and these general and specific amines and trihydrocarbylformates can be utilized, without limitation, to further describe the method to prepare the formamidine compound.

In an embodiment, the amine can have Structure A1. $R^1$ within amine Structure A1 is $R^1$—$NH_2$      Structure A1 independently described as a feature of the $N^2$-phosphinyl formamidine compound having Structure NPF1 and/or NPF2. Since amines having Structure A1 are ultimately utilized to prepare embodiments of $N^2$-phosphinyl formamidine compounds having Structures NPF1 and/or NPF2, the $R^1$ descriptions for the $N^2$-phosphinyl formamidine compounds can be utilized without limitation to further describe the amine Structure A1.

In an aspect, the amine having Structure A1 can be methylamine, an ethylamine, a propylamine, a butylamine, a pentylamine, a hexylamine, a heptylamine, an octylamine, a nonylamine, or a decylamine. In some embodiments, the amine having Structure A1 can be methylamine, ethylamine, n-propylamine, iso-propylamine, n-butylamine, iso-butylamine, sec-butylamine, tert-butylamine, n-pentylamine, iso-pentylamine, sec-pentylamine, or neopentylamine; alternatively, methylamine, ethylamine, iso-propylamine, tert-butylamine, or neopentylamine; alternatively, methylamine; alternatively, ethylamine; alternatively, n-propylamine; alternatively, iso-propylamine; alternatively, tert-butylamine; or alternatively, neopentylamine. In other aspects, the amine having Structure A1 can be cyclobutylamine, a substituted cyclobutylamine, cyclopentylamine, a substituted cyclopentylamine, cyclohexylamine, a substituted cyclohexylamine, cycloheptylamine, a substituted cycloheptylamine, cyclooctylamine, or a substituted cyclooctylamine. In an embodiment the amine having Structure A1 can be cyclopentylamine, a substituted cyclopentylamine, cyclohexylamine, or a substituted cyclohexylamine. In other embodiments, the amine having Structure A1 can be cyclobutylamine or a substituted cyclobutylamine; alternatively, a cyclopentylamine or a substituted cyclopentylamine; alternatively, a cyclohexylamine or a substituted cyclohexylamine; alternatively, a cycloheptylamine or a substituted cycloheptylamine; or alternatively, a cyclooctylamine, or a substituted cyclooctylamine. In further embodiments, the amine having Structure A1 can be cyclopentylamine; alternatively, a substituted cyclopentylamine; alternatively, a cyclohexylamine; or alternatively, a substituted cyclohexylamine. Substituents and substituents patterns for the $R^1$ cycloalkyl groups are described herein and can be utilized without limitation to further describe the substituted cycloalkylamines which can be utilized as the amine having Structure A1 in aspects and/or embodiments described herein.

In an aspect, the amine having Structure A1 can have Structure A6 or A7

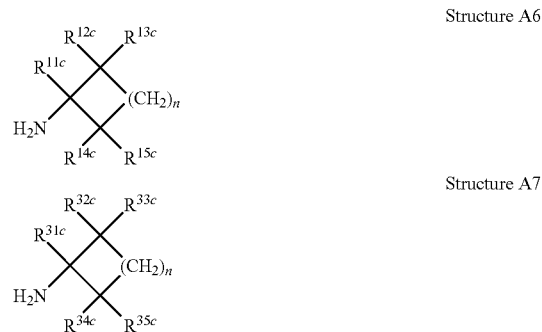

The $R^{11c}$, $R^{31c}$, $R^{12c}$, $R^{32c}$, $R^{13c}$, $R^{33c}$, $R^{14c}$, $R^{34c}$, $R^{15c}$ and $R^{35c}$ substituents, substituent patterns, and n for the $R^1$ group in Structure G1 are described herein and can be utilized without limitation to describe the amine having Structure A6 and/or Structure A7 which can be utilized in the various aspects and embodiments described herein.

In an aspect, the amine having Structure A1 can be aniline, a substituted aniline, a naphthylamine, or a substituted naphthylamine. In an embodiment, $R^1$ can be aniline or a substituted aniline; alternatively, a naphthylamine or a substituted naphthylamine; alternatively, an aniline or a naphthylamine; or alternatively, a substituted aniline or a substituted naphthylamine. Substituents and substituents patterns for $R^1$ are described herein and can be utilized without limitation to further describe the substituted anilines and substituted naphthylamines which can be utilized in aspects and/or embodiments described herein.

In an embodiment, the amine having Structure A1 can be a 2-substituted aniline, a 3-substituted aniline, a 4-substituted aniline, a 2,4-disubstituted aniline, a 2,6-disubstituted aniline, 3,5-disubstituted aniline, or a 2,4,6-trisubstituted aniline. In other embodiments, the $R^1$ substituted aniline can be a 2-substituted aniline, a 4-substituted aniline, a 2,4-disubstituted aniline, or a 2,6-disubstituted aniline; alternatively, a 3-substituted aniline or a 3,5-disubstituted aniline; alternatively, a 2-substituted aniline or a 4-substituted aniline; alternatively, a 2,4-disubstituted aniline or a 2,6-disubstituted aniline; alternatively, a 2-substituted aniline; alternatively, a 3-substituted aniline; alternatively, a 4-substituted aniline; alternatively, a 2,4-disubstituted aniline; alternatively, a 2,6-disubstituted aniline; alternatively, 3,5-disubstituted aniline; or alternatively, a 2,4,6-trisubstituted aniline. Substituents for the $R^1$ phenyl groups are generally disclosed herein and can be utilized without limitation to further describe the substituted anilines which can be utilized in the various aspects and/or embodiments described herein.

In an embodiment, the amine having Structure A1 can be 1-naphthylamine, a substituted 1-naphthylamine, 2-naphthylamine, or a substituted 2-naphthylamine. In some embodiments, the amine having Structure A1 can be 1-naphthylamine or a substituted 1-naphthylamine; alternatively, 2-naphthylamine or a substituted 2-naphthylamine; alternatively, 1-naphthylamine; alternatively, a substituted 1-naphthylamine; alternatively, 2-naphthylamine; or alternatively, a substituted 2-naphthylamine. In other embodiments, the amine having Structure A1 can be a 2-substituted 1-naphthylamine, a 3-substituted 1-naphthylamine, a 4-substituted 1-naphthylamine, or a 8-substituted 1-naphthylamine; alternatively, a 2-substituted 1-naphthylamine; alternatively, a 3-substituted 1-naphthylamine; alternatively, a 4-substituted 1-naphthylamine; or alternatively, a 8-substituted 1-naphthylamine. In further embodiments, the amine having Structure A1 can be a 1-substituted 2-naphthylamine, a 3-substituted 2-naphthylamine, or a 4-substituted 2-naphthylamine, or a 1,3-disubstituted 2-naphthylamine; alternatively, a 1-substituted 2-naphthylamine; alternatively, a 3-substituted 2-naphthylamine; alternatively, a 4-substituted 2-naphthylamine; alternatively, or a 1,3-disubstituted 2-naphthylamine. Substituents for the $R^1$ naphthyl groups are generally disclosed herein and can be utilized without limitation to further describe the substituted naphthylamines which can be utilized in the various aspects and/or embodiments described herein.

In an aspect, the amine having Structure A1 can have Structure A8.

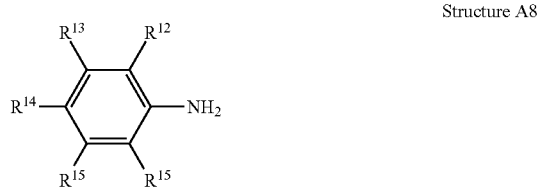

Structure A8

The $R^{12}$, $R^{13}$, $R^{14}$, $R^{15}$, and $R^{16}$ substituents and substituent patterns for the $R^1$ group having Structure G2 are described herein and can be utilized without limitation to describe the amine having Structure A8 which can be utilized in the various aspects and embodiments described herein.

In a non-limiting embodiment, the amine having Structure A1 can be aniline, a 2-alkylaniline, a 3-alkylaniline, a 4-alkylaniline, a 2,4-dialkylaniline a 2,6-dialkylaniline, a 3,5-dialkylaniline, or a 2,4,6-trialkylaniline; alternatively, a 2-alkylaniline, a 4-alkylaniline, a 2,4-dialkylaniline, a 2,6-dialkylaniline, or a 2,4,6-trialkylaniline; alternatively, a 2-alkylaniline or a 4-alkylaniline; alternatively, a 2,4-dialkylaniline a 2,6-dialkylaniline; alternatively, a 3-alkylaniline or a 3,5-dialkylaniline; alternatively, a 2-alkylaniline or a 2,6-dialkylaniline; alternatively, a 2-alkylaniline; alternatively, a 3-alkylaniline; alternatively, a 4-alkylaniline; alternatively, a 2,4-dialkylaniline; alternatively, a 2,6-dialkylaniline; alternatively, a 3,5-dialkylaniline; or alternatively, a 2,4,6-trialkylaniline. In another non-limiting embodiment, the amine having Structure A1 can be a 1-aminonaphthylene, a 2-aminonaphthylene, a 2-alkylnaphth-1-yl group, a 1-alkyl-2-aminonaphthylene, a 3-alkylnapth-2-yl group, or a 1,3-dialkyl-2-aminonaphthylene; alternatively, a 1-aminonaphthylene or a 2-alkyl-1-amino-naphthylene; alternatively, a 2-aminonaphthylene, a 1-alkyl-2-aminonaphthylene, a 3-alkylamin-napthylene, or a 1,3-dialkyl-2-aminonaphthylene; alternatively, 1-aminonaphthylene; alternatively, a 2-aminonaphthylene; alternatively, a 2-alkyl-1-aminonaphthylene; alternatively, a 1-alkyl-2-aminonaphthylene; alternatively, a 3-alkyl-2-aminonapthylene; or alternatively, a 1,3-dialkyl-2-aminonaphthylene. In other non-limiting embodiments, the amine having Structure A1 can be a cyclohexylamine, a 2-alkylcyclohexylamine, or a 2,6-dialkylcyclohexylamine; alternatively, cyclopentylamine, a 2-alkylcyclopentylamine, or a 2,5-dialkylcyclopentylamine; alternatively, cyclohexylamine; alternatively, a 2-alkylcyclohexylamine; alternatively, a 2,6-dialkylcyclohexylamine; alternatively, cyclopentylamine; alternatively, a 2-alkylcyclopentylamine; or alternatively, 2,5-dialkylcyclopentylamine. Alkyl group substituents are independently described herein and can be utilized, without limitation, to further describe the alkylanilines, dialkylanilines, trialkylanilines, alkylaminonaphthylenes, dialkylaminonaphthylenes, alkylcyclohexylamines, dialkylcyclohexylamines, alkylcyclopentylamines, or dialkylcyclopentylamine which can be utilized in the various aspects and/or embodiments described herein. Generally, the alkyl substituents of a dialkyl or trialkyl anilines, aminonaphthylenes, cyclohexylamines, or cyclopentylamines can be the same; or alternatively, can be different.

In another non-limiting embodiment, the amine having Structure A1 can be aniline, a 2-alkoxyaniline, a 3-alkoxyaniline, a 4-alkoxyaniline, or a 3,5-dialkoxyaniline; alternatively, a 2-alkoxyaniline or a 4-alkoxyaniline; alternatively, a 3-alkoxyaniline or 3,5-dialkoxyaniline; alternatively, a 2-alkoxyaniline, alternatively, a 3-alkoxyaniline; alternatively, a 4-alkoxyaniline; alternatively, a 3,5-dialkoxyaniline. Alkoxy group substituents are independently described herein and can be utilized, without limitation, to further describe the alkoxyanilines or dialkoxyanilines which can be utilized in the various aspects and/or embodiments described herein. Generally, the alkoxy substituents of a dialkoxyaniline can be the same; or alternatively, can be different.

In other non-limiting embodiments, the amine having Structure A1 can be aniline, a 2-haloaniline, a 3-haloaniline, a 4-haloaniline, a 2,6-dihalophenylgroup, or a 3,5-dialkylaniline; alternatively, a 2-haloaniline, a 4-haloaniline, or a 2,6-dihaloaniline; alternatively, a 2-haloaniline or a 4-haloaniline; alternatively, a 3-haloaniline or a 3,5-dihaloaniline; alternatively, a 2-haloaniline; alternatively, a 3-haloaniline; alternatively, a 4-haloaniline; alternatively, a 2,6-dihaloaniline; or alternatively, a 3,5-dialkylaniline. Halides are independently described herein and can be utilized, without limitation, to further describe the haloanilines or dihaloanilines which can be utilized in the various aspects and/or embodiments described herein. Generally, the halides of a dihaloaniline can be the same; or alternatively, can be different.

In a non-limiting embodiment, the amine having Structure A1 can be 2-methylaniline, 2-ethylaniline, 2-n-propylaniline, 2-isopropylaniline, 2-tert-butylaniline, 3-methylaniline, 2,6-dimethylaniline, 2,6-diethylaniline, 2,6-di-n-propylaniline, 2,6-diisopropylaniline, 2,6-di-tert-butylaniline, 2-isopropyl-6-methylaniline, or 2,4,6-trimethylaniline; alternatively, 2-methylaniline, 2-ethylaniline, 2-n-propylaniline, 2-isopropylaniline, or 2-tert-butylaniline; alternatively, 2,6-dimethylaniline, 2,6-diethylaniline, 2,6-di-n-propylaniline, 2,6-diisopropylaniline, 2,6-di-tert-butylaniline, or 2-isopropyl-6-methylaniline; alternatively, 2-methylaniline; alternatively, 2-ethylaniline; alternatively, 2-n-propylaniline; alternatively, 2-isopropylaniline; alternatively, 2-tert-butylaniline; alternatively, 3-methylaniline; alternatively, 2,6-dimethylaniline; alternatively, 2,6-diethylaniline; alternatively, 2,6-di-n-propylaniline; alternatively, 2,6-diisopropylaniline; alternatively, 2,6-di-tert-butylaniline; alternatively, 2-isopropyl-6-methylaniline; alternatively, 3,5-dimethylaniline; or alternatively, 2,4,6-trimethylaniline. In another non-limiting embodiment, the amine having Structure A1 can be 2-methylcyclohexylamine, 2-ethylcyclohexylamine, 2-isopropylcyclohexylamine, 2-tert-butylcyclohexylamine, 2,6-dimethylcyclohexylamine, 2,6-diethylcyclohexylamine, 2,6-diisopropylcyclohexylamine, or 2,6-di-tert-butylcyclohexylamine; alternatively, 2-methylcyclohexylamine, 2-ethylcyclohexylamine, 2-isopropylcyclohexylamine, or 2-tert-butylcyclohexylamine; alternatively, 2,6-dimethylcyclohexylamine, 2,6-diethylcyclohexylamine, 2,6-diisopropylcyclohexylamine, or 2,6-di-tert-butylcyclohexylamine; alternatively, 2-methylcyclohexyl; alternatively, 2-ethylcyclohexylamine; alternatively, 2-isopropylcyclohexylamine; alternatively, 2-tert-butylcyclohexylamine; alternatively, 2,6-dimethylcyclohexylamine; alternatively, 2,6-diethylcyclohexylamine; alternatively, 2,6-diisopropylcyclohexylamine; or alternatively, or 2,6-di-tert-butylcyclohexylamine. In another non-limiting embodiment, the amine having Structure A1 can be 2-methyl-1-aminonaphthylene, 2-ethyl-1-aminonaphthylene group, 2-n-propyl-1-aminonaphthylene, 2-isopropyl-1-aminoenaphthylene group, or 2-tert-butyl-1-aminonaphthylene group; alternatively, 2-methyl-1-aminonaphthylene group; alternatively, 2-ethyl-1-aminonaphthylene group; alternatively, 2-n-propyl-1-aminonaphthylene group; alternatively, 2-isopropyl-1-naphthylene group; or alternatively, 2-tert-butyl-1-amononaphthylene group.

In a non-limiting embodiment, the amine having Structure A1 can be 3-methoxyaniline, 3-ethoxyaniline, 3-isoprooxyaniline, 3-tert-butoxyaniline, 4-methoxyaniline, 4-ethoxyaniline, 4-isopropoxyaniline, 4-tert-butoxyaniline, 3,5-dimethoxyaniline, 3,5-diethoxyaniline, 3,5-diisopropoxyaniline, or 3,5-di-tert-butoxyaniline; alternatively, 3-methoxyaniline, 3-ethoxyaniline, 3-isopropoxyaniline, or 3-tert-butoxyaniline; alternatively, 4-methoxyaniline, 4-ethoxyaniline, 4-isopropoxyaniline, or 4-tert-butoxyaniline; or alternatively, 3,5-dimethoxyaniline, 3,5-diethoxyaniline, 3,5-diisopropoxyaniline, or 3,5-di-tert-butoxyaniline. In other non-limiting embodiments, the amine having Structure A1 can be 3-methoxyaniline; alternatively, 3-ethoxyaniline; alternatively, 3-isopropoxyaniline; alternatively, 3-tert-butoxyaniline; alternatively, 4-methoxyaniline; alternatively, 4-ethoxyaniline; alternatively, 4-isopropoxyaniline; alternatively, 4-tert-butoxyaniline; alternatively, 3,5-dimethoxyaniline; alternatively, 3,5-diethoxyaniline; alternatively, 3,5-diisopropoxyaniline; or alternatively, 3,5-di-tert-butoxyaniline.

In an embodiment, when a nitrogen atom of the amine group is attached to a ring atom (e.g. aminocycloalkane, aromatic amine, or aminoarene), the amine can comprise at least one substituent located on a carbon atom adjacent to the ring carbon atom attached to the nitrogen atom of the amine group; or alternatively, the amine can comprise at least one substituent at each carbon atom adjacent to the ring carbon atom attached to the nitrogen atom of the amine group. In some embodiments, when the nitrogen atom of the amine group is attached to a ring atom (e.g. aminocycloalkane, aromatic amine, or aminoarene,), the amine can consist of one substituent located on a carbon atom adjacent to the ring carbon atom attached to the nitrogen atom of the amine group. In some embodiments, when the nitrogen atom of the amine group is attached to a ring atom (e.g. aminocycloalkane, aromatic amine, or aminoarene), the amine can comprise only one substituent located on the carbon atom adjacent to the ring carbon atom attached to the nitrogen atom of the amine group; or alternatively, the amine can comprise only one substituent located on each carbon atom adjacent to the ring carbon atom attached to the nitrogen atom of the amine group. In yet other embodiments, when the nitrogen atom of the amine is attached to a ring atom (e.g. aminocycloalkane, aromatic amine, or aminoarene), the amine can consist of only one substituent located on a carbon atom adjacent to the ring carbon atom attached to the nitrogen atom of the amine group.

In an embodiment, the trihydrocarbylformate can have the formula $(R^fO)_3CH$. Generally, each $R^f$ independently can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In some embodiments, each $R^f$ independently can be $C_6$ to $C_{20}$ aromatic group; alternatively, a $C_6$ to $C_{15}$ aromatic group; alternatively, a $C_6$ to $C_{10}$ aromatic group; alternatively, a $C_1$ to $C_{20}$ alkyl group; alternatively, a $C_1$ to $C_{15}$ alkyl group; alternatively, a $C_1$ to $C_{10}$ alkyl group; or alternatively, a $C_1$ to $C_5$ alkyl group. In some embodiments, each $R^f$ independently can be a methyl group, an ethyl group, a propyl group, a butyl group, or a phenyl group; alternatively, a methyl group; alternatively, an ethyl group; alternatively, a propyl group; alternatively, a butyl group; or alternatively, a phenyl group. In an embodiment, the trihydrocarbylformate can be trimethylformate, triethylformate, or triphenylformate; alternatively, trimethylformate; alternatively, triethylformate; or alternatively, triphenylformate.

In an embodiment, the acid catalyst can be any acid which can facilitate the formation of the formamidine compound (or alternatively, the hydrocarboxymethanime compound). In an embodiment the acid catalyst can comprise, consist essentially of, or consist of, an inorganic acid or an organic acid; alternatively, an inorganic acid, or alternatively, an organic acid. In certain embodiments, the organic acid can comprise, consist essentially of, or consist of, a $C_1$ to $C_{30}$ organic acid; alternatively, a $C_1$ to $C_{20}$ organic acid; alternatively, a $C_1$ to $C_{15}$ organic acid; alternatively, a $C_1$ to $C_{10}$ organic acid; or alternatively, a $C_1$ to $C_5$ organic acid.

In an embodiment, the inorganic acid can comprise, consist essentially of, or consist of, hydrochloric acid, hydrobromic acid, hydroiodic acid, iodic acid, sulfuric acid, chlorosulfonic acid, sulfamic acid, nitric acid, phosphoric acid, meta-phosphoric acid, polyphorphoric acid, pyrophosphoric acid, fluorophosphoric acid, or any combination thereof. In some embodiments, the inorganic acid can comprise, consist essentially of, or consist of, hydrochloric acid, sulfuric acid, nitric acid, phosphoric acid, or any combination thereof; alternatively, hydrochloric acid; alternatively, hydrobromic acid; alternatively, hydroiodic acid; alternatively, iodic acid; alternatively, sulfuric acid; alternatively, chlorosulfonic acid; alternatively, sulfamic acid; alternatively, nitric acid; alternatively, phosphoric acid, alternatively, meta-phosphoric acid; alternatively, polyphorphoric acid; alternatively, pyrophosphoric acid; or alternatively, fluorophosphoric acid.

The organic acid can comprise, consist essentially of, or consist of, a carboxylic acid or an organic sulfonic acid; alternatively, a carboxylic acid; or alternatively, an organic sulfonic acid. Suitable carboxylic acids can have the same number of carbon atoms as the organic acid disclosed herein. In an embodiment, the carboxylic acid can have the same number of carbon atoms as the organic acid disclosed herein. In an embodiment, the organic sulfonic acid can have the same number of carbon atoms as the organic acid disclosed herein.

In an embodiment, the carboxylic acid can comprise, consist essentially of, or consist of formic acid, acetic acid, propionic acid, butyric acid, oxalic acid, trifluoroacetic acid, trichloroacetic acid, benzoic acid, a nitro substituted benzoic acid, a halo substituted benzoic acid, or any combination thereof; alternatively, trifluoroacetic acid; or alternatively, trichloroacetic acid. In an embodiment, the organic sulfonic acid can comprise, consist essentially of, or consist of an aryl sulfonic acid or an alkyl sulfonic acid; alternatively; an aryl sulfonic acid; or alternatively, an alkyl sulfonic acid. In some embodiments, the aryl sulfonic acid can comprise, consist essentially of, or consist of benzene sulfonic acid, a substituted benzene sulfonic acid, naphthalene sulfonic acid, a substituted naphthalene sulfonic acid, or any combination thereof. Substituent groups are independently disclosed herein and can be utilized without limitation to further describe the substituted benzene sulfonic acid or substituted naphthalene sulfonic acid which can be utilized as the acid catalyst. In some embodiments, the organic sulfonic acid can comprise, consist essentially of, or consist of, methane sulfonic acid, benzene sulfonic acid, toluene sulfonic acid (ortho, meta, and/or para), dodecylbenzene sulfonic acid, naphthalene sulfonic acid, dinonylnaphthalene disulfonic acid, or any combination thereof; alternatively, methane sulfonic acid; alternatively, benzene sulfonic acid; or alternatively, toluene sulfonic acid (ortho, meta, and/or para).

In an embodiment, the formamidine compound can be utilized without further isolation or purification. In some embodiments, the formamidine compound can be isolated; alternatively, purified; or alternatively, isolated and purified. In an embodiment, wherein the formamidine compound can be prepared in a solvent, the method to prepare the formamidine compound can include a step of isolating the formamidine compound by evaporating the solvent; or alternatively distilling the solvent from the formamidine. In an embodiment wherein the formamidine compound can be prepared in a solvent, the method to prepare the formamidine compound can include the step of isolating the formamidine compound by filtering the solution to remove particulate materials and/or byproducts of the reaction and evaporating the solvent (or distilling the solvent) from the formamidine compound. In embodiments, the method to prepare the formamidine compound can include a purification step wherein the formamidine compound can be purified by dissolving the formamidine compound in a solvent and filtering the solution to remove particulate materials and/or byproducts of the reaction. The solvent utilized to purify the formamidine compound can be the same solvent utilized to form the formamidine compound or it can be different than the solvent utilized to form the formamidine compound. In some embodiments, the method to prepare the formamidine compound can include a purification step wherein the formamidine can be purified by washing with a solvent. In other embodiments, the method to prepare the formamidine compound can include a purification step of recrystallizing the formamidine compound.

In an embodiment, the hydrocarboxymethanimine compound can have Structure HMA1.

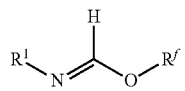

Structure HMA1

$R^1$ within hydrocarboxymethanimine compound Structure HMA1 is independently described as a feature of the $N^2$-phosphinyl formamidine compound Structures NPF1 and/or NPF2. Since the hydrocarboxymethanimine compound HMA1 can be utilized to prepare embodiments of $N^2$-phosphinyl formamidine compounds having Structures NPF1 and/or NPF2, the $R^1$ description for the $N^2$-phosphinyl formamidine compounds can be utilized without limitation to further describe the hydrocarboxymethanimine compound Structure HMA1. $R^f$ within the hydrocarboxymethanimine is described as a feature of the trihydrocarbyl formate from which the hydrocarboxymethanimine is prepared. The $R^f$ description for the trihydrocarbylformates can be utilized without limitation to further describe the hydrocarboxymethanimine compound Structures HMA1.

In an embodiment, the hydrocarboxymethanimine compound can be utilized without further isolation or purification. In some embodiments, the hydrocarboxymethanimine compound can be isolated; alternatively, purified; or alternatively, isolated and purified. In an embodiment, wherein the hydrocarboxymethanimine compound can be prepared in a solvent, the method to prepare the hydrocarboxymethanimine compound can include a step of isolating the hydrocarboxymethanimine compound by evaporating the solvent; or alternatively distilling the solvent from the hydrocarboxymethanimine compound. In an embodiment wherein the hydrocarboxymethanimine compound can be prepared in a solvent, the method to prepare the hydrocarboxymethanimine compound can include the step of isolating the hydrocarboxymethanimine compound by filtering the solution to remove particulate materials and/or byproducts of the reaction and evaporating the solvent (or distilling the solvent) from the hydrocarboxymethanimine compound. In embodiments, the method to prepare the hydrocarboxymethanimine compound can include a purification step wherein the formamidine compound can be purified by dissolving the hydrocarboxymethanimine compound in a solvent and filtering the solution to remove particulate materials and/or byproducts of the reaction. The solvent utilized to purify the hydrocarboxymethanimine compound can be the same solvent utilized to form the hydrocarboxymethanimine compound or it can be different than the solvent utilized to form the hydrocarboxymethanimine compound.

Ammonium compounds which can be utilized to form the formamidine compound from a hydrocarboxymethanime can be any ammonium compound which can substitute an —$NH_2$ group for the hydrocarboxy group of the hydrocarboxymethanime compound. In an embodiment, the ammonium compound can be ammonium acetate, ammonium fluoride, ammonium chloride, ammonium bromide, ammonium iodide, ammonium bicarbonate, ammonium carbonate, ammonium sulfate, ammonium bisulfate, ammonium phosphate, ammonium nitrate, or any combination thereof; alternatively, ammonium acetate; alternatively, ammonium chloride; alternatively, ammonium carbonate; alternatively, ammonium sulfate, or alternatively, ammonium nitrate.

When an amine and a trihydrocarbylformate are combined to form a formamidine compound, the amine and the trihydrocarbylformate can be combined in an amine to metal compound equivalent ratio of at least 1.8:1. In an embodiment, the amine and the trihydrocarbylformate can be combined in an amine to trihydrocarbylformate equivalent ratio of at least 1.9:1; alternatively, of at least 1.95:1; or alternatively, of at least 1.98:1. In some embodiments, the amine and the trihydrocarbylformate can be combined in an amine to trihydrocarbylformate equivalent ratio ranging from 1.8:1 to 2.5:1; alternatively, ranging from 1.9:1 to 2.4:1; alternatively, ranging from 1.95:1 to 2.3:1; or alternatively, ranging from 1.98:1 to 2.2:1. In other embodiments, the amine and the trihydrocarbylformate can be combined in an amine to trihydrocarbylformate equivalent ratio of about 2:1.

When an amine and a trihydrocarbylformate are combined to form a hydrocarboxymethanimine compound, the amine and the trihydrocarbylformate can be combined in an amine to metal compound equivalent ratio of at least 0.25:1. In an embodiment, the amine and the trihydrocarbylformate can be combined in an amine to trihydrocarbylformate equivalent ratio of at least 0.35:1; alternatively, of at least 0.4:1; or alternatively, of at least 0.45:1. In some embodiments, the amine and the trihydrocarbylformate can be combined in an amine to trihydrocarbylformate equivalent ratio ranging from 0.25:1 to 0.75:1; alternatively, ranging from 0.35:1 to 0.7:1; alternatively, ranging from 0.4:1 to 0.6:1; or alternatively, ranging from 0.45:1 to 0.55:1. In other embodiments, the amine and the trihydrocarbylformate can be combined in an amine to trihydrocarbylformate equivalent ratio of about 0.5:1.

In an embodiment where an amine and a trihydrocarbylformate are combined to form a hydrocarboxymethanime compound or a formamidine compound, the conditions capable of forming the hydrocarboxymethanime compound or the formamidine compound can include a temperature of at least 0° C.; alternatively, of at least 15° C.; alternatively, of at least 25° C.; or alternatively, of at least 40° C. In some embodiments where an amine and a trihydrocarbylformate are combined to form a hydrocarboxymethanime compound or a formamidine compound, the conditions capable of forming the hydrocarboxymethanime compound or a formamidine compound can include a temperature ranging from 0° C. to 200° C.; alternatively, ranging from 15° C. to 175° C.; alternatively, ranging from 25° C. to 150° C.; or alternatively, ranging from 40° C. to 125° C.

In an embodiment where an amine and a trihydrocarbylformate are combined to form a hydrocarboxymethanime compound or a formamidine compound, the conditions capable of forming the hydrocarboxymethanime compound or the formamidine compound can include a hydrocarboxymethanime compound or a formamidine compound formation time of at least 5 minutes; alternatively, of at least 30 minutes; alternatively, of at least 45 minutes; or alternatively, of at least 1 hour. In some embodiments where an amine and a trihydrocarbylformate are combined to form a hydrocarboxymethanime compound or a formamidine compound, the conditions capable of forming the hydrocarboxymethanime compound or the formamidine compound can include a hydrocarboxymethanime compound or a formamidine compound formation time ranging from 5 minutes to 48 hours; alternatively, ranging from 30 minutes to 36 hours; alternatively, ranging from 45 minutes to 30 hours; or alternatively, ranging from 1 hour to 24 hours.

In an embodiment where an amine and a trihydrocarbylformate are combined to form a hydrocarboxymethanime compound or a formamidine compound, the hydrocarboxymethanime compound or a formamidine compound can be formed in an aprotic solvent (or the amine and the trihydrocarbylformate can be contacted with an aprotic solvent). In some embodiments, the amine and the trihydrocarbylformate can be contacted in a polar aprotic solvent. Aprotic solvents which can be utilized include hydrocarbon solvents and ether solvents. Polar aprotic solvents which can be utilized include ether solvents. Solvents are generally disclosed herein and any general or specific aprotic solvent and/or polar aprotic solvent described herein can be utilized to further describe the method of preparing the hydrocarboxymethanime compound or a formamidine compound.

When a hydrocarboxylmethanime compound and an ammonium compound are combined to form a formamidine compound, the hydrocarboxylmethanime compound and the ammonium compound can be combined at an ammonium compound to hydrocarboxylmethanime compound equivalent ratio of at least 0.25:1. In an embodiment, the ammonium compound and the hydrocarboxylmethanime compound can be combined at an ammonium compound to hydrocarboxylmethanime compound equivalent ratio of at least 0.35:1; alternatively, of at least 0.4:1; or alternatively, of at least 0.45:1. In some embodiments, the ammonium compound and the hydrocarboxylmethanime compound can be combined at an ammonium compound to hydrocarboxylmethanime compound equivalent ratio ranging from 0.25:1 to 0.75:1; alternatively, ranging from 0.35:1 to 0.7:1; alternatively, ranging from 0.4:1 to 0.6:1; or alternatively, ranging from 0.45:1 to 0.55:1. In other embodiments, the ammonium compound and the hydrocarboxylmethanime compound can be combined at an ammonium compound to hydrocarboxylmethanime compound equivalent ratio of about 0.5:1.

In an embodiment where a hydrocarboxylmethanime compound and an ammonium compound are combined to form a formamidine compound, the conditions capable of forming the formamidine compound can include a temperature of at least 0° C.; alternatively, of at least 5° C.; alternatively, of at least 10° C.; or alternatively, of at least 15° C. In some embodiments where an amine and a trihydrocarbylformate are combined to form a formamidine compound, the conditions capable of forming the formamidine compound can include a temperature ranging from 0° C. to 60° C.; alternatively, ranging from 5° C. to 50° C.; alternatively, ranging from 10° C. to 45° C.; or alternatively, ranging from 15° C. to 40° C. In some embodiments where an amine and a trihydrocarbylformate are combined to form a formamidine compound, the conditions capable of forming the formamidine compound can include forming the formamidine compound at about ambient temperature.

In an embodiment where a hydrocarboxylmethanime compound and an ammonium compound are combined to form a formamidine compound, the conditions capable of forming the formamidine compound can include a formamidine compound formation time of at least 5 minutes; alternatively, of at least 30 minutes; alternatively, of at least 45 minutes; or alternatively, of at least 1 hour. In some embodiments where a hydrocarboxylmethanime compound and an ammonium compound are combined to form a formamidine compound, the conditions capable of forming the formamidine compound can include a formamidine compound formation time ranging from 5 minutes to 48 hours; alternatively, ranging from 30 minutes to 36 hours; alternatively, ranging from 45 minutes to 30 hours; or alternatively, ranging from 1 hour to 24 hours.

In an embodiment where a hydrocarboxylmethanime compound and an ammonium compound are combined to form a formamidine compound, the formamidine compound can be formed in a polar solvent (or the hydrocarboxymethanime compound and the ammonium compound can be contacted with a polar solvent). In some embodiments, the hydrocarboxylmethanime compound and the ammonium compound can be contacted with polar aprotic solvent; or alternatively, a polar protic solvent. Solvents are generally disclosed herein and any general or specific polar aprotic solvent and/or polar protic solvent described herein can be utilized to further describe the method of preparing the formamidine compound by contacting a hydrocarboxylmethanime compound and an ammonium compound.

Evaporation of the solvent, regardless of whether it is performed to separate 1) the formamidine compound from the solvent in the preparation of the formamidine compound by contacting an amine and a trihydrocarbylformate, 2) the hydrocarboxymethanime compound from the solvent in the preparation of the hydrocarboxymethanimine compound by contacting an amine and a trihydrocarbylformate, and/or 3) the formamidine compound from the solvent in the preparation of the formamidine compound by contacting a hydrocarboxymethanimine compound and an ammonium compound can be performed using any suitable method. In an embodiment, the solvent can be evaporated at ambient temperature (15-35° C.—no applied external heat source); alternatively, the solvent can be evaporated with gentle heating (e.g., at a temperature ranging from 25° C. to 50° C.); alternatively, the solvent can be evaporated at ambient temperature under reduced pressure; or alternatively, the solvent can be evaporated with gentle heating under reduced pressure. Distilling the solvent from the formamidine (or the hydrocarboxymethanimine) can be performed using any suitable method. In an embodiment, the distillation can be performed at ambient pressure; or alternatively, the distillation can be performed under reduced pressure. In some embodiments, the distillation can be utilized to separate other materials (e.g., excess amine utilized in the synthesis, and/or impurities formed during the synthesis, among other things) from the formamidine compound and/or the hydrocarboxymethanimine compound.

Methods of preparing a formamidine compound by contacting an amine and a trihydrocarbylformate to form a formamidine compound can produce a formamidine compound having Structure FA1 having the same group for $R^1$ and $R^3$. Methods of preparing a formamidine compound by contacting a hydrocarboxymethanimine compound and an ammonium compound to form a formamidine compound produce formamidine compounds having two $N^2$ hydrogens (e.g., formamidine compounds having Structure FA2). However, in some instances it may be desirable to have $N^2$-phosphinyl formamidine compounds having a non-hydrogen $R^3$ $N^2$ group which is different than the $R^1$ group; e.g., $N^2$-phosphinyl formamidine compounds having Structures NPF1 (where $R^1$ and $R^3$ are different). Two methods of preparing the $N^2$-phosphinyl formamidine compounds having a non-hydrogen $R^3$ $N^2$ group which is different than the $R^1$ group include: a) alkylating a formamidine compound having two $N^2$ hydrogen atoms (e.g., a formamidine compound having Structure FA2) to produce a formamidine compound having Structures FA1 wherein $R^3$ is an non-hydrogen group and converting the formamidine compound to an $N^2$-phosphinyl formamidine compound (e.g., $N^2$-phosphinyl formamidine compounds having Structure NPF1) utilizing methods described herein and b) alkylating an $N^2$-phosphinyl formamidine compound having an $N^2$ hydrogen atom (e.g., an $N^2$-phosphinyl formamidine compound having Structure NPF2).

Alkylation of Formamidine Compounds

In an aspect, a method of alkylating a formamidine compound can comprise: a) contacting a first formamidine compound having an $N^2$ hydrogen atom and a metallic compound capable of abstracting a proton from a —$NH_2$ group or a >NH group; b) forming a metal formamidinate; c) contacting a halogenated compound with the metal formamidinate and d) forming a second formamidine compound. Generally, the metal formamidinate can be formed under conditions capable of forming a metal formamidinate. In an embodiment, the metal formamidinate can be isolated; alternatively, purified; or alternatively, isolated and purified. Generally, the second formamidine compound can be formed under conditions capable of forming a formamidine compound. In an embodiment, the second formamidine compound can be isolated; alternatively, purified; or alternatively, isolated and purified. Methods steps, metallic compounds capable of abstracting a proton from a —$NH_2$ group or a >NH group, and method conditions for preparing metal formamidinates are described herein and can be utilized without limitation to further describe the method for alkylating a formamidine compound.

Generally, the halogenated compound and the metal formamidinate can be combined in a halogenated compound to metal formamidinate equivalent ratio of at least 0.9:1. In some embodiments, the halogenated compound and the metal formamidinate can be combined in a halogenated compound to metal formamidinate equivalent ratio of at least 0.95:1; alternatively, at least 0.975:1; or alternatively, at least 0.99:1. In some embodiments, the halogenated compound and the metal formamidinate can be combined in a halogenated compound to metal formamidinate equivalent ratio ranging from 0.9:1 to 1.25:1; alternatively, ranging from 0.95:1 to 1.20:1; alternatively, ranging from 0.975:1 to 1.15:1; or alternatively, ranging from 0.99:1 to 1.10:1. In other embodiments, the halogenated compound and the metal formamidinate can be combined in a halogenated compound to metal formamidinate equivalent ratio of about 1:1.

In an embodiment, the conditions capable of forming the second formamidine compound can include a reaction temperature of at least 0° C.; alternatively, of at least 5° C.; alternatively, of at least 10° C.; or alternatively, of at least 15° C. In some embodiments, the conditions capable of forming the second formamidine compound can include a reaction temperature ranging from 0° C. to 60° C.; alternatively, ranging from 5° C. to 50° C.; alternatively, ranging from 10° C. to 45° C.; or alternatively, ranging from 15° C. to 40° C. In an embodiment, the conditions capable of forming the second formamidine compound can include a reaction time of at least 5 minutes; alternatively, of at least 10 minutes; alternatively, of at least 15 minutes; or alternatively, of at least 20 minutes. In some embodiments, the conditions capable of forming the second formamidine compound can include a reaction time ranging from 5 minutes to 6 hours; alternatively, ranging from 10 minutes to 5 hours; alternatively, ranging from 15 minutes to 4.5 hours; or alternatively, ranging from 20 minutes to 4 hours.

In an embodiment, the halogenated compound and the metal formamidinate can be contacted in an aprotic solvent. In some embodiments, the halogenated compound and the metal formamidinate can be contacted in a polar aprotic solvent. Aprotic solvents which can be utilized include hydrocarbon solvents and ether solvents. Polar aprotic solvents which can be utilized include ether solvents. Solvents are generally disclosed herein and any general or specific aprotic solvent and/or polar aprotic solvent described herein can be utilized to further describe the method of preparing a formamidine compound comprising contacting a halogenated compound with a metal formamidinate and forming the formamidine compound.

In an embodiment, the second formamidine compound can be utilized without further isolation or purification. In some embodiments, the second formamidine compound can be isolated; alternatively, purified; or alternatively isolated and purified. In an embodiment, wherein the second formamidine compound can be prepared in a solvent (aprotic or polar aprotic), the method to alkylate a formamidine compound can include a step of isolating the second formamidine compound by evaporating the solvent. In an embodiment wherein the second formamidine compound can be prepared in a solvent (aprotic or polar aprotic), the method to alkylate a second formamidine compound can include the step of isolating the second formamidine compound by filtering the solution to remove particulate materials and/or byproducts of the reaction and evaporating the solvent. In embodiments, the method to alkylate a formamidine compound can include a purification step wherein the second formamidine compound can purified by dissolving the second formamidine compound in a solvent and filtering the solution to remove particulate materials and/or byproducts of the reaction. The solvent utilized to purify the second formamidine compound can be the same as the solvent utilized to form the second formamidine compound or it can be different than the solvent utilized to form the second formamidine compound. In some embodiments, the method to alkylate a formamidine compound can include purifying the second formamidine compound by washing the second formamidine compound with a solvent. In other embodiments, the method to alkylate a formamidine compound can include recrystallizing the second formamidine compound.

Generally, evaporation of the solvent can be performed using any suitable method. In some embodiments, the solvent can be evaporated at ambient temperature (15-35° C.—no applied external heat source). In other embodiments, the solvent can be evaporated with gentle heating (e.g., at a temperature ranging from 25° C. to 50° C.). In further embodiments, the solvent can be evaporated at ambient temperature under reduced pressure. In yet other embodiments, the solvent can be evaporated with gentle heating under reduced pressure.

Alkylation of $N^2$-Phosphinyl Formamidine Compounds

In an aspect, a method of alkylating an $N^2$-phosphinyl formamidine compound can comprise: a) contacting an $N^2$-phosphinyl formamidine compound having an $N^2$ hydrogen and a metallic compound capable of abstracting a proton from a —$NH_2$ group or a >NH group; b) forming a metal $N^2$-phosphinyl formamidinate; c) contacting a halogenated compound with the metal $N^2$-phosphinyl formamidinate and d) forming a second $N^2$-phosphinyl formamidine compound. Generally, the metal formamidinate can be formed under conditions capable of forming a metal formamidinate. In an embodiment, the metal $N^2$-phosphinyl formamidinate can be isolated; alternatively, purified; or alternatively, isolated and purified. Generally, the second $N^2$-phosphinyl formamidine compound can be formed under conditions capable of forming the second $N^2$-phosphinyl formamidine compound. In an embodiment, the second $N^2$-phosphinyl formamidine compound can be isolated; alternatively, purified; or alternatively, isolated and purified.

In an embodiment, the $N^2$-phosphinyl formamidine compound having an $N^2$ hydrogen can have Structure NPF2. In an embodiment, the second $N^2$-phosphinyl formamidine compound can have Structure NPF1. $N^2$-phosphinyl formamidine compounds having Structure NPF1 and NPF2 are described herein. These $N^2$-phosphinyl formamidine compounds can be utilized without limitation to further describe the method of alkylating an $N^2$-phosphinyl formamide compound.

In an embodiment, the metallic compound capable of abstracting a proton from a —$NH_2$ group or a >NH group are described herein (e.g., within methods for preparing metal formamidinates). These metallic compounds capable of abstracting a proton from a —$NH_2$ group or a >NH group can be utilized, without limitation, to further describe the method of alkylating an $N^2$-phosphinyl formamidine compound.

Generally, the first $N^2$-phosphinyl formamidine compound and the metallic compound capable of abstracting a proton from a —$NH_2$ group or a >NH group can be combined in an $N^2$-phosphinyl formamidine compound to metallic compound equivalent ratio of at least 0.9:1. In an embodiment, the $N^2$-phosphinyl formamidine compound and the metallic compound capable of abstracting a proton from a —$NH_2$ group or a >NH group can be combined in an $N^2$-phosphinyl formamidine compound to metallic compound equivalent ratio of at least 0.95:1; alternatively, of at least 0.975:1; or alternatively, of at least 0.99:1. In some embodiments, the $N^2$-phosphinyl formamidine compound and the metallic compound capable of abstracting a proton from a —$NH_2$ group or a >NH group can be combined in an $N^2$-phosphinyl formamidine compound and metallic compound equivalent ratio ranging from 0.9:1 to 1.25:1; alternatively, ranging from 0.95:1 to 1.20:1; alternatively, ranging from 0.975:1 to 1.15:1; or alternatively, ranging from 0.99:1 to 1.10:1. In other embodiments, the $N^2$-phosphinyl formamidine compound and the metallic compound capable of abstracting a proton from a —$NH_2$ group or a >NH group can be combined in an $N^2$-phosphinyl formamidine compound to metallic compound equivalent ratio of about 1:1.

In an embodiment, the conditions capable of forming the metal $N^2$-phosphinyl formamidinate can include a temperature of at least −45° C.; alternatively, of at least −30° C.; alternatively, of at least −25° C.; or alternatively, of at least −20° C. In some embodiments, the reaction conditions capable of forming a metal $N^2$-phosphinyl formamidinate can include a temperature ranging from −45° C. to 60° C.; alternatively, ranging from −30° C. to 50° C.; alternatively, ranging from −25° C. to 45° C.; or alternatively, ranging from −20° C. to 40° C.

In some embodiments, the conditions capable of forming the metal $N^2$-phosphinyl formamidinate can include an initial metallic compound capable of abstracting a proton from a —$NH_2$ group or a >NH group and first $N^2$-phosphinyl formamidine contact temperature and a second temperature to form the metal $N^2$-phosphinyl formamidinate. It should be noted the when the conditions capable of forming the metal $N^2$-phosphinyl formamidinate is described as occurring at two temperatures (one for the contact of the metallic compound capable of abstracting a proton from a —$NH_2$ group or a >NH group and the first $N^2$-phosphinyl formamidine and one for the formation of the metal $N^2$-phosphinyl formamidinate) that this description does not exclude the prospect that metal $N^2$-phosphinyl formamidinate can be formed at the contact temperature. The description just relates that, in some embodiments, the metal $N^2$-phosphinyl formamidinate formation can proceed better when the initial contact between the metallic compound capable of abstracting a proton from a —$NH_2$ group or a >NH group and first $N^2$-phosphinyl formamidine compound is performed at one temperature and the formation of the metal $N^2$-phosphinyl formamidinate is completed at a second different temperature.

In an embodiment, the metallic compound capable of abstracting a proton from a —$NH_2$ group or a >NH group and the first $N^2$-phosphinyl formamidine can be contacted at a temperature ranging from −45° C. to 20° C.; alternatively, ranging from −30° C. to 15° C.; alternatively, ranging from −25° C. to 45° C.; or alternatively, ranging from −20° C. to 40° C. In an embodiment, metal $N^2$-phosphinyl formamidinate can be formed at a temperature ranging from 0° C. to 20° C.; alternatively, ranging from 5° C. to 15° C.; alternatively, ranging from 10° C. to 45° C.; or alternatively, ranging from 15° C. to 40° C.

In an embodiment, the conditions capable of forming the metal $N^2$-phosphinyl formamidinate can include a metal $N^2$-phosphinyl formamidinate formation time of at least 5 minutes; alternatively, of at least 10 minutes; alternatively, of at least 15 minutes; or alternatively, of at least 20 minutes.

In some embodiments, the conditions capable of forming the metal $N^2$-phosphinyl formamidinate can include a metal $N^2$-phosphinyl formamidinate formation time ranging from 5 minutes to 6 hours; alternatively, ranging from 10 minutes to 5 hours; alternatively, ranging from 15 minutes to 4.5 hours; or alternatively, ranging from 20 minutes to 4 hours.

In an embodiment, the metallic compound capable of abstracting a proton from a —$NH_2$ group or a >NH group and the $N^2$-phosphinyl formamidine compound can be contacted in an aprotic solvent. In some embodiments, the metallic compound capable of abstracting a proton from a —$NH_2$ group or a >NH group and the $N^2$-phosphinyl formamidine compound can be contacted in a polar aprotic solvent. Aprotic solvents which can be utilized include hydrocarbon solvents and ether solvents. Polar aprotic solvents which can be utilized include ether solvents. Solvents are generally disclosed herein and any general or specific aprotic solvent and/or polar aprotic solvent described herein can be utilized to further describe the method of preparing the metal $N^2$-phosphinyl formamidinate by contacting a metallic compound capable of abstracting a proton from a —$NH_2$ group or a >NH group and an $N^2$-phosphinyl formamidine compound and forming a metal $N^2$-phosphinyl formamidinate.

In an embodiment, the metal $N^2$-phosphinyl formamidinate can be utilized without further isolation or purification. In some embodiments, the metal $N^2$-phosphinyl formamidinate can be isolated; alternatively, purified; or alternatively isolated and purified. In an embodiment, the method can include a step of isolating the metal $N^2$-phosphinyl formamidinate by filtering the metal $N^2$-phosphinyl formamidinate from the solution. In some embodiments, the method can include a step of purifying the metal $N^2$-phosphinyl formamidinate by washing the metal $N^2$-phosphinyl formamidinate with a solvent. Generally, the washing solvent is an aprotic solvent. In other embodiments, the washing solvent can be polar aprotic solvent. In other embodiments, the washing solvent can be a non-polar aprotic solvent.

In an embodiment, the halogenated compound can have Structure HC1. The halogenated compounds which can be utilized to alkylate a formamidine compound (via a reaction with a metal formamidinate) are the same halogenated compounds which can be utilized to alkylate an $N^2$-phosphinyl formamidine compound (via a reaction with a metal $N^2$-phosphinyl formamidinate). These halogenated compounds are disclosed herein and can be utilized, without limitation, to further describe the method to alkylate an $N^2$-phosphinyl formamidine compound.

Generally, the halogenated compound and the metal $N^2$-phosphinyl formamidinate can be combined in a halogenated compound to metal $N^2$-phosphinyl formamidinate equivalent ratio of at least 0.9:1. In some embodiments, the halogenated compound and the metal $N^2$-phosphinyl formamidinate can be combined in a halogenated compound to metal $N^2$-phosphinyl formamidinate equivalent ratio of at least 0.95:1; alternatively, of at least 0.975:1; or alternatively, of at least 0.99:1. In some embodiments, the halogenated compound and the metal $N^2$-phosphinyl formamidinate can be combined in a halogenated compound to metal $N^2$-phosphinyl formamidinate equivalent ratio ranging from 0.9:1 to 1.25:1; alternatively, ranging from 0.95:1 to 1.20:1; alternatively, ranging from 0.975:1 to 1.15:1; or alternatively, ranging from 0.99:1 to 1.10:1. In other embodiments, the halogenated compound and the metal $N^2$-phosphinyl formamidinate can be combined in a halogenated compound to metal $N^2$-phosphinyl formamidinate equivalent ratio of about 1:1.

In an embodiment, conditions capable of forming the second $N^2$-phosphinyl formamidine compound can include a reaction temperature of at least 0° C.; alternatively, of at least 5° C.; alternatively, of at least 10° C.; or alternatively, of at least 15° C. In some embodiments, conditions capable of forming the second $N^2$-phosphinyl formamidine compound can include a reaction temperature ranging from 0° C. to 60° C.; alternatively, ranging from 5° C. to 50° C.; alternatively, ranging from 10° C. to 45° C.; or alternatively, ranging from 15° C. to 40° C. In an embodiment, conditions capable of forming the second $N^2$-phosphinyl formamidine compound can include a reaction time of at least 5 minutes; alternatively, of at least 10 minutes; of at least 15 minutes; or alternatively, of at least 20 minutes. In some embodiments, conditions capable of forming the second $N^2$-phosphinyl formamidine compound can include a reaction time ranging from 5 minutes to 6 hours; alternatively, ranging from 10 minutes to 5 hours; alternatively, ranging from 15 minutes to 4.5 hours; or alternatively, ranging from 20 minutes to 4 hours.

In an embodiment, the halogenated compound and the metal $N^2$-phosphinyl formamidinate can be contacted in an aprotic solvent. In some embodiments, the halogenated compound and the metal $N^2$-phosphinyl formamidinate can be contacted in a polar aprotic solvent. Aprotic solvents which can be utilized include hydrocarbon solvents and ether solvents. Polar aprotic solvents which can be utilized include ether solvents. Solvents are generally disclosed herein and any general or specific aprotic solvent and/or polar aprotic solvent described herein can be utilized to further describe the method of preparing an $N^2$-phosphinyl formamidine compound comprising contacting a halogenated compound with a metal $N^2$-phosphinyl formamidinate and forming the $N^2$-phosphinyl formamidinate.

In an embodiment, the second $N^2$-phosphinyl formamidine compound can be utilized without further isolation or purification. In some embodiments, the second $N^2$-phosphinyl formamidine compound can be isolated; alternatively, purified; or alternatively isolated and purified. In an embodiment, wherein the second $N^2$-phosphinyl formamidine compound is prepared in a solvent (aprotic or polar aprotic), the method to alkylate the $N^2$-phosphinyl formamidine compound can include a step of isolating the second $N^2$-phosphinyl formamidine compound by evaporating the solvent. In an embodiment wherein the second $N^2$-phosphinyl formamidine compound is prepared in a solvent (aprotic or polar aprotic), the method to alkylate an $N^2$-phosphinyl formamidine compound can include the step of isolating the second $N^2$-phosphinyl formamidine compound by filtering the solution to remove particulate materials and/or byproducts of the reaction and evaporating the solvent. In embodiments, the method to alkylate an $N^2$-phosphinyl formamidine compound can include a purification step wherein the second $N^2$-phosphinyl formamidine compound is purified by dissolving the second $N^2$-phosphinyl formamidine compound in a solvent and filtering the solution to remove particulate materials and/or byproducts of the reaction. The solvent utilized to purify the second $N^2$-phosphinyl formamidine compound can be the same as the solvent utilized to form the second $N^2$-phosphinyl formamidine compound or it can be different than the solvent utilized to form the second $N^2$-phosphinyl formamidine compound. In some embodiments, the method to alkylate an $N^2$-phosphinyl formamidine compound can include purifying the second $N^2$-phosphinyl formamidine compound by washing the second $N^2$-phosphinyl formamidine compound with a solvent. In other embodiments, the method to alkylate an $N^2$-phosphinyl formamidine compound can include a recrystallizing the second $N^2$-phosphinyl formamidine compound.

Generally, evaporation of the solvent can be performed using any suitable method. In some embodiments, the solvent can be evaporated at ambient temperature (15-35° C.—no applied external heat source). In other embodiments, the solvent can be evaporated with gentle heating (e.g. at a temperature ranging from 25° C. to 50° C.). In further embodiments, the solvent can be evaporated at ambient temperature under reduced pressure. In yet other embodiments, the solvent can be evaporated with gentle heating under reduced pressure.

In an embodiment, the halogenated compound which can be utilized in the alkylation of the formamidine compounds or in the alkylation of the $N^2$-phosphinyl formamidine compounds can have Structure HC1.

$X^2R^3$     Structure HC1

$X^2$ of Structure HC1 represents a halide. In an embodiment, $X^2$ of the halogenated compound can be fluoride, chloride, bromide, or iodide; alternatively, fluoride; alternatively, chloride; alternatively, bromide; or alternatively, iodide. $R^3$ within halogenated compound Structure HC1 is independently described as a feature of the $N^2$-phosphinyl formamidine compounds having Structure NPF1. Since halogenated compound HC1 is utilized to prepare embodiments of $N^2$-phosphinyl formamidine compounds having Structure NPF1, the $R^3$ description for the $N^2$-phosphinyl formamidine compounds can be utilized without limitation to further describe halogenated compounds having Structure HC1. Halogenated compounds are disclosed herein and can be utilized, without limitation, to further describe the method to alkylate a formamidine compound or in the alkylation of the $N^2$-phosphinyl formamidine compounds.

In an aspect, the halogenated compound having Structure HC1 can be a methylhalide, an ethylhalide, a propylhalide, a butylhalide, a pentylhalide, a hexylhalide, a heptylhalide, an octylhalide, a nonylhalide, a decylhalide, a undecylhalide, a dodecylhalide, a tridecylhalide, a tetradecylhalide, a pentadecylhalide, a hexadecylhalide, a heptadecylhalide, an octadecylhalide, or a nonadecylhalide; or alternatively, a methylhalide, an ethylhalide, a propylhalide, a butylhalide, a pentylhalide, a hexylhalide, a heptylhalide, an octylhalide, a nonylhalide, or a decylhalide. In some embodiments, the halogenated compound having Structure HC1 can be a methylhalide, an ethylhalide, an n-propylhalide, an iso-propylhalide, butylhalide, an iso-butylhalide, a sec-butylhalide, a tert-butylhalide, an n-pentylhalide, an iso-pentylhalide, a sec-pentylhalide, or an neopentylhalide; alternatively, a methylhalide, an ethylhalide, an iso-propylhalide, a tert-butylhalide, or a neopentylhalide; alternatively, a methylhalide; alternatively, an ethylhalide; alternatively, an n-propylhalide; alternatively, an iso-propylhalide; alternatively, a tert-butylhalide; or alternatively, a neopentylhalide.

In an aspect, the halogenated compound having Structure HC1 can be a cyclobutylhalide, a substituted cyclobutylhalide, a cyclopentylhalide, a substituted cyclopentylhalide, a cyclohexylhalide, a substituted cyclohexylhalide, a cycloheptylhalide, a substituted cycloheptylhalide, a cyclooctylhalide, or a substituted cyclooctylhalide. In an embodiment the halide having Structure HC1 can be a cyclopentylhalide, a substituted cyclopentylhalide, a cyclohexylhalide, or a substituted cyclohexylhalide. In other embodiments, the halogenated compound having Structure HC1 can be a cyclopentylhalide or a substituted cyclopentylhalide; or alternatively, a cyclohexylhalide or a substituted cyclohexylhalide. In further embodiments, the halogenated compound having Structure HC1 can be a cyclopentylhalide; alternatively, a substituted cyclopentylhalide; a cyclohexylhalide; or alternatively, a substituted cyclohexylhalide. Substituents and substituents patterns for the $R^1$ cycloalkyl groups are described herein and can be utilized without limitation to further describe the substituted cycloalkylhalides which can be utilized in aspects and embodiments described herein.

In various embodiments, the halogenated compounds which can be utilized can have Structure HC2. $R^{31c}$, $R^{32c}$, $R^{33c}$, $R^{34c}$, and $R^{35c}$ substituents, substituent patterns, and n for the $R^3$ group having

Structure HC2

Structure G5 are described herein and can be utilized without limitation to describe halogenated compound having Structure HC2 which can be utilized in the various aspects and/or embodiments described herein. In an embodiment, $X^2$ of the halogenated compound having Structure HC2 can be fluoride, chloride, bromide, or iodide; alternatively, fluoride; alternatively, chloride; alternatively, bromide; or alternatively, iodide.

In an aspect, the halogenated compound can be a benzylhalide or a substituted benzylhalide. In an embodiment, the halogenated compound can be a benzylhalide; or alternatively, a substituted benzyl halide.

Generally, the method of preparing the formamidine compound, the method of preparing the metal formamidinate, and the $N^2$-phosphinyl formamidine compound can be combined in various embodiments to provide additional methods of forming an $N^2$-phosphinyl formamidine compound having only one $N^2$ hydrogen atom utilizing amines, trihydrocarboxyformates, compounds capable of abstracting a proton from a —$NH_2$ group or a >NH group, alkylating compounds, and phosphine halide. In a non-limiting embodiment, a method of preparing an $N^2$-phosphinyl formamidine compound can comprise, consist essentially of, or consist of: a) contacting an amine and a trihydrocarbylformate; b) forming the formamidine compound; c) contacting the formamidine compound and a metallic compound capable of abstracting a proton from a —$NH_2$ group or a >NH group; d) forming a metal formamidinate; e) contacting the metal formamidinate with a phosphine halide; and f) forming an $N^2$-phosphinyl formamidine compound. In another non-limiting embodiment, a method of preparing an $N^2$-phosphinyl formamidine compound can comprise, consist essentially of, or consist of: a) contacting an amine and a trihydrocarbylformate; b) forming a hydrocarboxymethanimine compound; c) contacting the hydrocarboxymethanimine compound and an ammonium compound; d) forming the formamidine compound; e) contacting the formamidine compound and a metallic compound capable of abstracting a proton from a —$NH_2$ group or a >NH group; 0 forming a metal formamidinate; g) contacting the metal formamidinate with a phosphine halide; and h) forming an $N^2$-phosphinyl formamidine compound. In yet another non-limiting embodiment, a method of preparing an $N^2$-phosphinyl formamidine compound can comprise, consist essentially of, or consist of: a) contacting an amine and a trihydrocarbylformate; b) forming a hydrocarboxymethanimine compound; c) contacting the hydrocarboxymethanimine compound and an ammonium compound; d) forming the formamidine compound; e) contacting the formamidine compound and a metallic compound capable of abstracting a proton from a —$NH_2$ group or a >NH group; f) forming a metal formamidinate; g) contacting the metal formamidinate with a halogenated compound; h) forming a second formamidine compound; i) contacting the second formamidine compound and a metallic compound capable of abstracting a proton from a —$NH_2$ group or a >NH group; j) forming a second metal formamidinate; k) contacting the second metal formamidinate with a phosphine halide; and l) forming an $N^2$-phosphinyl formamidine compound. In a further non-limiting embodiment, a method of preparing an $N^2$-phosphinyl formamidine compound can comprise, consist essentially of, or consist of: a) contacting an amine and a trihydrocarbylformate; b) forming a hydrocarboxymethanimine compound; c) contacting the hydrocarboxymethanimine compound and an ammonium compound; d) forming the formamidine compound; e) contacting the formamidine compound and a metallic compound capable of abstracting a proton from a —$NH_2$ group or a >NH group; 0 forming a metal formamidinate; g) contacting the metal formamidinate with a phosphine halide; h) forming an $N^2$-phosphinyl formamidine compound; i) contacting the $N^2$-phosphinyl formamidine compound and a metallic compound capable of abstracting a proton from a —$NH_2$ group or a >NH group; j) forming a metal $N^2$-phosphinyl formamidinate; k) contacting the metal $N^2$-phosphinyl formamidinate with a halogenated compound; and 1) forming a second $N^2$-phosphinyl formamidine compound. These methods can contain additional steps disclosed herein and/or features (e.g. reagent ratios, formation conditions, among other considerations) are described herein. It should be noted that when additional steps are included in the methods appropriate step identifiers (e.g. 1), 2), etc. . . . , a), b), etc. . . . , or i), ii), etc. . . . ) and compound/solvent identifiers (e.g. first, second, etc. . . . ) can be added and/or modified to indicate individual and/or different steps/compounds/solvents utilized within the preparation of the $N^2$-phosphinyl formamidine compound without detracting from the general disclosure.

Method of Preparing $N^2$-Phosphinyl Formamidine Metal Salt Complexes

In an aspect, this disclosure relates to a method of preparing an $N^2$-phosphinyl formamidine metal salt complex. Generally, the method of preparing the $N^2$-phosphinyl formamidine metal salt complex can comprise: a) contacting a metal salt with an $N^2$-phosphinyl formamidine compound; and b) forming the $N^2$-phosphinyl formamidine metal salt complex. Generally, the $N^2$-phosphinyl formamidine metal salt complex can be formed under conditions capable of forming an $N^2$-phosphinyl formamidine metal salt complex. In some embodiments, the $N^2$-phosphinyl formamidine metal salt complex can be isolated; alternatively purified; or alternatively, isolated and purified.

$N^2$-phosphinyl formamidine compounds are disclosed herein and can be utilized without limitation to further describe the method of preparing an $N^2$-phosphinyl formamidine metal salt complex. Metal salts are disclosed herein and can be utilized without limitation to further describe the method of preparing an $N^2$-phosphinyl formamidine metal salt complex.

Generally, the metal salt and the $N^2$-phosphinyl formamidine compound can be contacted at a metal salt to $N^2$-phosphinyl formamidine compound equivalent ratio of at least 0.9:1. In some embodiments, the metal salt and the $N^2$-phosphinyl formamidine compound can be contacted at a metal salt to $N^2$-phosphinyl formamidine compound equivalent ratio of at least 0.95:1; alternatively, of at least 0.975:1; or alternatively, of at least 0.99:1. In some embodiments, the metal salt and the $N^2$-phosphinyl formamidine compound can be contacted at a metal salt to $N^2$-phosphinyl formamidine compound equivalent ratio ranging from 0.9:1 to 1.25:1; alternatively, ranging from 0.95:1 to 1.20:1; alternatively, ranging from 0.975:1 to 1.15:1; or alternatively, ranging from 0.99:1 to 1.10:1. In other embodiments, the metal salt and the $N^2$-phosphinyl formamidine compound can be contacted at a metal salt to $N^2$-phosphinyl formamidine compound equivalent ratio of about 1:1.

In an embodiment, conditions capable of forming an $N^2$-phosphinyl formamidine metal salt complex can include a contact temperature of at least 0° C.; alternatively, of at least 5° C.; alternatively, of at least 10° C.; or alternatively, of at least 15° C. In some embodiments, conditions capable of forming the $N^2$-phosphinyl formamidine metal salt complex can include a contact temperature ranging from 0° C. to 60° C.; alternatively, ranging from 5° C. to 50° C.; alternatively, ranging from 10° C. to 45° C.; or alternatively, ranging from 15° C. to 40° C. In an embodiment, conditions capable of forming the $N^2$-phosphinyl formamidine metal salt complex can include a contact time of at least 15 minutes; alternatively, of at least 30 minutes; alternatively, of at least 45 minutes; or alternatively, of at least 1 hour. In some embodiments, conditions capable of forming the $N^2$-phosphinyl formamidine metal salt complex can include a contact time ranging from 15 minutes to 36 hours; alternatively, ranging from 30 minutes to 30 hours; alternatively, ranging from 45 minutes to 24 hours; or alternatively, ranging from 1 hour to 18 hours.

In an embodiment, the metal salt and the $N^2$-phosphinyl formamidine compound can be contacted in a solvent. In some embodiments, the metal salt and the $N^2$-phosphinyl formamidine compound can be contacted in a polar solvent. In some embodiments, the solvent is the same as the neutral ligand, Q, within some embodiments of the $N^2$-phosphinyl formamidine metal salt complex. Solvents (general and specific) are generally disclosed herein and can be utilized, without limitation, to further describe the method of preparing the $N^2$-phosphinyl formamidine metal salt complex.

In an embodiment, the $N^2$-phosphinyl formamidine metal salt complex can be utilized without further isolation or purification. In some embodiments, the $N^2$-phosphinyl formamidine metal salt complex can be isolated; alternatively, purified; or alternatively, isolated and purified. In an embodiment, wherein the $N^2$-phosphinyl formamidine metal salt complex is prepared in a solvent, the method to prepare the $N^2$-phosphinyl formamidine metal salt complex can include a step of isolating the $N^2$-phosphinyl formamidine metal salt complex by evaporating the solvent. In an embodiment wherein the $N^2$-phosphinyl formamidine metal salt complex is prepared in a solvent, the method to prepare the $N^2$-phosphinyl formamidine metal salt complex can include the step of isolating the $N^2$-phosphinyl formamidine metal salt complex by filtering the solution to remove particulate materials and/or byproducts of the reaction and evaporating the solvent. In embodiments, the method to prepare the $N^2$-phosphinyl formamidine metal salt complex can include a purification step wherein the $N^2$-phosphinyl formamidine compound is purified by dissolving the $N^2$-phosphinyl formamidine metal salt complex in a solvent and filtering the solution to remove particulate materials and/or byproducts of the reaction. The solvent utilized to purify the $N^2$-phosphinyl formamidine metal salt complex can be the same as the solvent utilized to form the $N^2$-phosphinyl formamidine metal salt complex or it can be different than the solvent utilized to form the $N^2$-phosphinyl formamidine metal salt complex. In some embodiments, the method of preparing the $N^2$-phosphinyl formamidine metal salt complex can include a purification step of isolating the $N^2$-phosphinyl formamidine metal salt complex by washing the $N^2$-phosphinyl formamidine metal salt complex with a solvent. In other embodiments, the method of preparing the $N^2$-phosphinyl formamidine metal salt complex can include a purification step of recrystallizing the $N^2$-phosphinyl formamidine metal salt complex.

Generally, evaporation of the solvent can be performed using any suitable method. In some embodiments, the solvent can be evaporated at ambient temperature (15-35° C.—no applied external heat source). In other embodiments, the solvent can be evaporated with gentle heating (e.g. at a temperature ranging from 25° C. to 50° C.). In further embodiments, the solvent can be evaporated at ambient temperature under reduced pressure. In yet other embodiments, the solvent can be evaporated with gentle heating under reduced pressure.

In an embodiment, the time between the isolation and/or purification of the $N^2$-phosphinyl formamidine metal salt complex and the formation of the catalyst system can have an impact on aspects of the oligomerization (or polymerization) process. In some embodiments, increasing the time between the isolation and/or purification of the $N^2$-phosphinyl formamidine metal salt complex and the formation of the catalyst system can increase the catalytic activity and/or increase the productivity of the catalyst system. In other embodiments, increasing the time between the isolation and/or purification of the $N^2$-phosphinyl formamidine metal salt complex and the formation of the catalyst system can increase the percentage of polymer produced by the catalyst system. Without being limited by theory, it is believed that these effects result from the disassociation of (or alternatively, evaporation of) neutral ligand, Q, from the $N^2$-phosphinyl formamidine metal salt complex and/or from the crystal lattice of the $N^2$-phosphinyl formamidine metal salt complex. Herein "formation of the catalyst system" refers to the point at which the minimal number of catalyst system components are contacted to produce a mixture capable of catalyzing an oligomerization process.

Controlling the time between the isolation and/or purification of the $N^2$-phosphinyl formamidine metal salt complex and the formation of the catalyst system can improve the oligomerization process. For instance, one can increase the activity and/or productivity of the catalyst system by increasing the time between the isolation and/or purification of the $N^2$-phosphinyl formamidine metal salt complex and formation of the catalyst system. Increasing the activity and/or the productivity of the catalyst system can provide increased oligomer product per unit of catalyst system.

However, it may not be possible to increase the time between the isolation and/or purification of the $N^2$-phosphinyl formamidine metal salt complex and formation of the catalyst system indiscriminately. As noted herein, increasing the time between the isolation and/or purification of the $N^2$-phosphinyl formamidine metal salt complex and the formation of the oligomerization catalyst system can increase the percentage of polymer produced by the catalyst system. If the polymer production of the catalyst system utilizing the $N^2$-phosphinyl formamidine metal salt complex increases too much, polymer production can adversely impact the oligomerization process. For example, polymer could adhere to the oligomerization reactor walls or cooling apparatus and cause fouling which can necessitate a reactor shut down to remove the polymer. Consequently, there can be a need to balance increases in catalyst system activity and/or productivity against increased polymer production.

In an embodiment, some of the effects of increasing the time between the isolation and/or purification of the $N^2$-phosphinyl formamidine metal salt complex and the formation of the catalyst system can be reversed by adding neutral ligand to the $N^2$-phosphinyl formamidine metal salt complex. The ability to reverse some of the effects of increasing the time between the isolation and/or purification of the $N^2$-phosphinyl formamidine metal salt complex and the formation of the catalyst system can negate potentially negative effects. Non-limiting examples of negative effects of increasing the time between the isolation and/or purification of the $N^2$-phosphinyl formamidine metal salt complex and the formation of the catalyst system can include 1) prohibiting the ability to use an $N^2$-phosphinyl formamidine metal salt complex by increasing the time between the isolation and/or purification of the $N^2$-phosphinyl formamidine metal salt complex and the formation of the catalyst system to a point wherein the formed catalyst system produces an undesirable quantity of polymer and 2) reducing the need to minimize the time between preparing the $N^2$-phosphinyl formamidine metal salt complex and the preparation of the catalyst system utilizing the $N^2$-phosphinyl formamidine metal salt complex. It should also be noted that the incremental loss of the neutral ligand can impact the catalyst system and its subsequent use in an oligomerization. Consequently, while adding neutral ligand can reverse the effect of neutral ligand loss from the $N^2$-phosphinyl formamidine metal salt complex, process and/or steps can be implemented that can limit the loss of neutral ligand loss from the $N^2$-phosphinyl formamidine metal salt complex as a method to control the effects associated with the neutral ligand loss from the $N^2$-phosphinyl formamidine metal salt complex. For example, the $N^2$-phosphinyl formamidine metal salt complex can be stored in a sealed container (among other methods know to those having ordinary skill in the art) to limit loss of neutral ligand from the $N^2$-phosphinyl formamidine metal salt complex. In an embodiment, the amount of neutral ligand present in the $N^2$-phosphinyl formamidine metal salt complex can be determined using any suitable methodology. In some aspects, the amount of neutral ligand in one or more $N^2$-phosphinyl formamidine metal salt complexes can be determined and/or monitored and the information utilized to determine suitable modifications to the $N^2$-phosphinyl formamidine metal salt complex to produce a user and/or process desired catalytic activity.

However, without being limited by theory, it has also been discovered that too much neutral ligand associated with the $N^2$-phosphinyl formamidine metal salt complex can significantly reduce or eliminate the catalyst system oligomer productivity. Consequently, in some embodiments, precautions to control the amount of neutral ligand provided to the $N^2$-phosphinyl formamidine metal salt complex can be taken. Generally, addition of the neutral ligand to the $N^2$-phosphinyl formamidine metal salt complex can be accomplished by any suitable method. For example, the $N^2$-phosphinyl formamidine metal salt complex can be recrystallized from a solution containing a neutral ligand or the $N^2$-phosphinyl formamidine metal salt complex can be placed in a solvent containing a neutral ligand. Excess neutral ligand can be removed from the $N^2$-phosphinyl formamidine metal salt complex by allowing the solvent to evaporate or by increasing the time between the treatment of the $N^2$-phosphinyl formamidine metal salt complex with the neutral ligand and the formation of the catalyst system.

In an aspect, the isolated and/or purified $N^2$-phosphinyl formamidine metal salt complex can be utilized in catalyst system. Consequently, in an aspect, any process of producing a catalyst system disclosed herein or any oligomerization (or polymerization) process can further comprise a step of aging the $N^2$-phosphinyl formamidine metal salt complex. In another aspect, any process of producing a catalyst system disclosed herein or any oligomerization (or polymerization) process can further comprise a step of treating the $N^2$-phosphinyl formamidine metal salt complex with a neutral ligand; or alternatively, 1) treating the $N^2$-phosphinyl formamidine metal salt complex with a neutral ligand and 2) allowing the treated $N^2$-phosphinyl formamidine metal salt complex to age. In another aspect, any process of producing a catalyst system disclosed herein or any oligomerization (or polymerization) process can further comprise a step of treating an aged $N^2$-phosphinyl formamidine metal salt complex with a neutral ligand; or alternatively, 1) treating the $N^2$-phosphinyl formamidine metal salt complex with a neutral ligand and 2) allowing the treated $N^2$-phosphinyl formamidine metal salt complex to age.

In an aspect, the activity of any catalyst system disclosed herein utilized in any oligomerization (or polymerization) method described herein can be controlled by aging the $N^2$-phosphinyl formamidine metal salt complex. In an aspect, the activity of any catalyst system disclosed herein utilized in any oligomerization (or polymerization) method described herein can be controlled by treating the $N^2$-phosphinyl formamidine metal salt complex with a neutral ligand; or alternatively, 1) treating the $N^2$-phosphinyl formamidine metal salt complex with a neutral ligand and 2) allowing the treated $N^2$-phosphinyl formamidine metal salt complex to age. In an aspect, the activity of any catalyst system disclosed herein utilized in any oligomerization (or polymerization) method described herein can be controlled by treating an aged $N^2$-phosphinyl formamidine metal salt complex with a neutral ligand; or alternatively, 1) treating the $N^2$-phosphinyl formamidine metal salt complex with a neutral ligand and 2) allowing the treated $N^2$-phosphinyl formamidine metal salt complex to age.

The catalytic activity of any catalyst system described herein comprising any $N^2$-phosphinyl formamidine metal salt complex described herein in an oligomerization process can be defined as the grams of oligomer product (or liquid oligomer product, or any other defined portion of the oligomerization product) produced per gram of metal of the metal salt in the $N^2$-phosphinyl formamidine metal salt complex utilized. In an embodiment, the catalyst system activity of any catalyst system described herein comprising any $N^2$-phosphinyl formamidine metal salt complex described herein can be increased by utilizing an aged $N^2$-phosphinyl formamidine metal salt complex. This activity increase can be described as a percentage increase in the catalyst system activity and can be related to the activity of the catalyst system prepared using a fresh $N^2$-phosphinyl formamidine metal salt complex, $a_0$. Generally, a fresh $N^2$-phosphinyl formamidine metal salt complex is one which has been utilized to prepare a catalyst system within 7 days of its isolation and/or purification. It should be noted, a fresh $N^2$-phosphinyl formamidine metal salt complex does not contain excess neutral ligand which can give an inactive catalyst system (i.e. a catalyst system that produces less than 500 grams oligomer per gram metal of metal salt in the $N^2$-phosphinyl formamidine metal salt complex). The activity of the catalyst system based upon an aged $N^2$-phosphinyl formamidine metal salt complex can be denoted $a_x$.

In an embodiment, the $N^2$-phosphinyl formamidine metal salt complex can be aged for a maximum of 730 days; alternatively, 550 days; alternatively, 450 days; alternatively, 365 days; alternatively, 330 days; alternatively, 300 days; alternatively, 270 days; alternatively, 240 days; alternatively, 210 days; or alternatively, 180 days. In some embodiments, the $N^2$-phosphinyl formamidine metal salt complex can be aged for a minimum of 1 day; alternatively, 3 days; alternatively, 7 days; alternatively, 14 days; alternatively, 28 days. In other embodiments, the $N^2$-phosphinyl formamidine metal salt complex can be aged from any minimum aging time provided herein to any maximum aging time provided herein. In a non-limiting embodiment, the $N^2$-phosphinyl formamidine metal salt complex can be aged can be aged from 1 day to 730 days; alternatively, from 3 days to 550 days; alternatively, from 3 days to 330 days; or alternatively, from 7 days to 180 days. Other aging times are readily apparent from the present disclosure.

In an embodiment, aging the $N^2$-phosphinyl formamidine metal salt complex (for any time period described herein) can increase the activity of any catalyst system described herein utilizing any $N^2$-phosphinyl formamidine metal salt complex described herein by a minimum of 10%; alternatively, by at least 20%; alternatively, by at least 30%; alternatively, by at least 40%; or alternatively, by at least 50%. In other embodiments, aging the $N^2$-phosphinyl formamidine metal salt complex (for any time period described herein) can increase the activity of any catalyst system described herein utilizing any $N^2$-phosphinyl formamidine metal salt complex described herein by a maximum of 1500%; alternatively, 1000%; alternatively, 750%; alternatively, 600%; or alternatively, 500% In some embodiments, aging the $N^2$-phosphinyl formamidine metal salt complex (for any time period described herein) can increase the activity of any catalyst system described herein utilizing any $N^2$-phosphinyl formamidine metal salt complex described herein from any minimum value described herein to any maximum value described herein. In a non-limiting example, aging the $N^2$-phosphinyl formamidine metal salt complex (for any time period described herein) can increase the activity of any catalyst system described herein utilizing any $N^2$-phosphinyl formamidine metal salt complex described herein from 10% to 1500%; alternatively, from 20% to 1000%; alternatively, from 30% to 750%; alternatively, from 40% to 600%; or alternatively, from 50% to 500%. Other catalyst system activity ranges are readily apparent from the present disclosure.

In an embodiment, aging the $N^2$-phosphinyl formamidine metal salt complex (for any time period described herein) for any catalyst system described herein utilizing any $N^2$-phosphinyl formamidine metal salt complex described herein can provide a catalyst system which can produce any defined percentage of polymer described herein. In an embodiment, aging the $N^2$-phosphinyl formamidine metal salt complex (for any time period described herein) for any catalyst system described herein utilizing any $N^2$-phosphinyl formamidine metal salt complex described herein can provide a catalyst system which can produce less than 5 weight percent polymer; alternatively, less than 2 weight % polymer; alternatively, less than 1.5 weight % polymer; alternatively, less than 1 weight % polymer; alternatively, less than 0.75 weight % polymer; alternatively, less than 0.5 weight % polymer; alternatively, less than 0.4 weight % polymer; alternatively, less than 0.3 weight % polymer; alternatively, less than 0.2 weight % polymer; or alternatively, equal to or less than 0.1 weight % polymer. Generally, the basis for weight percent polymer is based upon all products of the oligomerization (excluding unreacted monomer, catalyst system components, solvent, and other non-oligomerization products).

In some embodiments, any catalyst system described herein utilizing an aged $N^2$-phosphinyl formamidine metal salt complex can have a combination of any increased activity described herein and any amount of polymer described herein. The catalyst system described herein utilizing an aged $N^2$-phosphinyl formamidine metal salt complex can further be described utilizing, individually or in any combination, any other catalyst system feature or oligomerization product feature described herein.

In an embodiment, a calibration curve can be produced depicting oligomerization catalytic activity and/or polymer production of any catalyst system described herein comprising any $N^2$-phosphinyl formamidine metal salt complex described herein in response to aging the $N^2$-phosphinyl formamidine metal salt complex. In some embodiments, a calibration curve (for catalyst activity and/or polymer production) can be depicted as a function of the period of $N^2$-phosphinyl formamidine metal salt complex age in order to derive a predictive equation. The calibration curve or predictive equation relating catalyst system activity and/or polymer production in response to $N^2$-phosphinyl formamidine metal salt complex age can be utilized to adjust one or more user and/or process parameters based upon the interpolation or extrapolation the calibration curve and/or the predictive equation. It is contemplated that in some aspects, the extent to which $a_x$ increases with respect to $a_0$ can fall outside the instantly disclosed ranges and can be larger than would be expected based on the presently disclosed values depending on conditions under which the $N^2$-phosphinyl formamidine metal salt complex is aged. For example, the $N^2$-phosphinyl formamidine metal salt complex can be subjected to aging for time periods that are 5 to 10 times longer than those presently recited or under conditions of elevated temperature and/or reduced pressure. The effects of aging the $N^2$-phosphinyl formamidine metal salt complex under such conditions can be subject to the herein mentioned analysis to provide predictive information that can lead one to conditions under which aging the $N^2$-phosphinyl formamidine metal salt complex can increase catalyst system activity using an aged $N^2$-phosphinyl formamidine metal salt complexes outside of the recited numerical ranges. It is contemplated that given the benefits of this disclosure and using routine experimentation one having ordinary skill in the art can modify the methodologies disclosed herein to alter the oligomerization catalytic system activity using an aged $N^2$-phosphinyl formamidine metal salt complexes to a desired value or range. Such modifications fall within the scope of this disclosure.

In an embodiment, contacting of the $N^2$-phosphinyl formamidine metal salt complex (aged or otherwise) with a neutral ligand can be carried out using any suitable molar ratio of neutral ligand to $N^2$-phosphinyl formamidine metal salt. In an embodiment, the molar ratio of neutral ligand to $N^2$-phosphinyl formamidine metal salt complex can be at least 0.2:1; alternatively, at least 0.3:1; alternatively, at least 0.4:1; or alternatively, at least 0.5:1. In an embodiment, the molar ratio of neutral ligand to $N^2$-phosphinyl formamidine metal salt complex can be from 0.2:1 to 10,000:1; alternatively, 0.3:1 to 8,000:1; alternatively, from 0.4:1 to 6,000:1; or alternatively, from 0.5:1 to 5,000:1. In an embodiment, contact of the $N^2$-phosphinyl formamidine metal salt complex can occur in a solvent consisting essentially of the neutral ligand; or alternatively, in a solvent comprising, or consisting essentially of, the neutral ligand and a non-complexing solvent.

When the $N^2$-phosphinyl formamidine metal salt complex is contacted with a solvent consisting essentially of the neutral ligand, the molar ratio of neutral ligand to $N^2$-phosphinyl formamidine metal salt can be any molar ratio of neutral ligand to $N^2$-phosphinyl formamidine metal salt complex disclosed herein. In other embodiments wherein the $N^2$-phosphinyl formamidine metal salt complex is contacted with a solvent consisting essentially of the neutral ligand, the molar ratio of neutral ligand to $N^2$-phosphinyl formamidine metal salt complex can be at least 5:1; alternatively, at least 7.5:1; alternatively, at least 10:1; alternatively, at least 10:1; alternatively, at least 15:1; alternatively, 5:1; alternatively, range from 7.5:1 to 10,000:1; alternatively, range from 10:1 to 8,000:1; alternatively, range from 10:1 to 6,000:1; or alternatively, range from 15:1 to 5,000:1.

When the $N^2$-phosphinyl formamidine metal salt complex is contacted with a solvent comprising, or consisting essentially of, the neutral ligand and a non-complexing solvent, the molar ratio of neutral ligand to $N^2$-phosphinyl formamidine metal salt can be any molar ratio of neutral ligand to $N^2$-phosphinyl formamidine metal salt disclosed herein. In other embodiments wherein the $N^2$-phosphinyl formamidine metal salt complex is contacted with a solvent comprising, or consisting essentially of, the neutral ligand and a non-complexing solvent, the maximum molar ratio of neutral ligand to $N^2$-phosphinyl formamidine metal salt can be 500:1; alternatively, 300:1; alternatively, 200:1; alternatively, 100:1; alternatively, from 0.2:1 to 500:1; alternatively, from 0.3:1 to 300:1; alternatively, from 0.4:1 to 200:1; or alternatively, 0.5:1 to 100:1. In some embodiments, wherein the $N^2$-phosphinyl formamidine metal salt complex is contacted with a solvent comprising, or consisting essentially of, the neutral ligand and a non-complexing solvent, the volumetric ratio of neutral ligand to non-complexing solvent can range from 1:1 to 10,000:1; alternatively, range from 5:1 to 8,000:1; alternatively, range from 7.5:1 to 6,000:1; or alternatively, range from 10:1 to 5,000:1.

In an embodiment, the neutral ligand can be any neutral ligand disclosed herein. In some embodiments, the neutral ligand utilized to treat the $N^2$-phosphinyl formamidine metal salt complex can be the same or the same as the neutral ligand of the $N^2$-phosphinyl formamidine metal salt complex; or alternatively, the neutral ligand utilized to treat the $N^2$-phosphinyl formamidine metal salt complex can be different from the neutral ligand of the $N^2$-phosphinyl formamidine metal salt complex. In an embodiment, the non-complexing solvent utilized in an embodiment comprising, or consisting essentially of, a neutral ligand and a non-complexing solvent can be a hydrocarbon or a halogenated hydrocarbon; alternatively, a hydrocarbon or a halogenated hydrocarbon. Hydrocarbon and halogenated hydrocarbon solvents (general and specific) are disclosed herein and can be utilized, without limitation, to further describe any aspect and/or embodiment utilizing a solvent comprising, or consisting essentially of, a neutral ligand and a non-complexing solvent.

In an embodiment, the $N^2$-phosphinyl formamidine metal salt complex can be aged (whether or not it has been treated with a neutral ligand) utilizing any suitable methodology. In some embodiments, the $N^2$-phosphinyl formamidine metal salt complex can be aged (whether or not it has been treated with a neutral ligand) at ambient temperature (15-35° C.—no applied external heat source); or alternatively, at ambient temperature under an inert atmosphere. In other embodiments, the $N^2$-phosphinyl formamidine metal salt complex can be aged (whether or not it has been treated with a neutral ligand) with gentle heating (e.g., at a temperature ranging from 25° C. to 50° C.); alternatively, under reduced pressure; alternatively ambient temperature under reduced pressure; or alternatively, with gentle heating under reduced pressure.

In an embodiment, the aged $N^2$-phosphinyl formamidine metal salt complex, the neutral ligand treated $N^2$-phosphinyl formamidine metal salt complex, or the neutral ligand treated and aged $N^2$-phosphinyl formamidine metal salt complex can be utilized in a catalyst system, utilized in a process to prepare a catalyst system, and/or a method to oligomerize (or polymerize) an olefin. Generally, the steps of aging the $N^2$-phosphinyl formamidine metal salt complex, the steps of treating the $N^2$-phosphinyl formamidine metal salt complex with a neutral ligand, and/or treating the $N^2$-phosphinyl formamidine metal salt complex with a neutral ligand and aging the neutral ligand treated the $N^2$-phosphinyl formamidine metal salt complex can be utilized, without limitation, to further describe the catalyst system, the method of preparing the catalyst system, and/or the method to oligomerize (or polymerize) an olefin.

In an aspect, the step(s) for preparing the formamidine compound can be incorporated into the preparation of the $N^2$-phosphinyl formamidine metal salt complex. When the steps are combined, appropriate step identifiers (e.g. 1), 2), etc. . . . , a), b), etc. . . . , or i), ii), etc. . . . ) and compound/solvent identifiers (e.g. first, second, etc . . . ) can be added to indicate individual and/or different steps/compounds/solvents utilized within the preparation of the $N^2$-phosphinyl formamidine metal salt complex without detracting from the general disclosure.

Methods of Oligomerizing or Polymerizing Olefins.

In an embodiment, the process can comprise: a) contacting an olefin and a catalyst system; and b) forming an oligomer product. In some embodiments, the process can comprise, a) contacting an olefin, hydrogen, and a catalyst system; and b) forming an oligomer product. In an embodiment, the process can comprise: a) contacting an olefin and a catalyst system; and b) forming a polymer product. In some embodiments, the process can comprise a) contacting an olefin, hydrogen, and a catalyst system and b) forming a polymer product. The catalyst system, olefin, and features of the oligomer or polymer product are independently described herein and can be utilized, without limitation, to further describe the process. In an embodiment, the catalyst system can be prepared in a first solvent. In an embodiment, the olefin, catalyst system, and optionally hydrogen, can be contacted in a second solvent. Generally, a solvent in which the catalyst system can be prepared and the solvent in which the olefin and catalyst system can be contacted can be the same; or alternatively, can be different.

In an embodiment, the process can comprise: a) forming a catalyst system mixture comprising an $N^2$-phosphinyl formamidine metal salt complex and a metal alkyl; b) contacting the catalyst system mixture with an olefin; and c) forming an oligomer product. In an embodiment, the process can comprise: a) forming a catalyst system mixture comprising an $N^2$-phosphinyl formamidine metal salt complex and a metal alkyl; b) contacting the catalyst system mixture with an olefin; and c) forming an oligomer product. In some embodiments, the step of contacting the catalyst system mixture with the olefin can be a step of contacting the catalyst system mixture with an olefin and hydrogen. In some embodiments, the catalyst system mixture can further comprise a solvent (e.g. a first solvent). In some embodiments, the catalyst system mixture and olefin can be contacted in a solvent (e.g. a second solvent when the catalyst system is prepared in a solvent). In an embodiment, the process can comprise: a) forming a catalyst system mixture comprising, or consisting essentially of, an $N^2$-phosphinyl formamidine metal salt complex, a metal alkyl, and a first solvent; b) contacting the catalyst system mixture with an olefin and a second solvent; and c) forming an oligomer product. In an embodiment, the process can comprise: a) forming a catalyst system mixture comprising, or consisting essentially of, an $N^2$-phosphinyl formamidine metal salt complex, a metal alkyl, and a first solvent; b) contacting the catalyst system mixture with an olefin and a second solvent; and c) forming a polymer product. In some embodiments, the step of contacting the catalyst system mixture with the olefin and the second solvent can be a step of contacting the catalyst system mixture with an olefin, a second solvent, and hydrogen. The $N^2$-phosphinyl formamidine metal salt complex, metal alkyl, olefin, solvents, and features of the oligomer or polymer product are independently described herein (among other catalyst system and oligomerization or polymerization features) and can be utilized, without limitation to further describe the oligomerization or polymerization process. In some embodiments, the first and second solvent can be the same; or alternatively, the first and second solvent can be different. In some embodiments, the metal alkyl can comprise, or consist essentially of, an aluminoxane. Ratios for the metal of the $N^2$-phosphinyl formamidine metal salt complex to the metal of the metal alkyl are independently provided herein (among other catalyst system and oligomerization or polymerization features) and can be utilized without limitation to further describe the oligomerization or polymerization process.

In an embodiment, the process can comprise: a) forming a catalyst system mixture comprising an $N^2$-phosphinyl formamidine compound, a metal salt, and a metal alkyl; b) contacting the catalyst system mixture with an olefin; and c) forming an oligomer product. In an embodiment, the process can comprise: a) forming a catalyst system mixture comprising an $N^2$-phosphinyl formamidine compound, a metal salt, and a metal alkyl; b) contacting the catalyst system mixture with an olefin; and c) forming a polymer product. In some embodiments, the step of contacting the catalyst system mixture with the olefin can be a step of contacting the catalyst system mixture with an olefin and hydrogen. In some embodiments, the catalyst system mixture can further comprise a solvent (e.g. a first solvent). In some embodiments, the catalyst system mixture and olefin can be contacted in a solvent (e.g. a second solvent when the catalyst system is prepared in a solvent). In an embodiment, the process can comprise: a) forming a catalyst system mixture comprising, or consisting essentially of, an $N^2$-phosphinyl formamidine compound, a metal salt, a metal alkyl, and a first solvent; b) contacting the catalyst system mixture with an olefin and a second solvent; and c) forming an oligomer product. In an embodiment, the process can comprise: a) forming a catalyst system mixture comprising, or consisting essentially of an $N^2$-phosphinyl formamidine compound, a metal salt, a metal alkyl, and a first solvent; b) contacting the catalyst system mixture with an olefin and a second solvent; and c) forming a polymer product. In some embodiments, the step of contacting the catalyst mixture with the olefin and the second solvent can be a step of contacting the catalyst system mixture with an olefin, a second solvent, and hydrogen. In some embodiments, the first and second solvent can be the same; or alternatively, the first and second can be different. The $N^2$-phosphinyl formamidine compound, metal salt, metal alkyl, olefin, solvents, and features of the oligomer or polymer product are independently described herein (among other catalyst system and oligomerization or polymerization features) and can be utilized, without limitation to further describe the oligomerization or polymerization process. In some embodiments, the first and second solvent can be the same; or alternatively, the first and second solvent can be different. In some embodiments, the metal alkyl can comprise, or consist essentially of, an aluminoxane. The $N^2$-phosphinyl formamidine compound, metal salt, metal alkyl, olefin, solvents, and features of the oligomer or polymer product are independently described herein (among other catalyst system and oligomerization or polymerization features) and can be utilized, without limitation to further describe the process. Ratios for the $N^2$-phosphinyl formamidine compound to metal salt and ratios for the metal of the metal alkyl to metal of the metal salt are independently provided herein (among other catalyst system and oligomerization or polymerization features) and can be utilized without limitation to further describe the process.

In an embodiment, a solvent utilized with the catalyst system, a mixture comprising an $N^2$-phosphinyl formamidine metal salt complex, a mixture comprising an $N^2$-phosphinyl formamidine metal salt complex and a metal alkyl, a composition comprising an $N^2$-phosphinyl formamidine compound and a metal salt, or a composition comprising an $N^2$-phosphinyl formamidine compound, a metal salt, and a metal alkyl can be a hydrocarbon solvent, a halogenated hydrocarbon solvent, or any combination thereof; alternatively, a hydrocarbon solvent; or alternatively, a halogenated hydrocarbon solvent. In some embodiments, a solvent utilized with a mixture comprising an $N^2$-phosphinyl formamidine metal salt complex, a mixture comprising an $N^2$-phosphinyl formamidine metal salt complex and a metal alkyl, a composition comprising an $N^2$-phosphinyl formamidine compound and a metal salt, or a composition comprising an $N^2$-phosphinyl formamidine compound, a metal salt, and a metal alkyl can be an aliphatic hydrocarbon solvent, a halogenated aliphatic hydrocarbon solvent, an aromatic hydrocarbon solvent, a halogenated aromatic solvent, or any combination thereof; alternatively, an aliphatic hydrocarbon solvent, a halogenated aliphatic hydrocarbon solvent, or any combination thereof; alternatively, an aromatic hydrocarbon solvent, a halogenated aromatic solvent, or any combination thereof; alternatively, an aliphatic hydrocarbon solvent; alternatively, a halogenated aliphatic hydrocarbon solvent; alternatively, an aromatic hydrocarbon solvent; or alternatively, a halogenated aromatic solvent. General and specific hydrocarbon solvents, halogenated hydrocarbon solvents, aliphatic hydrocarbon solvents, halogenated aliphatic hydrocarbon solvents, aromatic hydrocarbon solvents, and halogenated aromatic solvents are described herein and can be utilized without limitation to further describe the process(es) described herein.

In an embodiment, a solvent utilized in any mixture including the olefin or utilized to form the oligomer product or polymer product can be hydrocarbon solvent, a halogenated hydrocarbon solvent, or any combination thereof; alternatively, a hydrocarbon solvent; or alternatively, a halogenated hydrocarbon solvent. In some embodiments, a solvent utilized in any mixture including the olefin or utilized to form the oligomer product or polymer product can be an aliphatic hydrocarbon solvent, a halogenated aliphatic hydrocarbon solvent, an aromatic hydrocarbon solvent, a halogenated aromatic solvent, or any combination thereof; alternatively, an aliphatic hydrocarbon solvent, a halogenated aliphatic hydrocarbon solvent, or any combination thereof; alternatively, an aromatic hydrocarbon solvent, a halogenated aromatic solvent, or any combination thereof; alternatively, an aliphatic hydrocarbon solvent; alternatively, a halogenated aliphatic hydrocarbon solvent; alternatively, an aromatic hydrocarbon solvent; or alternatively, a halogenated aromatic solvent. General and specific hydrocarbon solvents, halogenated hydrocarbon solvents, aliphatic hydrocarbon solvents, halogenated aliphatic hydrocarbon solvents, aromatic hydrocarbon solvents, and halogenated aromatic solvents are described herein and can be utilized without limitation to further describe the processes disclosed herein.

In some embodiments, the solvent utilized with the catalyst system, a mixture comprising an $N^2$-phosphinyl formamidine metal salt complex, a mixture comprising an $N^2$-phosphinyl formamidine metal salt complex and a metal alkyl, a composition comprising an $N^2$-phosphinyl formamidine compound and a metal salt, or a composition comprising an $N^2$-phosphinyl formamidine compound, a metal salt, and a metal alkyl and the solvent utilized in any mixture including the olefin or utilized to form the oligomer product or polymer product can be the same; or alternatively can be different. In an embodiment, the solvent utilized with the catalyst system, a mixture comprising an $N^2$-phosphinyl formamidine metal salt complex, a mixture comprising an $N^2$-phosphinyl formamidine metal salt complex and a metal alkyl, a composition comprising an $N^2$-phosphinyl formamidine compound and a metal salt, or a composition comprising an $N^2$-phosphinyl formamidine compound, a metal salt, and a metal alkyl and the solvent utilized in any mixture including the olefin or utilized to form the oligomer product or polymer product has a boiling point which allows for its easy separation (e.g. by distillation) from the oligomer product or polymer product.

Generally, the olefin which can be oligomerized or polymerized can comprise, or consist essentially of, a $C_2$ to $C_{30}$ olefin; alternatively, a $C_2$ to $C_{16}$ olefin; or alternatively, a $C_2$ to $C_{10}$ olefin. In an embodiment, the olefin can be an alpha olefin; alternatively, a linear alpha olefin; or alternatively a normal alpha olefin. In an embodiment, the olefin can comprise, or consist essentially of, ethylene, propylene, or a combination thereof; alternatively ethylene; or alternatively, propylene. When the olefin consists essentially of ethylene, the oligomerization process can be an ethylene oligomerization process or an ethylene polymerization process.

In an aspect, the process can be a trimerization process; alternatively, a tetramerization process; or alternatively, a trimerization and tetramerization process. When the olefin is ethylene, the process can be an ethylene trimerization process; alternatively, an ethylene tetramerization process; or alternatively, an ethylene trimerization and tetramerization process. When the process is an ethylene trimerization process, the oligomer product can comprise hexene; or alternatively, 1-hexene. When the process is an ethylene tetramerization process, the oligomer product can comprise octene; or alternatively, 1-octene. When the process is an ethylene trimerization and tetramerization process, the oligomer product can comprise hexene and octene; or alternatively, 1-hexene and 1-octene.

Unless otherwise specified, the terms contacted, combined, and "in the presence of" refer to any addition sequence, order, or concentration for contacting or combining two or more components of the oligomerization process. Combining or contacting of oligomerization components, according to the various methods described herein can occur in one or more contact zones under suitable contact conditions such as temperature, pressure, contact time, flow rates, etc. . . . . The contact zone can be disposed in a vessel (e.g. a storage tank, tote, container, mixing vessel, reactor, etc.), a length of pipe (e.g. a tee, inlet, injection port, or header for combining component feed lines into a common line), or any other suitable apparatus for bringing the components into contact. The processes can be carried out in a batch or continuous process as is suitable for a given embodiment.

In an embodiment, the process can be a continuous process carried out in one or more reactors. In some embodiments, the continuous reactor can comprise a circular recycle reactor, a tubular reactor, a continuous stirred tank reactor (CSTR), or combinations thereof. In other embodiments, the continuous reactor can be a recycle reactor; alternatively, a tubular reactor; or alternatively, a continuous stirred tank reactor (CSTR). In other embodiments, the continuous reactor can be employed in the form of different types of continuous reactors in combination, and in various arrangements.

In an embodiment, the oligomer product or polymer product can be formed under suitable reaction conditions such as reaction temperatures, reaction pressure, and/or reaction times. Reaction temperatures, reaction pressure, and/or reaction times can be impacted by a number of factors such as the metal complex stability, metal complex activity, cocatalyst identity, cocatalyst activity, desired product distribution, and/or desired product purity among other factors.

Generally, the processes can be performed using any $N^2$-phosphinyl formamidine compound, metal salt, or $N^2$-phosphinyl formamidine metal salt complex concentration that forms the desired oligomer product or polymer product. In an embodiment, the concentration of the $N^2$-phosphinyl formamidine compound, metal salt, or $N^2$-phosphinyl formamidine metal salt complex can be at least $1 \times 10^{-6}$ equivalents/liter; alternatively, at least $1 \times 10^{-5}$ equivalents/liter; or alternatively, at least $5 \times 10^{-4}$ equivalents/liter. In other embodiments, the concentration of the diphosphino aminyl complexed metal compound can range from $1 \times 10^{-6}$ equivalents/liter to 1 equivalents/liter; alternatively, range from $1 \times 10^{-5}$ equivalents/liter to $5 \times 10^{-1}$ equivalents/liter; or alternatively, range from $5 \times 10^{-4}$ equivalents/liter to $1 \times 10^{-1}$ equivalents/liter.

Generally, the reaction pressure can be any pressure that facilitates the oligomerization or polymerization of the olefin. In an embodiment, the reaction pressure of the process can be any reaction pressure required to produce the desired oligomer product or polymer product. In some embodiments, the pressure can be greater than or equal to 0 psig (0 KPa); alternatively, greater than or equal to 50 psig (344 KPa); alternatively, greater than or equal to 100 psig (689 KPa); or alternatively, greater than or equal to 150 psig (1.0 MPa). In other embodiments, the pressure can range from 0 psig (0 KPa) to 5,000 psig (34.5 MPa); alternatively, 50 psig (344 KPa) to 4,000 psig (27.6 MPa); alternatively, 100 psig (689 KPa) to 3,000 psig (20.9 MPa); or alternatively, 150 psig (1.0 MPa) to 2,000 psig (13.8 MPa). In embodiments wherein the monomer is a gas (e.g. ethylene), the pressure can be carried out under a monomer gas pressure. When the monomer is ethylene, the reaction pressure can be the monomer ethylene pressure. In some embodiments, the ethylene pressure can be greater than or equal to 0 psig (0 KPa); alternatively, greater than or equal to 50 psig (344 KPa); alternatively, greater than or equal to 100 psig (689 KPa); or alternatively, greater than or equal to 150 psig (1.0 MPa). In other embodiments, the ethylene pressure can range from 0 psig (0 KPa) to 5,000 psig (34.5 MPa); alternatively, 50 psig (344 KPa) to 4,000 psig (27.6 MPa); alternatively, 100 psig (689 KPa) to 3,000 psig (20.9 MPa); or alternatively, 150 psig (1.0 MPa) to 2,000 psig (13.8 MPa). In some cases when ethylene is the monomer, inert gases can form a portion of the total reaction pressure. In the cases where inert gases form a portion of the reaction pressure, the previously stated ethylene pressures can be the applicable ethylene partial pressures of the polymerization or oligomerization. In the situation where the monomer provides all or a portion of the oligomerization or polymerization pressure, the reaction system pressure can decrease as the gaseous monomer is consumed. In this situation, additional gaseous monomer and/or inert gas can be added to maintain a desired pressure or monomer partial pressure. In some embodiments, additional gaseous monomer can be added at a set rate (e.g. for a continuous flow reactor), or at different rates (e.g. to maintain a set system pressure in a batch reactor). In other embodiments, the pressure can be allowed to decrease without adding any additional gaseous monomer and/or inert gas.

In embodiments wherein hydrogen is utilized, hydrogen can be added in any amount that produces the desired effect. In some embodiments, the hydrogen partial pressure can be greater than or equal to 1 psig (kPa); alternatively, greater than or equal to 5 psig (34 kPa); alternatively, greater than or equal to 10 psig (69 kPa); or alternatively, greater than or equal to 15 psig (100 kPa). In other embodiments, the hydrogen partial pressure can range from 1 psig (6.9 kPa) to 500 psig (3.5 MPa); alternatively, 5 psig (34 kPa) to 400 psig (2.8 MPa); alternatively, 10 psig (69 kPa) to 300 psig (2.1 MPa); or alternatively, 15 psig (100 kPa) to 200 psig (1.4 MPa).

In an embodiment, a condition to form an oligomer product or polymer product can include an oligomerization temperature or polymerization temperature. Generally, the oligomerization temperature or polymerization temperature can be any temperature which forms the desired oligomer product or polymer product. In an embodiment, the temperature can be at least 0° C.; alternatively, at least 10° C.; alternatively, at least 20° C.; or alternatively, at least 30° C. In some embodiments, the temperature can range from 0° C. to 200° C.; alternatively, range from 10° C. to 160° C.; alternatively, ranges from 20° C. to 140° C.; or alternatively, ranges from 30° C. to 120° C.

In an embodiment, a condition to form an oligomer product or polymer product can include an oligomerization time or polymerization time. Generally, the time can be any time that produces the desired quantity of oligomer product or polymer product; or alternatively, provides a desired catalyst system productivity; or alternatively, provides a desired conversion of monomer. In some embodiments, the time can range from 1 minute to 5 hours; alternatively, ranges from 5 minutes to 2.5 hours; alternatively, ranges from 10 minutes to 2 hours; or alternatively, ranges from 15 minutes to 1.5 hours. In an embodiment, the oligomerization or polymerization can have a single pass olefin conversion of ethylene of at least 30 wt. % percent; alternatively, at least 35 wt. % percent; alternatively, at least 40 wt. % percent; or alternatively, at least 45 wt. % percent. When the olefin is ethylene, the olefin conversion is ethylene conversion.

In an aspect, the catalyst system productivity for the oligomerization process can be any catalyst system productivity which provides a desirable oligomer product. In an embodiment, the minimum catalyst system productivity can be $1 \times 10^3$ grams (g) oligomer product/mmol transition metal of the $N^2$-phosphinyl formamidine metal salt complex; alternatively, $5 \times 10^3$ g oligomer product/mmol $N^2$-phosphinyl formamidine metal salt complex; alternatively, $1 \times 10^4$ g oligomer product/mmol $N^2$-phosphinyl formamidine metal salt complex; alternatively, $5 \times 10^4$ g oligomer product/mmol $N^2$-phosphinyl formamidine metal salt complex; alternatively, $1 \times 10^5$ g oligomer product/mmol $N^2$-phosphinyl formamidine metal salt complex; or alternatively, $5 \times 10^3$ g oligomer product/mmol $N^2$-phosphinyl formamidine metal salt complex. In an embodiment, the maximum catalyst system productivity can be $1 \times 10^8$ g oligomer product/$N^2$-phosphinyl formamidine metal salt complex; alternatively, $5 \times 10^7$ g oligomer product/mmol $N^2$-phosphinyl formamidine metal salt complex; alternatively, $1 \times 10^7$ g oligomer product/mmol $N^2$-phosphinyl formamidine metal salt complex; alternatively, $5 \times 10^6$ g oligomer product/mmol $N^2$-phosphinyl formamidine metal salt complex; or alternatively, $1 \times 10^6$ g oligomer product/$N^2$-phosphinyl formamidine metal salt complex. In some embodiments, the catalyst system productivity can range from any minimum catalyst system productivity described herein to any maximum catalyst system productivity described herein. For example, in some non-limiting embodiments, the catalyst system productivity can range from $1 \times 10^3$ to $1 \times 10^8$ g oligomer product/$N^2$-phosphinyl formamidine metal salt complex; alternatively, $5 \times 10^3$ to $5 \times 10^7$ g oligomer product/$N^2$-phosphinyl formamidine metal salt complex; alternatively, $5 \times 10^4$ to $5 \times 10^7$ g oligomer product/mmol $N^2$-phosphinyl formamidine metal salt complex; or alternatively, $1 \times 10^5$ to $1 \times 10^7$ g oligomer product/mmol $N^2$-phosphinyl formamidine metal salt complex. Other catalyst system productivities are readily apparent from the present disclosure. When a specific transition metal of the transition metal complex is utilized, the catalyst system productivity can be provided utilizing the specific transition metal; for example when a chromium $N^2$-phosphinyl formamidine metal salt complex is utilized, the catalyst system productivity can be provided in units of g oligomer product/mmol Cr.

In an aspect, the catalyst system activity for the oligomerization process can be any catalyst system activity which provides a desirable amount of oligomer product under some user and/or process desired condition. Catalyst activity is defined as grams of a product produced per gram of metal of the metal compound (or metal complex) utilized in the catalyst system over the first 30 minutes of an oligomerization or polymerization reaction beginning from the time when the complete catalyst system is contacted with the olefin. Catalyst system activity can be stated in terms of various products of an oligomerization or polymerization. For example, in an ethylene oligomerization process utilizing a catalyst system comprising an iron complex as the metal complex, the catalyst system activities which can be utilized include (g ethylene oligomer)/(g Fe), and (total oligomer product)/(g Fe), among other activities.

In an embodiment, the process can produce an oligomer product comprising a trimer, a tetramer, or mixtures thereof. In some embodiments, when the olefin is ethylene the process can be an ethylene oligomerization process. In some embodiments, the process can produce an alpha olefin having at least four carbon atoms. In an embodiment, the ethylene oligomerization process can produce an oligomer product comprising an ethylene trimer (e.g. hexene, or alternatively, 1-hexene), an ethylene tetramer (e.g. octene, or alternatively, 1-octene), or a combination thereof; alternatively, hexene; alternatively, octene; alternatively hexene and octene. In other embodiments, the ethylene oligomerization process can produce an oligomer product comprising 1-hexene, 1-octene, or a combination thereof; alternatively, 1-hexene; alternatively, 1-octene; alternatively 1-hexene and 1-octene. In an embodiment, when the olefin is ethylene and the process can produce an alpha olefin (e.g. 1-hexene, 1-octene, or a combination thereof), the process can be an alpha olefin production process.

In an embodiment where the monomer comprises, consists essentially of, or consists of ethylene, the process can produce an oligomer product comprising a liquid product comprising at least 60 wt. % $C_6$ and $C_8$ olefins. In some embodiments where the monomer comprises, consists essentially of, or consists of ethylene, the oligomer product can comprise a liquid product comprising at least 70 wt. % $C_6$ and $C_8$ olefins; alternatively, at least 75 wt. % $C_6$ and $C_8$ olefins; alternatively, at least 80 wt. % $C_6$ and $C_8$ olefins; alternatively, at least 85 wt. % $C_6$ and $C_8$ olefins; or alternatively, at least 90 wt. % $C_6$ and $C_8$ olefins. In other embodiments where the monomer comprises, consists essentially of, or consists of ethylene, the process can produce an oligomer product comprising a liquid product having from 60 to 99.9 wt. % of $C_6$ and $C_8$ olefins; alternatively, from 70 to 99.8 wt. % $C_6$ and $C_8$ olefins; alternatively, from 75 to 99.7 wt. % $C_6$ and $C_3$ olefins; or alternatively, from 80 to 99.6 wt. % $C_6$ and $C_3$ olefins. Throughout this application, a liquid product refers to the oligomer product having from 4 to 18 carbon atoms.

In an embodiment where the monomer comprises, consists essentially of, or consists of ethylene, the process can produce an oligomer product comprising a liquid product comprising at least 60 wt. % $C_6$ olefins. In some embodiments where the monomer comprises, consists essentially of, or consists of ethylene, the process can produce an oligomer product comprising a liquid product comprising at least 70 wt. % $C_6$ olefins; alternatively, at least 75 wt. % $C_6$ olefins; alternatively, at least 80 wt. % $C_6$ olefins; alternatively, at least 85 wt. % $C_6$ olefins; or alternatively, at least 90 wt. % $C_6$ olefins. In other embodiments where the monomer comprises, consists essentially of, or consists of ethylene, the process can produce an oligomer product comprising a liquid product having from 60 to 99.9 wt. % of $C_6$ olefins; alternatively, from 70 to 99.8 wt. % $C_6$ olefins; alternatively, from 75 to 99.7 wt. % $C_6$ olefins; or alternatively, from 80 to 99.6 wt. % $C_6$ olefins; or alternatively, 85 to 99.6 wt. % $C_6$ olefins.

In an embodiment, the $C_6$ olefin product produced by the ethylene oligomerization process can comprise at least 85 wt. % 1-hexene. In some embodiments, the $C_6$ olefin product produced by the ethylene oligomerization process can comprise at least 87.5 wt. % 1-hexene; alternatively, at least 90 wt. % 1-hexene; alternatively, at least 92.5 wt. % 1-hexene; alternatively, at least 95 wt. % 1-hexene; alternatively, at least 97 wt. % 1-hexene; or alternatively at least 98 wt. % 1-hexene. In other embodiments, the $C_6$ olefin product produced by the ethylene oligomerization process can comprise from 85 to 99.9 wt. % 1-hexene; alternatively, from 87.5 to 99.9 wt. % 1-hexene; alternatively, from 90 to 99.9 wt. % 1-hexene; alternatively, from 92.5 to 99.9 wt. % 1-hexene; alternatively, from 95 to 99.9 wt. % 1-hexene; alternatively, from 97 to 99.9 wt. % 1-hexene; or alternatively, from 98 to 99.9 wt. % 1-hexene.

In an embodiment, the $C_8$ olefin product produced by the ethylene oligomerization process can comprise at least 85 wt. % 1-octene. In some embodiments, the $C_8$ olefin product produced by the ethylene oligomerization process can comprise at least 87.5 wt. % 1-octene; alternatively, at least 90 wt. % 1-octene; alternatively, at least 92.5 wt. % 1-octene; alternatively, at least 95 wt. % 1-octene; alternatively, at least 97 wt. % 1-octene; or alternatively at least 98 wt. % 1-octene. In other embodiments, the $C_8$ olefin product produced by the ethylene oligomerization process can comprise from 85 to 99.9 wt. % 1-octene; alternatively, from 87.5 to 99.9 wt. % 1-octene; alternatively, from 90 to 99.9 wt. % 1-octene; alternatively, from 92.5 to 99.9 wt. % 1-octene; alternatively, from 95 to 99.9 wt. % 1-octene; alternatively, from 97 to 99.9 wt. % 1-octene; or alternatively, from 98 to 99.9 wt. % 1-octene.

In some aspects and/or embodiments, aging the catalyst system (or catalyst system mixture) before contacting the catalyst system (or catalyst system mixture) with the olefin to be oligomerized and/or polymerized can improve aspects of the oligomerization and/or polymerization processes; or alternatively, aging the catalyst system (or a catalyst system mixture) in the substantial absence of an olefin can improve aspects of the oligomerization and/or polymerization processes. In some embodiments, aging the catalyst system can increase the productivity of the catalyst system. In other embodiments, aging the catalyst system can decrease the amount of polymer produced in an oligomerization process. In some oligomerization process aspects and/or embodiments, aging the catalyst system can increase the productivity of the catalyst system; alternatively, can decrease the amount of polymer produced in an oligomerization process; or alternatively, can increase the productivity of the catalyst system and decrease the amount of polymer produced in the oligomerization. In regards to aging the catalyst system (or catalyst system mixture) in the substantial absence of an olefin, this can be taken to mean that the catalyst system (or catalyst system mixture) can contain less than 1,000 ppm olefin, by weight. In some embodiments, the catalyst system (or catalyst system mixture) can contain less than 500 ppm, by weight, olefin; alternatively, 250 ppm, by weight, olefin; alternatively, 100 ppm, by weight, olefin; alternatively, 75 ppm, by weight, olefin; alternatively, 50 ppm, by weight, olefin; alternatively, 25 ppm, by weight, olefin; alternatively, 15 ppm, by weight, olefin; alternatively, 10 ppm, by weight, olefin; alternatively, 5 ppm, by weight, olefin; alternatively, 2.5 ppm, by weight, olefin; or alternatively, 1 ppm, by weight, olefin.

The catalyst system aging impacts can be utilized to provide positive benefits to an oligomerization and/or polymerization process. For example, increasing the activity and/or the productivity of the catalyst system can provide increased oligomer product per unit of catalyst system among other benefits. Additionally, in an oligomerization process, the decrease in polymer produced in an oligomerization process upon aging the catalyst system can reduce the amount of polymer which could adhere to the oligomerization reactor walls or cooling apparatus. The reduction in polymer produced in the oligomerization process can reduce the need to shut down a reactor to remove the polymer which can cause fouling.

In any aspect and/or embodiment, a mixture comprising the $N^2$-phosphinyl formamidine compound, the metal salt, and the metal alkyl can be allowed to age for a period of time prior to contacting the mixture with the olefin to be oligomerized or polymerized (or a mixture comprising the olefin to be oligomerized or polymerized); or alternatively, a catalyst system comprising the $N^2$-phosphinyl formamidine compound, the metal salt, and the metal alkyl can be allowed to age for a period of time in the substantial absence of (or in the absence of) the olefin to be oligomerized or polymerized (or a mixture comprising the olefin to be oligomerized or polymerized). In some embodiments, a mixture (or catalyst system) comprising an $N^2$-phosphinyl formamidine compound, a metal salt, and a metal alkyl can further comprise a solvent.

In any aspect and/or embodiment, a mixture comprising the $N^2$-phosphinyl formamidine metal salt complex and the metal alkyl can be allowed to age for a period of time prior to contacting the mixture with the olefin to be oligomerized or polymerized (or a mixture comprising the olefin to be oligomerized or polymerized); or alternatively, a catalyst system comprising the $N^2$-phosphinyl formamidine metal salt complex and the metal alkyl can be allowed to age for a period of time in the substantial absence of (or in the absence of) the olefin to be oligomerized or polymerized (or a mixture comprising the olefin to be oligomerized or polymerized). In some embodiments, a mixture (or catalyst system) comprising an $N^2$-phosphinyl formamidine metal salt complex and a metal alkyl can further comprise a solvent.

In a non-limiting embodiment, the oligomerization process can comprise: a) preparing a catalyst system; b) allowing the catalyst system to age for a period of time; c) contacting the aged catalyst system with an olefin; and d) forming an oligomer product. In some non-limiting embodiments, the oligomerization process can comprise, a) preparing a catalyst system; b) allowing the catalyst system to age for a period of time; c) contacting the aged catalyst system with an olefin and hydrogen; and d) forming an oligomer product. The catalyst system, olefin, and other features of the oligomer product are independently described herein and can be utilized, without limitation to further describe the oligomerization process. In some embodiments, the catalyst system can be prepared in a first solvent. In an embodiment, the olefin, aged catalyst system, and optionally hydrogen, can be contacted in a second solvent. Generally, a solvent in which the catalyst system can be prepared and the solvent in which the olefin and aged catalyst system can be contacted can be the same; or alternatively, can be different. The catalyst system, features of aging the catalyst system, features of the oligomer product, and features of the impacts of aging the catalyst system, among other features, are independently described herein and can be utilized, without limitation to further describe the oligomerization process. In some embodiments, the first and second solvent can be the same; or alternatively, the first and second solvent can be different.

In a non-limiting embodiment, the process can comprise: a) forming a catalyst system mixture comprising an $N^2$-phosphinyl formamidine metal salt complex and metal alkyl; b) aging the catalyst system mixture; c) contacting the aged catalyst system mixture with an olefin; and c) forming an oligomer product. In another non-limiting embodiment, the process can comprise: a) forming a catalyst system mixture comprising an $N^2$-phosphinyl formamidine compound, a metal salt, and a metal alkyl; b) aging the catalyst system mixture; c) contacting the aged catalyst system mixture with an olefin; and c) forming an oligomer product. In some embodiments the catalyst system mixture can further comprise a solvent (e.g. a first solvent). In some embodiments, the catalyst system mixture and the olefin can be contacted in a solvent (e.g. a second solvent). In yet another non-limiting embodiment, the process can comprise: a) forming a catalyst system mixture comprising (or consisting essentially of) an $N^2$-phosphinyl formamidine metal salt complex, a metal alkyl, and a first solvent; b) aging the catalyst system mixture; c) contacting the aged catalyst system mixture with an olefin and a second solvent; and c) forming an oligomer product. In a further non-limiting embodiment, the process can comprise: a) forming a catalyst system mixture comprising (or consisting essentially of) an $N^2$-phosphinyl formamidine compound, a metal salt, a metal alkyl, and a first solvent; b) aging the catalyst system mixture; c) contacting the aged catalyst system mixture with an olefin and a second solvent; and d) forming an oligomer product.

In some embodiments, the step of contacting the aged catalyst system mixture with the olefin (and optionally a solvent—e.g. second solvent) can be a step of contacting the aged catalyst system mixture with an olefin and hydrogen. The $N^2$-phosphinyl formamidine compound, metal salt, the metal salt, $N^2$-phosphinyl formamidine metal salt complex, the metal alkyl, the olefin, solvents, features of aging the catalyst system, features of the oligomer product, and features of the impacts of aging the catalyst system, among other features, are independently described herein and can be utilized, without limitation to further describe the oligomerization process. In some embodiments, the first and second solvent can be the same; or alternatively, the first and second solvent can be different. In some embodiments, the metal alkyl can comprise an aluminoxane. Ratios for the $N^2$-phosphinyl formamidine compound to metal salt and ratios for the metal of the metal alkyl to metal of the metal salt or the metal of the $N^2$-phosphinyl formamidine metal salt complex, among other features, are independently described herein and can be utilized without limitation to further describe the oligomerization process.

In an embodiment, the catalyst system (or catalyst system mixture) can be aged for up 14 days; alternatively, up to 10 days; alternatively, up to 8 days; alternatively, up to 6 days; alternatively, up to 4 days; alternatively, up to 3 days; alternatively, up to 48 hours; alternatively, up to 36 hours; alternatively, up to 24 hours; alternatively, up to 18 hours; alternatively, up to 10 hours; alternatively, up to 8 hours; alternatively, up to 6 hours; alternatively, up to 4 hours; or alternatively, up to 3 hours. In an embodiment, the catalyst system (or catalyst system mixture) can be aged for at least 15 minutes; alternatively, at least 20 minutes; or alternatively, at least 30 minutes. In an embodiment, the catalyst system (or catalyst system mixture) can be aged for a time ranging from any catalyst system (or catalyst system mixture) aging minimum time disclosed herein to any catalyst system (or catalyst system mixture) aging maximum time disclosed herein. In some non-limiting embodiments, the catalyst system (or catalyst system mixture) can be aged for from 15 minutes to 14 days; alternatively, from 15 minutes to 10 days; alternatively, from 15 minutes to 8 days; alternatively, from 15 minutes to 6 days; alternatively, from 20 minutes to 4 days; alternatively, from 20 minutes to 3 days; alternatively, from 30 minutes to 48 hours; alternatively, from 30 minutes to 36 hours; alternatively, from 30 minutes to 24 hours; alternatively, from 30 minutes to 18 hours; alternatively, from 30 minutes to 10 hours; alternatively, from 30 minutes to 8 hours; alternatively, from 30 minutes to 6 hours; alternatively, from 30 minutes to 4 hours; or alternatively, from 30 minutes to 3 hours. Other catalyst system (or catalyst system mixture) aging ranges are readily apparent from the present disclosure.

In an embodiment, any catalyst system (or catalyst system mixture) described herein can be aged at ambient temperature (15° C.-35° C.—no external heat source). In other embodiments, any catalyst system (or catalyst system mixture) described herein can be aged at a temperature from 10° C. to 130° C.; alternatively, from 25° C. to 100° C.; alternatively, from 30° C. to 80° C.; or alternatively, from 35° C. to 60° C. In some embodiments, any catalyst system (or catalyst system mixture) described herein can be aged under an inert atmosphere. Generally, one will recognize that the temperature at which the catalyst system (or catalyst system mixture) is aged can have an impact upon the time necessary to achieve an increase in catalyst system activity and/or reduction in catalyst system polymer production. In any aspect or embodiment, the catalyst system (or catalyst system mixture) can be aged at a combination of any catalyst system aging time described herein and any catalyst system aging temperature described herein.

The catalytic activity (oligomerization or polymerization) of any catalyst system (or catalyst system mixture) described herein comprising i) an $N^2$-phosphinyl formamidine metal salt complex and metal alkyl or ii) an $N^2$-phosphinyl formamidine compound, metal salt described herein can be defined as the grams of product produced per gram of metal of the metal salt in the $N^2$-phosphinyl formamidine metal salt complex and is measured over 30 minutes beginning from when complete catalyst system is contacted with the olefin. In an embodiment, any aged catalyst system (or catalyst system mixture) described herein (using any aging time period described herein and/or any aging temperature described herein) can increase the oligomerization or polymerization activity of the catalyst system by at least 10%; alternatively, at least 20%; alternatively, at least 30%; alternatively, at least 40%; or alternatively, at least 50%. In some embodiments, any aged catalyst system (or catalyst system mixture) described herein (using any aging time period described herein and/or any aging temperature described herein) can increase the oligomerization or polymerization activity of the catalyst system from 10 to 1000%; alternatively, from 20 to 800%; alternatively, from 30 to 600%; alternatively, from 40 to 500%; or alternatively, from 50 to 400%. Generally, the increase in the oligomerization or polymerization catalyst system activity as a result of aging the catalyst system (or catalyst system mixture) is determined by comparing the activity of the aged catalyst system to the activity of a catalyst system that has been aged for less than 12 minutes.

In an embodiment, any aged catalyst system (or catalyst system mixture) described herein (using any aging time period described herein and/or any aging temperature described herein) can provide a catalyst system (or catalyst system mixture) which can produce a reduction in the percentage of polymer produced in an oligomerization process described herein. In some embodiments, aging of any catalyst system (or catalyst system mixture) described herein can reduce (using any aging time period described herein and/or any aging temperature described herein) the amount of polymer produced in an oligomerization process by at least 5%; alternatively, at least 7.5%; alternatively, at least 10%; alternatively, at least 12.5%; or alternatively, at least 15%. In some embodiments, aging of any catalyst system described herein (for any time period described herein) can reduce the amount of polymer produced in an oligomerization by at least 20%; alternatively at least 25%; alternatively, at least 30%; or alternatively, at least 35%. Generally, the decrease in the catalyst system polymer production in an oligomerization process as a result of aging can be determined by comparing the polymer production of the aged catalyst system to the polymer production of a catalyst system that has been aged for less than 12 minutes.

In an embodiment, aging a catalyst system described herein can have a combination of any increase in activity described herein and any reduction in the amount of polymer produced described herein.

In an embodiment, a calibration curve can be produced depicting the catalyst system activity and/or polymer production of any aged catalyst system described herein in response to one or more catalyst system aging variables (e.g. time, temperature, or time and temperature). In some embodiments the calibration curve can be depicted graphically as a function of a catalyst system aging variable(s) (e.g. time, temperature, or time and temperature); or alternatively, the calibration curve can be depicted as a predictive equation of a catalyst system aging variable(s) (e.g. time, temperature, or time and temperature). The graphical representation and/or predictive equation relating catalyst system activity and/or polymer production in response to catalyst aging can be utilized to adjust one or more user and/or process parameters based upon the interpolation or extrapolation of the graphical representation or predictive equation. It is contemplated that in some aspects, the extent to which the catalyst system activity increases and/or the extent to which there is a decrease in polymer production with respect to catalyst system aging can fall outside the instantly disclosed ranges and can be larger than would be expected based on the presently disclosed values depending on the conditions under which the catalyst system is aged. For example, the catalyst system can be subjected to aging for time periods that are longer than those presently recited and/or at temperatures greater than those presently recited. The effects of aging the catalyst system under such conditions can be subject to the herein mentioned analysis to provide predictive information that can lead one to conditions under which catalyst system aging increases the catalyst system activity and/or reduces the polymer production in the oligomerization process to within some user and/or process desired range of values. It is contemplated that given the benefits of this disclosure and using routine experimentation one having ordinary skill in the art can modify the methodologies disclosed herein to alter the catalytic system activity of a disclosed catalyst system and/or reduce the amount of polymer produced in an oligomerization process to a desired value or range. Such modifications fall within the scope of this disclosure.

In embodiments where the metal alkyl is an alumoxane, aging the alumoxane can improve aspects of the oligomerization. For example, aging the alumoxane prior to its contact with the other components of the catalyst system can decrease the amount of polymer produced in an oligomerization process. In some embodiments, any process for preparing the catalyst system described herein and/or any oligomerization process described herein can include a step (or steps) for aging an alumoxane.

In an embodiment, the alumoxane can be aged at ambient temperature (15° C.-35° C.—no external heat source) for at least 60 days; at least 120 days; at least 180 days; or at least 240 days. In some embodiments, the alumoxane can be aged for up to 1,440 days; up to 1080 days; up to 900 days; or up to 720 days. In some embodiments, the alumoxane can be aged at ambient temperature (15° C.-35° C.—no external heat source) from 60 days to 1,440 days; from 120 days to 1080 days; from 180 to 900 days; or from 240 days to 720 days. In some embodiments, the alumoxane can be aged under an inert atmosphere.

The aging of the alumoxane can be performed at elevated temperature. Generally, aging the alumoxane at elevated temperature can reduce the time need to achieve the benefits observed when the aged alumoxane is utilized in a catalyst system. In an embodiment, the alumoxane can be aged at a temperature from 30° C. to 100° C., from 35° C. to 90° C., from 40° C. to 80° C., or from 45° C. to 70° C. In an embodiment, the alumoxane can be aged at any elevated temperature disclosed herein for at least 12 hours, at least 18 hours, at least 24 hours, or at least 36 hours. In an embodiment, the alumoxane can be aged at any elevated temperature disclosed herein for up to 360 days, up to 270 days, up to 180 days, or up to 90 days. In some embodiments, the alumoxane can be aged under an inert atmosphere. In an embodiment, the alumoxane can be aged for a time ranging from any alumoxane aging minimum time disclosed herein to any alumoxane aging maximum time disclosed herein. In some embodiments, the alumoxane can be aged at any elevated temperature disclosed herein and any alumoxane aging time disclosed herein. In a non-limiting example the alumoxane can be aged at any elevated temperature disclosed herein for a time ranging from 12 hours to 360 days; alternatively, from 12 hours to 270 days; alternatively, from 18 hours to 270 days; or alternatively, from 18 hours to 180 days. Other alumoxane aging times at elevated temperatures are readily apparent from the present disclosure. In some embodiments, the alumoxane can be aged under an inert atmosphere.

In an embodiment, aging of the alumoxane can provide a reduction in the percentage of polymer produced by the oligomerization process. In some embodiments, aging of the alumoxane can reduce the amount of polymer produced in an oligomerization process by at least 20%; at least 40%; at least 60%; at least 70%; at least 75%; at least 80%; or at least 85%.

In an embodiment, a calibration curve can be produced depicting the catalyst system polymer production utilizing an aged alumoxane in response to one or more alumoxane aging variables (e.g. time, temperature, or time and temperature). In some embodiments the alumoxane aging calibration curve can be depicted graphically as a function of an alumoxane aging variable(s) (e.g. time, temperature, or time and temperature); alternatively, the calibration curve can be depicted as a predictive equation of an alumoxane aging variable(s) (e.g. time, temperature, or time and temperature). The graphical representation and/or predictive equation relating catalyst system polymer production in response to alumoxane aging can be utilized to adjust one or more user and/or process parameters based upon the interpolation or extrapolation of the graphical representation or predictive equation. It is contemplated that in some aspects, the extent to which the polymer production of the catalyst system decreases with respect to alumoxane aging can fall outside the instantly disclosed ranges and can be larger than would be expected based on the presently disclosed values depending on the conditions under which alumoxane is aged. For example, the catalyst system can be subjected to aging for time periods that are longer than those presently recited and/or at temperatures greater than those presently recited. The effects of alumoxane aging under such conditions can be subject to the herein mentioned analysis to provide predictive information that can lead to conditions under which alumoxane aging can reduce the polymer production of the catalyst system in the oligomerization process. It is contemplated that given the benefits of this disclosure and using routine experimentation one having ordinary skill in the art can modify the methodologies disclosed herein to alter a reduction in the amount of polymer produced in an oligomerization process. Such modifications fall within the scope of this disclosure.

Substituent Groups

Various aspect and embodiments described herein refer to non-hydrogen substituents such as halogen (or halo, halide), hydrocarbyl, hydrocarboxy, alkyl, and/or alkoxy substituents. In an embodiment, each non-hydrogen substituent of any aspect or embodiment calling for a sub stituent can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In an embodiment, each hydrocarbyl substituent can be a $C_1$ to $C_{10}$ hydrocarbyl group; or alternatively, a $C_1$ to $C_5$ hydrocarbyl group. In an embodiment, each hydrocarboxy substituent of any aspect or embodiment calling for a substituent can be a $C_1$ to $C_{10}$ hydrocarboxy group; or alternatively, a $C_1$ to $C_5$ hydrocarboxy group. In an embodiment, any halide substituent of any aspect or embodiment calling for a substituent can be a fluoride, chloride, bromide, or iodide; alternatively, a fluoride or chloride. In some embodiments, any halide substituent of any aspect or embodiment calling for a substituent can be a fluoride; alternatively, a chloride; alternatively, a bromide; or alternatively, an iodide.

In an embodiment, any hydrocarbyl substituent of any aspect or embodiment calling for a substituent can be an alkyl group, an aryl group, or an aralkyl group; alternatively, an alkyl group; alternatively, an aryl group; or alternatively, an aralkyl group. In an embodiment, any alkyl substituent of any aspect or embodiment calling for a substituent can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, any aryl substituent of any aspect or embodiment calling for a substituent can be phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an embodiment, any aralkyl substituent of any aspect or embodiment calling for a substituent can be benzyl group or an ethylphenyl group (2-phenyleth-1-yl or 1-phenyleth-1-yl); alternatively, a benzyl group; alternatively, an ethylphenyl group; alternatively a 2-phenyleth-1-yl group; or alternatively, a 1-phenyleth-1-yl group.

In an embodiment, any hydrocarboxy substituent of any aspect or embodiment calling for a substituent can be an alkoxy group, an aryloxy group, or an aralkoxy group; alternatively, an alkoxy group; alternatively, an aryloxy group, or an aralkoxy group. In an embodiment, any alkoxy substituent of any aspect or embodiment calling for a substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aryloxy substituent of any aspect or embodiment calling for a substituent can be phenoxy group, a toloxy group, a xyloxy group, or a 2,4,6-trimethylphenoxy group; alternatively, a phenoxy group; alternatively, a toloxy group, alternatively, a xyloxy group; or alternatively, a 2,4,6-trimethylphenoxy group. In an embodiment, any aralkoxy substituent of any aspect or embodiment calling for a substituent can be benzoxy group.

Solvents

The methods described herein can utilize one or more solvents. Solvents which can be utilized in aspects of the present disclosure include without limitation water, hydrocarbons, halogenated hydrocarbons, ethers, carbonates, esters, ketones, aldehydes, alcohols, nitriles and combinations thereof. In some embodiments, an aspect of the present disclosure can call for a polar solvent. Polar solvents which can be utilized include without limitation water ethers, carbonates, esters, ketones, aldehydes, alcohols, nitriles, and mixtures thereof; alternatively, ethers, carbonates, esters, ketones, aldehydes, alcohols, nitriles, and mixtures thereof; alternatively, ethers, esters, ketones, alcohols, nitriles, and mixtures thereof; alternatively, ethers; alternatively, carbonates; alternatively, esters; alternatively, ketones; alternatively, aldehydes; alternatively, alcohols; or alternatively, nitriles. In some embodiments, an aspect of the present disclosure can call for an aprotic polar solvent. Aprotic polar solvents which can be utilized include without limitation ethers, esters, ketones, aldehydes, nitriles, and mixtures thereof; alternatively, ethers, nitriles and mixtures thereof; alternatively, esters, ketones, aldehydes and mixtures thereof; alternatively, ethers; alternatively, esters; alternatively, ketones; alternatively, aldehydes; or alternatively, nitriles. In other embodiments, an aspect of the disclosure can call for a non-polar solvent. Non-polar solvents include without limitation hydrocarbons, halogenated hydrocarbons, or mixtures thereof; alternatively, a hydrocarbon; or alternatively, a halogenated hydrocarbon. In another embodiment, an aspect of the present disclosure can call for a solvent that is substantially unreactive with a metal alkyl. Solvents which are unreactive with a metal alkyl include without limitation ethers, hydrocarbons, and mixtures thereof; alternatively, ethers; or alternatively, hydrocarbons.

Hydrocarbons and halogenated hydrocarbon can include, for example, aliphatic hydrocarbons, aromatic hydrocarbons, petroleum distillates, halogenated aliphatic hydrocarbons, halogenated aromatic hydrocarbons, or combinations thereof; alternatively aliphatic hydrocarbons, aromatic hydrocarbons, halogenated aliphatic hydrocarbons, halogenated aromatic hydrocarbons, and combinations thereof; alternatively, aliphatic hydrocarbons; alternatively, aromatic hydrocarbons; alternatively, halogenated aliphatic hydrocarbons; or alternatively, halogenated aromatic hydrocarbons. Aliphatic hydrocarbons which can be useful as a solvent include $C_3$ to $C_{20}$ aliphatic hydrocarbons; alternatively $C_4$ to $C_{15}$ aliphatic hydrocarbons; or alternatively, $C_5$ to $C_{10}$ aliphatic hydrocarbons. The aliphatic hydrocarbons can be cyclic or acyclic and/or can be linear or branched, unless otherwise specified. Non-limiting examples of suitable acyclic aliphatic hydrocarbon solvents that can be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, propane; alternatively, iso-butane; alternatively, n-butane; alternatively, butane (n-butane or a mixture of linear and branched $C_4$ acyclic aliphatic hydrocarbons); alternatively, pentane (n-pentane or a mixture of linear and branched $C_5$ acyclic aliphatic hydrocarbons); alternatively, hexane (n-hexane or mixture of linear and branched $C_6$ acyclic aliphatic hydrocarbons); alternatively, heptane (n-heptane or mixture of linear and branched $C_7$ acyclic aliphatic hydrocarbons); or alternatively, octane (n-octane or a mixture of linear and branched $C_8$ acyclic aliphatic hydrocarbons). Non-limiting examples of suitable cyclic aliphatic hydrocarbon solvents include cyclohexane, methyl cyclohexane; alternatively cyclohexane; or alternatively, methylcyclohexane. Aromatic hydrocarbons which can be useful as a solvent include $C_6$ to $C_{20}$ aromatic hydrocarbons; or alternatively, $C_6$ to $C_{10}$ aromatic hydrocarbons. Non-limiting examples of suitable aromatic hydrocarbons that can be utilized singly or in any combination include benzene, toluene, xylene (including ortho-xylene, meta-xylene, para-xylene, or mixtures thereof), and ethylbenzene, or combinations thereof; alternatively, benzene; alternatively, toluene; alternatively, xylene (including ortho-xylene, meta-xylene, para-xylene or mixtures thereof); or alternatively, ethylbenzene.

Halogenated aliphatic hydrocarbons which can be useful as a solvent include $C_1$ to $C_{15}$ halogenated aliphatic hydrocarbons; alternatively, $C_1$ to $C_{10}$ halogenated aliphatic hydrocarbons; or alternatively, $C_1$ to $C_5$ halogenated aliphatic hydrocarbons. The halogenated aliphatic hydrocarbons can be cyclic or acyclic and/or can be linear or branched, unless otherwise specified. Non-limiting examples of suitable halogenated aliphatic hydrocarbons which can be utilized include methylene chloride, chloroform, carbon tetrachloride, dichloroethane, trichloroethane, and combinations thereof; alternatively, methylene chloride, chloroform, dichloroethane, trichloroethane, and combinations thereof; alternatively, methylene chloride; alternatively, chloroform; alternatively, carbon tetrachloride; alternatively, dichloroethane; or alternatively, trichloroethane. Halogenated aromatic hydrocarbons which can be useful as a solvent include $C_6$ to $C_{20}$ halogenated aromatic hydrocarbons; or alternatively, $C_6$ to $C_{10}$ halogenated aromatic hydrocarbons. Non-limiting examples of suitable halogenated aromatic hydrocarbons include chlorobenzene, dichlorobenzene, and combinations thereof; alternatively chlorobenzene and dichlorobenzene.

Ethers, carbonates, esters, ketones, aldehydes, or alcohols which can be useful as a solvent include $C_2$ to $C_{20}$ ethers, carbonates, esters, ketones, aldehydes, or alcohols; alternatively, $C_2$ to $C_{10}$ ethers, carbonates, esters, ketones, aldehydes, or alcohols; or alternatively, $C_2$ to $C_5$ ethers, carbonates, esters, ketones, aldehydes, or alcohols. Suitable ether solvents can be cyclic or acyclic. Non-limiting examples of suitable ethers which can be useful as a solvent include dimethyl ether, diethyl ether, methyl ethyl ether, monoethers or diethers of glycols (e.g., dimethyl glycol ether), furans, substituted furans, dihydrofuran, substituted dihydrofurans, tetrahydrofuran (THF), substituted tetrahydrofurans, tetrahydropyrans, substituted tetrahydropyrans, 1,3-dioxanes, substituted 1,3-dioxanes, 1,4-dioxanes, substituted 1,4-dioxanes, or mixtures thereof. In an embodiment, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group. $C_1$ to $C_5$ alkyl substituent group are disclosed herein and can be utilized without limitation of further describe the substituted tetrahydrofuran, dihydrofuran, furan, 1,3-dioxane, or 1,4 dioxane solvents. Non-limiting examples of suitable carbonates which can be utilized as a solvent include ethylene carbonate, propylene carbonate, diethyl carbonate, diethyl carbonate, glycerol carbonate, and combinations thereof. Non-limiting examples of suitable esters which can be utilized as a solvent include ethyl acetate, propyl acetate, butyl acetate, isobutyl isobutyrate, methyl lactate, ethyl lactate, and combinations thereof. Non-limiting examples of suitable ketones which can be utilized as a solvent include acetone, ethyl methyl ketone, methyl isobutyl ketone, and combinations thereof. Non-limiting examples of suitable alcohols which can be utilized as a solvent include methanol, ethanol, propanol, isopropanol, n-butanol, isobutanol, pentanol, hexanol, heptanol, octanol, benzyl alcohol, phenol, cyclohexanol, and the like, or combinations thereof.

General Disclosure Information

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can suggest themselves to one of ordinary skill in the art without departing from the spirit of the present invention or the scope of the appended claims.

The data and descriptions provided in the following examples are given to show particular aspects and embodiments of the compounds, catalyst systems, and oligomerization and/or polymerization methods disclosed, and to demonstrate a number of the practices and advantages thereof. The examples are given as a more detailed demonstration of some of the aspects and embodiments described herein and are not intended to limit the disclosure or claims in any manner.

EXAMPLES

Unless otherwise stated, all operations were carried out under argon in a glove box or using standard Schlenk techniques. Tetrahydrofuran and diethyl ether were purified by standard drying procedures and distilled (under argon) from sodium/benzophenone prior to use. All other solvents were purchased in anhydrous form, degassed prior to use and stored over activated molecular sieves in a glovebox. All chemical reagents were purchased from commercial sources and used as received. Proton NMR spectra were obtained on a Bruker AVANCE 11400 MHz spectrometer operating at room temperature.

Synthesis of Hydrocarboxymethanimine Compounds

Hydrocarboxymethanimine Synthesis 1—(E)-N-(2-ethylphenyl)methoxymethanimine (HMA I)

To a dry 100 mL Schlenk flask was added 50 mL of anhydrous benzene, 6.1 mL (50 mmoles) 2-ethylaniline, 11.0 mL (100 mmoles) trimethylorthoformate, and 80 mg p-toluenesulfonic acid monohydrate (catalyst). The solution became clear orange and was refluxed for twelve hours, during which it became a darker clear orange solution. Volatiles were removed under vacuum leaving an orange oil. This oil was heated under vacuum and a clear oil was distilled (60° C., 0.1 Torr), yielding 3.76 grams (46.1 mole % yield) of the desired product. $^1$H NMR (400 MHz, CDCl$_3$): δ=7.66, s, 1H (N=CH); 7.18, d, 1H; 7.11, m, 2H; 6.75, d, 2H; 3.89, s, 3H (OMe); 2.65, q, 2H (2-CH$_2$CH$_3$); 1.17, t, 3H (2-CH$_2$CH$_3$).

Hydrocarboxymethanimine Synthesis 2—(E)-N-(2,6-dimethylphenyl)methoxymethanimine (HMA II)

To a dry 100 mL Schlenk flask was added 50 mL of anhydrous benzene, 6.2 mL (50 mmoles) 2,6-dimethylaniline, 11.0 mL (100 mmoles) trimethylorthoformate, and 80 mg p-toluenesulfonic acid monohydrate (catalyst). The solution became clear and was refluxed for twelve hours, during which there was no observed color change. Volatiles were removed under vacuum leaving a cloudy white oil. This oil was heated under vacuum and a clear oil was distilled (60° C., 0.1 Torr), yielding 4.90 grams (66.1 mole % yield) of the desired product. $^1$H NMR (400 MHz, CDCl3): δ=7.51, s, 1H (N=CH); 7.01, d, 2H; 6.89, t, 1H; 3.94, s, 3H (OMe); 2.16, s, 6H (2,6-di-CH3).

Hydrocarboxymethanimine Synthesis 3—(E)-N-(2-tert-butylphenyl)methoxymethanimine (HMAIII)

To a dry 100 ml Schlenk flask was added 50 mL of anhydrous benzene, 6.0 ml (38.5 mmoles) 2-t-butylaniline, 8.5 ml (77.0 mmoles) trimethylorthoformate, and 80 mg p-tolusulfonic acid monohydrate (catalyst). The solution became clear red and was refluxed for twelve hours, during which there was no observed color change. Volatiles were removed under vacuum leaving an orange oil. This oil was heated under vacuum and a clear oil was distilled {60° C., 0.1 Torr), yielding 5.54 grams (75.3 mole % yield) of the desired product. $^1$H NMR (400 MHz, CDCb): δ=7.62, s, 1H (N=CH); 7.35, d, 1H; 7.14, t, 1H; 7.07, t, 1H; 6.68, d, 1H; 3.92, s, 3H (OMe); 1.41, s, 9H (2-C(CH$_3$)$_3$).

TABLE I

Hydrocarboxymethanimine Compounds

| | |
|---|---|
| [structure] | HMA I |
| [structure] | HMA II |
| [structure] | HMA III |

Synthesis of Formamidine Compounds

Formamidine Synthesis 1—(E)-N-(2,6-dimethylphenyl)formamidine (FA I)

(E)-N-(2,6-dimethylphenyl)methoxymethanimine, HMA II, (4.90 grams, 30.03 mmoles) and 1.44 grams (15.12 mmoles) ammonium carbonate were added to a dry 100 mL Schlenk flask containing 50 mL methanol. The solution became clear and was stirred for twelve hours, during which no color change was observed. Volatiles were removed by vacuum, leaving a white solid. This solid was heated under vacuum and a clear oil was distilled (60° C., 0.1 Torr), yielding 3.07 grams (69.1 mole % yield) of a white solid. $^1$H NMR (400 MHz, CDCl$_3$): δ=7.29, s, 1H (N=CH); 7.00, d, 2H; 6.87, t, 1H; 4.42, broad singlet, 2H (NH$_2$); 2.13, s, 6H (2,6-di-CH$_3$).

Formamidine Synthesis 2—(E)-N,N'-bis(2-ethylphenyl)formamidine (FA II)

To a dry 50 mL Schlenk flask was added 25 mL of anhydrous benzene, 1.1 mL (10 mmoles) of trimethylorthoformate, 2.5 mL (20 mmoles) of 2-ethylaniline, and 80 mg p-toluenesulfonic acid monohydrate (catalyst). The solution became clear red and was refluxed for twelve hours. The mixture was cooled, treated with saturated aqueous NaHCO$_3$, and extracted with 2×20 mL benzene. The combined benzene layers were dried with Na$_2$SO$_4$ and filtered. Benzene was removed under vacuum leaving an orange solid. The solid was heated at 60° C. under vacuum to remove unreacted aniline via distillation (0.1 Torr). An orange solid remained (1.60 grams, 63.5 mole % yield). $^1$H NMR (400 MHz, CDCl$_3$): δ=8.04, s, 1H (N=CH); 7.19, m, 4H; 7.05, m, 4H; 6.75, d, 2H; 2.68, q, 4H (2-CH$_2$CH$_3$); 1.24, t, 6H (2-CH$_2$CH$_3$).

(E)-N, N'-bis(phenyl)formamidine (Formamidine compound FA III), (E)-N,N'-bis(4-tert-butylphenyl)formamidine (Formamidine compound FA IV), and (E)-N,N'-bis(2,6-dimethylphenyl)-formamidine (Formamidine compound FA V) were prepared according to the procedure of Formamidine Synthesis 2 using the appropriate amine and the appropriate molar ratios. (E)-N-(2,5-di-tert-butylphenyl)formamidine (Formidine compound FA VI) was prepared according to the procedure of Formamidine Synthesis 2 using the appropriate hydrocarboxymethanimine (prepared using the appropriate amine and the procedure of Hydrocarboxylmethanimine Synthesis 1) and the appropriate molar ratios.

TABLE II

Formamidine Compounds

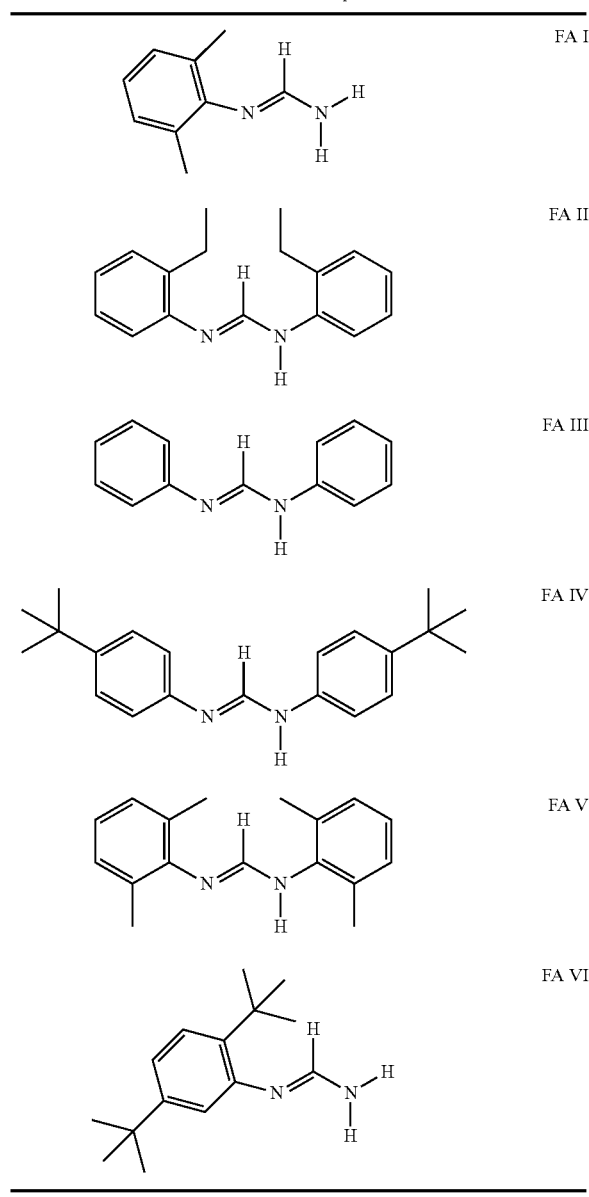

| FA I |
| FA II |
| FA III |
| FA IV |
| FA V |
| FA VI |

Synthesis of N$^2$-Phosphinyl Formamidine Compounds

Phosphinylformamidine Synthesis 1—(E)-N'-(2,6-dimethylphenyl)-N-(diisopropylphosphinyl)-formamidine (NP I)

(E)-N-(2,6-dimethylphenyl)formamidine, FA I, (0.74 grams, 5.0 mmoles) was dissolved in 50 mL of diethyl ether, cooled to 0° C., and treated dropwise with 2.5 mL (5.0 mmoles) of 2.0 M butyllithium in pentane. The color changed instantly from clear to cloudy white. The mixture was stirred for three hours at room temperature and treated with 0.80 mL (5.0 mmoles) chlorodiisopropylphosphine. This mixture was stirred for an additional hour at room temperature resulting in a cloudy white slurry. Filtration through diatomaceous earth and removal of volatiles under vacuum provided a thick pale yellow oil (0.7995 grams, 60.5 mole % yield).

Phosphinylformamidine Synthesis 2—(E)-N'-(2,6-dimethylphenyl)-N-(diphenylphosphinyl)formamidine (NP II)

(E)-N-(2,6-dimethylphenyl)formamidine, FA I, (0.74 grams, 5.0 mmoles) was dissolved in 50 mL of diethyl ether, cooled to 0° C., and treated dropwise with 2.5 mL (5.0 mmoles) of 2.0 M butyllithium in pentane. The color changed instantly from clear to cloudy white. The mixture was stirred for three hours at room temperature and treated with 0.90 mL (5.0 mmoles) chlorodiphenylphosphine. This mixture was stirred for an additional hour at room temperature resulting in a cloudy white slurry. Filtration through diatomaceous earth and removal of volatiles under vacuum provided a quantitative yield of thick pale white oil.

Phosphinylformamidine Synthesis 3—(E)-N,N'-bis(2-ethylphenyl)-N-(diisopropylphosphinyl)-formamidine (NP III)

(E)-N,N'-bis(2-ethylphenyl)formamidine, FA II, (0.656 g, 2.6 mmol) was dissolved in 50 mL of diethyl ether, cooled to 0° C., and treated dropwise with 1.3 mL (2.6 mmol) of 2.0 M butyllithium in pentane. The color changed instantly from pale orange to pale green. The mixture was stirred for three hours at room temperature and treated with 0.40 mL (2.6 mmol) of chlorodiisopropylphosphine. This mixture was stirred for an additional hour at room temperature resulting in a cloudy, pale green slurry. Filtration through diatomaceous earth and removal of volatiles under vacuum provided a clear, pale yellow oil (0.752 grams, 78.5 mole % yield).

Phosphinylformamidine Synthesis 4—(E)-N,N'-bis(2-ethylphenyl)-N-(diphenylphosphinyl)formamidine (NP IV)

(E)-N,N'-bis(2-ethylphenyl)formamidine, FA II, (0.656 g, 2.6 mmol) was dissolved in 50 mL of diethyl ether, cooled to 0° C., and treated dropwise with 1.3 mL (2.6 mmol) of 2.0 M butyllithium in pentane. The resulting solution was stirred for three hours at room temperature, yielding a cloudy pale green slurry. Chlorodiphenylphosphine (0.47 mL, 2.6 mmol) was added dropwise and the pale yellow solution was stirred for one hour at room temperature. Filtration through diatomaceous earth and removal of volatiles provided 1.14 g (98.2 mole % yield) of pale orange oil.

(E)-N,N'-bis(phenyl)-N-(diisopropylphosphinyl)formamidine ($N^2$ Phosphinylformamidine Compound NPF V), (E)-N,N'-bis(phenyl)-N-(diphenylphosphinyl)formamidine ($N^2$ Phosphinylformamidine Compound NPF VI), (E)-N,N'-bis(4-tert-butylphenyl)-N-(diisopropylphosphinyl)-formamidine ($N^2$ Phosphinylformamidine Compound NPF VII), (E)-N,N'-bis(4-tert-butylphenyl)-N-(diphenylphosphinyl)formamidine ($N^2$ Phosphinylformamidine Compound NPF VIII), (E)-N,N'-bis(2,6-dimethylphenyl)-N-(diisopropylphosphinyl)formamidine ($N^2$ Phosphinylformamidine compound NPF IX), (E)-N,N'-bis(2,6-dimethylphenyl)-N-(diphenylphosphinyl)formamidine ($N^2$ Phosphinylformamidine Compound NPF X), and (E)-N'-(2,5-di-tert-butylphenyl)-N-(diphenylphosphinyl)formamidine ($N^2$ Phosphinylformamidine Compound NPF XI) were prepared according to the procedure of Phosphinylformamidine Synthesis 1 using the appropriate formamidine compound, the appropriate phosphine chloride, and the appropriate molar ratios.

TABLE III

| $N^2$ Phosphinylformamidine Compounds | |
|---|---|
| 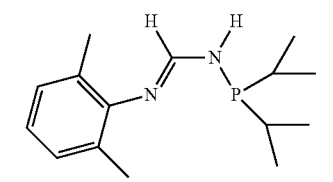 [SMILES: Cc1cccc(C)c1/N=C/NP(C(C)C)C(C)C] | NPF I |
| 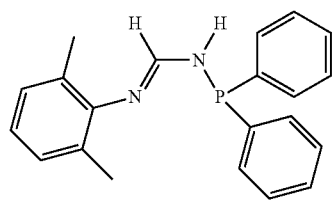 [SMILES: Cc1cccc(C)c1/N=C/NP(c1ccccc1)c1ccccc1] | NPF II |
| 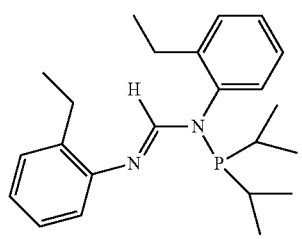 [SMILES: CCc1ccccc1/N=C/N(c1ccccc1CC)P(C(C)C)C(C)C] | NPF III |
| 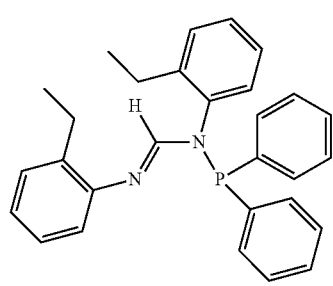 [SMILES: CCc1ccccc1/N=C/N(c1ccccc1CC)P(c1ccccc1)c1ccccc1] | NPF IV |

TABLE III-continued

| $N^2$ Phosphinylformamidine Compounds | |
|---|---|
| 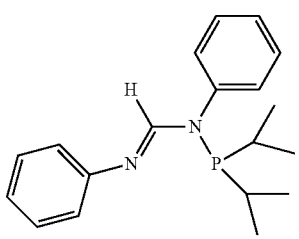 [SMILES: CC(C)P(C(C)C)N(/C=N/c1ccccc1)c1ccccc1] | NPF V |
| 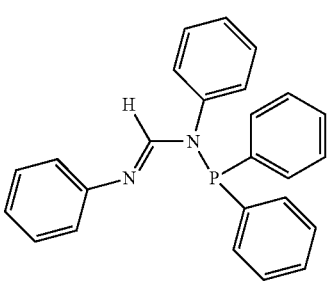 [SMILES: C(=N\c1ccccc1)/N(c1ccccc1)P(c1ccccc1)c1ccccc1] | NPF VI |
| 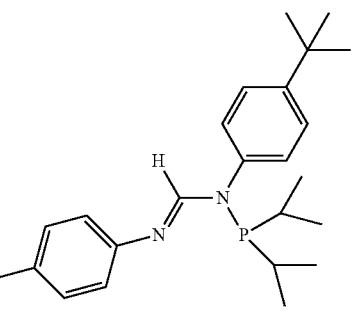 | NPF VII |
| 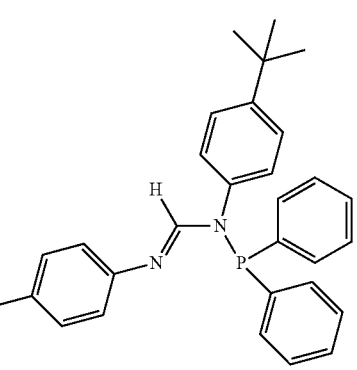 | NPF VIII |
| 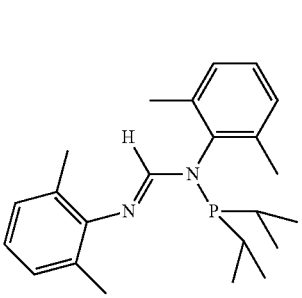 [SMILES: Cc1cccc(C)c1/N=C/N(c1c(C)cccc1C)P(C(C)C)C(C)C] | NPF IX |

TABLE III-continued

N² Phosphinylformamidine Compounds

NPF X

NPF XI

Synthesis of N²-Phosphinyl Formamidine Metal Salt Complexes

Phosphinyl Formamidine Metal Complex Synthesis 1—[(E)-N'-(2,6-dimethylphenyl)-N-(diisopropylphosphino)formamidine] (THF)CrCl3 (NPFMC I)

(E)-N'-(2,6-dimethylphenyl)-N-(diisopropylphosphinyl) formamidine, NP I, (0.132 grams, 0.5 mmoles) was dissolved in THF and added dropwise to a solution of THF containing 0.187 grams (0.5 mmoles) of $CrCl_3(THF)_3$ resulting in an immediate color change from purple to blue. This solution was stirred for twelve hours, during which it became cloudy light blue. It was filtered and volatiles were removed by vacuum, yielding 0.145 grams (57.0 mole % yield) of a blue solid.

Phosphinyl Formamidine Metal Complex Synthesis 2—[(E)-N'-(2,6-dimethylphenyl)-N-(diphenylphosphino)formamidine] (THF)$CrCl_3$ (NPFMC II)

(E)-N'-(2,6-dimethylphenyl)-N-(diphenylphosphinyl)formamidine, (NP II, (0.166 grams, 0.5 mmoles) was dissolved in THF and added dropwise to a solution of THF containing 0.187 grams (0.5 mmoles) of $CrCl_3(THF)_3$ resulting in an immediate color change from purple to blue. This solution was stirred for twelve hours and volatiles were removed by vacuum resulting in a blue solid. This solid was rinsed with pentane and dried (0.277 grams, 96.2 mole % yield).

Phosphinyl Formamidine Metal Complex Synthesis 3—[(E)-N,N'-bis(2-ethylphenyl)-N-(diisopropylphosphino) formamidine] (THF)$CrCl_3$ (NPFMC III)

(E)-N,N'-bis(2-ethylphenyl)-N-(diisopropylphosphinyl) formamidine, NP III, (0.218 grams, 0.5 mmoles) was dissolved in THF and added dropwise to a solution of THF containing 0.187 grams (0.5 mmoles) of $CrCl_3(THF)_3$. This solution was stirred for twelve hours, during which it became blue. Volatiles were removed by vacuum resulting in a blue solid. This solid was rinsed with pentane and dried (0.251 grams, 73.6 mole % yield).

Phosphinyl Formamidine Metal Complex Synthesis 4—[(E)-N,N'-bis(2-ethylphenyl)-N-(diphenylphosphino)formamidine] (THF)$CrCl_3$ (NPFMC IV)

(E)-N,N'-bis(2-ethylphenyl)-N-(diphenylphosphinyl)formamidine, NP IV, (0.184 grams, 0.5 mmoles) was dissolved in THF and added dropwise to a solution of THF containing 0.187 grams (0.5 mmoles) of $CrCl_3(THF)_3$. This solution was stirred for twelve hours, during which it became blue. Volatiles were removed by vacuum resulting in a blue solid. This solid was rinsed with pentane and dried (0.222 grams, 72.3 mole % yield).

(E)-N,N'-bis(phenyl)-N-(diisopropylphosphinyl)formamidine(THF)$CrCl_3$ (N² Phosphinylformamidine Metal Complex NPFMC V), (E)-N,N'-bis(phenyl)-N-(diphenylphosphinyl)-formamidine (THF)$CrCl_3$ (N² Phosphinylformamidine Metal Complex NPFMC VI), (E)-N,N'-bis(4-tert-butylphenyl)-N-(diisopropylphosphinyl)formamidine (THF)$CrCl_3$ (N² Phosphinylformamidine Metal Complex NPFMC VII), (E)-N,N'-bis(4-tert-butylphenyl)-N-(diphenylphosphinyl)-formamidine (THF)$CrCl_3$ (N² Phosphinylformamidine Metal Complex NPFMC VIII), (E)-N,N'-bis(2,6-dimethylphenyl)-N-(diisopropylphosphinyl) formamidine (THF)$CrCl_3$ (N² Phosphinylformamidine Metal Complex NPFMC IX), (E)-N,N'-bis(2,6-dimethylphenyl)-N-(diphenylphosphinyl) (THF)$CrCl_3$ (N² Phosphinylformamidine Metal Complex NPFMC X), and (E)-N'-(2, 5-di-tert-butylphenyl)-N-(diphenylphosphinyl)formamidine (N² Phosphinylformamidine Metal Complex NPFMC XI) were prepared according to the procedure of Phosphinylformamidine Metal Complex Synthesis 1 using the appropriate N²-phosphinylformamidine formamidine compound, the appropriate metal salt, and the appropriate molar ratios.

TABLE IV

N² Phosphinylformamidine Metal Salt Complexes
(NFP Formamidine Metal Salt Complexes)

NPFMC I

NPFMC II

NPFMC III

TABLE IV-continued

N² Phosphinylformamidine Metal Salt Complexes
(NFP Formamidine Metal Salt Complexes)

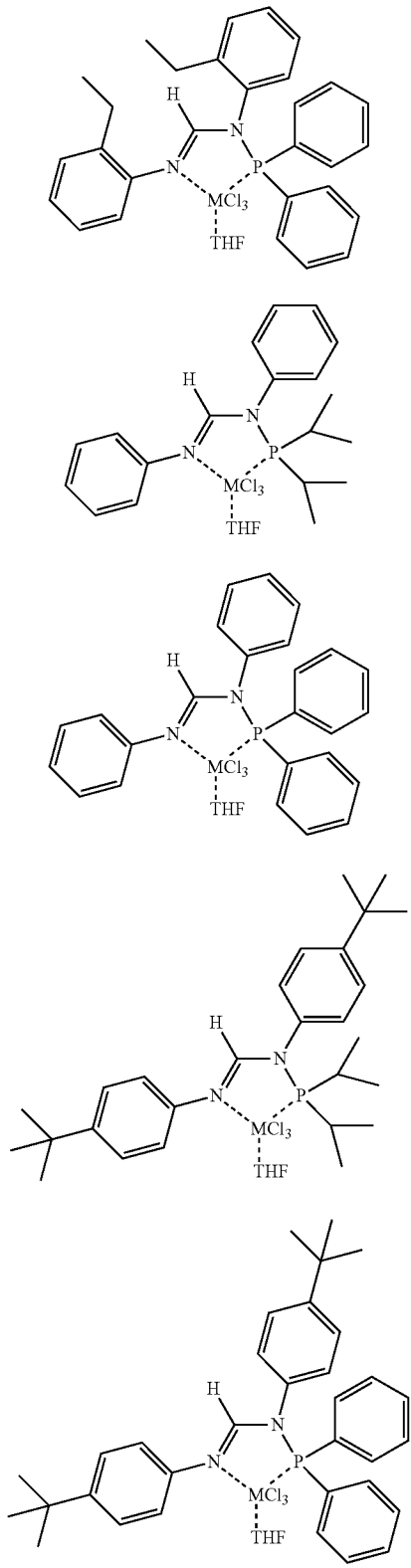

NPFMC IV

NPFMC V

NPFMC VI

NPFMC VII

NPFMC VIII

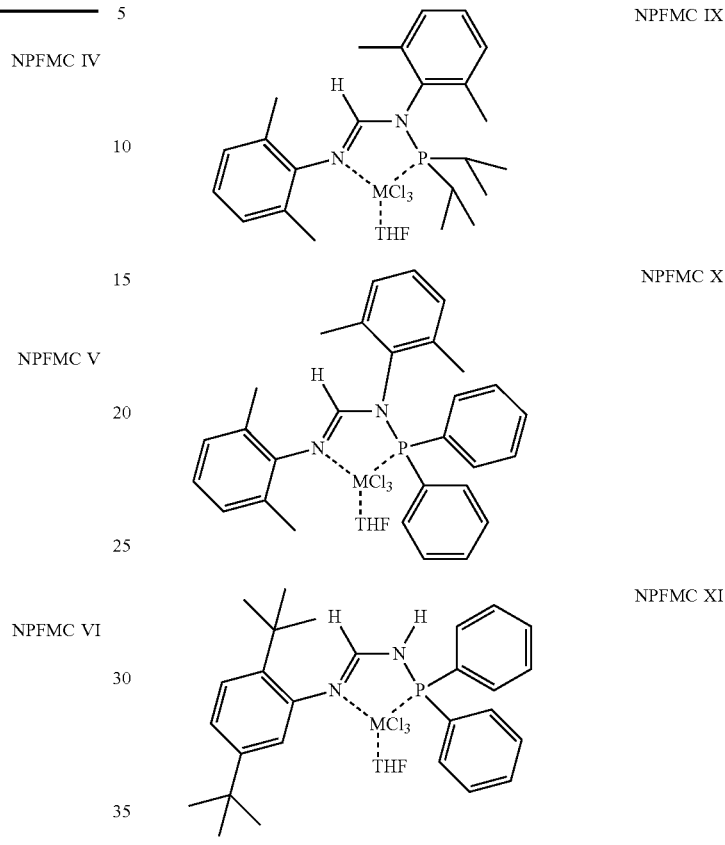

NPFMC IX

NPFMC X

NPFMC XI

Olefin Oligomerization

The N²-phosphinylformamidine metal salt complexes were utilized as prepared using the methods described herein. The MMAO-3A (7 wt. % aluminum in heptanes) was utilized as obtained from the chemical supplier Akzo-Nobel. The solvents were dried and/or purified using conventional methods and stored under conditions to limit their ability to pick-up water. In the product analyses, reference to an amount of C6 or C8 products refer to all oligomer products having 6 or 8 carbon atoms, respectively, within the oligomer product. References to weight percent of 1-hexene or 1-octene refer to the weight percent of 1-hexene or 1-octene in the C6 or C8 product portion of the oligomer product, respectively (e.g., product purities).

Ethylene Oligomerization Run—Standard Method

A 1 L stainless steel reactor was dried under vacuum at 110° C. for at least 8 hours prior to use. The reactor was then cooled to 50° C. In the drybox, a 20 mL glass vial was charged with an N²-phosphinyl formamidine metal salt complex and ethylbenzene (1.0 g). MMAO-3A was added to the blue heterogeneous solution of the N2-phosphinyl metal salt complex resulting in formation of a yellow solution. The catalyst system was then allowed to age a room temperature for 4 hours. The yellow solution was then added to 0.5 L glass charger containing cyclohexane. This solution was removed from the drybox and charged into the reactor. Hydrogen was added to the reactor followed by ethylene. The reaction was allowed to proceed for 30 minutes (starting from the introduction of ethylene) at 70° C. with ethylene fed to maintain reactor pressure and heating or cooling as necessary to maintain the desired temperature. After 30 minutes, water cooling was applied to the reactor system. Once the temperature reached 35° C., the unreacted ethylene and hydrogen gas was vented to the atmosphere. A liquid sample was collected and analyzed by GC-FID; for this run ethylbenzene was used as the internal standard. Solids were collected by filtering the solution and cleaning the reactor walls and cooling coil. The $N^2$-phosphinyl formamidine metal salt complexes and amount of materials utilized for each ethylene oligomerization are provided are summarized in Table V along with the results of each oligomerization run.

Background is not an admission that it is prior art to the present invention, especially any reference that can have a publication date after the priority date of this application. The disclosures of all patents, patent applications, and publications cited herein are hereby incorporated by reference, to the extent that they provide exemplary, procedural or other details supplementary to those set forth herein.

The following are enumerated embodiments, designated Group A, which are provided as non-limiting examples:

Embodiment 1

An $N^2$-phosphinyl formamidine compound having the formula:

TABLE V

N²-Phosphinyl Formamidine Complex, Catalyst System Ratios, and Reaction Condition for Ethylene Oligomerization Runs 5-26.

| | Run # | | | | | | | | | |
|---|---|---|---|---|---|---|---|---|---|---|
| | 1 | 2 | 3 | 4 | 5 | 6 | 7 | 8 | 9 | 10 |
| Ethylene Oligomerization Conditions | | | | | | | | | | |
| Complex | 8a | 8a | 8b | 9a | 10a | 10b | 11a | 11b | 12a | 13b |
| Complex GMW[1] | 566.91 | 566.91 | 634.95 | 671.06 | 614.96 | 682.99 | 727.17 | 795.2 | 671.06 | 719.1 |
| Complex Amount (mg) | 7 | 7 | 7 | 7 | 7 | 7 | 7 | 7 | 7 | 7 |
| Cr (mg) | 0.64 | 0.64 | 0.57 | 0.54 | 0.59 | 0.53 | 0.50 | 0.46 | 0.54 | 0.51 |
| Al:Cr molar ratio | 600 | 600 | 700 | 700 | 600 | 700 | 800 | 800 | 700 | 800 |
| Cyclohexane Solvent | 0.4 L | 0.4 L | 0.4 L | 0.4 L | 0.4 L | 0.4 L | 0.4 L | 0.4 L | 0.4 L | 0.4 L |
| Reaction Time (min) | 30 | 30 | 30 | 30 | 30 | 30 | 30 | 30 | 30 | 30 |
| $C_2H_4$ pressure (psi) | 875 | 875 | 875 | 875 | 875 | 875 | 875 | 875 | 875 | 875 |
| $H_2$ pressure (psi) | 25 | 25 | 25 | 25 | 25 | 25 | 25 | 25 | 25 | 25 |
| Reaction Temperature (° C.) | 70 | 70 | 70 | 70 | 70 | 70 | 70 | 70 | 70 | 70 |
| Ethylene Oligamerization Product Analysis | | | | | | | | | | |
| Solid Product (g) | <2 | <2 | <2 | <2 | 6 | <2 | >2 | <2 | <2 | <2 |
| Liquid Product (g) | 339.8 | 316 | 60.7 | 5.8 | 1 | 0.3 | 6.8 | 0.4 | 4.7 | 116 |
| Carbon Number Distribution (wt. %) | | | | | | | | | | |
| $C_6$ | 93.7 | 93.9 | 80.6 | 83.9 | 51.6 | NA | 38.1 | NA | 91.4 | 95.1 |
| $C_8$ | 0.8 | 0.8 | 18.2 | 5.2 | 26.3 | NA | 27.4 | NA | 8.1 | 2.4 |
| $C_{10+}$ | 5.5 | 5.3 | 1.2 | 10.9 | 22.1 | NA | 34.5 | NA | 0.5 | 2.5 |
| $g(C_6 + C_8)/gCr$ | 500,113 | 466,069 | 104,613 | 9,527 | 1,316 | inactive | 8,898 | inactive | 8,621 | 223,435 |
| 1-hexene in $C_6$'s (wt. %) | 99.71 | 99.69 | 99.2 | 96.76 | 5994 | NA | 38.16 | NA | 98.85 | 99.63 |
| 1-octene in $C_8$'s (wt. %) | 97.74 | 98.01 | 99.64 | 82.89 | 83.13 | NA | 72.48 | NA | 95.26 | 98.28 |

[1]Assumed two THF neutral ligand per complex molecule.

While preferred embodiments of the invention have been shown and described, modifications thereof can be made by one skilled in the art without departing from the spirit and teachings of the disclosure. The embodiments described herein are exemplary only, and are not intended to be limiting. Many variations and modifications of the disclosure are possible and are within the scope of the invention. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the

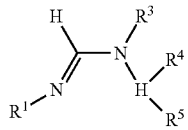

wherein: $R^1$ is a $C_1$ to $C_{30}$ organyl group, $R^3$ is hydrogen, a $C_1$ to $C_{30}$ organyl group, or a $C_1$ to $C_{30}$ organyl group consisting essentially of inert functional groups, and $R^4$ and $R^5$ are each independently a $C_1$ to $C_{30}$ organyl group consisting essentially of inert functional groups.

Embodiment 2

The $N^2$-phosphinyl formamidine compound of embodiment 1, wherein $R^1$ is a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group.

Embodiment 3

The $N^2$-phosphinyl formamidine compound of embodiment 1, wherein $R^1$ is a phenyl group or a $C_6$ to $C_{20}$ substituted phenyl group.

Embodiment 4

The $N^2$-phosphinyl formamidine compound of embodiment 1, wherein $R^1$ is a phenyl group, a 2-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group.

Embodiment 5

The $N^2$-phosphinyl formamidine compound of embodiment 3 or 4, wherein each substituent of the substituted phenyl group is independently a halide, a $C_1$ to $C_5$ alkyl group, or a $C_1$ to $C_5$ alkoxy group.

Embodiment 6

The $N^2$-phosphinyl formamidine compound of embodiment 1, wherein $R^1$ is a phenyl group, a 2-methylphenyl group, a 2-ethylphenyl group, a 2-isopropylphenyl group, a 2-tert-butylphenyl group, a 4-methylphenyl group, a 4-ethylphenyl group, a 4-isopropylphenyl group, a 4-tert-butylphenyl group, a 2,6-dimethylphenyl group, a 2,6-diethylphenyl group, a 2,6-diisopropylphenyl group, a 2-methyl-6-isopropylphenyl group, a 3,5-dimethylphenyl group, a 2,4,6-trimethylphenyl group, or a 2,6-dimethyl-4-tert-butylphenyl group.

Embodiment 7

The $N^2$-phosphinyl formamidine compound of any of embodiments 1 to 6, wherein $R^3$ is hydrogen, a $C_1$ to $C_{10}$ alkyl group, a $C_1$ to $C_{15}$ cycloalkyl group, a $C_1$ to $C_{15}$ substituted cycloalkyl group, a $C_3$ to $C_{15}$ aliphatic heterocyclic group, a $C_3$ to $C_{15}$ substituted aliphatic heterocyclic group, a $C_6$ to $C_{15}$ aryl group, a $C_6$ to $C_{15}$ substituted aryl group, a $C_3$ to $C_{15}$ heteroaryl group, or a substituted $C_3$ to $C_{15}$ heteroaryl group.

Embodiment 8

The $N^2$-phosphinyl formamidine compound of any of embodiments 1 to 6, wherein $R^3$ is hydrogen.

Embodiment 9

The $N^2$-phosphinyl formamidine compound of any of embodiments 1 to 8, wherein $R^4$ and $R^5$ are independently a $C_1$ to $C_{15}$ alkyl group, a $C_4$ to $C_{20}$ cycloalkyl group, a $C_4$ to $C_{20}$ substituted cycloalkyl group, a $C_3$ to $C_{15}$ aliphatic heterocyclic group, a $C_3$ to $C_{15}$ substituted aliphatic heterocyclic group, a $C_6$ to $C_{20}$ aryl group, a $C_6$ to $C_{20}$ substituted aryl group, a $C_3$ to $C_{20}$ heteroaryl group, or a $C_3$ to $C_{20}$ substituted heteroaryl group.

Embodiment 10

The $N^2$-phosphinyl formamidine compound of any of embodiments 1 to 8, wherein $R^4$ and $R^5$ are independently a methyl group, an ethyl group, an n-propyl group, an n-butyl group, an n-pentyl group, or an n-hexyl group.

Embodiment 11

The $N^2$-phosphinyl formamidine compound of any of embodiments 1 to 8, wherein $R^4$ and $R^5$ are independently a methyl group, an ethyl group, an isopropyl group, a tert-butyl group, or a neopentyl group.

Embodiment 12

The $N^2$-phosphinyl formamidine compound of any of embodiments 1 to 8, wherein $R^4$ and $R^5$ are each independently a cyclopentyl group, a substituted cyclopentyl group, a cyclohexyl group, or a substituted cyclohexyl group.

Embodiment 13

The $N^2$-phosphinyl formamidine compound of any of embodiments 1 to 8, wherein $R^4$ and $R^5$ are independently a phenyl group or a $C_6$ to $C_{20}$ substituted phenyl group.

Embodiment 14

The $N^2$-phosphinyl formamidine compound of any of embodiments 1 to 8, wherein $R^4$ and $R^5$ are independently a phenyl group, a 2-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group.

Embodiment 15

The $N^2$-phosphinyl formamidine compound of embodiment 1, wherein $R^1$ is a phenyl group or a $C_6$ to $C_{20}$ substituted phenyl group, $R^3$ is hydrogen, and $R^4$ and $R^5$ are independently a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group.

Embodiment 16

A method of preparing an $N^2$-phosphinyl formamidine compound of any of embodiments 1-21 comprising: a) contacting a metal alkyl with a formamidine to form a metal formamidinate; and b) contacting a phosphine halide with the metal formamidinate to form a compound comprising an $N^2$-phosphinyl formamidine group.

Embodiment 17

The method of embodiment 16, wherein the formamidine compound has the formula

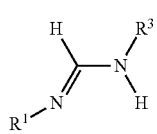

and the phosphine halide has the formula

wherein X is chloride, bromide, or iodide.

Embodiment 18

The method of embodiment 16, wherein the formamidine compound is prepared by contacting an amine having the formula $R^1NH_2$ and a trihydrocarbylformate.

Embodiment 19

The method of embodiment 16, wherein the formamidine compound is prepared by contacting ammonium carbonate with a hydrocarboxymethanimine compound having the formula

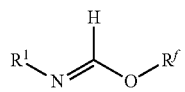

wherein $R^f$ is a $C_1$ to $C_{10}$ hydrocarbyl group.

Embodiment 20

The method of embodiment 19, wherein the hydrocarboxymethanimine compound is prepared by contacting trihydrocarbyl formate with amine having formula $R^1NH_2$.

Embodiment 21

A metal salt complex of the $N^2$-phosphinyl formamidine compound of any of embodiments 1 to 15, having the formula

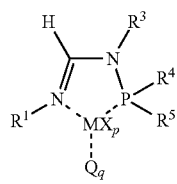

or the formula

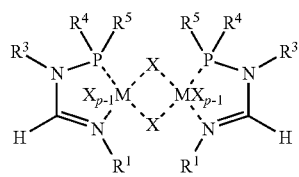

wherein $MX_p$ represents the metal salt where M is a transition metal, X is a monoanion and p ranges from 2 to 6, or X is dianionic and p ranges from 1 to 3, Q is a neutral ligand, and q ranges from 0 to 6.

Embodiment 22

The metal salt complex of embodiment 21, wherein the metal of the metal salt is in a +2 or +3 oxidation state.

Embodiment 23

The metal salt complex of embodiment 21 or 22, wherein the metal salt comprises chromium.

Embodiment 24

The metal salt complex of embodiment 21, wherein the metal salt is a chromium(III) chloride.

Embodiment 25

A method of preparing the $N^2$-phosphinyl formamidine metal salt complex of any of embodiments 21 to 24 having the formula

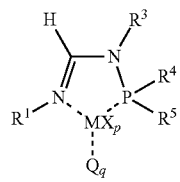

comprising: a) contacting a transition metal salt with an $N^2$-phosphinyl formamidine compound according to claim 1; and b) forming the $N^2$-phosphinyl formamidine metal salt complex.

Embodiment 26

The method of embodiment 25, wherein the transition metal salt and the $N^2$-phosphinyl formamidine compound are contacted at a transition metal salt to $N^2$-phosphinyl formamidine compound equivalent ratio of at least 0.9:1.

Embodiment 27

The method of embodiment 25 or 26, wherein the transition metal salt and the $N^2$-phosphinyl formamidine compound are contacted in a solvent.

Embodiment 28

A catalyst system comprising a) the $N^2$-phosphinyl formamidine metal salt complex of any of embodiments 21 to 24 and b) a metal alkyl.

Embodiment 29

The catalyst system of embodiment 28, wherein the metal alkyl comprises an aluminoxane.

Embodiment 30

The catalyst system of embodiment 29, wherein the aluminoxane comprises methylaluminoxane (MAO), modified methylaluminoxane (MMAO), ethylaluminoxane, n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neo-pentylaluminoxane, or mixtures thereof.

Embodiment 31

The catalyst system of embodiment 29, wherein the aluminoxane comprises modified methylaluminoxane (MMAO).

Embodiment 32

The catalyst system of any of embodiments 29 to 31, wherein a molar ratio of the aluminum of the aluminoxane to the metal of the metal complex is at least 5:1.

Embodiment 33

A method of preparing a catalyst system according to any of embodiments 28 to 32, comprising forming a catalyst system mixture comprising a) the $N^2$-phosphinyl formamidine metal salt complex of any of embodiments 21 to 24 and b) the metal alkyl.

Embodiment 34

A process comprising: a) contacting an olefin and the catalyst system of any of embodiments 28 to 32, wherein the metal alkyl is an aluminoxane; and b) forming an oligomer product.

Embodiment 35

A process comprising: a) forming a catalyst system mixture according to embodiment 33, wherein the metal alkyl is an aluminoxane; b) contacting the catalyst system mixture with an olefin; and c) forming an oligomer product.

Embodiment 36

The process of embodiment 34 or 35, wherein the catalyst system or catalyst system mixture further comprises a solvent.

Embodiment 37

The process of embodiment 34 or 35, wherein the catalyst system or the catalyst system mixture is aged in the substantial absence of the olefin to form an aged catalyst system.

Embodiment 38

The process of embodiment 37, wherein the catalyst system or the catalyst system mixture is aged at a temperature from 10° C. to 130° C.

Embodiment 39

The process of embodiment 37 or 38, wherein the catalyst system mixture is aged for at least 20 minutes Embodiment 40

The process of any of embodiments 34 to 39, wherein the oligomer product is formed at reaction conditions capable of forming an oligomer product comprising a temperature ranging from 20° C. to 150° C.

Embodiment 41

The process of any of embodiments 34 to 40, wherein the olefin comprises ethylene.

Embodiment 42

The process of embodiment 41, wherein the ethylene partial pressure at which the oligomer product is formed is at least 50 psig.

Embodiment 44

The process of embodiment 41 or 42, wherein the olefin consists essentially of ethylene and a liquid oligomer product comprising at least 70 wt. % $C_6$ and $C_8$ olefins.

Embodiment 45

The process of embodiments 44, wherein the $C_6$ product in the oligomer product comprises at least 90 wt. % 1-hexene.

Embodiment 46

The process of embodiment 44 or 45, wherein the $C_8$ product in the oligomer product comprises at least 90 wt. % 1-octene.

Embodiment 47

The process of any of embodiments 34 to 46, wherein the catalyst system or catalyst system mixture is contacted with the olefin and hydrogen and the hydrogen partial pressure is at least 5 psig.

Embodiment 48

The process of any of embodiments 34 to 47, wherein $R^1$ is a phenyl group or a $C_6$ to $C_{20}$ substituted phenyl group, $R^3$ is hydrogen, $R^4$ and $R^5$ are independently a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group, $MX_p$ comprises a chromium (III) halide, Q is a THF, and q ranges from 0 to 6.

The following are enumerated embodiments, designated Group B, which are provided as non-limiting examples:

A first embodiment which is an $N^2$-phosphinyl formamidine compound having the formula:

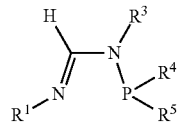

wherein:
$R^1$ is a $C_1$ to $C_{30}$ organyl group,
$R^3$ is hydrogen, a $C_1$ to $C_{30}$ organyl group, or a $C_1$ to $C_{30}$ organyl group consisting essentially of inert functional groups, and
$R^4$ and $R^5$ are each independently a $C_1$ to $C_{30}$ organyl group consisting essentially of inert functional groups.

A second embodiment which is a method of preparing an $N^2$-phosphinyl formamidine compound according to the first embodiment, comprising:

a) contacting a metal alkyl with a formamidine compound to form a metal formamidinate; and b) contacting a phosphine halide with the metal formamidinate to form a compound comprising an $N^2$-phosphinyl formamidine group.

A third embodiment which is a metal salt complex of an $N^2$-phosphinyl formamidine compound according to the first embodiment, having the formula

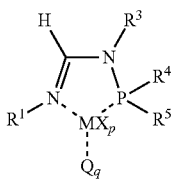

or the formula

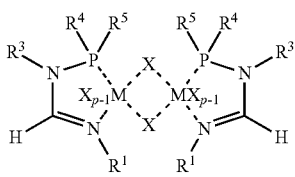

wherein:

$R^1$ is a $C_1$ to $C_{30}$ organyl group, $R^3$ is hydrogen, a $C_1$ to $C_{30}$ organyl group, or a $C_1$ to $C_{30}$ organyl group consisting essentially of inert functional groups, $R^4$ and $R^5$ are each independently a $C_1$ to $C_{30}$ organyl group consisting essentially of inert functional groups, $MX_p$ represents the metal salt where M is a transition metal, X is a monoanion and p ranges from 2 to 6, or X is a dianion and p ranges from 1 to 3, Q is a neutral ligand, and q ranges from 0 to 6.

A fourth embodiment which is a method of preparing an $N^2$-phosphinyl formamidine metal salt complex according to the third embodiment having the formula

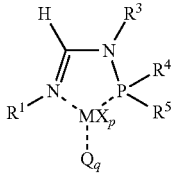

comprising:

a) contacting a transition metal salt with an $N^2$-phosphinyl formamidine compound according to embodiment 1; and b) forming the $N^2$-phosphinyl formamidine metal salt complex.

A fifth embodiment which is a catalyst system comprising a) an $N^2$-phosphinyl formamidine metal salt complex according to the third embodiment and b) a metal alkyl.

A sixth embodiment which is a method of preparing a catalyst system according to the fifth embodiment, comprising forming a catalyst system mixture comprising a) the $N^2$-phosphinyl formamidine metal salt complex according to embodiment 3 and b) the metal alkyl.

A seventh embodiment which is a process comprising:

a) contacting an olefin and the catalyst system according to embodiment 5, wherein the metal alkyl is an aluminoxane; and b) forming an oligomer product.

An eighth embodiment which is a process comprising:

a) forming a catalyst system mixture according to the sixth embodiment, wherein the metal alkyl is an aluminoxane;

b) contacting the catalyst system mixture with an olefin; and c) forming an oligomer product.

A ninth embodiment which is subject matter of any of the first through the eighth embodiments, wherein $R^1$ is a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group.

A tenth embodiment which is the subject matter of any of the first through the eighth embodiments, wherein $R^1$ is a phenyl group or a $C_6$ to $C_{20}$ substituted phenyl group.

An eleventh embodiment which is the subject matter of any of the first through the eighth embodiments, wherein $R^1$ is a phenyl group, a 2-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group.

A twelfth embodiment which is the subject matter of any of the tenth or the eleventh embodiment, wherein each substituent of the substituted phenyl group is independently a halide, a $C_1$ to $C_5$ alkyl group, or a $C_1$ to $C_5$ alkoxy group.

A thirteenth embodiment which is the subject matter of any of the first through the eighth embodiments, wherein $R^1$ is a phenyl group, a 2-methylphenyl group, a 2-ethylphenyl group, a 2-isopropylphenyl group, a 2-tert-butylphenyl group, a 4-methylphenyl group, a 4-ethylphenyl group, a 4-isopropylphenyl group, a 4-tert-butylphenyl group, a 2,6-dimethylphenyl group, a 2,6-diethylphenyl group, a 2,6-diisopropylphenyl group, a 2-methyl-6-isopropylphenyl group, a 3,5-dimethylphenyl group, a 2,4,6-trimethylphenyl group, or a 2,6-dimethyl-4-tert-butylphenyl group.

A fourteenth embodiment which is the subject matter of any preceding embodiments, wherein $R^3$ is hydrogen, a $C_1$ to $C_{10}$ alkyl group, a $C_1$ to $C_{15}$ cycloalkyl group, a $C_1$ to $C_{15}$ substituted cycloalkyl group, a $C_3$ to $C_{15}$ aliphatic heterocyclic group, a $C_3$ to $C_{15}$ substituted aliphatic heterocyclic group, a $C_6$ to $C_{15}$ aryl group, a $C_6$ to $C_{15}$ substituted aryl group, a $C_3$ to $C_{15}$ heteroaryl group, or a substituted $C_3$ to $C_{15}$ heteroaryl group.

A fifteenth embodiment which is the subject matter of any preceding embodiments, wherein $R^3$ is hydrogen.

A sixteenth embodiment which is the subject matter of any preceding embodiments, wherein $R^4$ and $R^5$ are independently a $C_1$ to $C_{15}$ alkyl group, a $C_4$ to $C_{20}$ cycloalkyl group, a $C_4$ to $C_{20}$ substituted cycloalkyl group, a $C_3$ to $C_{15}$ aliphatic heterocyclic group, a $C_3$ to $C_{15}$ substituted aliphatic heterocyclic group, a $C_6$ to $C_{20}$ aryl group, a $C_6$ to $C_{20}$ substituted aryl group, a $C_3$ to $C_{20}$ heteroaryl group, or a $C_3$ to $C_{20}$ substituted heteroaryl group.

A seventeenth embodiment which is the subject matter of any preceding embodiments, wherein $R^4$ and $R^5$ are independently a methyl group, an ethyl group, an isopropyl group, a tert-butyl group, or a neopentyl group.

An eighteenth embodiment which is the subject matter of any preceding embodiments, wherein $R^4$ and $R^5$ are independently a methyl group, an ethyl group, an n-propyl group, an n-butyl group, an n-pentyl group, or an n-hexyl group.

A nineteenth embodiment which is the subject matter of any of the first through the sixteenth embodiments, wherein $R^4$ and $R^5$ are each independently a cyclopentyl group, a substituted cyclopentyl group, a cyclohexyl group, or a substituted cyclohexyl group.

A twentieth embodiment which is the subject matter of any of the first through the sixteenth embodiments, wherein $R^4$ and $R^5$ are independently a phenyl group or a $C_6$ to $C_{20}$ substituted phenyl group.

A twenty-first embodiment which is the subject matter of any of the first through the sixteenth embodiments, wherein $R^4$ and $R^5$ are independently a phenyl group, a 2-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group.

A twenty-second embodiment which is the subject matter of any of the first through the eighth embodiments, wherein
$R^1$ is a phenyl group or a $C_6$ to $C_{20}$ substituted phenyl group,
$R^3$ is hydrogen, and
$R^4$ and $R^5$ are independently a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group.

A twenty-third embodiment which is the method of the second embodiment, wherein the formamidine compound is prepared by contacting an amine having the formula $R^1NH_2$ and a trihydrocarbylformate.

A twenty-fourth embodiment which is the method of the second embodiment, wherein the formamidine compound is prepared by contacting ammonium carbonate with a hydrocarboxymethanimine compound having the formula

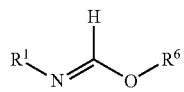

wherein $R^1$ is a $C_1$ to $C_{30}$ organyl group and $R^6$ is a $C_1$ to $C_{10}$ hydrocarbyl group.

A twenty-fifth embodiment which is the method of the twenty-fourth embodiment, wherein the hydrocarboxymethanimine compound is prepared by contacting trihydrocarbyl formate with amine having formula $R^1NH_2$ wherein $R^1$ is a $C_1$ to $C_{30}$ organyl group.

A twenty-sixth embodiment which is the subject matter of any of the third through the eighth embodiments, wherein the metal of the metal salt is in a +2 or +3 oxidation state.

A twenty-seventh embodiment which is the subject matter of any of the third through the eighth embodiments, wherein the metal salt comprises chromium.

A twenty-eighth embodiment which is the subject matter of any of the third through the eighth embodiments, wherein the metal salt is a chromium(III) chloride.

A twenty-ninth embodiment which is the method of the fourth embodiment, wherein the transition metal salt and the $N^2$-phosphinyl formamidine compound are contacted at a transition metal salt to $N^2$-phosphinyl formamidine compound equivalent ratio of at least 0.9:1.

A thirtieth embodiment which is the method of the fourth embodiment, wherein the transition metal salt and the $N^2$-phosphinyl formamidine compound are contacted in a solvent.

A thirty-first embodiment which is the subject matter of any of the fifth through the eighth embodiments, wherein the metal alkyl comprises an aluminoxane and the aluminoxane comprises methylaluminoxane (MAO), modified methylaluminoxane (MMAO), ethylaluminoxane, n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, or mixtures thereof.

A thirty-second embodiment which is the subject matter of the thirty-first embodiment, wherein the aluminoxane comprises modified methylaluminoxane (MMAO).

A thirty-third embodiment which is the subject matter of the thirty-first embodiment, wherein a molar ratio of the aluminum of the aluminoxane to the metal of the metal complex is at least 5:1.

A thirty-fourth embodiment which is the subject matter of any of the sixth or the eighth embodiment, wherein the catalyst system or catalyst system mixture further comprises a solvent.

A thirty-fifth embodiment which is the process of any of the seventh or the eighth embodiment, wherein the catalyst system or the catalyst system mixture is aged in the substantial absence of the olefin to form an aged catalyst system.

A thirty-sixth embodiment which is the process of the thirty-fifth embodiment, wherein the catalyst system or the catalyst system mixture is aged at a temperature from 10° C. to 130° C.

A thirty-seventh embodiment which is the process of any of the thirty-fifth or the thirty-sixth embodiment, wherein the catalyst system mixture is aged for at least 20 minutes A thirty-eighth embodiment which is the process of any of the seventh, the eighth or the thirty-fifth through thirty-seventh embodiments, wherein the oligomer product is formed at reaction conditions capable of forming an oligomer product comprising a temperature ranging from 20° C. to 150° C.

A thirty-ninth embodiment which is the process of any of the seventh, the eighth or the thirty-fifth through thirty-seventh embodiments, wherein the olefin comprises ethylene.

A fourteenth embodiment which is the process of the thirty-ninth embodiment, wherein the ethylene partial pressure at which the oligomer product is formed is at least 50 psig.

A forty-first embodiment which is the process of any of the seventh, the eighth or the thirty-fifth through thirty-seventh embodiments, wherein the olefin consists essentially of ethylene and a liquid oligomer product comprising at least 70 wt. % $C_6$ and $C_8$ olefins.

A forty-second embodiment which is the process of the forty-first embodiment, wherein the $C_6$ product in the oligomer product comprises at least 90 wt. % 1-hexene.

A forty-third embodiment which is the process of the forty-first embodiment, wherein the $C_8$ product in the oligomer product comprises at least 90 wt. % 1-octene.

A forty-fourth embodiment which is the process of the eighth embodiment, wherein the catalyst system mixture is contacted with the olefin and hydrogen and the hydrogen partial pressure is at least 5 psig.

A forty-fifth embodiment which is the process of any of the seventh, the eighth or the thirty-fifth through forty-second embodiments, wherein
$R^1$ is a phenyl group or a $C_6$ to $C_{20}$ substituted phenyl group, $R^3$ is hydrogen,
$R^4$ and $R^5$ are independently a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group,
$MX_p$ comprises a chromium (III) halide,
Q is a THF, and
q ranges from 0 to 6.

What is claimed:
1. A catalyst system comprising
a) an $N^2$-phosphinyl formamidine metal salt complex having the formula

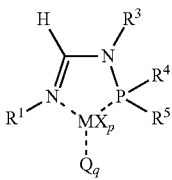

or the formula

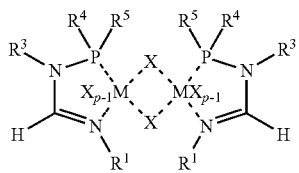

wherein:
$R^1$ is a $C_1$ to $C_{30}$ organyl group,
$R^3$ is hydrogen,
$R^4$ and $R^5$ are each independently a $C_1$ to $C_{30}$ organyl group consisting essentially of inert functional groups, wherein each inert functional group independently is a halo group, a nitro group, a hydrocarboxy group, a sulfidyl group, or a hydrocarbyl group,
$MX_p$ represents the metal salt where M is a Group 6 transition metal, X is a monoanion and p ranges from 2 to 6, or X is a dianion and p ranges from 1 to 3,
O is a neutral ligand, and
q ranges from 0 to 6, and
b) a metal alkyl.
2. The catalyst system of claim 1, wherein
$R^1$ is a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group, and
$R^4$ and $R^5$ are independently a $C_1$ to $C_{15}$ alkyl group, a $C_4$ to $C_{20}$ cycloalkyl group, a $C_4$ to $C_{20}$ substituted cycloalkyl group, a $C_3$ to $C_{15}$ aliphatic heterocyclic group, a $C_3$ to $C_{15}$ substituted aliphatic heterocyclic group, a $C_6$ to $C_{20}$ aryl group, a $C_6$ to $C_{20}$ substituted aryl group, a $C_3$ to $C_{20}$ heteroaryl group, or a $C_3$ to $C_{20}$ substituted heteroaryl group.
3. The catalyst system of claim 1, wherein
$R^1$ is a phenyl group or a $C_6$ to $C_{20}$ substituted phenyl group,
$R^4$ and $R^5$ are independently a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group,
M is chromium,
X is a halide, a $C_1$ to $C_{20}$ carboxylate, a $C_1$ to $C_{20}$ β-diketonate, or a $C_1$ to $C_{20}$ hydrocarboxide,
p is ranges from 2 to 3, and
Q is a $C_2$ to $C_{20}$ nitrile or a $C_2$ to $C_{40}$ either.
4. The catalyst system of claim 3, wherein the metal alkyl comprises an aluminoxane and the aluminoxane comprises methylaluminoxane (MAO), modified methylaluminoxane (MMAO), ethylaluminoxane, n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, or mixtures thereof.
5. The catalyst system of claim 4, wherein a molar ratio of the aluminum of the aluminoxane to the metal of the metal complex is at least 5:1.
6. A method of preparing a catalyst system of claim 1, comprising forming a catalyst system mixture comprising a) the $N^2$-phosphinyl formamidine metal salt complex and h) the metal alkyl.
7. The method of claim 6, wherein the catalyst system or the catalyst system mixture is aged for at least 20 minutes in the substantial absence of the olefin to form an aged catalyst system.
8. A process comprising:
a) forming a catalyst system mixture according to claim 6, wherein the metal alkyl is an aluminoxane;
b) contacting the catalyst system mixture with an olefin; and
c) forming an oligomer product.
9. The process of claim 8, wherein the catalyst system or the catalyst system mixture is aged for at least 20 minutes in the substantial absence of the olefin to form an aged catalyst system.
10. A process comprising:
a) contacting an olefin and the catalyst system of claim 1, wherein the metal alkyl is an aluminoxane; and
b) forming an oligomer product.
11. The process of claim 10, wherein
$R^1$ is a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group, and
$R^4$ and $R^5$ are independently a $C_1$ to $C_{15}$ alkyl group, a $C_4$ to $C_{20}$ cycloalkyl group, a $C_4$ to $C_{20}$ substituted cycloalkyl group, a $C_3$ to $C_{15}$ aliphatic heterocyclic group, a $C_3$ to $C_{15}$ substituted aliphatic heterocyclic group, a $C_6$ to $C_{20}$ aryl group, a $C_6$ to $C_{20}$ substituted aryl group, a $C_3$ to $C_{20}$ heteroaryl group, or a $C_3$ to $C_{20}$ substituted heteroaryl group.
12. The process of claim 10, wherein
$R^1$ is a phenyl group or a $C_6$ to $C_{20}$ substituted phenyl group,
$R^4$ and $R^5$ are independently a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group,
M is chromium,
X is a halide, a $C_1$ to $C_{20}$ carboxylate, a $C_1$ to $C_{20}$ β-diketonate, or a $C_1$ to $C_{20}$ hydrocarboxide,
p is ranges from 2 to 3, and
Q is a $C_2$ to $C_{20}$ nitrile or a $C_2$ to $C_{40}$ ether.
13. The process of claim 12, wherein the aluminoxane comprises methylaluminoxane (MAO), modified methylaluminoxane (MMAO), ethylaluminoxane, n-propylaluminoxane, iso-propylaluminoxane, n-butylaluminoxane, sec-butylaluminoxane, iso-butyl aluminoxane, t-butyl aluminoxane, 1-pentylaluminoxane, 2-pentylaluminoxane, 3-pentylaluminoxane, iso-pentylaluminoxane, neopentylaluminoxane, or mixtures thereof.

14. The process of claim 13, wherein the olefin comprises ethylene and the ethylene partial pressure ranges from 50 psig to 4,000 psig.

15. The process of claim 14, wherein the a molar ratio of the aluminum of the aluminoxane to the metal of the metal salt complex is at least 5:1, the oligomer product is formed at a temperature ranging from 20° C. to 150° C., and optionally wherein hydrogen is contacted with the catalyst system mixture and the olefin and the hydrogen partial pressure ranges from 5 psig to 400 psig.

16. The process of claim 15, wherein a liquid oligomer product comprises at least 70 wt. % $C_6$ and $C_8$ olefins.

* * * * *